US012729199B2

(12) United States Patent
Stauffer et al.

(10) Patent No.: US 12,729,199 B2
(45) Date of Patent: Sep. 8, 2026

(54) CITRON KINASE INHIBITORS

(71) Applicant: The Cleveland Clinic Foundation, Cleveland, OH (US)

(72) Inventors: Shaun R. Stauffer, Cleveland, OH (US); Hannelore V. Heemers, Cleveland, OH (US); Jonathan D. Macdonald, Cleveland, OH (US); Salma Ben-Salem, Cleveland, OH (US); Joshua Maw, Cleveland, OH (US); Tarun Arya, Cleveland, OH (US); Dhiraj P. Sonawane, Cleveland, OH (US); Jesse A. Coker, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 231 days.

(21) Appl. No.: 18/553,968

(22) PCT Filed: Apr. 5, 2022

(86) PCT No.: PCT/US2022/023494
§ 371 (c)(1),
(2) Date: Oct. 4, 2023

(87) PCT Pub. No.: WO2022/216717
PCT Pub. Date: Oct. 13, 2022

(65) Prior Publication Data

US 2025/0243196 A1 Jul. 31, 2025

Related U.S. Application Data

(60) Provisional application No. 63/170,898, filed on Apr. 5, 2021.

(51) Int. Cl.
*C07D 471/04* (2006.01)
*A61K 31/437* (2006.01)
*A61K 31/444* (2006.01)

(52) U.S. Cl.
CPC .......... *C07D 471/04* (2013.01); *A61K 31/437* (2013.01); *A61K 31/444* (2013.01)

(58) Field of Classification Search
CPC .................................................... C07D 471/04
See application file for complete search history.

(56) References Cited

U.S. PATENT DOCUMENTS

| | | | |
|---|---|---|---|
| 5,033,252 | A | 7/1991 | Carter |
| 5,052,558 | A | 10/1991 | Carter |
| 5,323,907 | A | 6/1994 | Kalvelage |
| 2011/0038835 | A1 | 2/2011 | Feng et al. |

FOREIGN PATENT DOCUMENTS

| | | |
|---|---|---|
| WO | WO 03/000688 | 1/2003 |
| WO | WO 2007/070514 | 6/2007 |
| WO | WO 2007/076423 | 7/2007 |
| WO | WO 2007/125310 | 11/2007 |
| WO | WO 2007/125321 | 11/2007 |
| WO | WO 2008/034860 | 3/2008 |
| WO | WO 2008/145688 | 12/2008 |
| WO | WO 2009/079009 | 6/2009 |
| WO | WO 2013/173506 | 11/2013 |

OTHER PUBLICATIONS

International Search Report and Written Opinion for PCT/US22/23494. mailed Aug. 12, 2022. 15 pages.
Davies et al., CRISPRi enables isoform-specific loss-of-funciton screens and identification of gastric cancer-specific isoform dependencies. Genome Biology, 2021, 22:47. 19 pages.
Hartz et al., Discovery, Structure-Activity Relationships, and In Vivo Evaluation of Novel Aryl Amides as Brain Penetrant Adaptor Protein 2-Associated Kinase 1 (AAK1) Inhibitors for the Treatment of Neuropathic Pain. J Med Chem. Aug. 12, 2021;64(15):11090-11128.
Lu et al., High Expression of Citron Kinase Contributes to the Development of Esophagael Squamous Cell Carcinoma. Frontiers in Genetics. Jul. 2021. vol. 12 Article 628547. 9 pages.
Mckenzie et al., Investigating cytokinesis failure as a strategy in cancer therapy. Oncotarget, 2016, 7(52), 87323-87341.
Meng et al., Citron kinase (CIT-K) promotes aggressiveness and tumorigenesis of breast cancer cells in vitro and in vivo: preliminary study of the underlying mechanism. Clinical and Translational Oncology. 2019; 21:910-923.
Pallavicini et al., Inactivaiton of Citron Kinase Inhibits Medulloblastoma progression by Inducing Apoptosis and Cell Senescence. Cancer Res. 2018, 78(16), 4599-4612.
PubChem-SID-135477400. Modify Date: Mar. 30, 2012. Retrieved from internet Jul. 20, 2022, 5 pages.
Sahin et al., Citron Rho-interacting kinase silencing causes cytokinesis failure and reduces tumor growth in multiple myeloma. 2019, 3(7), 995-1002.
Wu et al., Up-regulation of CIT promotes the growth of colon cancer cells. Oncotarget, 2017, 8(42), 71954-71964.

*Primary Examiner* — Rei Tsang Shiao
(74) *Attorney, Agent, or Firm* — Casimir Jones, S.C.; Anne M. Reynolds

(57) ABSTRACT

Disclosed herein are compounds that are citron kinase inhibitors, pharmaceutical compositions comprising the compounds, and methods of using the compounds, e.g., in a method of treating cancer, such as medulloblastoma or prostate cancer.

20 Claims, 8 Drawing Sheets

FIG. 1A
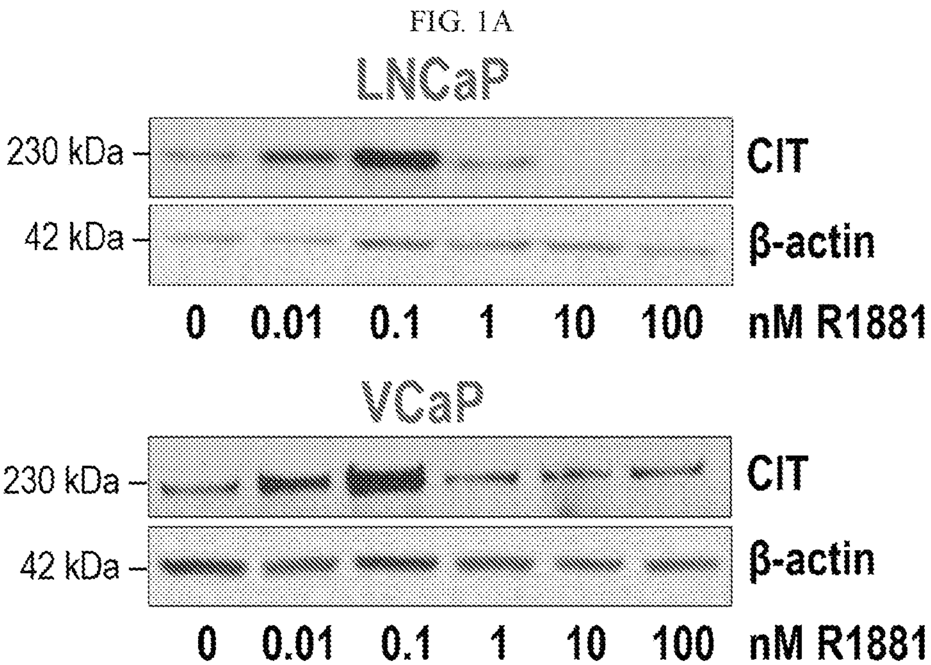
FIG. 1B
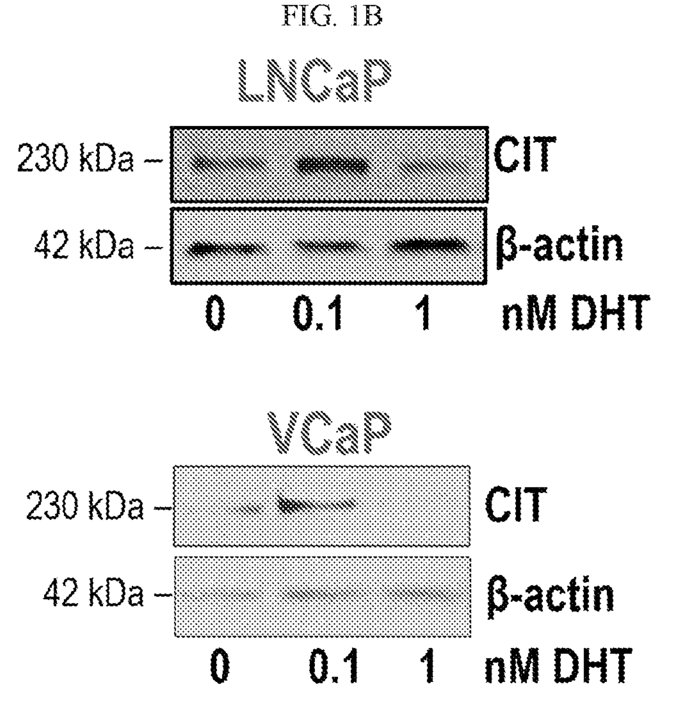
FIGS. 1A-1B

FIG. 2A FIG. 2B FIG. 2C
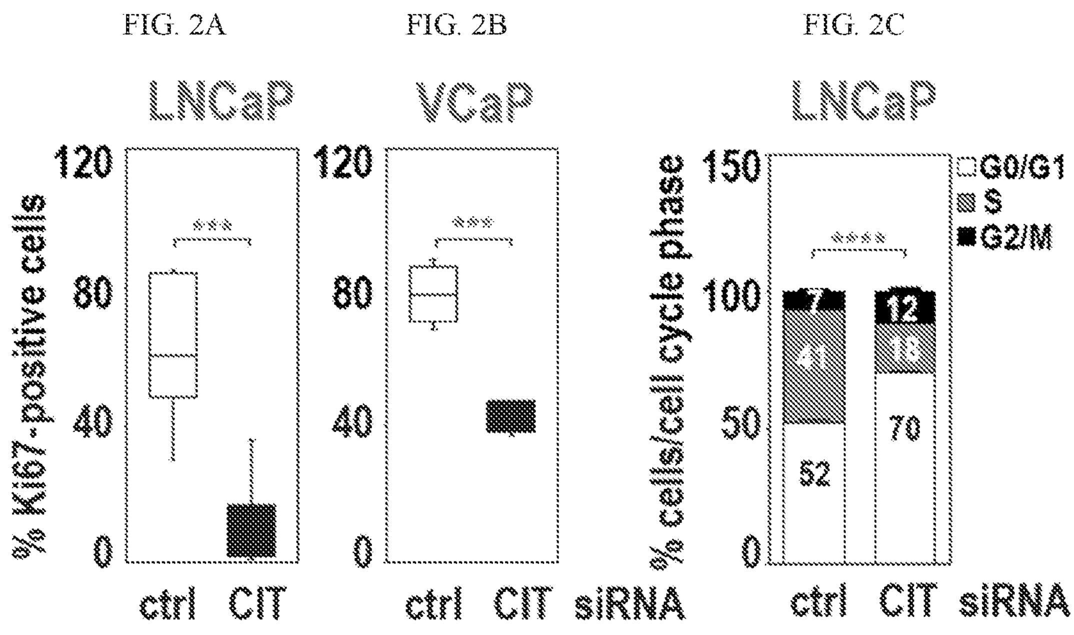
FIG. 2D
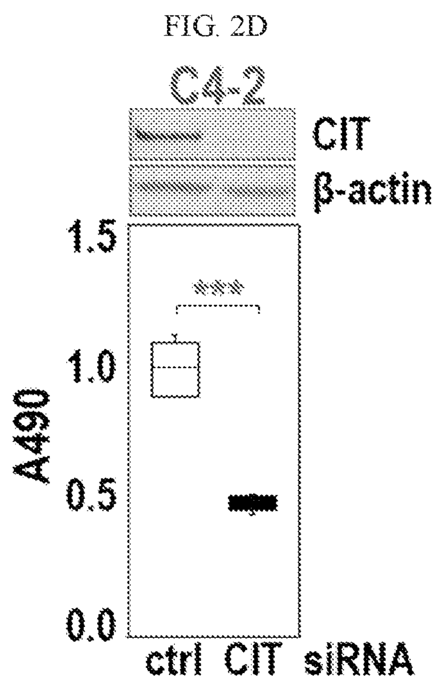
FIGS. 2A-2D

FIG. 3A
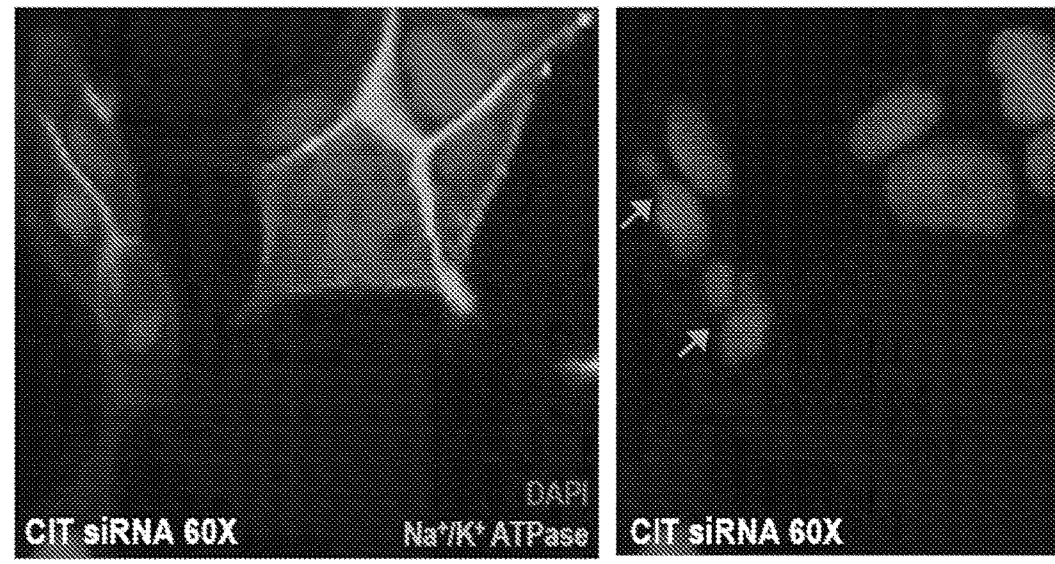
FIG. 3B
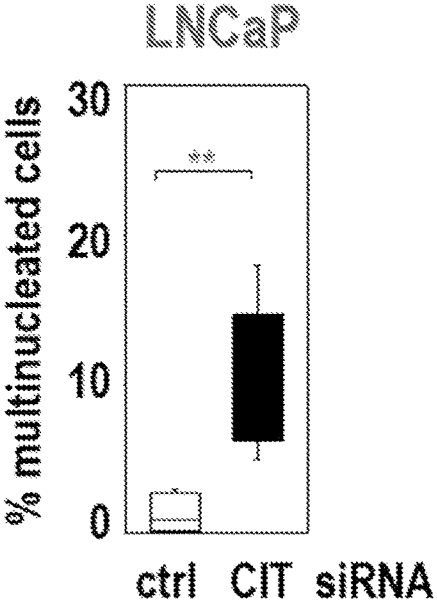
FIGS. 3A-3B

FIG. 5A
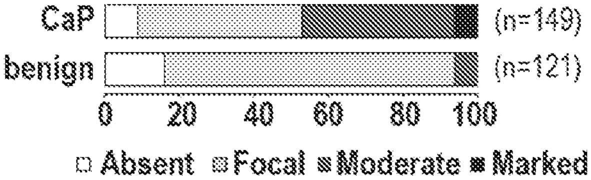
FIG. 5B
FIG. 5C
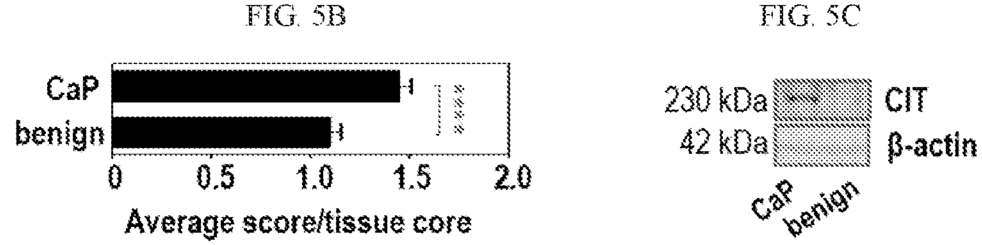
FIG. 5D
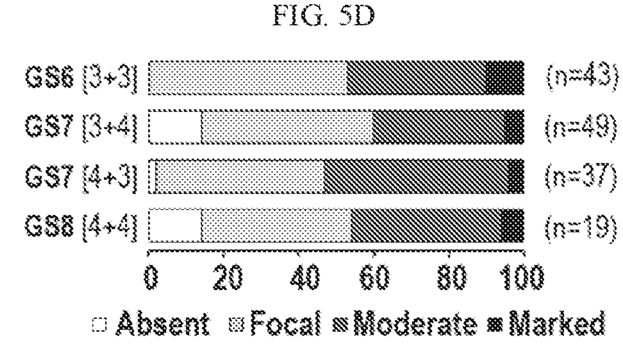
FIG. 5E
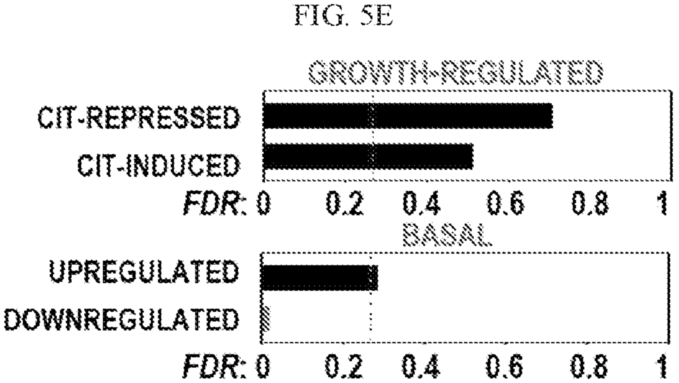
FIGS. 5A-5E FIG. 6A
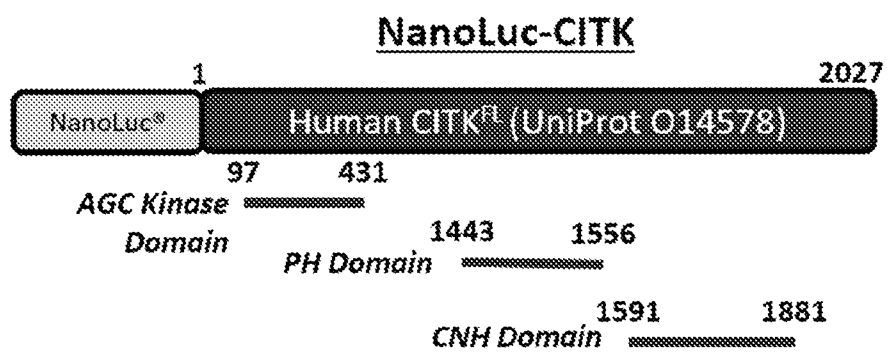
FIG. 6B
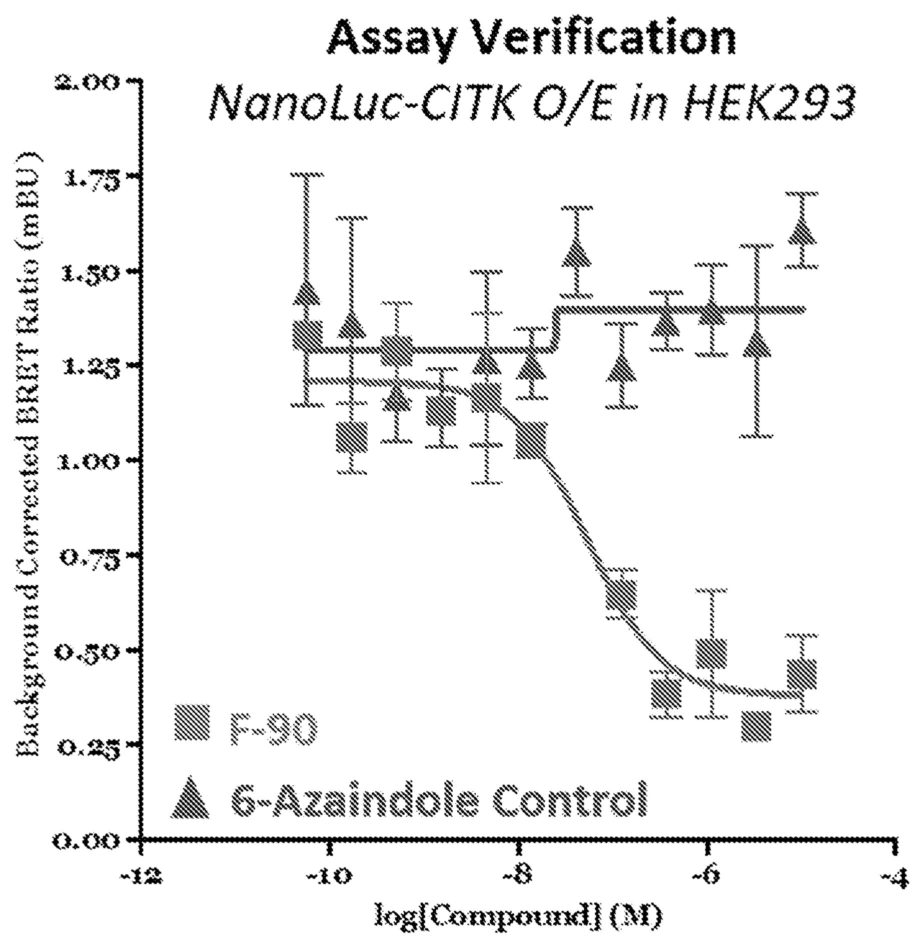
FIGS. 6A-6B

CITRON KINASE INHIBITORS

CROSS-REFERENCE TO RELATED APPLICATIONS

This application is a national stage filing under 35 U.S.C. § 371 of International Application No. PCT/US2022/023494, filed on Apr. 5, 2022, which claims priority to and the benefit of U.S. Provisional Patent Application No. 63/170,898, filed on Apr. 5, 2021, which is incorporated herein by reference in its entirety.

STATEMENT REGARDING FEDERALLY SPONSORED RESEARCH

This invention was made with government support under CA166440 awarded by the National Institutes of Health. The government has certain rights in this invention.

TECHNICAL FIELD

Disclosed herein are compounds that are citron kinase inhibitors, pharmaceutical compositions comprising the compounds, and methods of using the compounds, e.g., in a method of treating cancer, such as medulloblastoma or prostate cancer.

BACKGROUND

Citron kinase (CIT-K) is a serine/threonine protein kinase that plays an important role in cytokinesis, and also has roles earlier in mitosis and in DNA damage control. Citron kinase has also been identified as a potential target in cancer therapy.

SUMMARY

In one aspect, disclosed is a compound of formula (I)

(I)

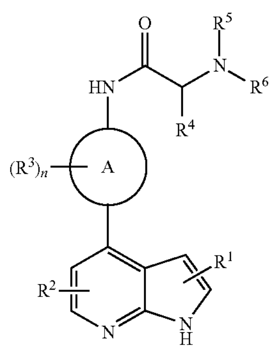

or a pharmaceutically acceptable salt thereof, wherein:

A is phenyl or a monocyclic 5- or 6-membered heteroaryl;

$R^1$ is selected from hydrogen, $C_1$-$C_3$ alkyl, $C_1$-$C_3$ haloalkyl, and $C_3$-$C_5$ cycloalkyl;

$R^2$ is selected from hydrogen, $C_1$-$C_3$ alkyl, $C_1$-$C_3$ haloalkyl, and $C_3$-$C_5$ cycloalkyl;

n is 0, 1, or 2;

each $R^3$ is independently selected from $C_1$-$C_3$ alkyl, $C_1$-$C_3$ haloalkyl, $C_3$-$C_5$ cycloalkyl, $C_1$-$C_3$ alkoxy, $C_1$-$C_3$ haloalkoxy, halo, and cyano;

$R^4$ is selected from hydrogen, $C_1$-$C_6$ alkyl, $C_1$-$C_6$ haloalkyl, $C_3$-$C_6$ cycloalkyl, aryl-$C_1$-$C_3$-alkyl, $C_3$-$C_6$ cycloalkyl-$C_1$-$C_3$-alkyl, hydroxy-$C_1$-$C_6$-alkyl, $C_1$-$C_3$-alkoxy-$C_1$-$C_6$-alkyl, and heterocyclyl-$C_1$-$C_3$-alkyl, wherein each cycloalkyl, aryl, and heterocyclyl is independently unsubstituted or substituted with 1-2 substituents independently selected from $C_1$-$C_3$ alkyl, $C_1$-$C_3$ haloalkyl, $C_1$-$C_3$ alkoxy, hydroxy, and halo; and $R^5$ and $R^6$ are each independently selected from hydrogen, $C_1$-$C_3$ alkyl, $C_1$-$C_3$ haloalkyl, $C_3$-$C_5$ cycloalkyl, $C_1$-$C_3$-alkoxy-$C_1$-$C_3$-alkyl, and $C_3$-$C_6$ cycloalkyl-$C_1$-$C_3$-alkyl.

In some embodiments, A is selected from phenyl, pyridyl, and thiazolyl. In some embodiments, A is phenyl.

In some embodiments, the compound has formula (Ia):

(Ia)

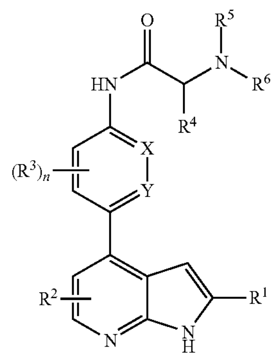

wherein: X and Y are each independently selected from CH and N.

In some embodiments, the compound has formula (Ib):

(Ib)

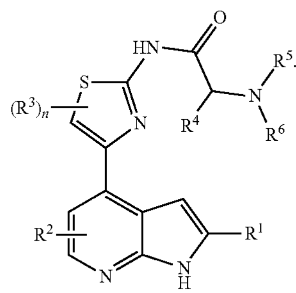

In some embodiments, $R^1$ is selected from hydrogen, $C_1$-$C_2$ alkyl, $C_1$-$C_2$ fluoroalkyl, and $C_3$-$C_4$ cycloalkyl. In some embodiments, $R^1$ is selected from hydrogen, methyl, ethyl, difluoromethyl, trifluoromethyl, and cyclopropyl.

In some embodiments, $R^2$ is selected from hydrogen and $C_1$-$C_3$ alkyl. In some embodiments, $R^2$ is selected from hydrogen and methyl.

In some embodiments, n is 0. In some embodiments, n is 1 or 2.

In some embodiments, each $R^3$ is independently selected from $C_1$-$C_2$ alkyl, $C_1$-$C_2$ haloalkyl, $C_1$-$C_2$ alkoxy, $C_1$-$C_2$ haloalkoxy, halo, and cyano. In some embodiments, each $R^3$ is independently selected from methyl, ethyl, difluoromethyl, trifluoromethyl, methoxy, trifluoromethoxy, fluoro, chloro, and cyano.

In some embodiments, $R^4$ is selected from hydrogen, $C_1$-$C_5$ alkyl, $C_1$-$C_3$ haloalkyl, $C_3$-$C_4$ cycloalkyl, aryl-$C_1$-$C_2$-alkyl, $C_3$-$C_5$ cycloalkylmethyl, hydroxy-$C_1$-$C_4$-alkyl, and methoxy-$C_1$-$C_2$-alkyl. In some embodiments, $R^4$ is selected from hydrogen, methyl, ethyl, n-propyl, iso-propyl, n-butyl, sec-butyl, iso-butyl, tert-butyl, iso-pentyl, neo-pentyl, trifluoromethyl, 1-fluoro-1-methylethyl, 2,2,2-trifluoroethyl, 3,3,3-trifluoropropyl, cyclopropyl, benzyl, 3-chlorobenzyl, 4-chlorobenzyl, 3-hydroxybenzyl, 4-hydroxybenzyl, 3-methoxybenzyl, 4-methoxybenzyl, hydroxymethyl, 1-hydroxyethyl, 2-hydroxyisopropyl, 1-hydroxy-2-methylpropyl, 1-hydroxy-2,2-dimethylpropyl, methoxymethyl, 2-methoxyethyl, cyclopropylmethyl, cyclobutylmethyl, cyclopentylmethyl, and tetrahydro-2H-pyran-4-ylmethyl.

In some embodiments, $R^5$ and $R^6$ are each independently selected from hydrogen, $C_1$-$C_2$ alkyl, $C_1$-$C_2$ haloalkyl, $C_3$-$C_4$ cycloalkyl, methoxy-$C_1$-$C_2$-alkyl, and $C_3$-$C_4$-cycloalkylmethyl. In some embodiments, $R^5$ and $R^6$ are each independently selected from hydrogen, methyl, ethyl, 2,2,2-trifluoroethyl, cyclopropyl, 2-methoxyethyl, and cyclopropylmethyl. In some embodiments, $R^5$ and $R^6$ are each hydrogen.

In some embodiments, the compound is a compound disclosed herein, or pharmaceutically acceptable salt thereof.

Also disclosed herein is a pharmaceutical composition comprising a compound of formula (I), or a pharmaceutically acceptable salt thereof, and a pharmaceutically acceptable carrier.

Also disclosed herein is a method of treating cancer in a subject in need thereof, comprising administering to the subject a therapeutically effective amount of a compound of formula (I), or a pharmaceutically acceptable salt thereof. In some embodiments, the cancer is selected from prostate cancer, breast cancer, a central nervous system (CNS) cancer (e.g., medulloblastoma), cervical cancer, colon cancer, esophageal cancer, gastric cancer, leukemia, melanoma, lung cancer, ovarian cancer, renal cancer, and multiple myeloma. In some embodiments, the cancer is medulloblastoma. In some embodiments, the cancer is prostate cancer.

In some embodiments, the method further comprises treating the subject with one or more additional therapies. In some embodiments, the one or more additional therapies are selected from surgery, chemotherapy, radiation therapy, hormone therapy, immunotherapy, and bisphosphonate therapy.

Also disclosed herein is a method of inhibiting cancer cell proliferation, comprising contacting cancer cells with a compound of formula (I), or a pharmaceutically acceptable salt thereof, in an amount effective to inhibit the cancer cell proliferation. In some embodiments, the cancer cells are selected from the cancer cells are selected from prostate cancer, breast cancer, a central nervous system (CNS) cancer (e.g., medulloblastoma), cervical cancer, colon cancer, esophageal cancer, gastric cancer, leukemia, melanoma, lung cancer, ovarian cancer, renal cancer, and multiple myeloma cells. In some embodiments, the cancer cells are medulloblastoma cancer cells. In some embodiments, the cancer cells are prostate cancer cells. In some embodiments, the step of contacting the cancer cells with the compound comprises administering the compound to a subject suffering from cancer.

BRIEF DESCRIPTION OF THE DRAWINGS

FIGS. 1A-1B show data demonstrating that growth stimuli induce citron kinase expression. FIG. 1A: LNCaP (top panel) and VCaP cells (bottom panel) were treated with increasing doses of the synthetic androgen R1881 for 48 hours. CIT and β-actin expression were analyzed by western blotting. FIG. 1B: LNCaP (left panel) and VCaP cells (right panel) were treated with increasing doses of the natural androgen dihydrotestosterone (DHT) and analyzed as for FIG. 1A.

FIGS. 2A-2D show data demonstrating that citron kinase is a key regulator of CaP cell proliferation. LNCaP (FIG. 2A) or VCaP (FIG. 2B) cells were transfected with siRNA targeting CIT (CIT) or with non-specific control (ctrl) siRNA. 96 hours after transfection, CaP cell proliferation was measured via Ki67 immunostaining (7 independent images with >1,000 (LNCaP) or 500 (VCaP) cells per siRNA condition (n=7, *p<0.001, t test). FIG. 2C: LNCaP cells were transfected as under A. Cell cycle analysis was evaluated by propidium iodide cell sorting. The average percentage of cells in G0/G1, S, and G2/M phase is shown (assay performed in triplicate, p<0.0001, two-way ANOVA). FIG. 2D: CRPC C4-2 cells were transfected as under A. 96 hours after transfection, cell viability was measured. *p<0.001, t test.

FIGS. 3A-3B show data demonstrating that citron kinase controls prostate cancer cell division. LNCaP cells were transfected with siRNA targeting CIT (CIT) or with non-specific control siRNA. 96 hours after transfection, multinucleation was analyzed by immunofluorescence staining using the cell membrane marker Na/K ATPase (green), counterstained with nuclear marker stain DAPI (blue). FIG. 3A shows representative images at magnification 60× FIG. 3B shows quantification of percentage of multinucleated cells recorded from 8 independent images with >75 cells per siRNA condition (n=8, **p<0.01, t test).

FIGS. 5A-5E show data demonstrating that citron kinase is overexpressed in clinical prostate cancer. FIG. 5A: Percentage of cores with absent, focal, moderate or marked CIT immunohistochemical staining from TMAs that contain 149 CaP cores and 121 matching benign cores is shown. FIG. 5B: Average CIT expression score per tissue core as evaluated in benign versus prostate cancer tissues (n=149, **p<0.0001, t test). FIG. 5C: Protein lysates from a localized treatment-naïve CaP tissue that contains >90% neoplastic nuclei and an adjacent non-malignant prostate tissue were analyzed for CIT and β-actin expression via western blotting. FIG. 5D: Percentage of Gleason score 6 (3+3), 7 (3+4 and 4+3), and 8 (4+4) cores with absent, focal, moderate or marked CIT immunohistochemical staining from TMAs. FIG. 5**E: GSEA analysis of growth-regulated and basal CIT-dependent gene signatures, comparing to CRPC and treatment-naïve CaP (GSE32269). Black bars, no significant enrichment; red bars, significant positive enrichment in CRPC compared to treatment-naïve CaP. Red dashed line indicates FDR<0.25, which is considered significant.

FIGS. 6A-6B show an illustration of the NanoLuc-CITK fusion protein construct used for NanoBRET target engagement assays (FIG. 6A), and dose-response curves for compounds F-90 and a negative control compound using the NanoBRET target engagement assay (FIG. 6B).

DETAILED DESCRIPTION

Figure 4:
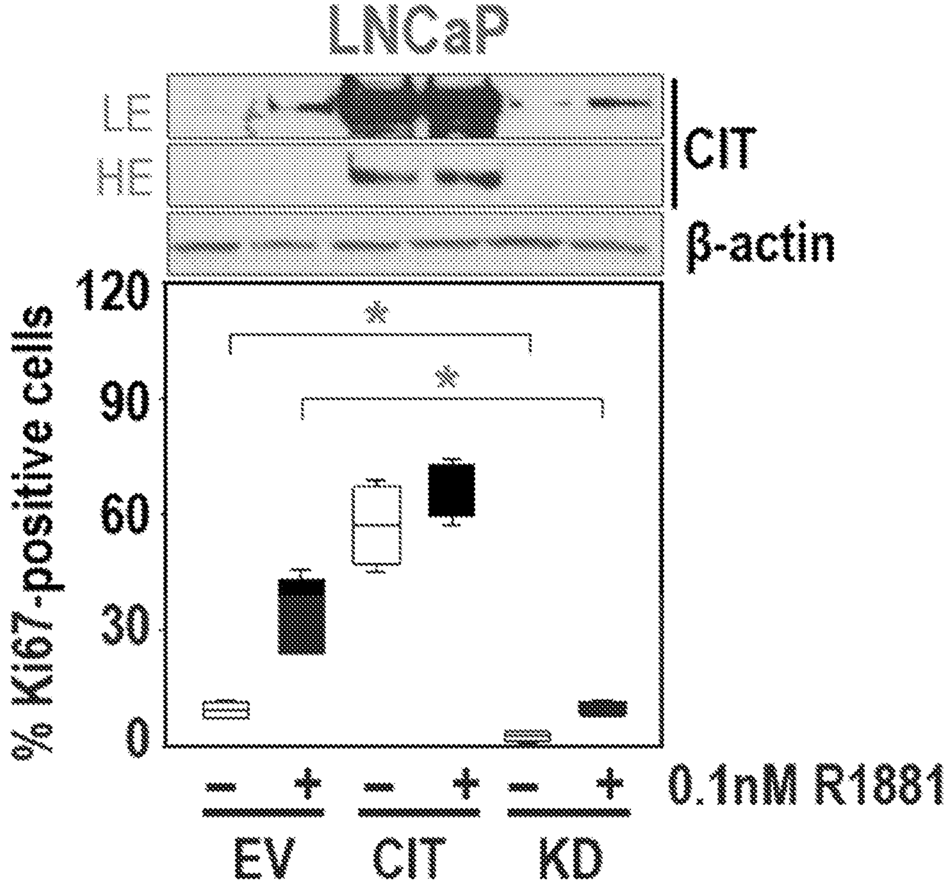
FIG. 4 shows data demonstrating that citron kinase is a druggable target for prostate cancer treatment. LNCaP were transiently transfected with expression constructs encoding wild-type CIT (CIT), citron kinase-dead (CIT-KD) or empty vector (EV) and stimulated with 0.1 nM of R1881 for 48 h. Ki67 immunostaining was evaluated using 4 independent images with >100 cells per condition (n=4, *p<0.05, t test).

As disclosed herein, citron kinase has been identified as a druggable target that acts downstream of androgen receptor (AR), and compounds of formula (I) have been identified as citron kinase inhibitors. Accordingly, the disclosure relates to compounds of formula (I), pharmaceutical compositions comprising the compounds, and methods of using the compounds, e.g., in methods of inhibiting the proliferation of cancer cells, and in methods of treating cancer, such as prostate cancer, breast cancer, central nervous system (CNS) cancers (e.g., medulloblastoma), cervical cancer, colon cancer, esophageal cancer, gastric cancer, leukemia, melanoma, lung cancer, ovarian cancer, renal cancer, and multiple myeloma.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents, and other references mentioned herein are incorporated by reference in their entirety. The materials, methods, and examples disclosed herein are illustrative only and not intended to be limiting.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Sorrell, Organic Chemistry, $2^{nd}$ edition, University Science Books, Sausalito, 2006; Smith, March's Advanced Organic Chemistry: Reactions, Mechanism, and Structure, $7^{th}$ Edition, John Wiley & Sons, Inc., New York, 2013; Larock, Comprehensive Organic Transformations, $3^{rd}$ Edition, John Wiley & Sons, Inc., New York, 2018; and Carruthers, Some Modern Methods of Organic Synthesis, $3^{rd}$ Edition, Cambridge University Press, Cambridge, 1987; the entire contents of each of which are incorporated herein by reference.

As used herein, the term "alkyl" means a straight or branched saturated hydrocarbon chain containing from 1 to 30 carbon atoms, for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_5$ alkyl), 1 to 6 carbon atoms ($C_1$-$C_6$ alkyl), 1 to 4 carbon atoms ($C_1$-$C_4$ alkyl), 6 to 20 carbon atoms ($C_6$-$C_{20}$ alkyl), or 8 to 14 carbon atoms ($C_8$-$C_{14}$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

As used herein, the term "aryl" refers to an aromatic carbocyclic ring system having a single ring (monocyclic) or multiple rings (bicyclic or tricyclic) including fused ring systems, and zero heteroatoms. As used herein, aryl contains 6-20 carbon atoms ($C_6$-$C_{20}$ aryl), 6 to 14 ring carbon atoms ($C_6$-$C_{14}$ aryl), 6 to 12 ring carbon atoms ($C_6$-$C_{12}$ aryl), or 6 to 10 ring carbon atoms ($C_6$-$C_{10}$ aryl). Representative examples of aryl groups include, but are not limited to, phenyl, naphthyl, anthracenyl, and phenanthrenyl.

As used herein, the term "cyano" means a —CN group.

As used herein, the term "cycloalkyl" refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

As used herein, the term "halogen" or "halo" means F, Cl, Br, or I.

As used herein, the term "haloalkyl" means an alkyl group, as defined herein, in which at least one hydrogen atom (e.g., one, two, three, four, five, six, seven or eight hydrogen atoms) is replaced by a halogen. Representative examples of haloalkyl include, but are not limited to, fluoromethyl, difluoromethyl, trifluoromethyl, 2,2,2-trifluoroethyl, and 3,3,3-trifluoropropyl.

As used herein, the term "haloalkoxy" means a haloalkyl group, as defined herein, is appended to the parent molecular moiety through an oxygen atom. Representative examples of haloalkoxy include, but are not limited to, difluoromethoxy, trifluoromethoxy, and 2,2,2-trifluoroethoxy.

As used herein, the term "heteroaryl" refers to an aromatic group having a single ring (monocyclic) or multiple rings (bicyclic or tricyclic) having one or more ring heteroatoms independently selected from O, N, and S. The aromatic monocyclic rings are five- or six-membered rings containing at least one heteroatom independently selected from O, N, and S (e.g. 1, 2, 3, or 4 heteroatoms independently selected from O, N, and S). The five-membered aromatic monocyclic rings have two double bonds, and the six-membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein, and a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

As used herein, the term "heterocycle" or "heterocyclic" refers to a saturated or partially unsaturated non-aromatic cyclic group having one or more ring heteroatoms independently selected from O, N, and S. The heterocycle can be monocyclic heterocycle, a bicyclic heterocycle, or a tricyclic heterocycle. The monocyclic heterocycle is a three-, four-, five-, six-, seven-, or eight-membered ring containing at least one heteroatom independently selected from O, N, and S. The three- or four-membered ring contains zero or one double bond, and one heteroatom selected from O, N, and S. The five-membered ring contains zero or one double bond and one, two or three heteroatoms selected from O, N, and S. The six-membered ring contains zero, one, or two double bonds and one, two, or three heteroatoms selected from O, N, and S. The seven- and eight-membered rings contains zero, one, two, or three double bonds and one, two, or three heteroatoms selected from O, N, and S. The heteroatom in the ring can be oxidized (e.g., a if the ring heteroatom is S, it can be oxidized to SO or $SO_2$). Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan,hexahydro-1H-1,4-methanocyclopenta[c]furan, aza-adamantane (1-azatricyclo[3.3.1.$1^{3,7}$]decane), and oxa-adamantane (2-oxatricyclo[3.3.1.$1^{3,7}$]decane). The monocyclic, bicyclic, and tricyclic heterocycles are connected to the parent molecular moiety through any carbon atom or any nitrogen atom contained within the rings.

As used herein, the term "hydroxy" means an —OH group.

As used herein, the term "substituent" refers to a group substituted on an atom of the indicated group. When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below), provided that the designated atom's normal valence is not exceeded. Substituent groups include, but are not limited to, alkyl, alkenyl, alkynyl, alkoxy, acyl, amino, amido, amidino, aryl, azido, carbamoyl, carboxyl, carboxyl ester, cyano, cycloalkyl, cycloalkenyl, guanidino, halo, haloalkyl, haloalkoxy, heteroalkyl, heteroaryl, heterocyclyl, hydroxy, hydrazino, imino, oxo, nitro, phosphate, phosphonate, sulfonic acid, thiol, thione, or combinations thereof.

As used herein, in chemical structures the indication:

represents a point of attachment of one moiety to another moiety (e.g., a substituent group to the core compound).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., $—CH_2O—$ optionally also recites $—OCH_2—$, and —OC(O)NH— also optionally recites —NHC(O)O—.

The terms "administer," "administering," "administered," or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Effective amount," as used herein, refers to a dosage of a compound or a composition effective for eliciting a desired effect. This term as used herein may also refer to an amount effective at bringing about a desired in vivo effect in a subject, such as a human.

As used herein, the term "subject" is intended to include human and non-human animals. Exemplary human subjects include a human patient having a disorder, e.g., an opioid addiction. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Compounds

The present disclosure provides a compound of formula (I):

(I)

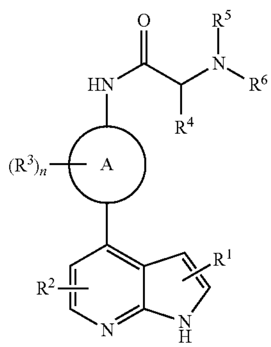

or a pharmaceutically acceptable salt thereof, wherein:

A is phenyl or a monocyclic 5- or 6-membered heteroaryl;

$R^1$ is selected from hydrogen, $C_1$-$C_3$ alkyl, $C_1$-$C_3$ haloalkyl, and $C_3$-$C_5$ cycloalkyl;

$R^2$ is selected from hydrogen, $C_1$-$C_3$ alkyl, $C_1$-$C_3$ haloalkyl, and $C_3$-$C_5$ cycloalkyl;

n is 0, 1, or 2;

each $R^3$ is independently selected from $C_1$-$C_3$ alkyl, $C_1$-$C_3$ haloalkyl, $C_3$-$C_5$ cycloalkyl, $C_1$-$C_3$ alkoxy, $C_1$-$C_3$ haloalkoxy, halo, and cyano;

$R^4$ is selected from hydrogen, $C_1$-$C_6$ alkyl, $C_1$-$C_6$ haloalkyl, $C_3$-$C_6$ cycloalkyl, aryl-$C_1$-$C_3$-alkyl, $C_3$-$C_6$ cycloalkyl-$C_1$-$C_3$-alkyl, hydroxy-$C_1$-$C_6$-alkyl, $C_1$-$C_3$-alkoxy-$C_1$-$C_6$-alkyl, and heterocyclyl-$C_1$-$C_3$-alkyl, wherein each cycloalkyl, aryl, and heterocyclyl is independently unsubstituted or substituted with 1-2 substituents independently selected from $C_1$-$C_3$ alkyl, $C_1$-$C_3$ haloalkyl, $C_1$-$C_3$ alkoxy, hydroxy, and halo; and $R^5$ and $R^6$ are each independently selected from hydrogen, $C_1$-$C_3$ alkyl, $C_1$-$C_3$ haloalkyl, $C_3$-$C_5$ cycloalkyl, $C_1$-$C_3$-alkoxy-$C_1$-$C_3$-alkyl, and $C_3$-$C_6$ cycloalkyl-$C_1$-$C_3$-alkyl.

In some embodiments, A is selected from phenyl, pyridyl, and thiazolyl. In some embodiments, A is selected from phenyl and pyridyl. In some embodiments, A is phenyl. In some embodiments, A is pyridyl. In some embodiments, A is thiazolyl.

In some embodiments, the compound of formula (I) is a compound of formula (Ia):

(Ia)

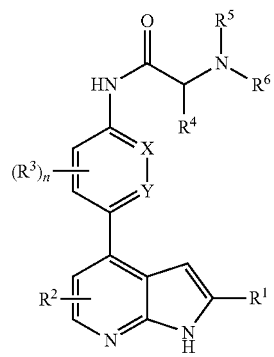

or a pharmaceutically acceptable salt thereof, wherein:

X and Y are each independently selected from CH and N.

In some embodiments, X and Y are not simultaneously N. In some embodiments, X is CH and Y is CH. In some embodiments, X is CH and Y is N. In some embodiments, X is N and Y is CH.

In some embodiments, the compound of formula (I) is a compound of formula (Ib):

(Ib)

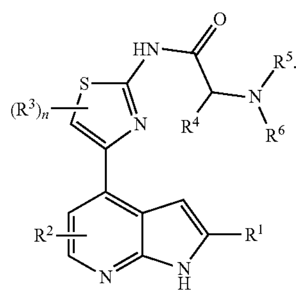

or a pharmaceutically acceptable salt thereof.

In some embodiments, $R^1$ is selected from hydrogen, $C_1$-$C_2$ alkyl, $C_1$-$C_2$ fluoroalkyl, and $C_3$-$C_4$ cycloalkyl. In some embodiments, $R^1$ is selected from hydrogen, methyl, ethyl, difluoromethyl, trifluoromethyl, and cyclopropyl. In some embodiments, $R^1$ is selected from hydrogen and methyl. In some embodiments, $R^1$ is hydrogen. In some embodiments, $R^1$ is $C_1$-$C_3$ alkyl. In some embodiments, $R^1$ is $C_1$-$C_2$ alkyl. In some embodiments, $R^1$ is methyl. In some embodiments, $R^1$ is ethyl. In some embodiments, $R^1$ is $C_1$-$C_3$ haloalkyl. In some embodiments, $R^1$ is $C_1$-$C_2$ haloalkyl. In some embodiments, $R^1$ is difluoromethyl. In some embodiments, $R^1$ is trifluoromethyl. In some embodiments, $R^1$ is $C_3$-$C_5$ cycloalkyl. In some embodiments, $R^1$ is $C_3$-$C_4$ cycloalkyl. In some embodiments, $R^1$ is cyclopropyl.

In some embodiments, $R^2$ is selected from hydrogen and $C_1$-$C_3$ alkyl. In some embodiments, $R^2$ is selected from hydrogen and methyl. In some embodiments, $R^2$ is hydrogen. In some embodiments, $R^2$ is $C_1$-$C_3$ alkyl. In some embodiments, $R^2$ is $C_1$-$C_2$ alkyl. In some embodiments, $R^2$ is methyl.

In some embodiments, n is 0. In some embodiments, n is 1. In some embodiments, n is 2. In some embodiments, n is 0 or 1. In some embodiments, n is 1 or 2.

In some embodiments, ring A has a structure selected from:

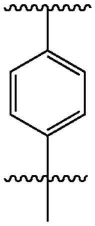, 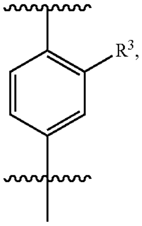 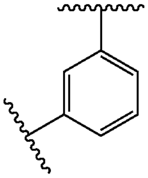, 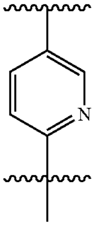,

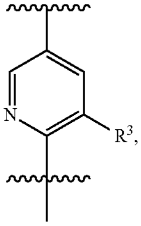 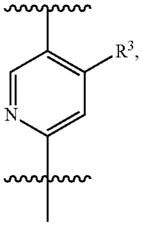 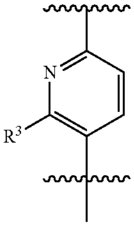,

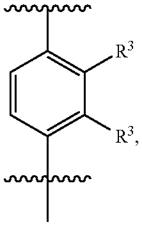 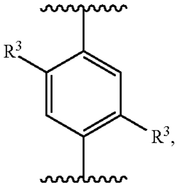 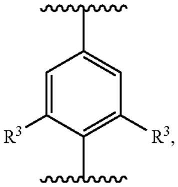

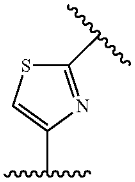, and 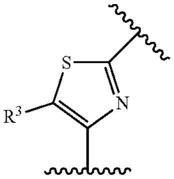.

In the structures illustrated above for ring A, the rings can be oriented in either direction (i.e. the "top" point of attachment can link to either the amide or to the pyrrolopyridine ring in formula (I), and the "bottom" point of attachment can link to the other moiety).

In some embodiments, each $R^3$ is independently selected from $C_1$-$C_2$ alkyl, $C_1$-$C_2$ haloalkyl, $C_1$-$C_2$ alkoxy, $C_1$-$C_2$ haloalkoxy, halo, and cyano. In some embodiments, each $R^3$ is independently selected from methyl, ethyl, difluoromethyl, trifluoromethyl, methoxy, difluoromethoxy, trifluoromethoxy, fluoro, chloro, and cyano.

In some embodiments, n is 1, and $R^3$ is selected from $C_1$-$C_2$ alkyl, $C_1$-$C_2$ haloalkyl, $C_1$-$C_2$ alkoxy, $C_1$-$C_2$ haloalkoxy, halo, and cyano. In some embodiments, n is 1, and $R^3$ is selected from methyl, ethyl, difluoromethyl, trifluoromethyl, methoxy, difluoromethoxy, trifluoromethoxy, fluoro, chloro, and cyano.

In some embodiments, n is 2, and each $R^3$ is independently selected from $C_1$-$C_2$ alkyl, $C_1$-$C_2$ haloalkyl, $C_1$-$C_2$ alkoxy, $C_1$-$C_2$ haloalkoxy, halo, and cyano. In some embodiments, n is 2, and each $R^3$ is independently selected from methyl, ethyl, difluoromethyl, trifluoromethyl, methoxy, difluoromethoxy, trifluoromethoxy, fluoro, chloro, and cyano. In some embodiments, n is 2, and each $R^3$ is independently selected from $C_1$-$C_3$ alkyl and halo. In some embodiments, n is 2, and each $R^3$ is independently selected from $C_1$-$C_2$ alkyl and halo. In some embodiments, n is 2, and each $R^3$ is independently selected from methyl and fluoro.

In some embodiments, $R^4$ is selected from $C_1$-$C_6$ alkyl, $C_1$-$C_6$ haloalkyl, $C_3$-$C_6$ cycloalkyl, aryl-$C_1$-$C_3$-alkyl, $C_3$-$C_6$ cycloalkyl-$C_1$-$C_3$-alkyl, hydroxy-$C_1$-$C_6$-alkyl, $C_1$-$C_3$-alkoxy-$C_1$-$C_6$-alkyl, and heterocyclyl-$C_1$-$C_3$-alkyl, wherein each cycloalkyl, aryl, and heterocyclyl is independently unsubstituted or substituted with 1-2 substituents independently selected from $C_1$-$C_3$ alkyl, $C_1$-$C_3$ haloalkyl, $C_1$-$C_3$ alkoxy, hydroxy, and halo. In some embodiments, $R^4$ is selected from hydrogen, $C_1$-$C_5$ alkyl, $C_1$-$C_3$ haloalkyl, $C_3$-$C_4$ cycloalkyl, aryl-$C_1$-$C_2$-alkyl, $C_3$-$C_5$ cycloalkylmethyl, hydroxy-$C_1$-$C_4$-alkyl, and methoxy-$C_1$-$C_2$-alkyl. In some embodiments, $R^4$ is selected from $C_1$-$C_5$ alkyl, $C_1$-$C_3$ haloalkyl, $C_3$-$C_4$ cycloalkyl, $C_3$-$C_5$ cycloalkylmethyl, aryl-$C_1$-$C_2$-alkyl, hydroxy-$C_1$-$C_4$-alkyl, and methoxy-$C_1$-$C_2$-alkyl. In some embodiments, $R^4$ is selected from hydrogen, methyl, ethyl, n-propyl, iso-propyl, n-butyl, sec-butyl, iso-butyl, tert-butyl, iso-pentyl, neo-pentyl, trifluoromethyl, 1-fluoro-1-methylethyl, 2,2,2-trifluoroethyl, 3,3,3-trifluoropropyl, cyclopropyl, benzyl, 3-chlorobenzyl, 4-chlorobenzyl, 3-hydroxybenzyl, 4-hydroxybenzyl, 3-methoxybenzyl, 4-methoxybenzyl, hydroxymethyl, 1-hydroxyethyl, 2-hydroxyisopropyl, 1-hydroxy-2-methylpropyl, 1-hydroxy-2,2-dimethylpropyl, methoxymethyl, 2-methoxyethyl, cyclopropylmethyl, cyclobutylmethyl, cyclopentylmethyl, and tetrahydro-2H-pyran-4-ylmethyl. In some embodiments, $R^4$ is selected from methyl, ethyl, n-propyl, iso-propyl, n-butyl, sec-butyl, iso-butyl, tert-butyl, iso-pentyl, neo-pentyl, trifluoromethyl, 2,2,2-trifluoroethyl, 3,3,3-trifluoropropyl, cyclopropyl, hydroxymethyl, 1-hydroxyethyl, methoxymethyl, 2-methoxyethyl, cyclopropylmethyl, cyclobutylmethyl, cyclopentylmethyl, and tetrahydro-2H-pyran-4-ylmethyl. In some embodiments, $R^4$ is $C_1$-$C_6$ alkyl. In some embodiments, $R^4$ is selected from methyl, ethyl, n-propyl, iso-propyl, n-butyl, sec-butyl, iso-butyl, tert-butyl, iso-pentyl, and neo-pentyl.

In some embodiments, $R^5$ and $R^6$ are each independently selected from hydrogen, $C_1$-$C_2$ alkyl, $C_1$-$C_2$ haloalkyl, $C_3$-$C_4$ cycloalkyl, methoxy-$C_1$-$C_2$-alkyl, and $C_3$-$C_4$-cycloalkylmethyl. In some embodiments, $R^5$ and $R^6$ are each independently selected from hydrogen, methyl, ethyl, 2,2,2-trifluoroethyl, cyclopropyl, 2-methoxyethyl, and cyclopropylmethyl. In some embodiments, $R^5$ and $R^6$ are each hydrogen. In some embodiments, $R^5$ is hydrogen, and $R^6$ is selected from $C_1$-$C_3$ alkyl, $C_1$-$C_3$ haloalkyl, $C_3$-$C_5$ cycloalkyl, $C_1$-$C_3$-alkoxy-$C_1$-$C_3$-alkyl, and $C_3$-$C_6$ cycloalkyl-$C_1$-$C_3$-alkyl. In some embodiments, $R^5$ is hydrogen, and $R^6$ is selected from $C_1$-$C_2$ alkyl, $C_1$-$C_2$ haloalkyl, $C_3$-$C_4$ cycloalkyl, methoxy-$C_1$-$C_2$-alkyl, and $C_3$-$C_4$-cycloalkylmethyl. In some embodiments, $R^5$ is hydrogen, and $R^6$ is selected from methyl, ethyl, 2,2,2-trifluoroethyl, cyclopropyl, 2-methoxyethyl, and cyclopropylmethyl. In some embodiments, $R^5$ and $R^6$ are each $C_1$-$C_3$ alkyl. In some embodiments, $R^5$ and $R^6$ are each methyl.

In some embodiments, the compound is selected from:
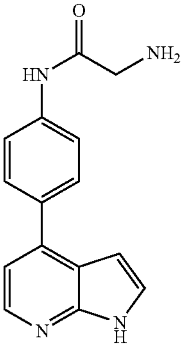
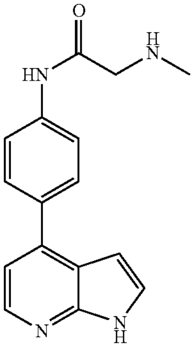
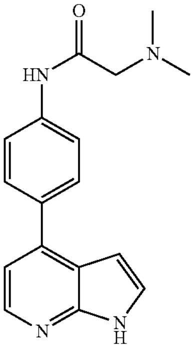
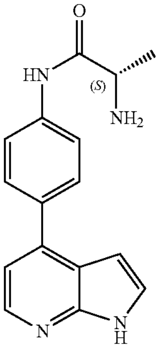
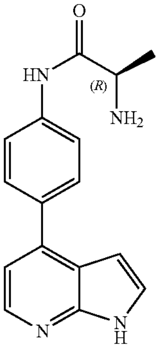
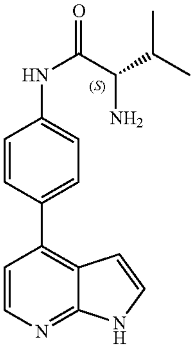
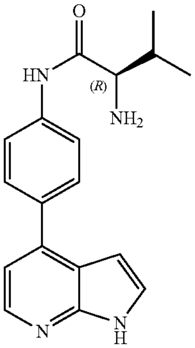
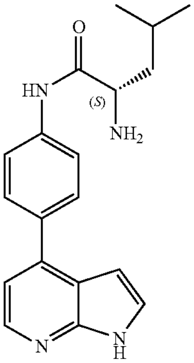
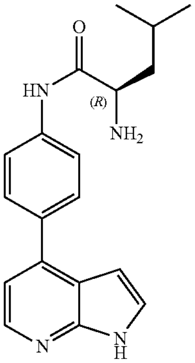
-continued
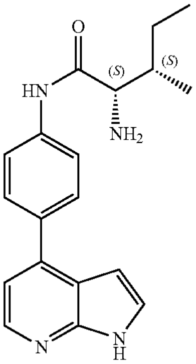
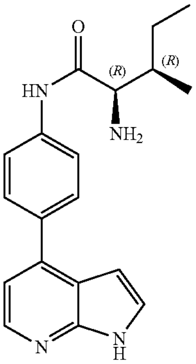
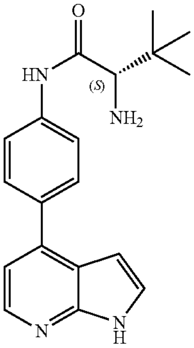
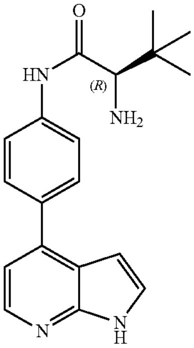
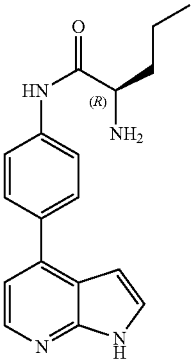
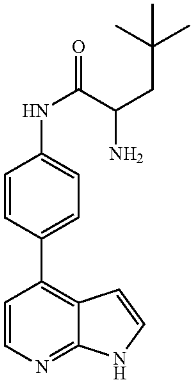
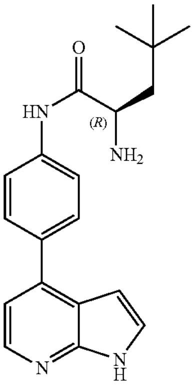
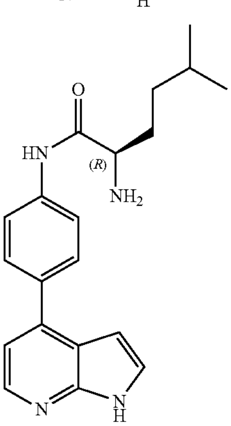

-continued
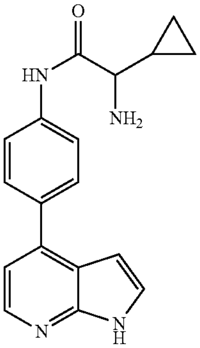
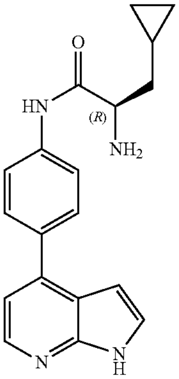
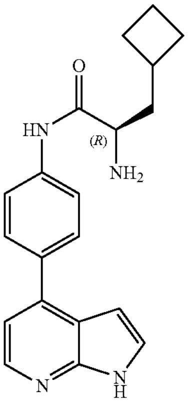
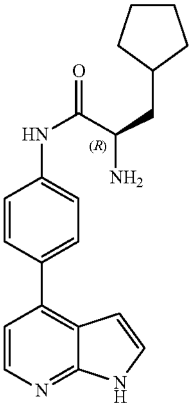
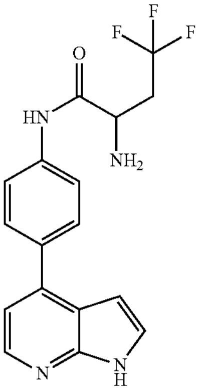
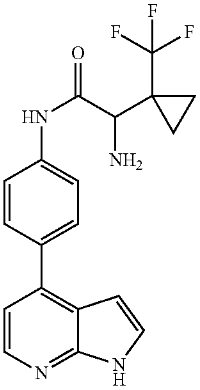
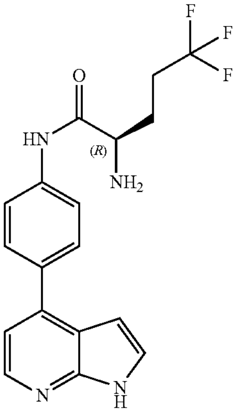
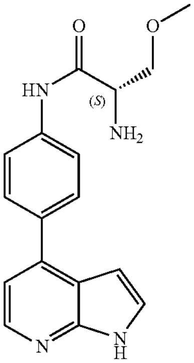
-continued
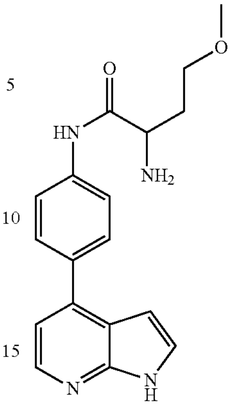
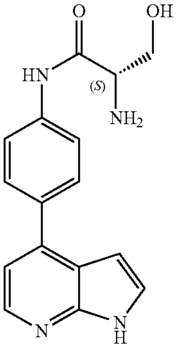
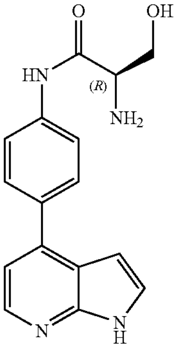
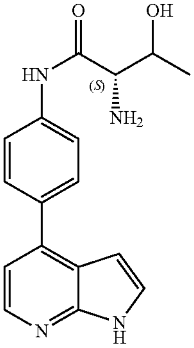
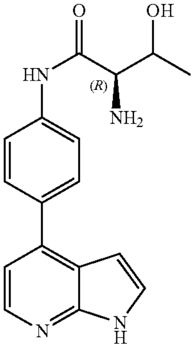
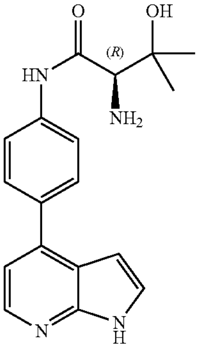
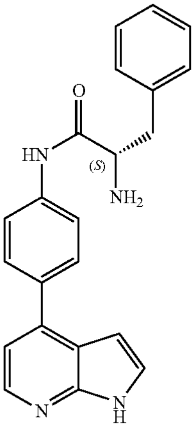
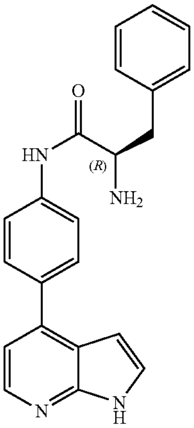
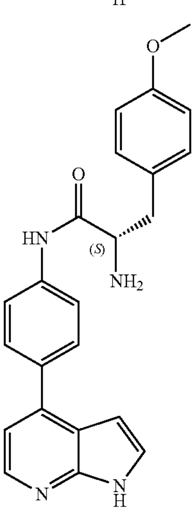

-continued
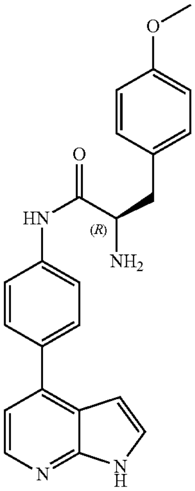
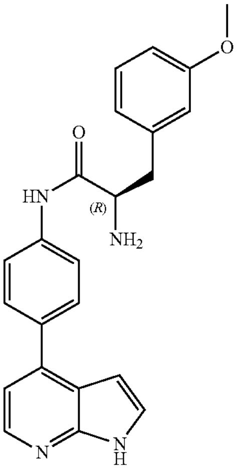
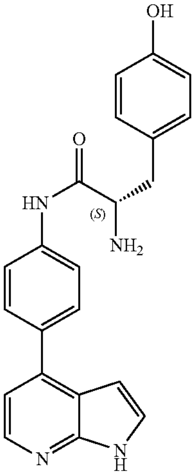
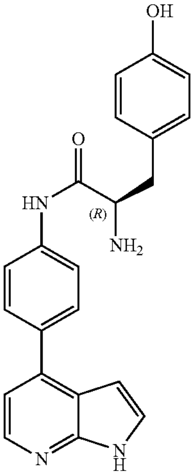
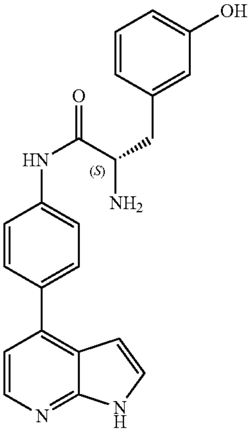
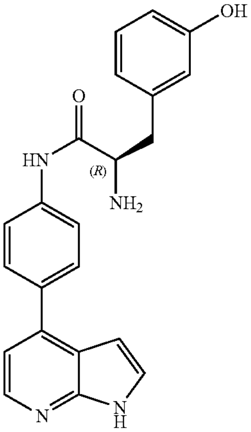
-continued
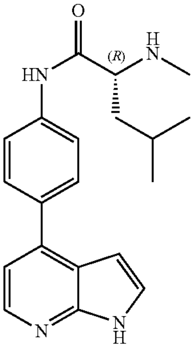
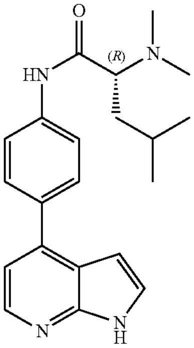
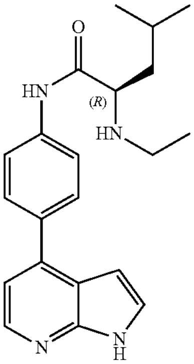
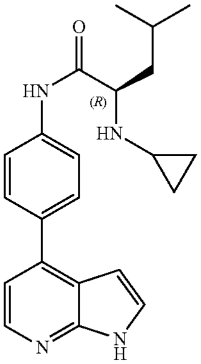
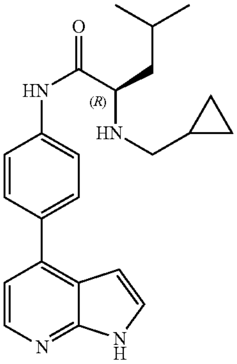
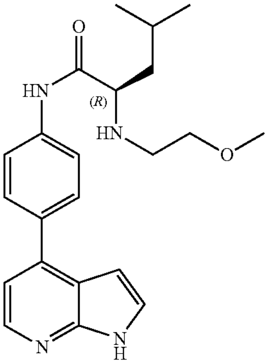
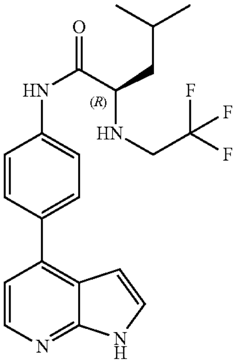
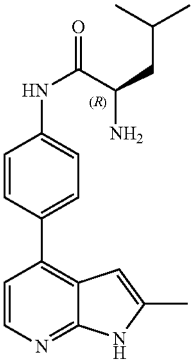

-continued
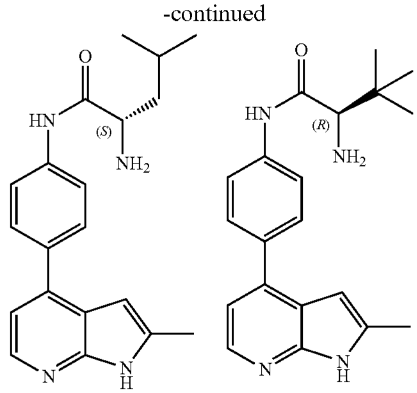
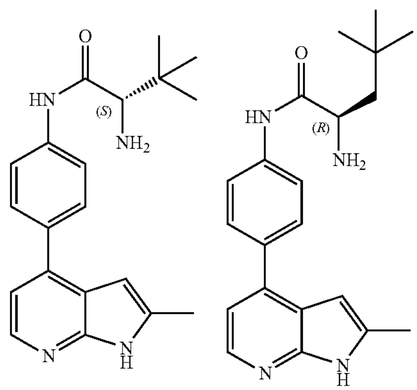
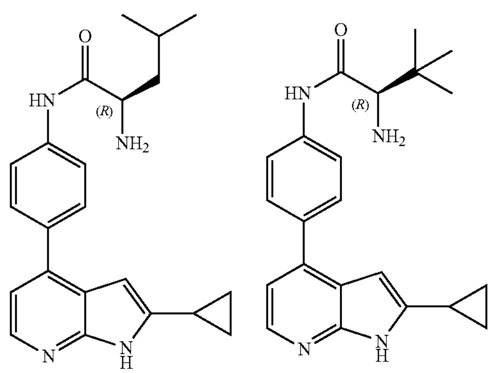
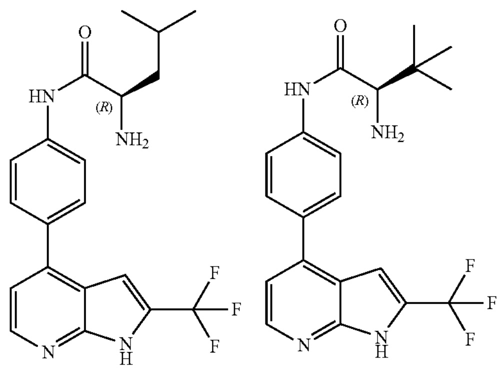
-continued
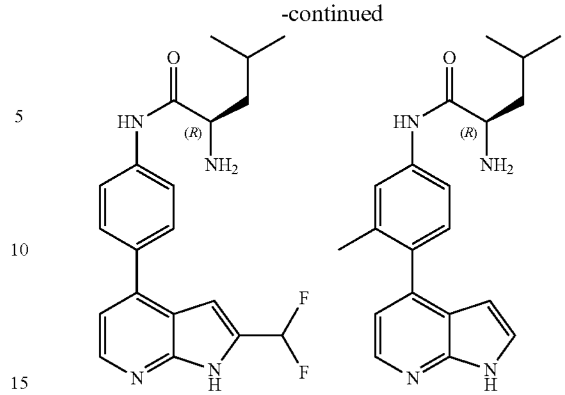
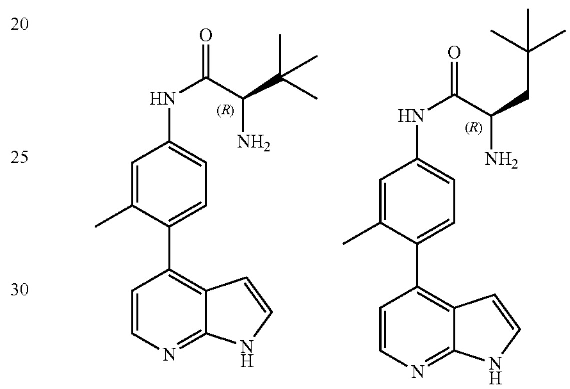
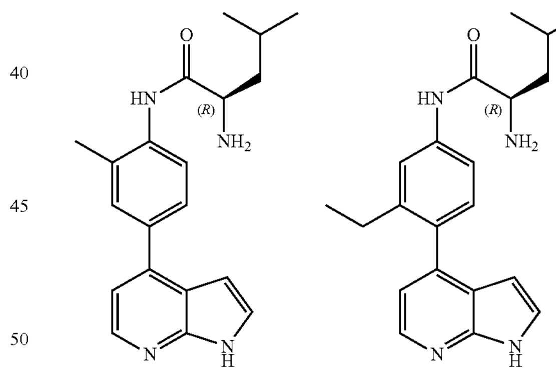
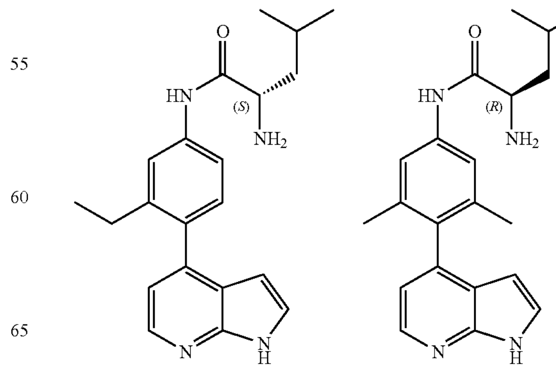

-continued
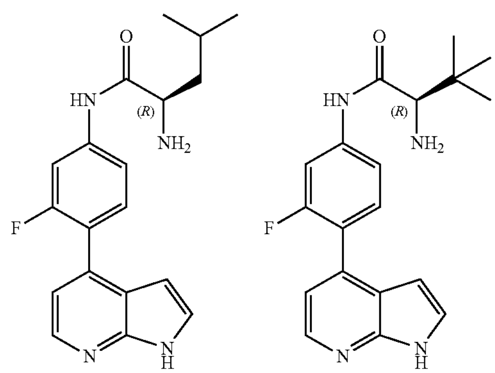
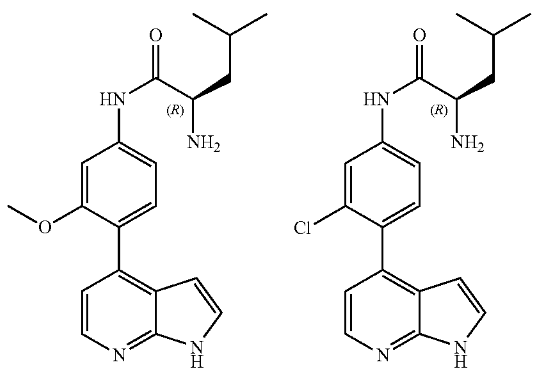
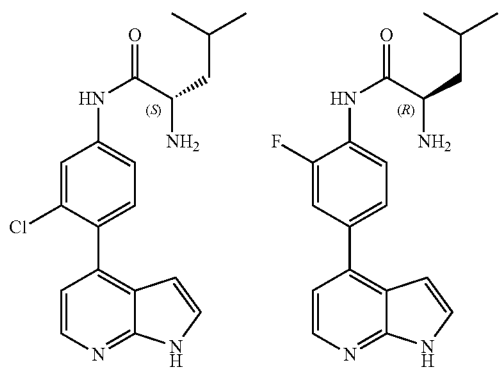
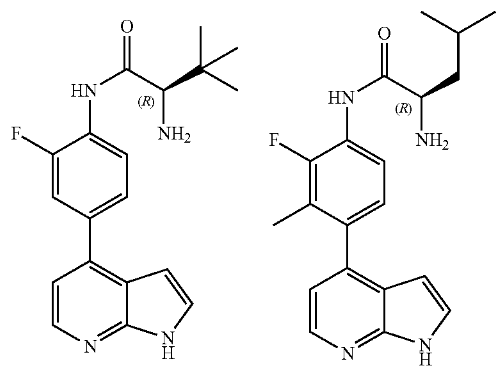
-continued
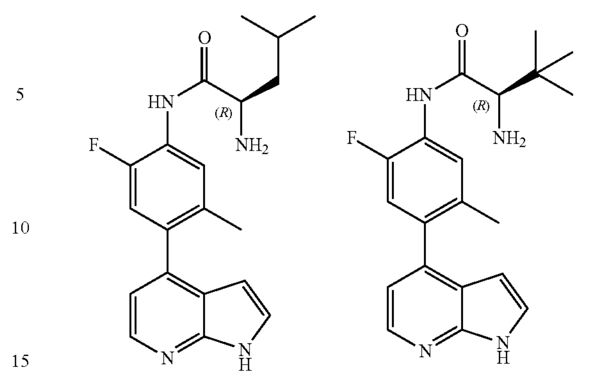
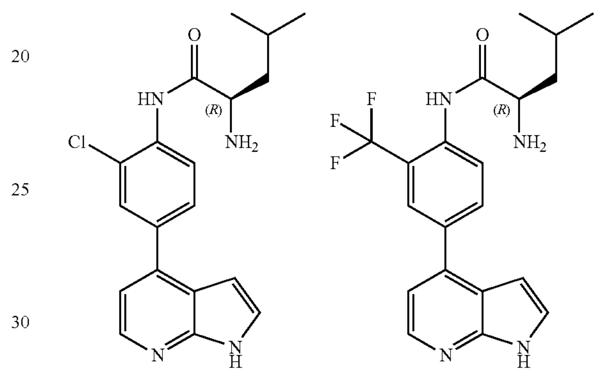
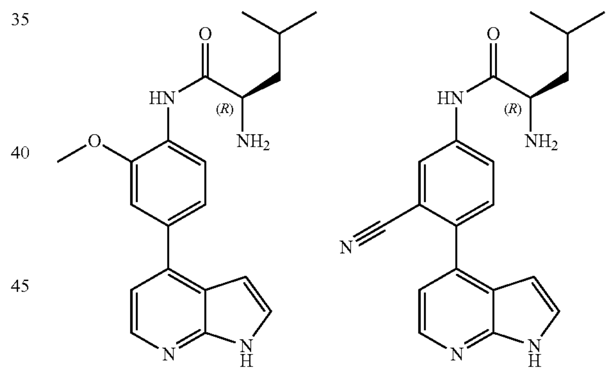
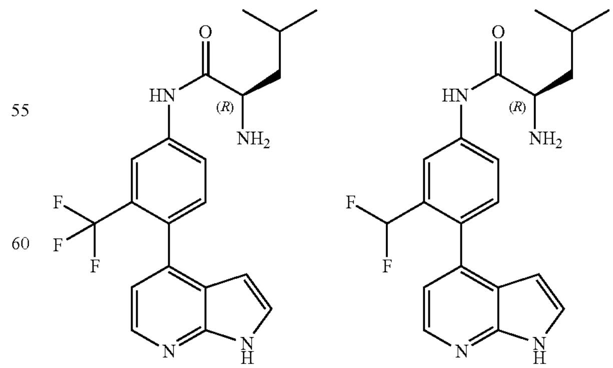

-continued
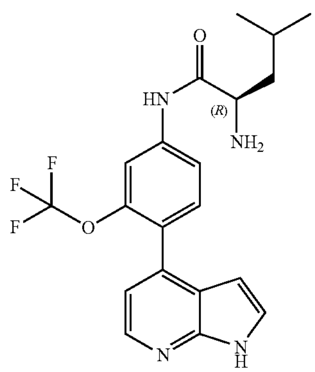
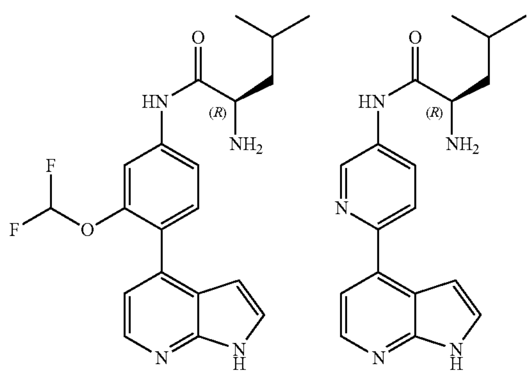
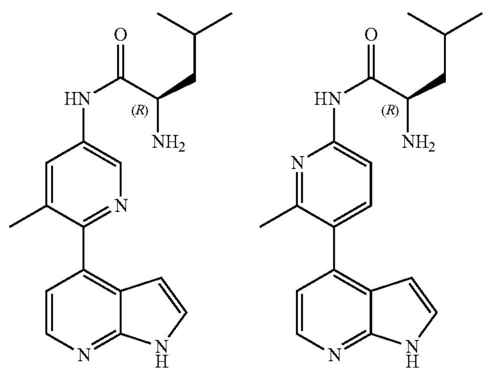
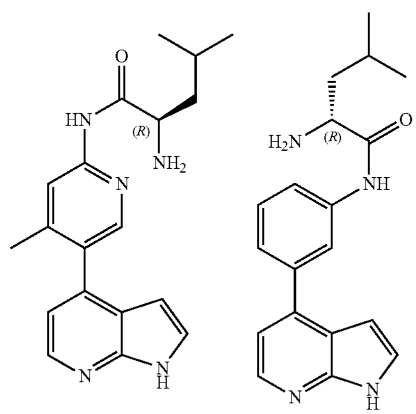
-continued
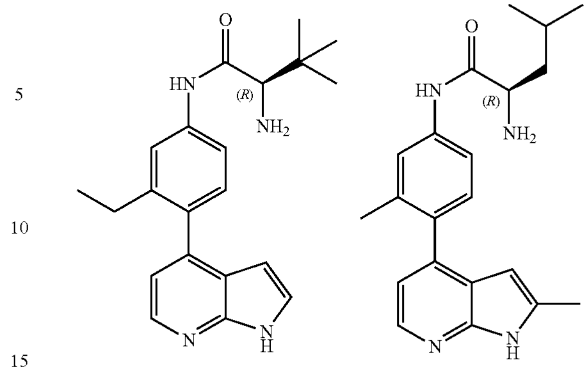
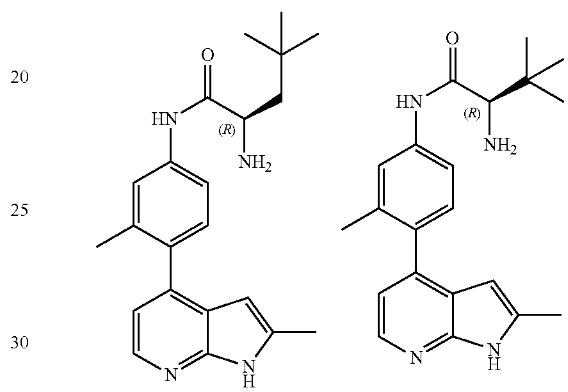
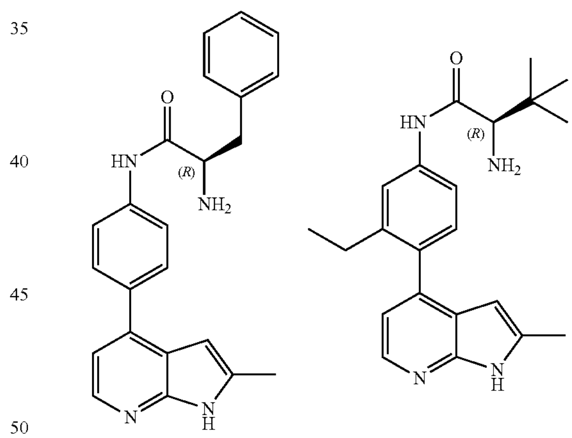
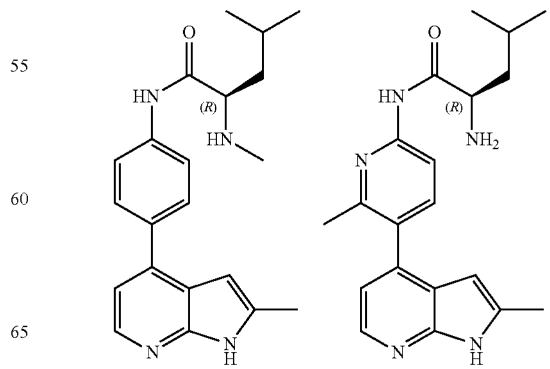

-continued
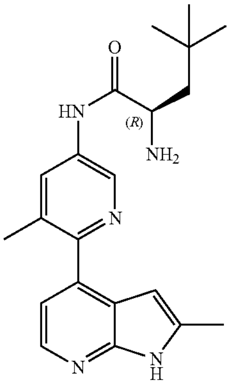
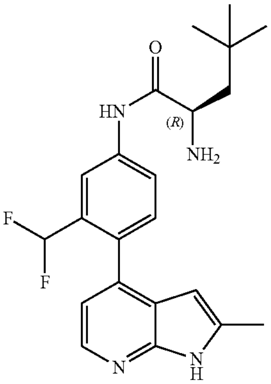
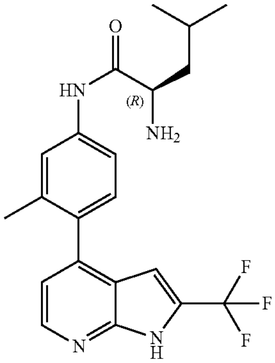
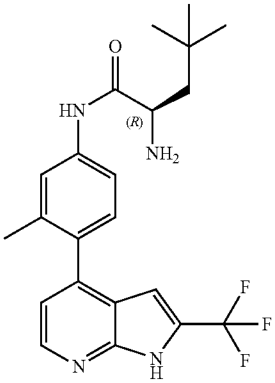
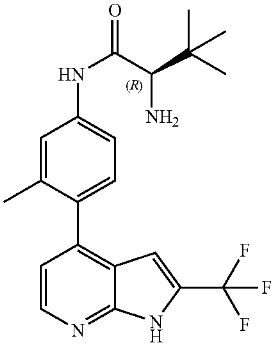
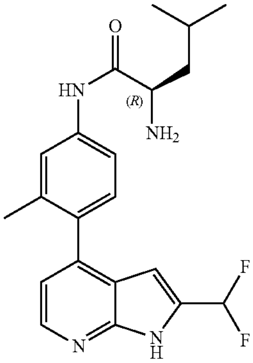
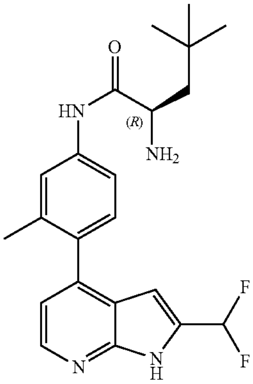
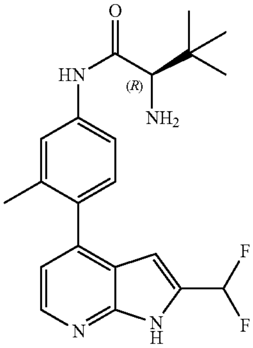
-continued
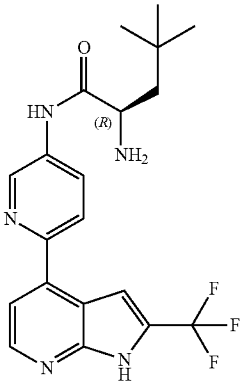
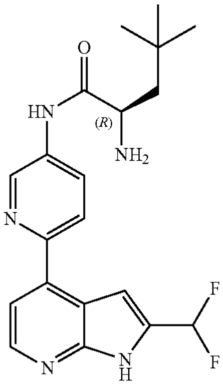
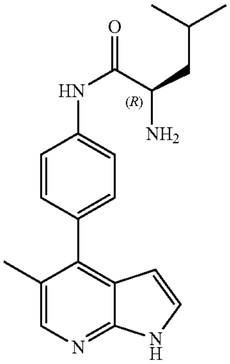
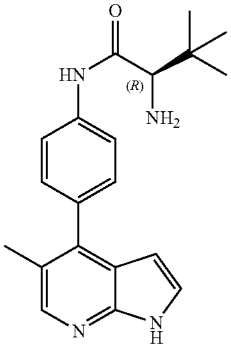
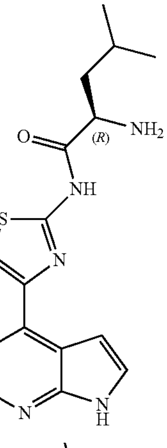
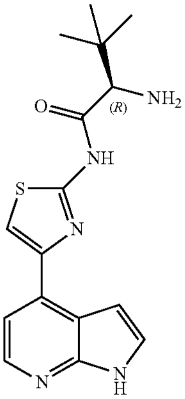
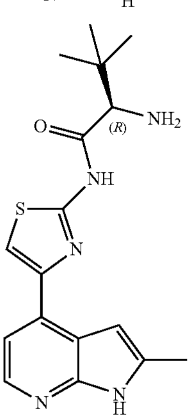
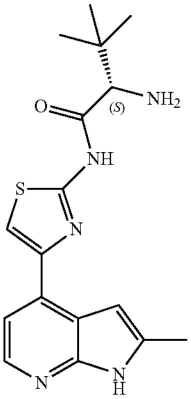

-continued
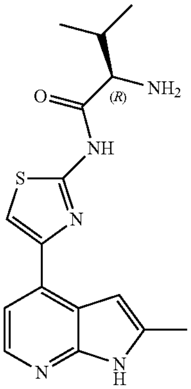
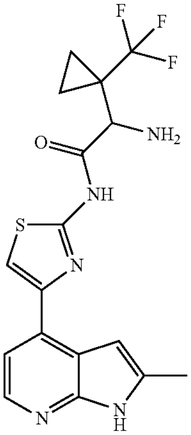
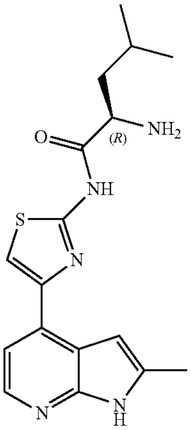
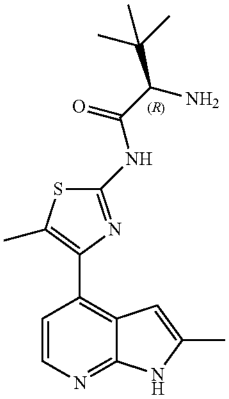
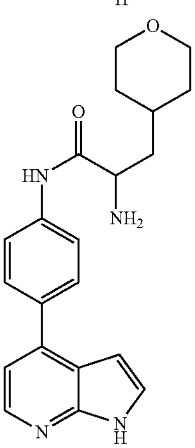
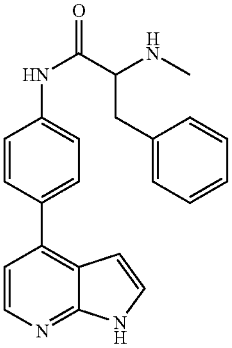
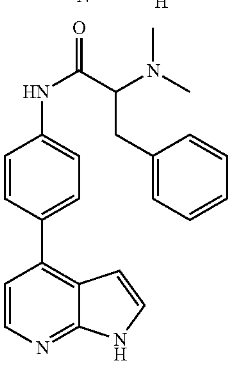
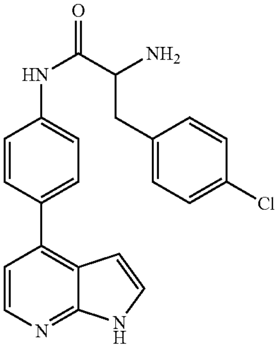
-continued
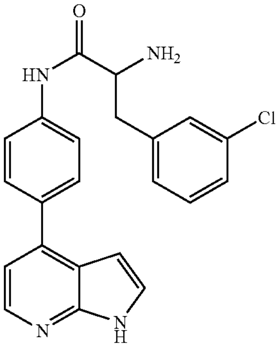
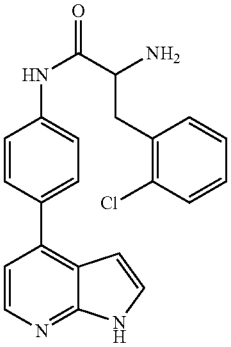
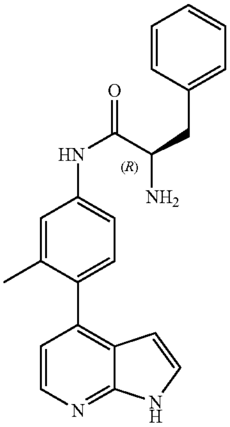
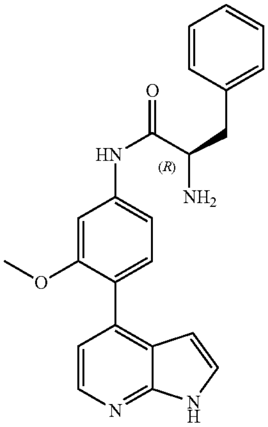
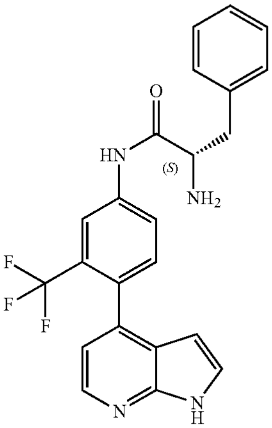
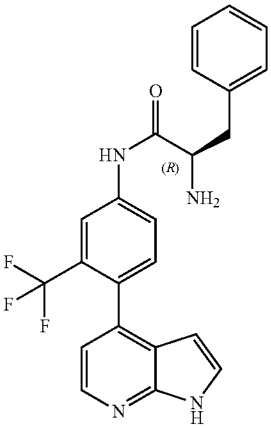
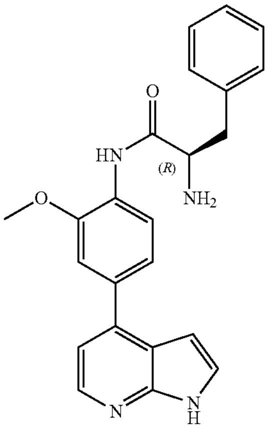
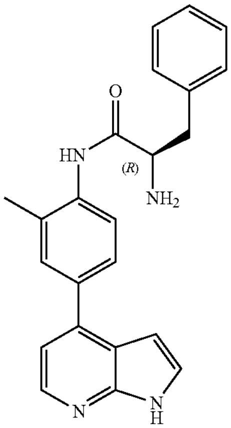

-continued
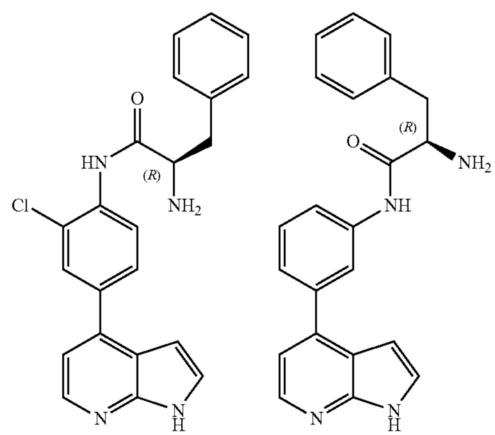
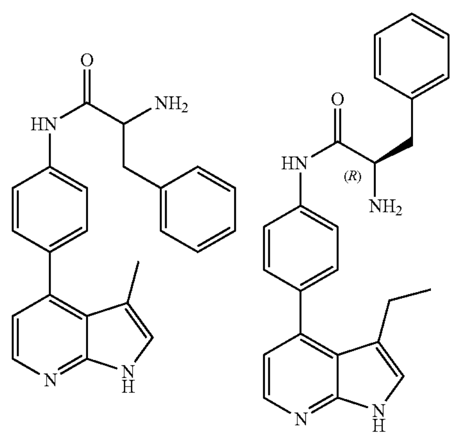
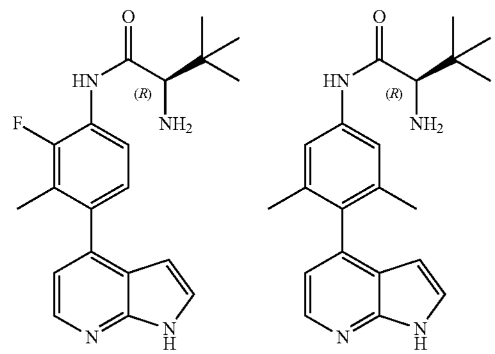
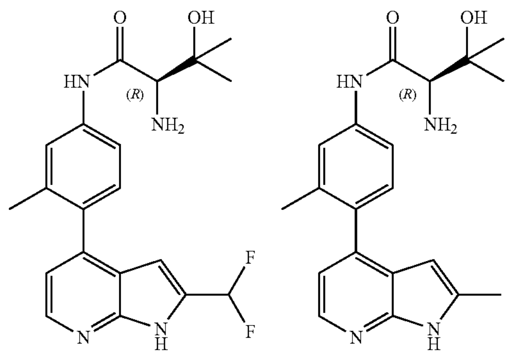
-continued
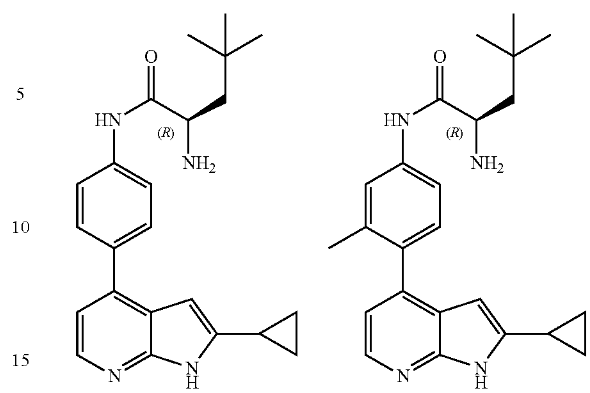
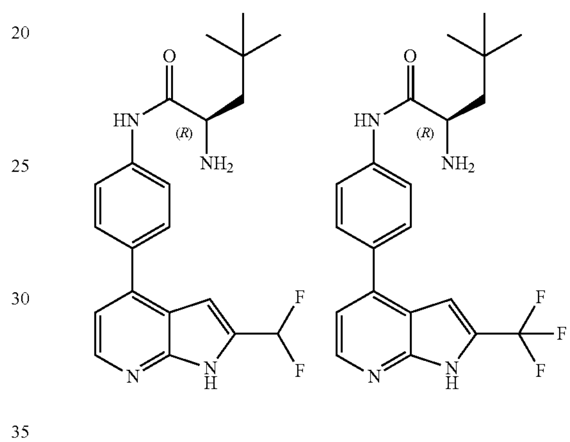
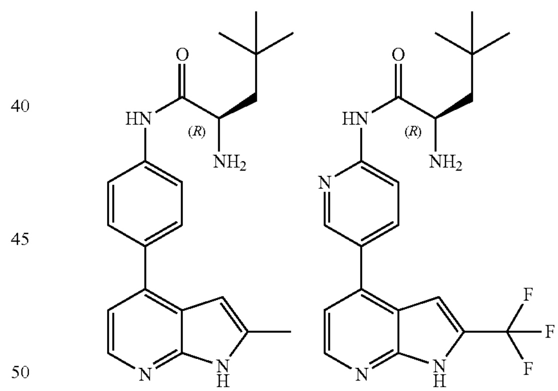
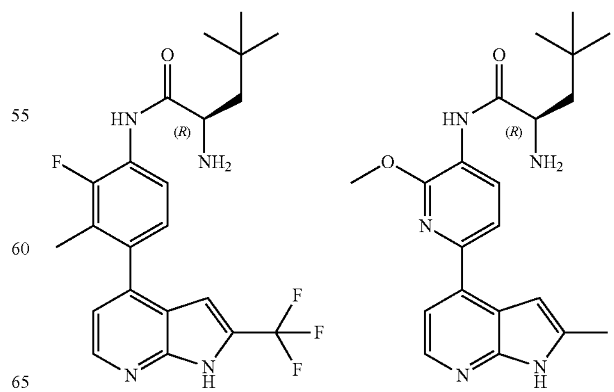

-continued
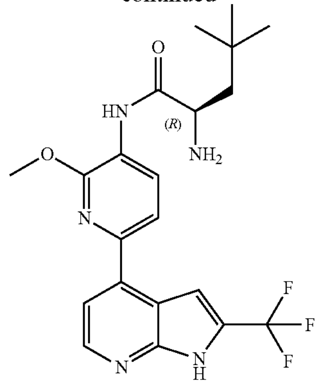
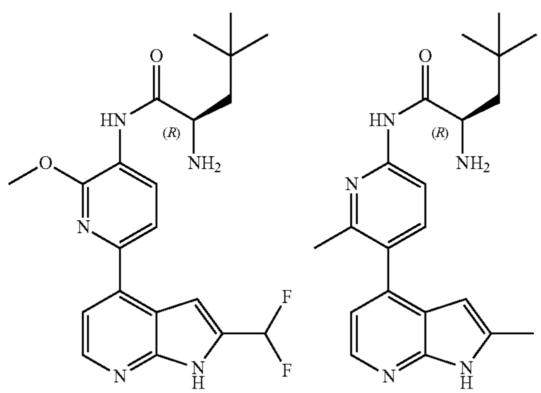
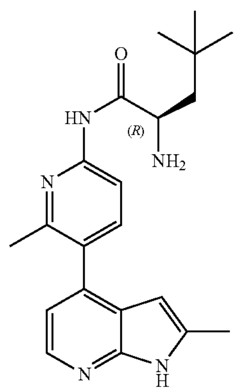
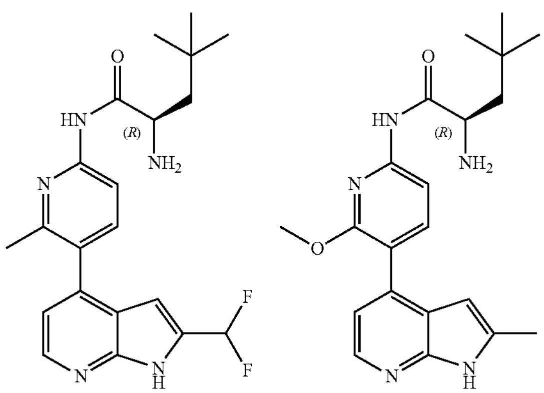
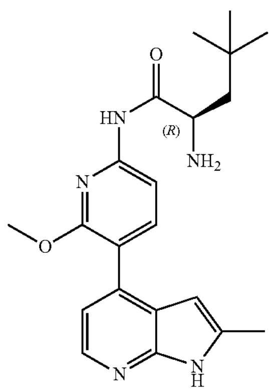
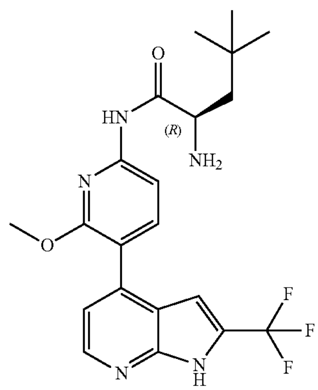
-continued
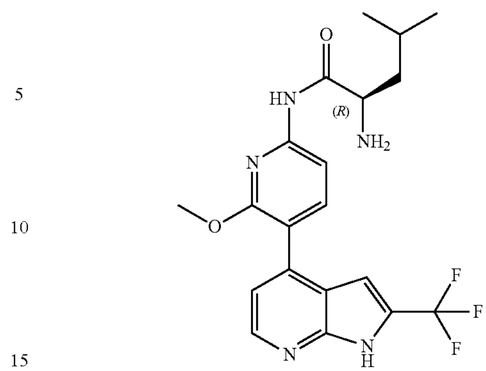
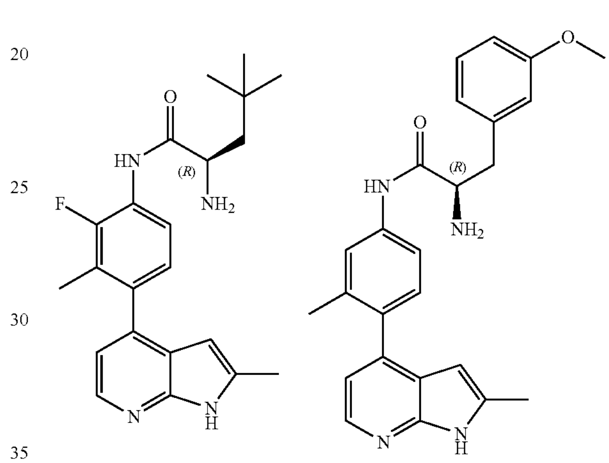
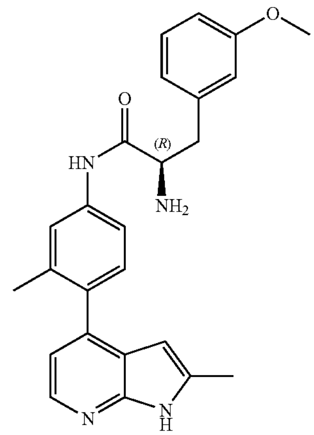
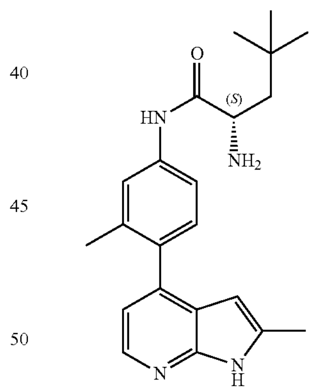
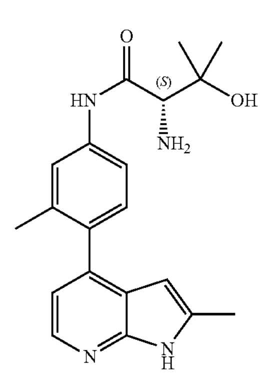
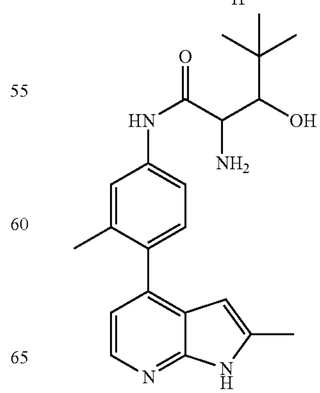
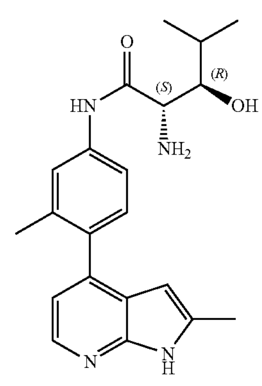

-continued

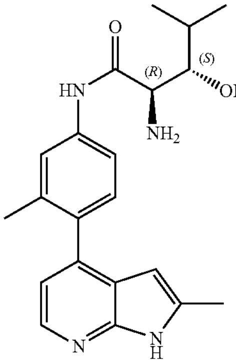

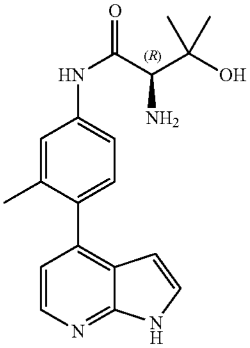

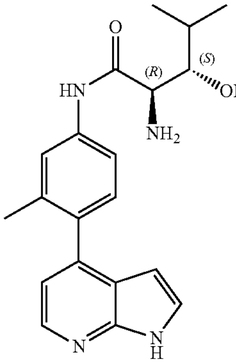

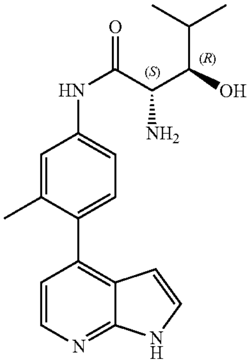

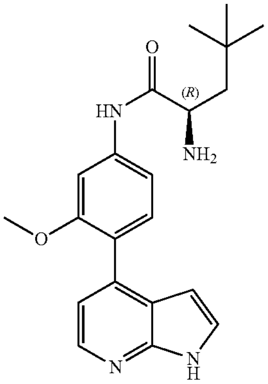

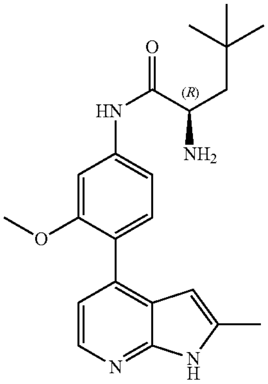

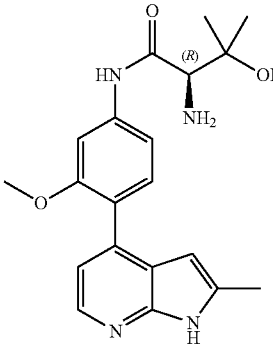

-continued

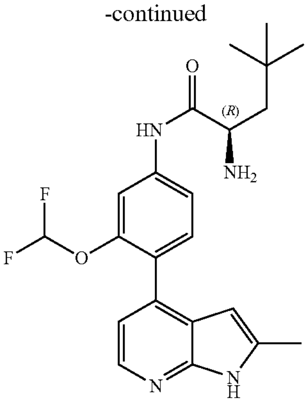

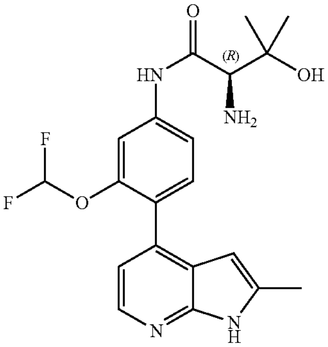

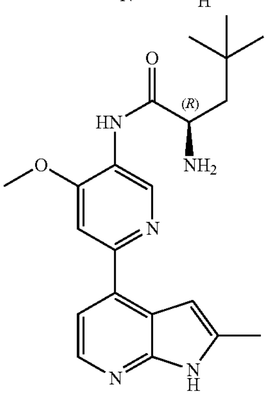

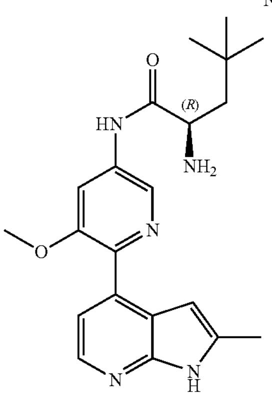

and

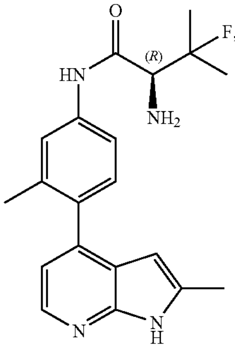

, or pharmaceutically acceptable salt thereof.

Some of the compounds of the present disclosure have at least one asymmetric center. Additional asymmetric centers may be present depending upon the nature of the various substituent groups. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this disclosure.

The independent syntheses of the enantiomerically or diastereomerically enriched compounds, or their chromatographic separations, may be achieved as known in the art by appropriate modification of the methodology disclosed herein. The absolute stereochemistry of a compound may be determined by using X-ray crystallography to determine the crystal structure of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

The compound (e.g., a compound of formula (I)) may possess tautomeric forms, and tautomers also constitute embodiments of the disclosure.

The present disclosure also includes isotopically-labeled compounds (e.g., an isotopically-labeled compound of formula (I)), which are identical to those recited in formula (I), but for the fact that one or more atoms are replaced by an atom having an atomic mass or mass number different from the atomic mass or mass number usually found in nature. Examples of isotopes suitable for inclusion in the compounds of the disclosure are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{31}P$ $^{35}S$, $^{18}F$, and $^{36}Cl$, respectively. Substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described herein using an appropriate isotopically-labeled reagent in place of a non-isotopically-labeled reagent.

Compounds disclosed herein can exist in solvated as well as unsolvated forms with pharmaceutically acceptable solvents such as water, ethanol, and the like, and it is intended that the disclosure encompass both solvated and unsolvated forms. In one embodiment, the compound is amorphous. In one embodiment, the compound is a single polymorph. In another embodiment, the compound is a mixture of polymorphs. In another embodiment, the compound is in a crystalline form.

Compounds of formula (I) can be synthesized by a variety of methods. Exemplary approaches are outlined in General Schemes 1-4. In the method shown in General Scheme 1, an appropriate 7-azaindole derivative is coupled to a protected aniline derivative via a palladium mediated Suzuki-Miyaura reaction. This deprotected aniline can then be used in an amide coupling reaction with amino acid derivatives. The desired product is obtained after deprotection of relevant protecting groups. Alternately, as shown in General Scheme 2, the amide coupling of the amino acid can be performed on a halogenated amino-substituted aromatic group, and this intermediate can then be used in the palladium mediated Suzuki-Miyaura coupling. Again, the desired product is obtained after deprotection of the relevant protecting groups. As shown in General Scheme 3, in some instances, this sequence of steps can be performed without protection of the 7-azaindole derivative, allowing for a one-step deprotection of the amino acid. Finally, N-substitution on the amino acid could be introduced by SN2-displacement of the alkyl bromide, as shown in General Scheme 4.

General Scheme 1

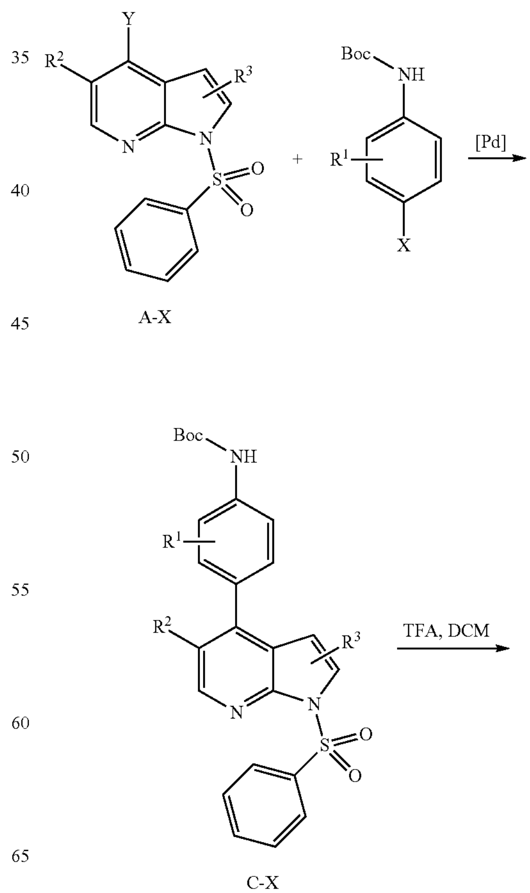

A-X

C-X

-continued
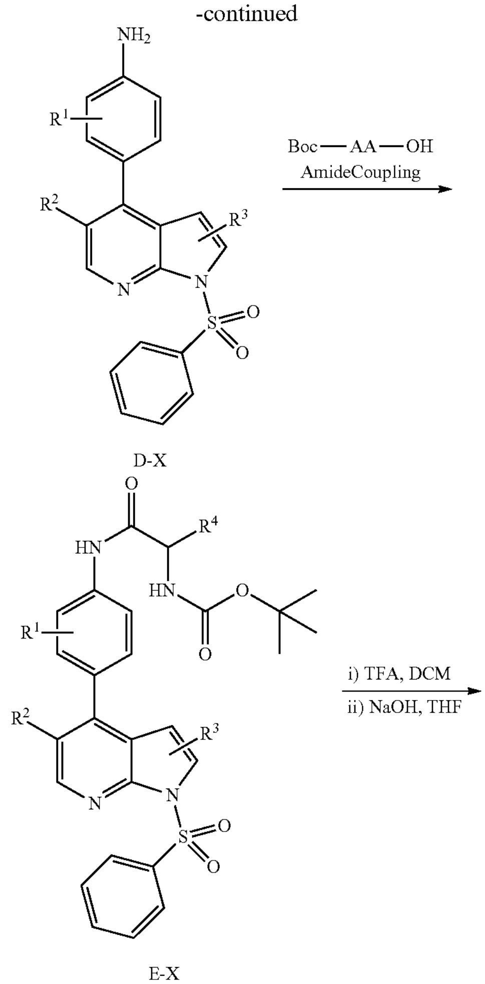
D-X
E-X
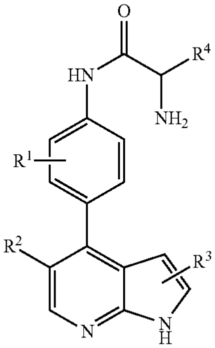
F-X
General Scheme 2
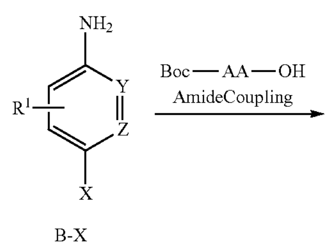
B-X
-continued
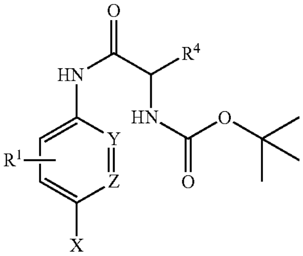
G-X
+
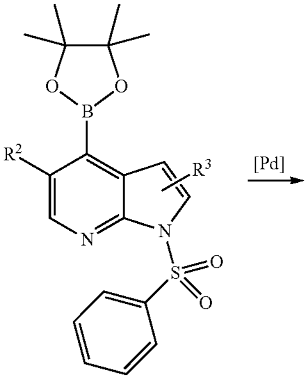
A-X
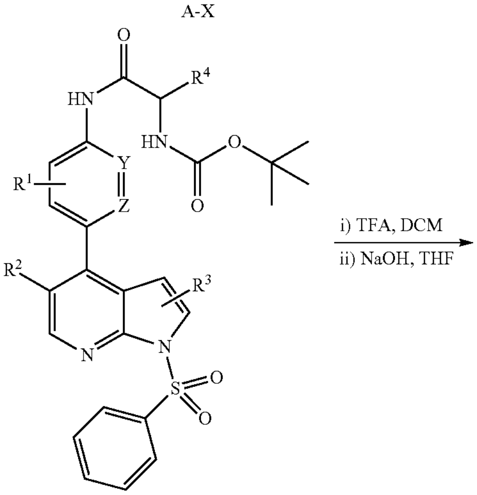
E-X
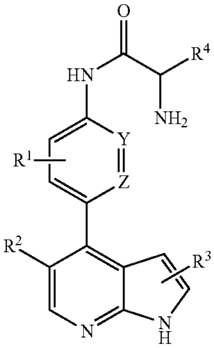
F-X General Scheme 3

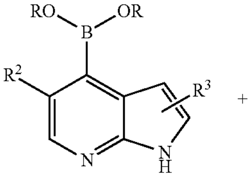

A-X

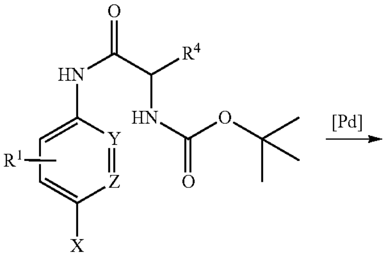

G-X

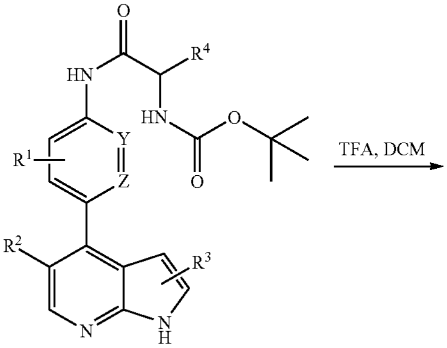

H-X

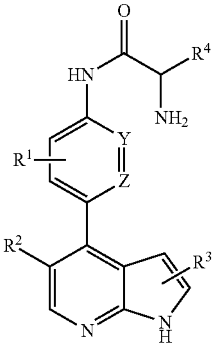

F-X

General Scheme 4

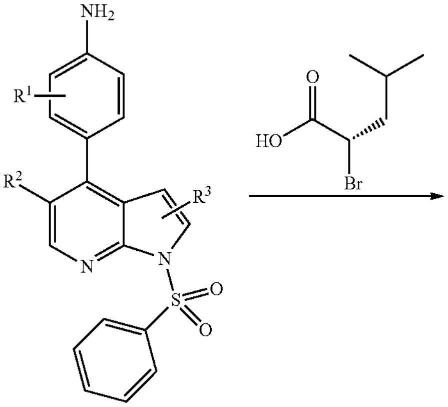

D-X

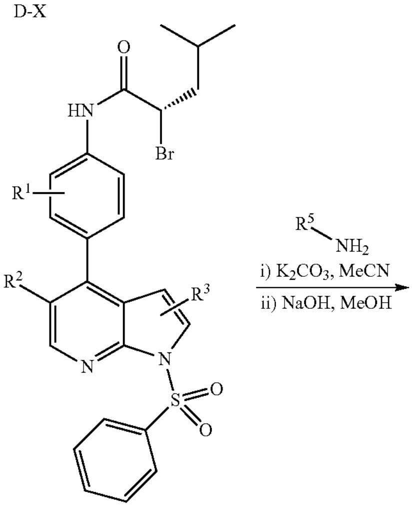

J-X

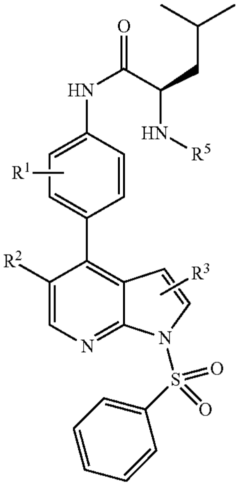

F-X

Compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Reactions can be worked up in a conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Standard experimentation, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006).

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the procedures described herein using a pure geometric isomer as a starting material, or by resolution of a mixture of the geometric isomers of the compound or intermediates using a standard procedure such as chromatographic separation.

The synthetic schemes and specific examples as described are illustrative and are not to be read as limiting the scope of the disclosure or the claims. Alternatives, modifications, and equivalents of the synthetic methods and specific examples are contemplated.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, or allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl, and the like. In one embodiment, the compound is in the form of a trifluoroacetate salt.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Compounds disclosed herein can exist in unsolvated forms as well as solvated forms, including hydrated forms. In general, the solvated forms are equivalent to unsolvated forms and are encompassed within the scope of the present disclosure. Certain compounds of the disclosure may also exist in multiple crystalline or amorphous forms. In general, all physical forms are equivalent for the uses contemplated by the present disclosure and are intended to be within the scope of the present disclosure.

The present disclosure also provides compounds that are in a prodrug form. Prodrugs of the compounds described herein are those compounds that readily undergo chemical changes under physiological conditions to provide the compounds disclosed herein (e.g., a compound of formula (I)). Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Pharmaceutical Compositions

The disclosed compounds (e.g., compounds of formula (I), including compounds of formula (Ia) and (Ib)) may be incorporated into pharmaceutical compositions suitable for administration to a subject (such as a patient, which may be a human or non-human). The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the disclosure are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease or condition, the prophylactically effective amount will be less than the therapeutically effective amount.

For example, a therapeutically effective amount of a compound of formula (I) may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their pharmaceutically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerin, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)), and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this disclosure.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I), or a pharmaceutically acceptable salt thereof), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this disclosure are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

Methods of Use

The present disclosure provides methods of using the compounds and compositions described herein (e.g., compounds of formula (I) or pharmaceutically acceptable salts thereof, including compounds of formula (Ia) and (Ib) or pharmaceutically acceptable salts thereof, or pharmaceutical compositions comprising such compounds). The methods include methods of treating diseases such as cancer, and methods of inhibiting the proliferation of cancer cells. For example, the methods include methods of treating prostate cancer, breast cancer, a central nervous system (CNS) cancer (e.g., medulloblastoma, glioblastoma), cervical cancer, colon cancer, esophageal cancer (e.g., esophageal squamous cell carcinoma), gastric cancer, leukemia, melanoma, lung cancer (e.g., non-small cell lung cancer), ovarian cancer, renal cancer, and multiple myeloma.

Citron kinase has been implicated in several types of cancers. In particular, cytokinesis failure caused by depletion of citron kinase has been found to decrease cell proliferation in breast, cervical and colorectal cancer cells (McKenzie et al. *Oncotarget* 2016, 7(52):87323-87341). Citron kinase has also been identified as a target for medulloblastoma therapy; in certain medulloblastoma cell lines, CITK knockdown impaired cell proliferation and induced cell senescence and apoptosis (Pallavicini et al. *Cancer Res.* 2018, 78(16):4599-4612). Reports have also indicated a role for citron kinase in gastric cancer (Davies et al. *Genome Biol.* 2021, 22(1):88), breast cancer (Meng et al. *Clin. Transl. Oncol.* 2019, 21:910-923), colon cancer (Wu et al. *Oncotarget* 2017, 8(42):71954-71964), multiple myeloma (Sahin et al. *Blood Adv.* 2019, 3(7):995-1002), and esophageal squamous cell carcinoma (Lu et al. Front. Genet. 2021, 12:628547). Data presented in the examples additionally shows that compounds disclosed herein have activity against several cancer cell lines.

As also demonstrated herein, citron kinase promotes prostate cancer cell cycle progression and cell division. It was previously known that AR activity is critical for prostate cancer growth, but the molecular mechanism by which AR regulates cell cycle progression was poorly understood. AR activity is targeted therapeutically by preventing its ligand activation. Although androgen deprivation initially induces remission, prostate cancer recurs that is no longer responsive to androgen deprivation but is still driven by AR action. As shown herein, citron kinase has now been identified as a mediator of prostate cancer cell proliferation. Expression of citron kinase is induced by low androgen concentrations, which induce cell proliferation, and reduced by high androgen concentrations, which limit prostate cancer cell proliferation and induce differentiation. The kinase domain of citron kinase is critical for prostate cancer cell proliferation, and targeting citron kinase activity downstream activated AR has accordingly been identified as a viable prostate cancer therapy.

Accordingly, in some embodiments, the disclosure provides a method of treating cancer in a subject in need thereof (e.g., a subject suffering from cancer), comprising administering to the subject a therapeutically effective amount of a compound described herein (e.g., a compound of formula (I), or a pharmaceutically acceptable salt thereof), or a pharmaceutical composition described herein (e.g., a pharmaceutical composition comprising a compound of formula (I) or a pharmaceutically acceptable salt thereof). In some embodiments, the cancer is selected from prostate cancer, breast cancer, a central nervous system (CNS) cancer (e.g., medulloblastoma, glioblastoma), cervical cancer, colon cancer, esophageal cancer, gastric cancer, leukemia, melanoma, lung cancer (e.g., non-small cell lung cancer), ovarian cancer, renal cancer, and multiple myeloma. In some embodiments, the cancer is prostate cancer. In some embodiments, the cancer is medulloblastoma. In some embodiments, the cancer is breast cancer. In some embodiments, the cancer is cervical cancer. In some embodiments, the cancer is colon cancer. In some embodiments, the cancer is esophageal cancer (e.g., esophageal squamous cell carcinoma). In some embodiments, the cancer is gastric cancer. In some embodiments, the cancer is leukemia. In some embodiments, the cancer is melanoma. In some embodiments, the cancer is lung cancer (e.g., non-small cell lung cancer). In some embodiments, the cancer is ovarian cancer. In some embodiments, the cancer is renal cancer. In some embodiments, the cancer is multiple myeloma.

In another aspect, disclosed is a method of inhibiting cancer cell proliferation, comprising contacting cancer cells with a compound described herein (e.g., a compound of formula (I) or a pharmaceutically acceptable salt thereof), or a pharmaceutical composition described herein (e.g., a pharmaceutical composition comprising a compound of formula (I) or a pharmaceutically acceptable salt thereof), in an amount effective to inhibit the cancer cell proliferation. In some embodiments, the cancer cells are selected from prostate cancer, breast cancer, a central nervous system (CNS) cancer (e.g., medulloblastoma, glioblastoma), cervical cancer, colon cancer, esophageal cancer, gastric cancer, leukemia, melanoma, lung cancer (e.g., non-small cell lung cancer), ovarian cancer, renal cancer, and multiple myeloma cells. In some embodiments, the cancer cells are prostate cancer cells. In some embodiments, the cancer cells are medulloblastoma cells. In some embodiments, the cancer cells are breast cancer cells. In some embodiments, the cancer cells are cervical cancer cells. In some embodiments, the cancer cells are colon cancer cells. In some embodiments, the cancer cells are esophageal cancer cells (e.g., esophageal squamous cell carcinoma cells). In some embodiments, the cancer cells are gastric cancer cells. In some embodiments, the cancer cells are leukemia cells. In some embodiments, the cancer cells are melanoma cells. In some embodiments, the cancer cells are lung cancer cells (e.g., non-small cell lung cancer cells). In some embodiments, the cancer cells are ovarian cancer cells. In some embodiments, the cancer cells are renal cancer cells. In some embodiments, the cancer cells are multiple myeloma cells. In some embodiments, the step of contacting the cancer cells with the compound comprises administering the compound to a subject suffering from cancer.

In another aspect, disclosed is a method of inhibiting citron kinase in a sample, comprising contacting the sample with a compound described herein (e.g., a compound of formula (I) or a pharmaceutically acceptable salt thereof), or a pharmaceutical composition described herein (e.g., a pharmaceutical composition comprising a compound of formula (I) or a pharmaceutically acceptable salt thereof), in an amount effective to inhibit citron kinase. In some embodiments, the step of contacting the sample with the compound comprises administering the compound to a subject (e.g., a subject) suffering from cancer. Methods of determining kinase inhibition are well known in the art. For example, kinase activity of an enzyme and the inhibitory capacity of a test compound can be determined by measuring enzyme specific phosphorylation of a substrate. Commercial assays and kits can be employed. For example, kinase inhibition can be determined using a radiometric binding assay, such as using KinaseProfiler™ technology (Eurofins Discovery). This assay method directly detects product formation without the use of modified substrates or coupling enzymes. Test compounds are incubated with kinase, substrate, required cofactors and radioisotope labeled ATP. Following incubation, unreacted radioactive ATP is removed by washing and incorporation of the radiolabeled phosphate into the kinase substrate is assayed to detect phosphoryltransferase activity, which is directly proportional to the amount of phosphorylated substrate. Inhibition of the kinase by a kinase inhibitor prevents phosphorylation of the substrate and thereby limits the incorporation of radiolabeled phosphate. Such an assay is compatible with a microwell assay format, allowing simultaneous determination of $IC_{50}$ of multiple compounds.

i. Dosages

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

ii. Combination Therapies

A compound or composition described herein may be used in combination with other known therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound or composition described herein and the at least one additional therapeutic agent can be administered simultaneously, in the same or in separate compositions, or sequentially. For sequential administration, the compound described herein can be administered first, and the additional agent can be administered subsequently, or the order of administration can be reversed.

In some embodiments, a compound or composition described herein is administered in combination with at least one of surgery, chemotherapy, radiation therapy, hormone therapy, immunotherapy, and bisphosphonate therapy. In some embodiments a compound or composition described herein is administered in combination with two or more of surgery, chemotherapy, radiation therapy, hormone therapy, immunotherapy, and bisphosphonate therapy.

In some embodiments, a compound or composition described herein is used in combination with surgery. Surgery is a standard treatment for prostate cancer. The surgery may be a radical prostatectomy, in which the prostate, surrounding tissue, and seminal vesicles are removed, and nearby lymph nodes may also be removed. Particular types of radical prostatectomy include open radical prostatectomy, radical laparoscopic prostatectomy, and robot-assisted laparoscopic radical prostatectomy. Other types of surgery include pelvic lymphadenectomy, which removes the lymph nodes in the pelvis, and transurethral resection of the prostate, which removes the tissue from the prostate using a resectoscope.

In some embodiments, a compound or composition described herein is used in combination with radiation therapy, which uses high doses of radiation to kill cancer cells. In some embodiments, the radiation therapy is external radiation therapy, which uses a machine outside the body to send radiation toward the affected area of the body. Hypofractionated radiation therapy may be used, in which a larger total dose of radiation is given once a day over a shorter period of time compared to standard radiation therapy. In some embodiments, the radiation therapy is internal radiation therapy, in which a radioactive substance is placed directly into or near the cancer. For example, radioactive seeds may be placed in the prostate using needles that are inserted through the skin between the scrotum and rectum. In some embodiments, the radiation therapy is radiopharmaceutical therapy, in which radium-223 is injected through a vein and travels through the bloodstream, collecting in areas with cancer.

In some embodiments, a compound or composition described herein is used in combination with hormone therapy. In some embodiments, the hormone therapy includes one or more of abiraterone acetate treatment; orchiectomy (surgical removal of one or both testicles, the main source of male hormones such as testosterone); estrogen treatment; luteinizing hormone-releasing hormone agonist treatment (e.g., leuprolide, goserelin, or buserelin); antiandrogen treatment (e.g., flutamide, bicalutamide, enzalutamide, apalutamide, or nilutamide); and drugs that prevent the adrenal glands from making androgens (e.g., ketoconazole, aminoglutethimide, hydrocortisone, or progesterone).

In some embodiments, a compound or composition described herein is used in combination with immunotherapy. In immunotherapy, treatment boosts, directs, or restores the body's natural immune defenses against cancer. In some embodiments, the immunotherapy is conducted using Sipuleucel-T.

In some embodiments, a compound or composition described herein is used in combination with bisphosphonate therapy. Subjects treated with antiandrogen therapy or orchiectomy are at an increased risk of bone loss, and bisphosphonate drugs lessen the risk of bone fracture (breaks). Particular examples of bisphosphonate drugs include clodronate and zoledronate.

In some embodiments, a compound or composition described herein is used in combination with chemotherapy. For example, a compound or composition described herein can be used in combination with any of the following: actinomycins, alkylating agents, anthracyclines, antifolates, antiestrogen agents, anti-metabolites, anti-androgens, antimicrotubule agents, aromatase inhibitors, bleomycins, bromodomain inhibitors, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds (e.g., cisplatin, carboplatin, oxaliplatin, nedaplatin, satraplatin, or triplatin tetranitrate), receptor tyrosine kinase inhibitors, ribonucleotide reductase inhibitors, thrombospondin mimetics, uracil analogs, vinca alkaloids, vitamin D3 analogs, DOT1L inhibitors, agents targeting epigenetic mechanisms, or an additional chemotherapeutic agent such as N-Ac-Sar-Gly-Val-D-alloIle-Thr-Nva-Ile-Arg-Pro-$NHCH_2CH_3$ or a salt thereof, actinomycin D, AG13736, 17-allylamino-17-demethoxygeldanamycin, 9-aminocamptothecin, N-(4-(3-amino-1H-indazol-4-yl)phenyl}-N'-(2-fluoro-5-methylphenyl)urea or a salt thereof, N-(4-(4-aminothieno[2,3-d]pyrimidin-5-yl)phenyl}-N'-(2-fluoro-5-(trifluoromethyl)phenyl)urea or a salt thereof, temozolomide, procarbazine, altretamine, mitozolomide, anastozole, AP-23573, asparaginase, azacitidine, bevacizurnab, bicalutamide, bleomycin a2, bleomycin b2, bortezemib, busulfan, campathecins, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN518, MLN4924, MS-275, mycophenolic acid, mitomycin C, nitrosoureas, oprelvekin, paclitaxel, PD98059, peplomycin, photosensitizer Pc4, phthalocyanine, pirarubicin, plicamycin, prednisone, procarbazine, PTK787, PU24FC1, PU3, radicicol, raloxifene, rapamycin, raltitrexed, retinoids such as fenretinide, ribavirin, rituximab (Rituxin®), sorafenib, staurosporine, steroids such as dexamethasone and prednisone, suberoylanilide hydroxamic acid, tamoxifen, taxol, temozolomide, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin, bevacizumab, enzastaurin, temsirolimus, cilengitide, lapatinib, sunitinib, axitinib, pazopanib, vemurafenib, dabrafenib, JQ1, or combinations thereof.

In some embodiments, a compound or composition described herein is administered in combination with one or more of abiraterone acetate, apalutamide, bicalutamide, cabazitaxel, darolutamide, degarelix, docetaxel, enzalutamide, flutamide, goserelin acetate, leuprolide acetate, mitoxantrone hydrochloride, nilutamide, olaparib, radium-223 dichloride, rucaparib camsylate, and Sipuleucel-T.

Kits

For use in the therapeutic applications described herein, kits and articles of manufacture are also provided, which include a compound or pharmaceutical composition described herein (e.g., a compound of formula (I), or a pharmaceutically acceptable salt thereof, or a pharmaceutical composition comprising a compound of formula (I) or a pharmaceutically acceptable salt thereof). In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, in some embodiments the container(s) includes a compound of formula (I, or a pharmaceutically acceptable salt thereof, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

The following examples further illustrate aspects of the disclosure but, of course, should not be construed as in any way limiting its scope.

EXAMPLES

The following abbreviations are used in the Examples: "β-cyclopropyl-D-Ala-OH" means (R)-2-amino-3-cyclopropylpropanoic acid, "$B(OiPr)_3$" means triisopropyl borate, "Boc" means tert-butyloxycarbonyl, "Boc-D-Neo-OH" means (R)-2-((tert-butoxycarbonyl)amino)-4,4-dimethylpentanoic acid, "Boc-Ser(Me)-OH" means N-(tert-butoxycarbonyl)-O-methyl-L-serine, "Boc-Tle-OH" means (S)-2-((tert-butoxycarbonyl)amino)-3,3-dimethylbutanoic acid, "Boc-D-Tle-OH" means (R)-2-((tert-butoxycarbonyl)amino)-3,3-dimethylbutanoic acid, "COMU" means (1-cyano-2-ethoxy-2-oxoethylidenaminooxy)dimethylamino-morpholino-carbenium hexafluorophosphate, "conc." means concentration, "DAD" means diode-array-detection, "DAST" means diaminosulfur trifluoride, "DCM" means dichloromethane, "DIPEA" means diisopropylethylamine, "DMAP" means 4-cimethylaminopyridine, "DMF" means N,N-dimethylformamide, "DMSO" means dimethyl sulfoxide, "DMSO-$d_6$" means dimethyl sulfoxide (deuterated), "EDC" means 1-ethyl-3-(3-dimethylaminopropyl)carbodiimide, "$Et_3N$" means triethylamine, "EtOAc" means ethyl acetate, "Fmoc-D-Tle-OH" means (R)-2-((((9H-fluoren-9-yl)methoxy)carbonyl)amino)-3,3-dimethylbutanoic acid, "h" means hours, "HATU" means hexafluorophosphate azabenzotriazole tetramethyl uronium, "HPLC" means high performance liquid chromatography, "HRMS" means high resolution mass spectrometry, "KOAc" means potassium acetate, "LCMS" means liquid chromatography mass spectrometry, "$[M+H]^+$" means the protonated mass of the free base of the compound, "m-CPBA" means 3-chloroperbenzoic acid, "MeCN" means acetonitrile, "MeOH" means methanol, "MeOH-$d_4$" means methanol (deuterated), "min" means minutes, "$Ms_2O$" means methanesulfonic anhydride, "n-BuLi" means n-butyllithium, "NMR" means nuclear magnetic resonance, "PdAmphos" means bis(di-tert-butyl(4-dimethylaminophenyl)phosphine)dichloropalladium(II), "$Pd(dppf)Cl_2 \cdot DCM$" means [1,1'-Bis(diphenylphosphino)ferrocene]dichloropalladium(II) complex with dichloromethane, "r.t." means room temperature, "sat. aq." means saturated aqueous, "SCX" means strong cation exchange, "S-Phos Palladacycle G2" means chloro(2-dicyclohexylphosphino-2',6'-dimethoxy-1,1'-biphenyl)[2-(2'-amino-1,1'-biphenyl)]palladium(II), "TFA" means trifluoroacetic acid, "THF" means tetrahydrofuran, "TMAB" means tetramethylammonium bromide, "$t_R$" means retention time, and "Xphos Palladacycle G2" means chloro(2-dicyclohexylphosphino-2',4',6'-triisopropyl-1,1'-biphenyl)[2-(2'-amino-1,1'-biphenyl)]palladium(II).

EXPERIMENTAL

All chemical reagents and reaction solvents were purchased from commercial suppliers and used as received. Normal phase chromatography was performed on a Teledyne ISCO CombiFlash NextGen300 system using Teledyne RediSep normal phase silica cartridges, with average particle size 35-70 micron. Preparative reversed-phase HPLC was performed using either Gilson GX-271 preparative liquid handler, or Teledyne ACCQ-Prep purification system. Both instruments were equipped with Phenomenex Kinetex C18 columns, using gradients of MeCN in $H_2O$ as mobile phase with 0.1% TFA modifier, unless stated. Compounds that are obtained as a TFA salt after purification were afforded as free base, by dissolving the salt in EtOAc and washing with sat. aq. $K_2CO_3$, or by elution through a Biotage ISOLUTE SCX-II cartridge, loading and washing with MeOH and eluting with 2N $NH_3$ in MeOH. Proton nuclear magnetic resonance ($^1H$ NMR) spectra were recorded at 400 MHz on a Bruker Avance Neo NanoBay 400 spectrometer with standard pulse sequences, or at 500 MHz on a Bruker Ascend Avance III HD. For $^1H$ NMR spectra, chemical shifts are reported in parts per million (ppm) and are reported relative to residual non-deuterated solvent signals. Coupling constants are reported in hertz (Hz). The following abbreviations (or a combination, thereof) are used to describe splitting patterns: s, singlet; d, doublet; t, triplet; q, quartet; pent, pentet; m, multiplet; br, broad. Analytical thin layer chromatography (TLC) was performed on Kieselgel 60 F254 glass plates precoated with a 0.25 mm thickness of silica gel. TLC plates were visualized with UV light and iodine. Hydrogenation reactions are performed using an atmospheric balloon.

All compounds were of 95% purity or higher, unless otherwise noted, as measured by analytical reversed-phase HPLC. High resolution mass spectra were recorded on an Agilent 1290 Infinity II Series 6230B TOF LC/MS. Detection methods are diode array (DAD) at 210, 254 nM and positive/negative electrospray ionization (ESI), mass range capable of 25-20,000 m/z. The MS detector was configured to mass range 100 to 1700 m/z, with nitrogen used as the nebulizer gas. High-resolution acquisition rate mass spectra (MS mode) were acquired in electrospray mode by scanning at a rate up to 40 spectra per second. The system maintains a 2 ppm mass accuracy/stability within 2° C. drift per hour. Data acquisition was performed with MassHunter Walkup software. Unless stated, all methods use an Agilent InfinityLab Poroshell 120 EC-C18 column, dimensions 4.6×50 mm, 2.7 μm, fitted with Poroshell 120 EC-C18, 2.1 mm, 1.9 μm guard. Mobile phase A was 0.1% TFA in $H_2O$, mobile phase B was 0.1% TFA in $CH_3CN$.

For LCMS characterization of the compounds, the following methods were used:

Method A: Reverse phase HPLC was carried out with a flow rate of 0.4 mL/min, at 55° C., using positive ESI mode. Injection volume 1 μL. The gradient conditions used are 5% mobile phase B for 0.2 min., then a gradient of 5-95% mobile phase B over 2.0 min, then hold at 95% mobile phase B for 0.45 min.

Method B: Reversed phase HPLC was carried out with a flow rate of 0.4 mL/min, at 55° C., using positive ESI mode. Injection volume 1 μL. The gradient conditions used are 40% mobile phase B for 0.2 min., then a gradient of 40-95% mobile phase B over 2.5 min, then hold at 95% mobile phase B for 0.5 min.

For reverse-phase HPLC the following method was used (unless otherwise stated): Teledyne ACCQ-Prep HPLC equipped with a Phenomenex Gemini 5 μM C18 110 Å column, 100×30 mm. Flow rate 40 mL/min, gradient 5-40% B in A over a 14 min gradient, then 100% B for 3 min. A: $H_2O$+0.10% TFA; B: MeCN+0.10% TFA.

General Synthetic Procedures

General Procedure A: Suzuki-Miyaura 1. A vial was charged with corresponding aryl halide (1 eq), aryl boronic acid or equivalent (1.2 eq), $Pd(dppf)Cl_2$ (0.05 eq), $K_2CO_3$ (2.2 eq). A mixture of dioxane:water (4:1) was added and degassed with argon for 0-15 min before heating to 100° C. for 1-16 h. Upon cooling the mixture was filtered through celite, washing with EtOAc, and the filtrate was washed with water, brine, dried ($Na_2SO_4$) and concentrated. Purification by ISCO flash chromatography, unless stated.

General Procedure B: Suzuki-Miyaura 2. A vial was charged with corresponding aryl halide (1 eq), aryl boronic acid or equivalent (1.2 eq), $Pd(dppf)Cl_2$ (0.05 eq), $K_2CO_3$ (2M aq. 3 eq.). THE (0.2 m) was added and degassed with argon for 15 min before stirring in a pre-heated block at 75° C. for 1-16 h. Upon cooling the mixture was filtered through celite, washing with EtOAc, and the filtrate was washed with water, brine, dried ($Na_2SO_4$) and concentrated. Purification by ISCO flash chromatography, unless stated.

General Procedure C: Suzuki-Miyaura 3. A vial was charged with corresponding aryl halide (1 eq), aryl boronic acid or equivalent (1.5 eq), SPhos Palladacycle G2 (0.05 eq.) or XPhos Palladacycle G2 (0.05 eq), $K_2CO_3$ (2M aq. 3 eq.). 1-butanol (0.2 m) was added and degassed with argon for 15 min before heating to 100-110° C. for 1-16 h. Upon cooling the mixture was filtered through celite, washing with EtOAc, and the filtrate was washed with water, brine, dried ($Na_2SO_4$) and concentrated. Purification by ISCO flash chromatography, unless stated.

General Procedure D: HATU Mediated Amide Coupling. Carboxylic acid derivative (1.5 eq) and HATU (1.5 eq) were dissolved in DCM and cooled to 0° C. $Et_3N$ (3 eq) was added and the mixture stirred for 1 h before the addition of amine (1 eq). The mixture was stirred for 16 h. Upon complete reaction the mixture was diluted with DCM and washed with water, then concentrated and purified by ISCO flash chromatography, unless stated.

General Procedure E: COMU Mediated Amide Coupling. COMU (1.5 eq.) was added to a solution of carboxylic acid derivate (1.5 eq.), amine (1 eq.) and DIPEA (3 eq.) in DCM and stirred at rt for 1-16 h. Water was added and the mixture extracted with DCM. The extracts were dried ($Na_2SO_4$) and concentrated then purified by ISCO flash chromatography unless stated.

General Procedure F: Amide Coupling via Mixed Anhydride. A THF (0.4 M) solution of carboxylic acid derivative (1 eq) and 4-methylmorpholine (1.1 eq) was cooled to 0° C. and to this was added drop-wise a solution of ethyl chloroformate (1.1 eq) in THE (0.4 M). Upon complete addition the mixture was stirred for 15 min before the addition of amine derivative (1.2 eq) as solid or THE solution. The mixture was stirred at r.t. for 16 h, then diluted with DCM and washed with water, concentrated and purified by ISCO flash chromatography, unless stated.

General Procedure G: Schotten-Baumann Boc Protection and Amide Coupling. To a solution of amino acid derivative (1 eq) in THE and 1M NaOH (3 eq) was added di-tert-butyl decarbonate (1.1 eq) and the mixture stirred at r.t. for 16 h, then acidified with 1M HCl and extracted with EtOAc. The organic extract was dried over $MgSO_4$ and concentrated. The crude material was dissolved in DCM and cooled to 0° C. before the addition of triethylamine (1.1 eq), then ethyl chloroformate (1.1 eq) and the mixture stirred for 1 h. A solution of amine intermediate in DCM was added, and the solution was stirred at r.t. for 1-16 h. The mixture was diluted with DCM and washed with water, concentrated and purified by ISCO flash chromatography.

General Procedure H: Amide Coupling via Fmoc Acyl Chloride. To an ice-cold solution of Fmoc-amino acid derivative (1.2 eq) in DCM was added oxalyl chloride (1.4 eq) and the mixture stirred for 1 h at 0° C., then concentrated in vacuo. The mixture was redissolved in THF and aniline derivative (1 eq) and $NaHCO_3$ (1.4 eq) added, then heated to 60° C. for 16-24 h. The cooled reaction was filtered, concentrated and purified by ISCO flash chromatography.

General Procedure I: Boc Deprotection. The protected intermediate (1 eq) was dissolved in DCM and TFA (5-10 eq) added. The mixture was stirred for 1-16 h. Upon complete reaction the mixture was poured into sat. aq. $NaHCO_3$ and stirred for 1 h, then extracted with DCM. Combined organics were washed with sat. aq. NaCl and concentrated to afford a crude brown solid. Purification by ISCO flash chromatography.

General Procedure J: Benzenesulfonyl Deprotection. The protected intermediate (1 eq) was dissolved in MeOH and NaOH (5-10 eq) added, the mixture was heated to 60° C. for 15-60 min. Upon cooling the mixture was filtered and immediately purified by reverse-phase HPLC or ISCO flash column chromatography.

General Procedure K: Double Deprotection. The protected intermediate (1 eq.) was dissolved in DCM (0.2 m) and TFA (5-10 eq) added. The mixture was stirred for 1-16 h, then concentrated. The residue was dissolved in MeOH and NaOH (5-10 eq.) added, the mixture was heated to 65° C. for 15-60 min. Upon cooling the mixture was filtered and immediately purified by reverse-phase HPLC. Unless stated otherwise, the free base was obtained by Biotage ISOLUTE® SCX-II cartridge, loading and washing with MeOH and elution with 2N $NH_3$ in MeOH.

General Procedure L: Deprotection from Fmoc Amino Acid. The protected intermediate was dissolved in a DCM: Piperidine (5:1) mixture and stirred at r.t. for 1 h, then concentrated. Redissolved in MeOH and NaOH (5-10 eq) added, then stirred at 60° C. for 30-60 mins. The cooled mixture was filtered and purified by reverse-phase HPLC. Unless stated otherwise, the free base was obtained by Biotage ISOLUTE® SCX-II cartridge, loading and washing with MeOH and elution with 2N $NH_3$ in MeOH.

General Procedure M: Amide coupling via Acyl Fluoride. Pyridine (1.2 eq.) and Boc-amino acid (1 eq.) were combined in DCM and cooled to −10° C. under an atmosphere of Ar. Cyanuric fluoride (1.16 eq.) was added dropwise and the mixture stirred for 1.5 h. The reaction was quenched by the addition of ice water and diluted with DCM. The biphasic mixture was filtered and the filtrate extracted with DCM. The extracts were dried over $Na_2SO_4$ and concentrated to afford a white powder of Amino Acid Fluoride which was immediately used in amide coupling reactions. Amino acid fluoride (3-5 eq.), amine (1 eq.) and trimethylamine (3-5 eq.) were combined in THE and stirred at 60° C. for 0.25-16 h. The reaction was cooled, water was added and the reaction stirred for 30 mins. The mixture was extracted with DCM, the extracts washed with water, dried over $Na_2SO_4$, concentrated then purified by ISCO flash chromatography.

General Procedure N: Double deprotection with TBAF/TFA. The protected intermediate (1 eq.) was dissolved in THE and TBAF (3 eq.) was added and the mixture stirred at 60° C. for 10-30 mins. Upon cooling sat. aq. $NH_4Cl$ was added followed by extraction with EtOAc. The extracts were washed with brine, dried over $Na_2SO_4$, concentrated and the NHBoc intermediate purified by ISCO flash chromatography. The intermediate was dissolved in DCM, TFA (5-10 eq.) was added, the mixture stirred for 1 h then concentrated and purified by reverse-phase HPLC. Unless stated otherwise, the free base was obtained by Biotage ISOLUTE® SCX-II cartridge, loading and washing with MeOH and elution with 2N $NH_3$ in MeOH.

Example 1: Preparation of Common Intermediates

Scheme 1. Preparation of intermediates A-2 and A-3

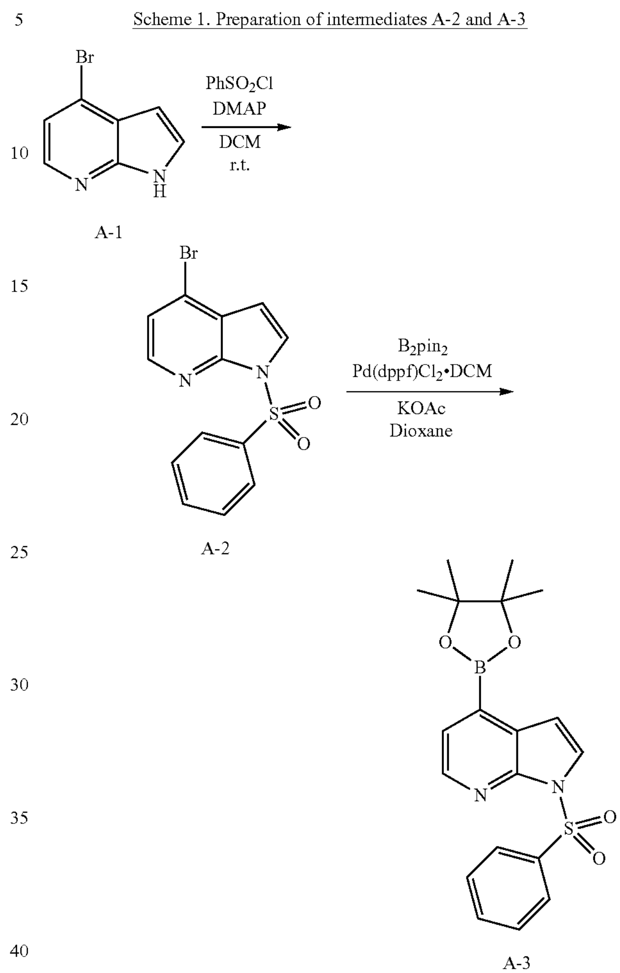

A-1

A-2

A-3

4-Bromo-1-(phenylsulfonyl)-1H-pyrrolo[2,3-b]pyridine, A-2. To a solution of 4-bromo-1H-pyrrolo[2,3-b]pyridine, A-1 (11.8 g, 59.89 mmol) in DCM (150 mL) was added benzenesulfonyl chloride (9.17 mL, 71.87 mmol), DIPEA (25.0 mL, 143.73 mmol) and DMAP (0.37 g, 2.99 mmol) and stirred at rt for 18 h. Reaction was washed with 1M HCl and water, dried ($Na_2SO_4$) and concentrated in vacuo. Purification by ISCO flash chromatography (10-90% EtOAc in hexanes) to afford a cream powder (19.4 g, 57.5 mmol, 96%). LCMS (Method A) $t_R$=1.69 min, m/z=336.9811 and 338.9791 $[M+H]^+$. $^1H$ NMR (400 MHz, DMSO-$d_6$) δ 8.25 (d, J=5.2 Hz, 1H), 8.16-8.08 (m, 2H), 8.06 (d, J=4.1 Hz, 1H), 7.78-7.69 (m, 1H), 7.68-7.57 (m, 3H), 6.80 (d, J=4.1 Hz, 1H).

1-(Benzenesulfonyl)-4-(4,4,5,5-tetramethyl-1,3,2-dioxaborolan-2-yl)pyrrolo[2,3-b]pyridine, A-3. A-2 (2.02 g, 6.00 mmol), bis(pinacolato)diboron (1.82 g, 7.20 mmol) and KOAc (1.77 g, 18.00 mmol) were combined in dioxane (15 mL) and degassed under a stream of Ar. $Pd(dppf)Cl_2 \cdot DCM$ (244 mg, 0.30 mmol) was added and the reaction heated in a sealed tube at 100° C. for 1 h. Reaction was filtered through celite washing with MeOH then concentrated in vacuo. Purification by ISCO flash chromatography (10-80% EtOAc in hexanes) to afford a colourless solid (2.17 g, 5.64 mmol, 94%). LCMS (Method A) $t_R$=1.77 min, m/z=303.0618 $[M+H]^+$ (mass of $B(OH)_2$ observed by MS, NMR confirms Bpin). $^1H$ NMR (400 MHz, DMSO-$d_6$) δ 8.40-8.37 (m, 1H), 8.10-8.05 (m, 2H), 7.99-7.96 (m, 1H), 7.74-7.66 (m, 1H), 7.63-7.57 (m, 2H), 7.49-7.46 (m, 1H), 6.99-6.93 (m, 1H), 1.31 (s, 12H).

Scheme 2. Preparation of intermediates A-4 and A-5.

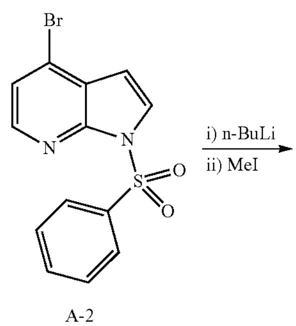

A-2

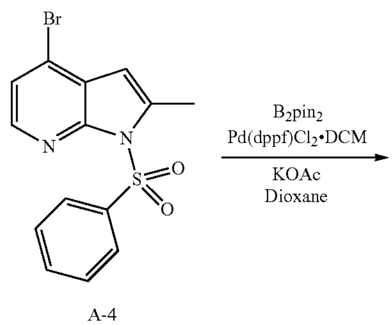

A-4

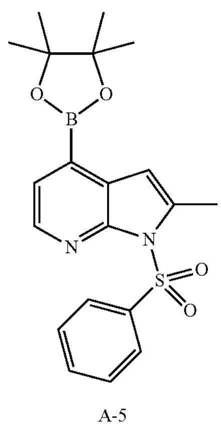

A-5

1-(Benzenesulfonyl)-4-bromo-2-methyl-pyrrolo[2,3-b] pyridine, A-4. Diisopropylamine (0.77 mL, 5.5 mmol) was taken in THF (15 mL) under an inert atmosphere and cooled to −78° C. in an acetone/dry ice bath. n-Butyllithium (2.2 mL, 5.5 mmol) was added and the mixture was stirred for 1 h before the drop-wise addition of A-2 (1.69 g, 5 mmol) in THF (15 mL). Upon complete addition the mixture was stirred for 1 h before the addition of iodomethane (374 μL, 6 mmol); the mixture was stirred for 16 h allowing to warm to r.t. The solution was concentrated, redissolved in EtOAc (100 mL) and washed with sat. aq. $NH_4Cl$ (100 mL) and concentrated. Purification by preparative HPLC (40-95% MeCN in H2O, 0.1% TFA) affords a colourless solid (1.51 g, 4.3 mmol, 86%). LCMS (Method B) $t_R$=1.87 min, m/z=352.98 $[M+H]^+$; $^1H$ NMR (400 MHz, $CDCl_3$) δ 8.16-8.12 (m, 3H), 7.57 (d, J=7.3 Hz, 1H), 7.48 (t, J=7.3 Hz, 2H), 7.34-7.29 (m, 1H), 6.36 (s, 1H), 2.75 (s, 3H).

1-(Benzenesulfonyl)-2-methyl-4-(4,4,5,5-tetramethyl-1,3,2-dioxaborolan-2-yl)pyrrolo[2,3-b]pyridine, A-5. A-4 (3.50 g, 9.97 mmol), bis(pinacolato)diboron (3.04 g, 11.96 mmol) and KOAc (2.93 g, 29.90 mmol) were combined in Dioxane (19.9 mL), Pd(dppf)Cl2·DCM (243 mg, 0.30 mmol) was added, degassed under a stream of Ar for 30 mins and the reaction heated at 100° C. for 1 h. Reaction was filtered through celite washing with MeOH then concentrated in vacuo. Purification by ISCO flash chromatography (0-75% EtOAc in hexanes) to afford a cream powder (3.15 g, 7.91 mmol, 79%). LCMS (Method A); $t_R$=1.81 min, m/z=317.0750 $[M+H]^+$ (mass of $B(OH)_2$ observed by MS, NMR confirms Bpin). $^1H$ NMR (400 MHz, DMSO-$d_6$) δ 8.28 (d, J=4.7 Hz, 1H), 8.06 (dt, J=7.3, 1.4 Hz, 2H), 7.72-7.63 (m, 1H), 7.58 (t, J=7.9 Hz, 2H), 7.41 (d, J=4.8 Hz, 1H), 6.72 (d, J=1.5 Hz, 1H), 2.76-2.71 (m, 3H), 1.31 (s, 12H).

Scheme 3. Synthesis of intermediates A-7 and A-8.

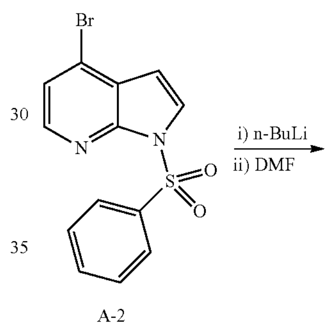

A-2

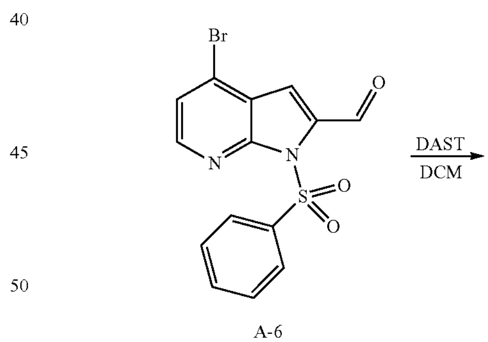

A-6

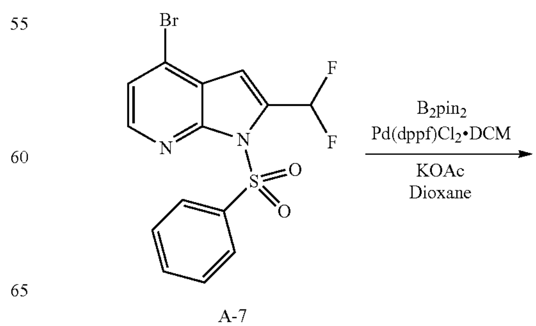

A-7

-continued

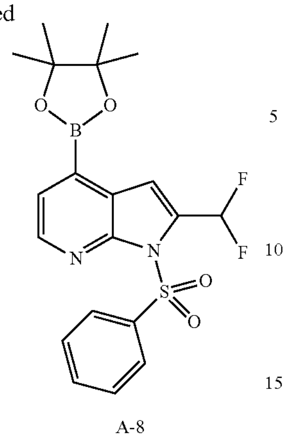

A-8

1-(Benzenesulfonyl)-4-bromo-pyrrolo[2,3-b]pyridine-2-carbaldehyde, A-6. n-Butyllithium (1.44 mL, 3.6 mmol) was added dropwise to a solution of diisopropylamine (0.5 mL, 3.6 mmol) in THE (4.5 mL) at −78° C. under an atmosphere of Ar. The reaction was stirred for 30 mins at −78° C., followed by the dropwise addition of a solution of A-2 (1.01 g, 3.00 mmol) in THF (2 mL). The resulting solution was stirred at −78° C. for 1 h, followed by the dropwise addition of a solution of DMF (0.93 mL, 12.00 mmol) in THE (1 mL). The resulting reaction was stirred at −78° C. for 1 h then quenched with sat. aq. ammonium chloride solution (10 mL). The mixture was extracted with ethyl acetate. The organic extracts were washed with brine, dried ($Na_2SO_4$) and concentrated in vacuo. Purification by ISCO flash chromatography (0-100% EtOAc in hexanes to afford a colourless solid (917 mg, 2.51 mmol, 84%). LCMS (Method A) $t_R$=2.26 min, m/z=366.9398 $[M+H]^+$; $^1H$ NMR (400 MHz, DMSO-$d_6$) δ 10.45 (s, 1H), 8.44 (d, J=5.2 Hz, 1H), 8.27-8.20 (m, 2H), 7.81-7.71 (m, 2H), 7.66 (t, J=7.8 Hz, 2H), 7.45 (s, 1H).

1-(Benzenesulfonyl)-4-bromo-2-(difluoromethyl)pyrrolo[2,3-b]pyridine, A-7. DAST (0.29 mL, 2.19 mmol) was added to a solution of A-6 (400 mg, 1.10 mmol) in DCM (5.5 mL) and stirred at rt for 2 h. The reaction was poured into sat. aq. $NaHCO_3$ solution and extracted with DCM. The extracts were dried ($Na_2SO_4$) and concentrated in vacuo. Purification by ISCO flash chromatography (0-100% EtOAc in hexanes) to afford a colourless solid (320 mg, 0.83 mmol, 75%). LCMS (Method A) $t_R$=2.46 min, m/z=388.9457 $[M+H]^+$; $^1H$ NMR (400 MHz, MeOH-$d_4$) δ 8.26 (d, J=5.3 Hz, 1H), 8.22 (dd, J=7.6, 1.7 Hz, 2H), 7.71-7.37 (m, 5H), 7.10 (s, 1H); $^{19}F$ NMR (376 MHz, MeOH-$d_4$) δ −114.81.

2-(Difluoromethyl)-1-(phenylsulfonyl)-4-(4,4,5,5-tetramethyl-1,3,2-dioxaborolan-2-yl)-1H-pyrrolo[2,3-b]pyridine, A-8. A-7 (5.72 g, 14.77 mmol), Bis(pinacolato)diboron (4.5 g, 17.73 mmol), Pd(dppf)$Cl_2$·DCM (481 mg, 0.59 mmol) and KOAc (4.35 g, 44.36 mmol) were combined in dioxane (60 mL) and degassed under a stream of Ar for 20 mins followed by heating at 100° C. for 4 h. The reaction mixture was filtered through celite, washed with EtOAc (60 mL), concentrated in vacuo and purified by ISCO flash chromatography (35% EtOAc in hexanes) to afford a cream powder (5.9 g, 13.58 mmol, 91%). LCMS (Method A) $t_R$=1.98 min, m/z=353.05 $[M+H]^+$ (mass of $B(OH)_2$ observed by MS, NMR confirms Bpin); $^1H$ NMR (400 MHz, $CDCl_3$) δ 8.52 (d, J=4.6 Hz, 1H), 8.28-8.21 (m, 2H), 7.63-7.31 (m, 6H), 1.36 (s, 12H); $^{19}F$ NMR (376 MHz, $CDCl_3$) δ −112.89.

Scheme 4. Synthesis of intermediate A-12.

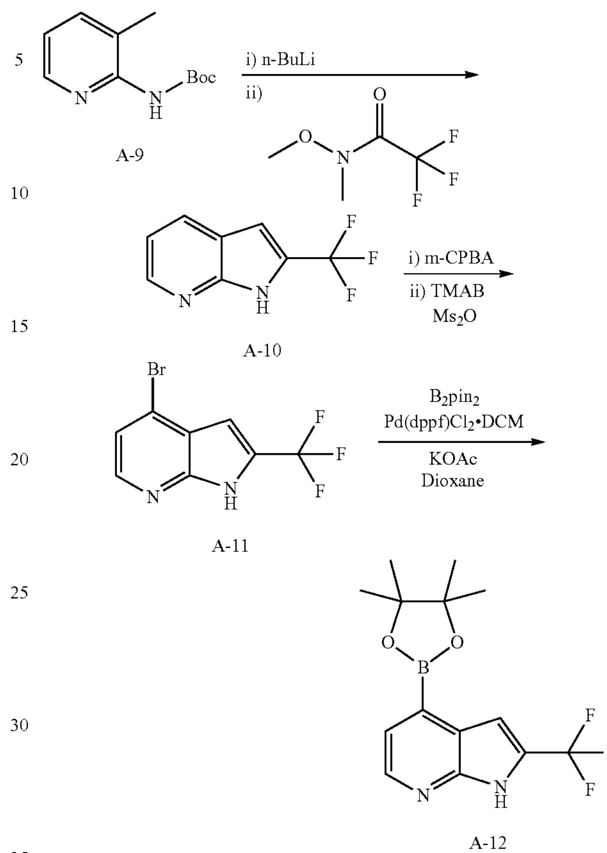

A-9

A-10

A-11

A-12

2-(Trifluoromethyl)-1H-pyrrolo[2,3-b]pyridine, A-10. 2-(N-Boc-Amino)-3-methylpyridine, A-9 (10 g, 48.02 mmol) was stirred in dry THE (100 mL) and cooled in an ice bath (ice/salt) to −10° C. The mixture was treated with 2.5 M hexane solution of n-BuLi (38.41 mL, 96.03 mmol) under nitrogen in a drop-wise fashion over 20 mins while maintaining the temperature below 0° C. The red suspension was further stirred for 1 h min at <0° C. then treated with 2,2,2-trifluoro-N-methoxy-N-methylacetamide (6.97 mL, 57.62 mmol) slowly. The reaction was continued stirring for 1.5 h then slowly added to stirring 5M HCl (106 mL) over 10 mins at 0° C., then continued stirring for 25 min. The mixture was then heated to 80° C. for 2 h. The phases were separated and the aq. phase was made alkaline with 10 M sodium hydroxide (approx. 70 mL). The mixture was extracted with EtOAc (2×100 mL). The organic phase was dried ($Na_2SO_4$) then evaporated to give a pale orange solid which was purified by ISCO flash chromatography (20% EtOAc in hexane) to afford a white solid (5.4 g, 29.01 mmol, 60%). LCMS (Method A) $t_R$=1.63 min, m/z=187.04 $[M+H]^+$; $^1H$ NMR (400 MHz, $CDCl_3$) δ 8.49 (dd, J=4.9, 1.6 Hz, 1H), 8.11 (dd, J=8.0, 1.6 Hz, 1H), 7.25-7.19 (m, 1H), 6.92 (q, J=1.3 Hz, 1H); $^{19}F$ NMR (376 MHz, $CDCl_3$) δ −61.20.

4-Bromo-2-(trifluoromethyl)-1H-pyrrolo[2,3-b]pyridine, A-11. A stirred solution of A-10 (5.4 g, 29.01 mmol) in EtOAc (100 mL) was treated drop wise with a solution of m-CPBA (8.3 g, 1.12 eq.) in EtOAc (100 mL) at 0° C. The reaction was warmed to 5-10° C. over ~2 h. Before re-cooling to 0° C. and treated with an additional portion of m-CPBA (2.3 g, 0.28 eq.) in EtOAc (30 mL). The reaction was warmed to room temperature over 16 h. The solid precipitate was collected to give the pyridine N-oxide intermediate as a white powder (3.7 g, 18.30 mmol). LCMS (Method A) $t_R$=1.40 min, m/z=203.04 $[M+H]^+$. The intermediate (3.7 g, 18.30 mmol) was taken in anhydrous DMF (75 mL), Tetramethylammonium bromide (4.22 g, 27.45 mmol) was added to it at room temperature. The reaction mixture was cooled to 0° C. followed by addition of methane sulfonic anhydride (6.37 g, 36.61 mmol) portion-wise and the reaction was allowed to warm to ambient temperature over 16 h. The reaction was further treated with tetramethylammonium bromide (1.40 g, 9.15 mmol) and methane sulfonic anhydride (1.59 g, 9.15 mmol). After 2 h the reaction was poured onto water (250 mL) and the resultant yellow solid was collected by filtration, and dried under vacuum to afford A-11 (3.3 g, 12.45 mmol, 43% yield over two steps). LCMS (Method A) $t_R$=2.14 min, m/z=264.97 $[M+H]^+$; $^1H$ NMR (400 MHz, $CDCl_3$) δ 8.26 (d, J=5.4 Hz, 1H), 7.49 (d, J=5.4 Hz, 1H), 7.01 (q, J=1.3 Hz, 1H); $^{19}F$ NMR (376 MHz, $CDCl_3$) δ −61.48.

4-(4,4,5,5-Tetramethyl-1,3,2-dioxaborolan-2-yl)-2-(trifluoromethyl)-1H-pyrrolo[2,3-b]pyridine, A-12. A-11 (2.87 g, 10.83 mmol), bis(pinacolato)diboron (3.3 g, 13 mmol), $Pd(dppf)Cl_2 \cdot DCM$ (0.44 g, 0.54 mmol) and KOAc (3.19 g, 32.51 mmol) were combined in dioxane (40 mL) and degassed under a stream of Ar for 20 mins, followed by heating to 100° C. for 16 h. The reaction mixture was filtered through celite, washed with EtOAc (50 mL), concentrated in vacuo and purified by ISCO flash chromatography (20% EtOAc in hexanes) to afford a cream powder (2.1 g, 6.72 mmol, 62%). LCMS (Method A) $t_R$=1.35 min, m/z=231.07 $[M+H]^+$ (mass of $B(OH)_2$ observed by MS, NMR confirms Bpin); $^1H$ NMR (400 MHz, $CDCl_3$) δ 8.49 (d, J=4.7 Hz, 1H), 7.60 (d, J=4.7 Hz, 1H), 7.29 (q, J=1.4 Hz, 1H), 1.42 (s, 12H); $^{19}F$ NMR (376 MHz, $CDCl_3$) δ −61.05.

Scheme 5. Synthesis of intermediate A-15.

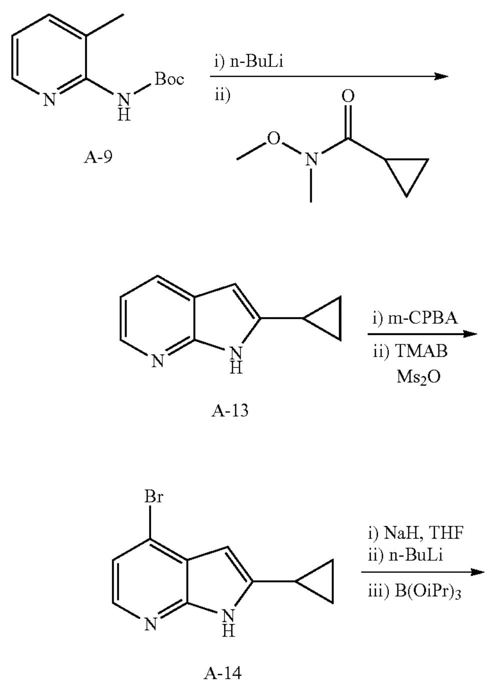

A-9

A-13

A-14

-continued

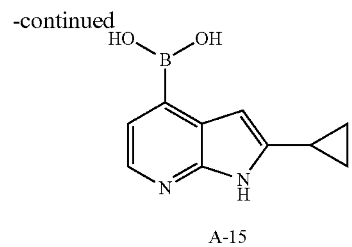

A-15

2-Cyclopropyl-1H-pyrrolo[2,3-b]pyridine, A-13. 2-(N-Boc-amino)-3-methylpyridine, A-9 (5.7 g, 27.37 mmol) in anhydrous THE (50 mL) was cooled in a salt/ice bath to −10° C. The mixture was treated with 2.5 M hexane solution of n-BuLi (21.89 mL, 54.73 mmol) under nitrogen in a drop-wise fashion over 20 mins while maintaining the temperature below 0° C. The red suspension was further stirred for 1 h 15 min at <0° C. then treated with a solution of N-methoxy-N-methylcyclopropanecarboxamide (3.89 g, 30.11 mmol) in THE (4 mL) and stirred for 2 h. The yellow solution was added to 5 M HCl (60 mL) over 10 mins at 0° C., then heated at 60° C. for 2 h. The phases were separated and the aq. phase was made alkaline with 10 M sodium hydroxide (approx. 20 mL). The mixture was extracted with EtOAc (2×50 mL). The organic phase was dried ($Na_2SO_4$) then evaporated to give a pale orange solid which was purified by ISCO flash chromatography (40% EtOAc in hexanes) to afford a white powder (3.6 g, 22.75 mmol, 83%). LCMS (Method A) $t_R$=1.37 min, m/z=159.15 $[M+H]^+$; $^1H$ NMR (400 MHz, $CDCl_3$) δ 10.09 (s, 1H), 8.20 (dd, J=4.9, 1.6 Hz, 1H), 7.81 (dd, J=7.8, 1.6 Hz, 1H), 7.04 (dd, J=7.8, 4.9 Hz, 1H), 6.15 (s, 1H), 2.09-2.03 (m, 1H), 1.11-1.00 (m, 2H), 0.94-0.85 (m, 2H).

4-Bromo-2-cyclopropyl-1H-pyrrolo[2,3-b]pyridine, A-14. A stirred solution of A-13 (3.6 g, 22.76 mmol) in 1,2-dimethoxyethane (60 mL) was treated drop wise with a solution of m-CPBA (6.81 g, 29.58 mmol) in 1,2-dimethoxyethane (20 mL) at 20° C. The reaction was stirred for 1 h. The solid precipitate was collected and washed with EtOAc (5 mL) to afford a yellow solid (1.6 g, 9.18 mmol). LCMS (Method A) $t_R$=1.40 min, m/z=175.14 $[M+H]^+$. The pyridine N-oxide intermediate (1.6 g, 9.18 mmol) was taken in anhydrous DMF (40 mL), methane sulfonic anhydride (3.2 g, 18.37 mmol) added and stirred under nitrogen at 25° C. Tetramethylammonium bromide (2.12 g, 13.77 mmol) was added to it in one charge. The reaction mixture was stirred at 25° C. for 30 h. The reaction was poured onto water (150 mL) and stirred for 1 h. The aqueous was adjusted to pH>11 with 10 N aqueous sodium hydroxide (8 mL). The suspension was stirred for 1 h. The precipitate was collected by filtration. The solid was purified by ISCO flash column chromatography (35% EtOAc in hexanes) to afford a pale yellow solid (1.22 g, 5.14 mmol, 23% yield over two steps). LCMS (Method A) $t_R$=1.76 min, m/z=237.07 $[M+H]^+$; $^1H$ NMR (400 MHz, $CDCl_3$) δ 10.96 (s, 1H), 8.03 (d, J=5.3 Hz, 1H), 7.23 (d, J=5.3 Hz, 1H), 6.19 (s, 1H), 2.11-2.04 (m, 1H), 1.15-1.06 (m, 2H), 0.98-0.91 (m, 2H).

2-Cyclopropyl-4-(4,4,5,5-tetramethyl-1,3,2-dioxaborolan-2-yl)-1H-pyrrolo[2,3-b]pyridine, A-15. To a solution of A-14 (103 mg, 0.434 mmol) in anhydrous THE (3 mL) stirred under nitrogen at 10° C. was added solid sodium hydride (60 wt. % in mineral oil, 22 mg, 0.543 mmol) in one charge. The reaction mixture was allowed to warm to 20° C. and stirred for 45 mins. The reaction was cooled to −78° C. and 2.5 M hexane solution of n-BuLi (0.4 mL, 0.999 mmol) was added dropwise over 15 min, then stirred at −78° C. for 45 mins. Triisopropylborate (0.3 mL, 1.30 mmol) was added dropwise during 15 min. The reaction mixture was stirred at −78° C. for 20 min, followed by stirring at 20° C. for 2 h. The reaction mixture was quenched with water (2 mL) and the reaction mixture was diluted with EtOAc (2 mL). The organic layer was separated and the aqueous layer was adjusted to pH 7 with 2 N aqueous hydrochloric acid. The suspension was extracted with ethyl acetate (2×5 mL). The combined organics were dried ($Na_2SO_4$) and concentrated in vacuo to get an off-white solid (40 mg, 0.198 mmol, 45%). LCMS (Method A); $t_R$=1.27 min, m/z=203.16 $[M+H]^+$; $^1H$ NMR (400 MHz, MeOH-$d_4$) δ 8.00 (d, J=5.0 Hz, 1H), 7.17 (s, 1H), 6.21 (s, 1H), 2.06 (td, J=8.4, 4.2 Hz, 1H), 1.08-0.95 (m, 2H), 0.93-0.81 (m, 2H).

Scheme 6. Synthesis of intermediate A-18

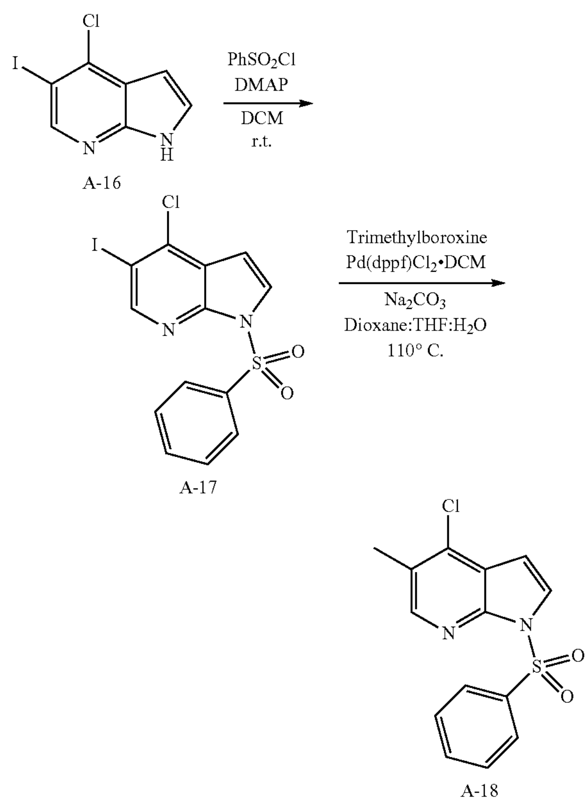

A-16

A-17

A-18

1-(Benzenesulfonyl)-4-chloro-5-iodo-pyrrolo[2,3-b]pyridine, A-17. To a solution of 4-chloro-5-iodo-1H-pyrrolo[2,3-b]pyridine, A-16 (1.0 g, 3.6 mmol) and DMAP (44 mg, 0.36 mmol) in DCM (34 mL) was added benzenesulfonyl chloride (0.55 mL, 4.3 mmol) and DIPEA (1.54 mL, 8.6 mmol), the mixture was stirred at r.t. for 4 h, with solid precipitate forming. The precipitate was collected by vacuum filtration, then purified by ISCO flash chromatography (0-100% EtOAc in hexanes) affording a colourless solid (0.76 g, 1.82 mmol, 51%). LCMS (Method B) $t_R$=2.07 min, m/z=418.91 $[M+H]^+$; $^1H$ NMR (400 MHz, DMSO-$d_6$) δ 8.72 (s, 1H), 8.15-8.08 (m, 2H), 8.03 (d, J=4.0 Hz, 1H), 7.80-7.72 (m, 1H), 7.65 (t, J=7.9 Hz, 2H), 6.89 (d, J=4.0 Hz, 1H).

1-(Benzenesulfonyl)-4-chloro-5-methyl-pyrrolo[2,3-b]pyridine, A-18. To a vial containing A-17 (530 mg, 1.27 mmol), Pd(dppf)$Cl_2$·DCM (52 mg, 0.06 mmol), and $Na_2CO_3$ (268 mg, 2.53 mmol) in dioxane (5 mL) and water (0.5 mL) was added trimethylboroxine (50% w/w solution in THF, 0.53 mL, 1.90 mmol). The mixture heated to 110° C. for 16 h, then filtered. The filtrate was diluted with EtOAc and washed with water, sat. aq. NaCl and concentrated. Purification by ISCO flash chromatography affords a colourless solid (265 mg, 0.86 mmol, 68%). LCMS (Method B) $t_R$=1.77 min, m/z=307.03 $[M+H]^+$; $^1H$ NMR (400 MHz, $CDCl_3$) δ 8.25 (s, 1H), 8.20-8.13 (m, 2H), 7.71 (d, J=4.0 Hz, 1H), 7.62-7.53 (m, 1H), 7.52-7.44 (m, 2H), 6.66 (d, J=4.0 Hz, 1H), 2.40 (s, 3H).

Scheme 7. Synthesis of intermediate A-20

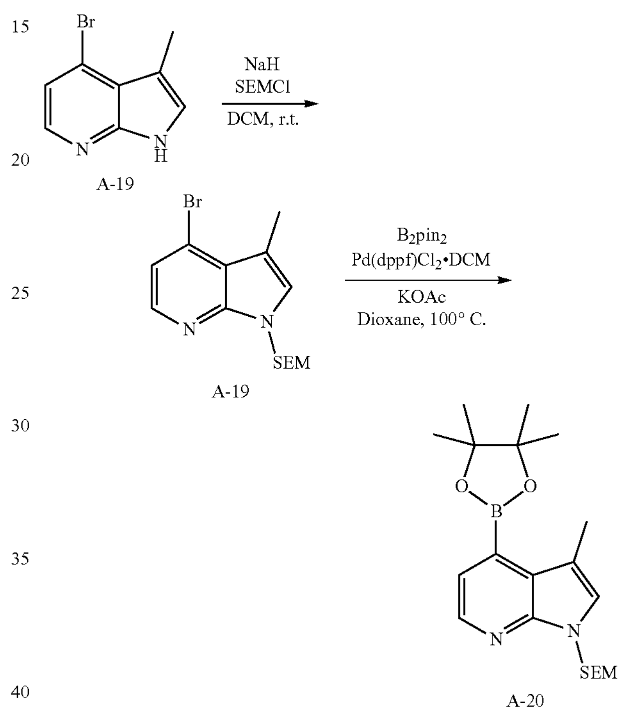

A-19

A-19

A-20

4-Bromo-3-methyl-1-((2-(trimethylsilyl)ethoxy)methyl)-1H-pyrrolo[2,3-b]pyridine, A-19. To a solution of A-19 (1 g, 4.74 mmol) in DMF (10 mL) was added sodium hydride (284 mg, 7.11 mmol, 60% w/w dispersion in mineral oil) at 0° C. and stirred for 30 min. (2-(Chloromethoxy)ethyl)trimethylsilane (1.11 g, 6.64 mmol) in DMF (1 mL) was added dropwise and stirred for 1 h at r.t. Water (50 mL) was added and the solution was extracted with EtOAc (3×25 mL). The combined organics were washed with brine (30 mL), dried over anhydrous sodium sulfate and concentrated. The residue was purified on silica gel column chromatography (0-20% EtOAc/Petroether) to provide A-19 as a colourless solid (1.39 g, 86% yield) as a white solid. LCMS m/z=341.0 $[M+H]^+$.

3-Methyl-4-(4,4,5,5-tetramethyl-1,3,2-dioxaborolan-2-yl)-1-((2-(trimethylsilyl)ethoxy)methyl)-1H-pyrrolo[2,3-b]pyridine, A-20. A mixture of A-19 (1.39 g, 4.08 mmol), bis(pinacolato)diboron (1.24 g, 4.89 mmol, 1.2 equiv), Pd(dppf)$Cl_2$·DCM (335 mg, 0.41 mmol) and KOAc (801 mg, 8.16 mmol) in 1,4-dioxane (20 mL) was heated to 100° C. for 16 h. Water (20 mL) was added and the solution was extracted with EtOAc (3-30 mL). The combined organics were washed with brine (30 mL), dried over anhydrous sodium sulfate and concentrated. The residue was purified on silica gel column chromatography (0-35% EtOAc/

Petroether) to provide the title compound A-20 (1.46 g, 92% yield) as a colourless solid. LCMS m/z=389.0 $[M+H]^+$.

Scheme 8. Synthesis of intermediate D-1.

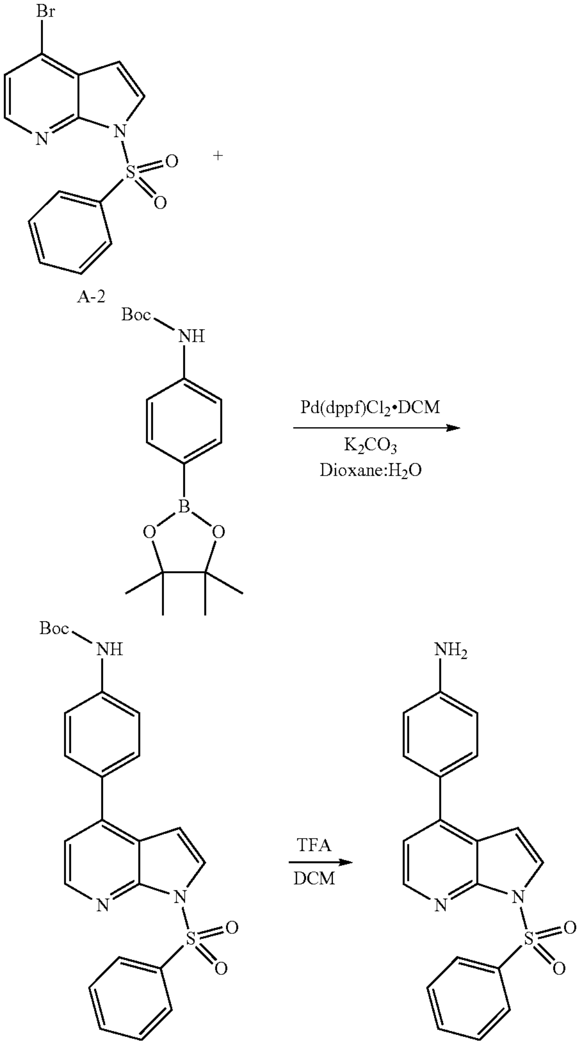

tert-Butyl (4-(1-(phenylsulfonyl)-1H-pyrrolo[2,3-b]pyridine-4-yl)phenyl)carbamate, C-1. A-2 (1.69 g, 5 mmol) was reacted with 4-(Boc-amino)benzeneboronic acid (1.30 g, 5.5 mmol) following General Procedure A. The reaction was run in quadruplicate in 4×40 mL vials. Upon complete reaction the material was combined for filtration and purification by ISCO flash column chromatography (40-80% EtOAc in hexanes) to afford a pale cream solid (8.27 g, 18.4 mmol, 92%). LCMS (Method B) $t_R$=2.12 min, m/z=450.15 $[M+H]^+$; $^1H$ NMR (400 MHz, $CDCl_3$) $\delta_H$ 8.44 (d, J=5.0 Hz, 1H), 8.25-8.18 (m, 2H), 7.76 (d, J=4.1 Hz, 1H), 7.62-7.45 (m, 7H), 7.21 (d, J=5.0 Hz, 1H), 6.77 (d, J=4.1 Hz, 1H), 6.59 (s, 1H), 1.54 (s, 9H).

4-(1-(Phenylsulfonyl)-1H-pyrrolo[2,3-b]pyridine-4-yl) aniline, D-1. C-1 (8.27 g, 18.4 mmol) was reacted following General Procedure I. Purification by ISCO flash chromatography (0-100% EtOAc in hexanes) affords a fluffy cream solid (5.96 g, 17.1 mmol, 92.7%). LCMS (Method A) $t_R$=1.79 min, m/z=350.10 $[M+H]^+$; $^1H$ NMR (400 MHz, $CDCl_3$) $\delta_H$ 8.48 (d, J=5.1 Hz, 1H), 8.28-8.23 (m, 3H), 7.80 (d, J=4.1 Hz, 1H), 7.62-7.56 (m, 3H), 7.56-7.49 (m, 3H), 7.22 (d, J=5.1 Hz, 1H), 6.76 (d, J=4.1 Hz, 1H).

Scheme 9. Synthesis of intermediate D-3.

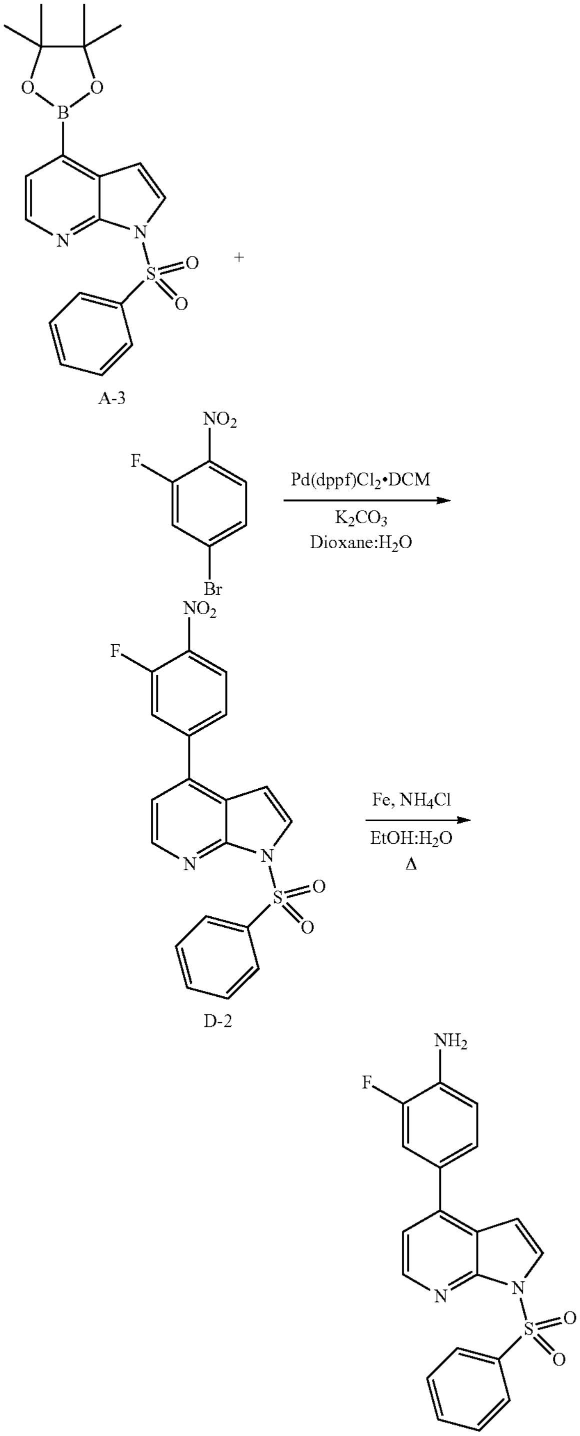

1-(Benzenesulfonyl)-4-(3-fluoro-4-nitro-phenyl)pyrrolo[2,3-b]pyridine, D-2. A-3 (1.0 g, 2.6 mmol) and 4-bromo-2-fluoro-1-nitro-benzene (687 mg, 3.12 mmol) were reacted according to General Procedure A at 110° C. for 2 h.

Purification by ISCO flash chromatography (20-100% EtOAc in hexanes) affords a cream powder (0.87 g, 1.86 mmol, 72%). LCMS (Method A) $t_R$=2.38 min, m/z=398.0597 $[M+H]^+$; $^1H$ NMR (400 MHz, DMSO-$d_6$) δ 8.52 (d, J=4.9 Hz, 1H), 8.30 (t, J=8.5 Hz, 1H), 8.13 (dd, J=28.8, 5.9 Hz, 3H), 7.94 (d, J=12.3 Hz, 1H), 7.75 (dd, J=13.2, 8.0 Hz, 2H), 7.66 (d, J=7.5 Hz, 2H), 7.58-7.52 (m, 1H), 7.01 (t, J=3.2 Hz, 1H); $^{19}F$ NMR (376 MHz, DMSO-$d_6$) δ −117.73 (d, J=8.0 Hz).

4-[1-(Benzenesulfonyl)pyrrolo[2,3-b]pyridin-4-yl]-2-fluoro-aniline, D-3. A flask was charged with iron (215 mg, 3.85 mmol), $NH_4Cl$ (25 mg, 0.48 mmol), D-2 (300 mg, 0.64 mmol), water (0.75 mL) and ethanol (3 mL) then stirred at 80° C. for 18 h. The reaction was filtered, washing with EtOAc. The filtrate was washed with water and brine, dried ($Na_2SO_4$) and concentrated in vacuo. Purification by ISCO flash chromatography (20-100% EtOAc in hexanes) to afford a yellow oil (188 mg, 0.51 mmol, 79%). LCMS (Method A) $t_R$=2.16 min, m/z=368.1 $[M+H]^+$; $^1H$ NMR (400 MHz, DMSO-$d_6$) δ 8.33 (d, J=5.1 Hz, 1H), 8.18-8.10 (m, 2H), 7.93 (d, J=4.1 Hz, 1H), 7.77-7.68 (m, 1H), 7.67-7.58 (m, 2H), 7.37 (dd, J=12.7, 2.0 Hz, 1H), 7.32 (d, J=5.1 Hz, 1H), 7.29 (dd, J=8.3, 2.1 Hz, 1H), 6.97 (d, J=4.1 Hz, 1H), 6.89 (dd, J=9.4, 8.3 Hz, 1H), 5.60 (s, 2H); $^{19}F$ NMR (376 MHz, DMSO-$d_6$) δ −134.48.

Scheme 10. Synthesis of intermediate D-6.

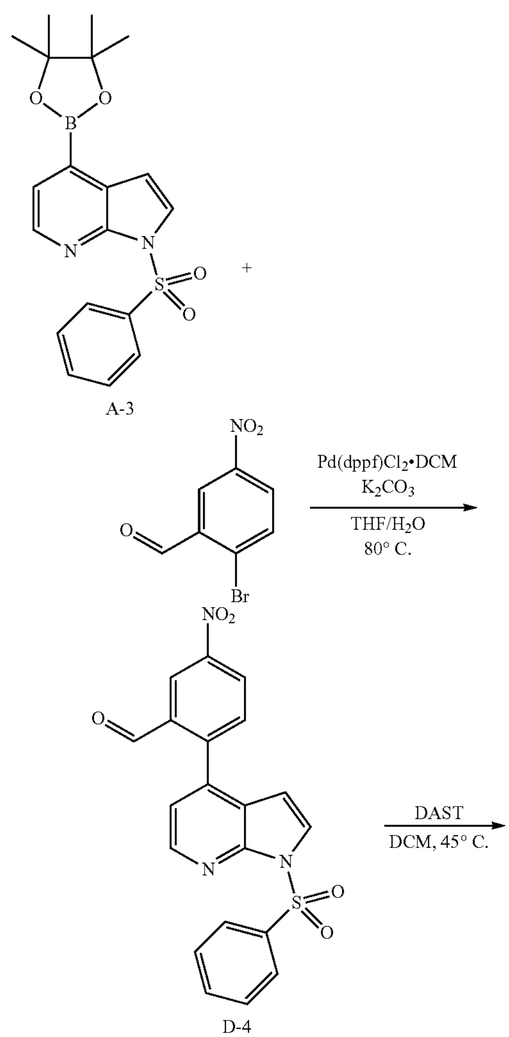

A-3

D-4

-continued

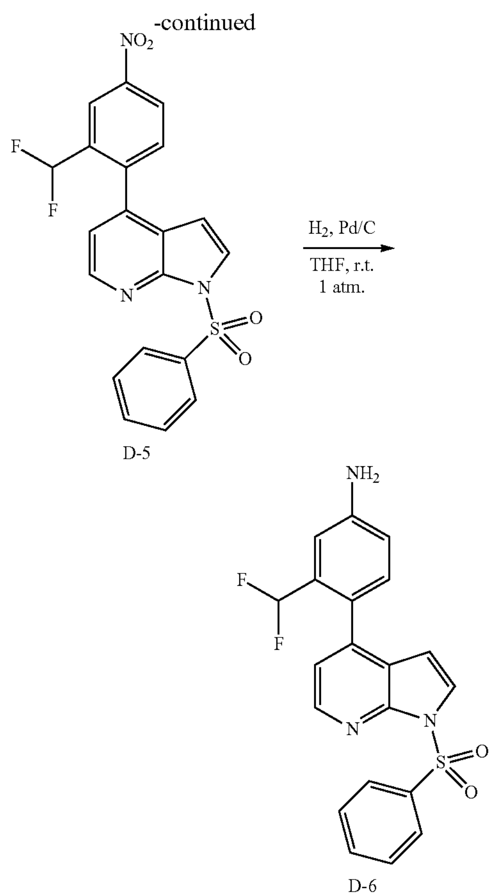

D-5

D-6

2-[1-(Benzenesulfonyl)pyrrolo[2,3-b]pyridin-4-yl]-5-nitro-benzaldehyde, D-4. A-3 (768 mg, 2.00 mmol) was reacted with 2-bromo-5-nitro-benzaldehyde (552 mg, 2.40 mmol) following General Procedure B. Purification by ISCO flash chromatography (10-80% EtOAc in hexanes) affords as a beige powder (191 mg, 0.47 mmol, 23%). LCMS (Method A) $t_R$=2.26 min, m/z=408.0663 $[M+H]^+$; $^1H$ NMR (400 MHz, DMSO-$d_6$) δ 9.81 (s, 1H), 8.70 (d, J=2.5 Hz, 1H), 8.58 (dd, J=8.5, 2.5 Hz, 1H), 8.52 (d, J=5.0 Hz, 1H), 8.23-8.14 (m, 2H), 8.04 (d, J=4.1 Hz, 1H), 7.86 (d, J=8.5 Hz, 1H), 7.81-7.72 (m, 1H), 7.67 (t, J=7.8 Hz, 2H), 7.45 (d, J=5.0 Hz, 1H), 6.60 (d, J=4.1 Hz, 1H).

1-(Benzenesulfonyl)-4-[2-(difluoromethyl)-4-nitro-phenyl]pyrrolo[2,3-b]pyridine, D-5. DAST (0.23 mL, 1.77 mmol) was added to a suspension of D-4 (180 mg, 0.44 mmol) in DCM (2.21 mL) and stirred at 45° C. for 1 h. Reaction was carefully poured into sat. aq. $NaHCO_3$ solution and extracted with DCM. The extracts were dried ($Na_2SO_4$) and concentrated in vacuo. Purification by ISCO flash chromatography (20-100% EtOAc in hexanes) to afford a cream powder (165 mg, 0.38 mmol, 87%). LCMS (Method A) $t_R$=2.37 min, m/z=430.0676 $[M+H]^+$; H NMR (400 MHz, DMSO-$d_6$) δ 8.56-8.44 (m, 3H), 8.23-8.16 (m, 2H), 8.02 (d, J=4.0 Hz, 1H), 7.77 (t, J=7.9 Hz, 2H), 7.67 (dd, J=8.6, 7.0 Hz, 2H), 7.32 (d, J=5.0 Hz, 1H), 6.95 (t, J=53.7 Hz, 1H), 6.53 (d, J=4.1 Hz, 1H); $^{19}F$ NMR (376 MHz, DMSO-$d_6$) δ −109.50 (d, J=444.6 Hz).

4-[1-(Benzenesulfonyl)pyrrolo[2,3-b]pyridin-4-yl]-3-(difluoromethyl)aniline, D-6. Pd/C (10%) (36 mg, 0.03 mmol) and D-5 (145 mg, 0.34 mmol) were combined in THF (1.69 mL) and stirred under an atmosphere of $H_2$ at r.t. for 3.5 h.

The reaction mixture was filtered through celite and concentrated in vacuo, then purified by ISCO flash chromatography (0-10% MeOH in DCM to afford a cream powder (87 mg, 0.22 mmol, 65%). LCMS (Method A) $t_R$=2.05 min, m/z=400.0939 $[M+H]^+$.

Scheme 11. Synthesis of intermediate D-8.

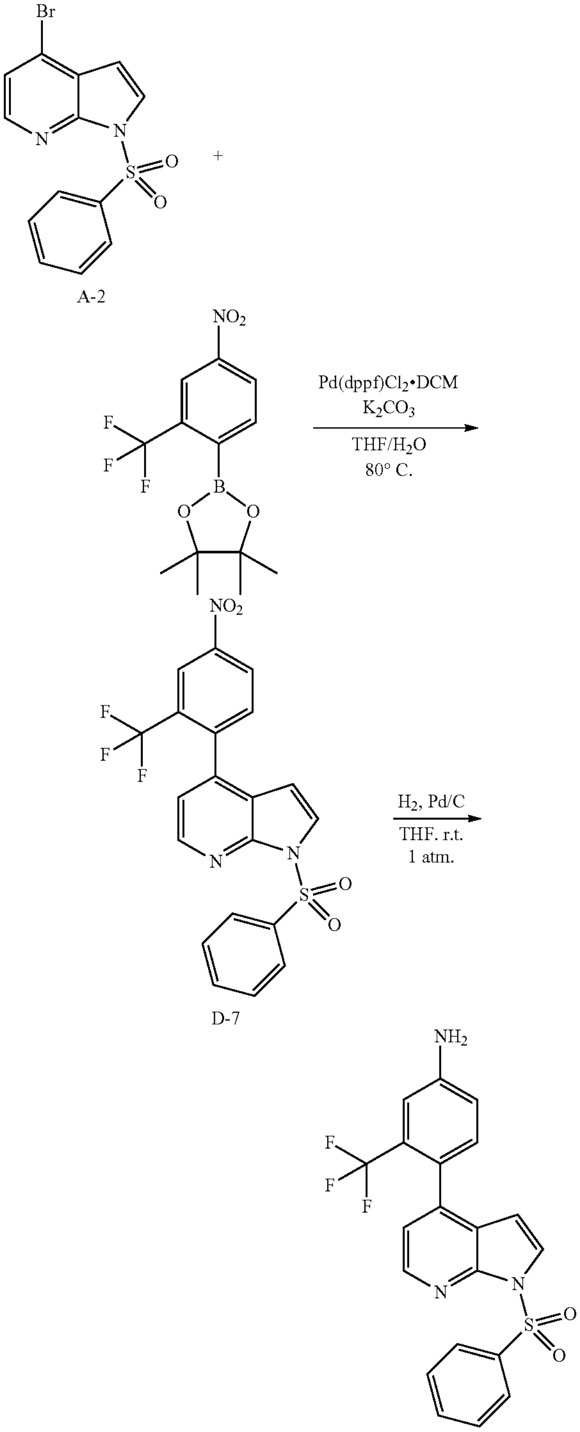

A-2

D-7

D-8

1-(Benzenesulfonyl)-4-[4-nitro-2-(trifluoromethyl)phenyl]pyrrolo[2,3-b]pyridine, D-7. A-2 (337 mg, 1.00 mmol) and 4,4,5,5-tetramethyl-2-[4-nitro-2-(trifluoromethyl)phenyl]-1,3,2-dioxaborolane (380 mg, 1.20 mmol) were reacted following General Procedure B to afford a yellow solid (276 mg, 0.62 mmol, 62%). LCMS (Method A) $t_R$=2.42 min, m/z=448.0520 $[M+H]^+$; $^1$H NMR (400 MHz, DMSO-$d_6$) δ 8.62 (d, J=2.3 Hz, 1H), 8.58 (dd, J=8.5, 2.3 Hz, 1H), 8.49 (d, J=4.9 Hz, 1H), 8.18 (d, J=7.5 Hz, 2H), 7.99 (d, J=4.1 Hz, 1H), 7.85-7.72 (m, 2H), 7.67 (t, J=7.5 Hz, 2H), 7.30 (d, J=4.9 Hz, 1H), 6.46 (d, J=4.1 Hz, 1H); $^{19}$F NMR (376 MHz, DMSO-$d_6$) δ −57.26.

4-[1-(Benzenesulfonyl)pyrrolo[2,3-b]pyridin-4-yl]-3-(trifluoromethyl)aniline, D-8. D-7 (270 mg, 0.6 mmol) was dissolved in ethanol (3 mL) under an atmosphere of Ar. Pd/C 10% (64 mg, 0.06 mmol) was added then the reaction vessel was purged and placed under an atmosphere of $H_2$ for 13 h. The mixture was filtered through celite then purified by ISCO flash chromatography (4 0-10% MeOH in DCM) to afford a tan solid (219 mg, 0.52 mmol, 87%). LCMS (Method A) $t_R$=2.18 min, m/z=418.0843 $[M+H]^+$.

Scheme 12. Synthesis of intermediate D-9.

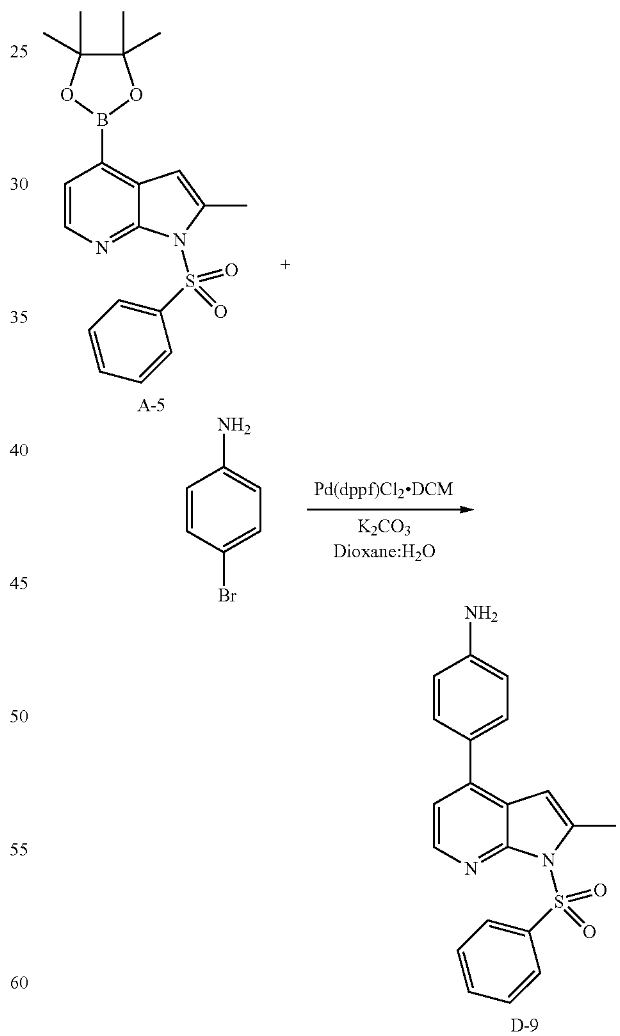

A-5

D-9

4-[1-(Benzenesulfonyl)-2-methyl-pyrrolo[2,3-b]pyridin-4-yl]aniline, D-9. A-5 (797 mg, 2.0 mmol) was reacted with 4-bromoaniline (516 mg, 3.0 mmol) following General Procedure A, affording a pale brown solid (479 mg, 1.32 mmol, 66%) after purification. LCMS (Method A) $t_R$=1.82 min, m/z=364.11 $[M+H]^+$; $^1H$ NMR (400 MHz, DMSO-$d_6$) δ 8.21 (d, J=5.2 Hz, 1H), 8.15-8.11 (m, 2H), 7.75-7.66 (m, 1H), 7.61 (t, J=7.8 Hz, 2H), 7.38 (d, J=8.4 Hz, 2H), 7.22 (d, J=5.2 Hz, 1H), 6.75 (d, J=1.2 Hz, 1H), 6.68 (d, J=8.5 Hz, 2H), 5.51 (s, 2H), 2.73 (d, J=1.2 Hz, 3H).

Scheme 13. Synthesis of intermediate D-10.

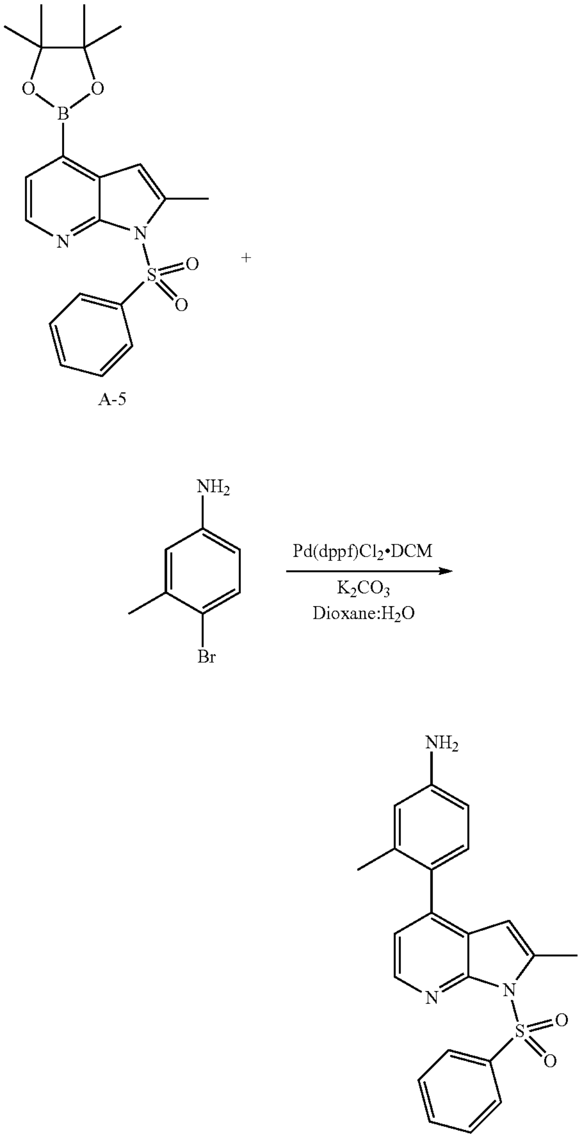

A-5

D-10

4-[1-(Benzenesulfonyl)-2-methyl-pyrrolo[2,3-b]pyridin-4-yl]-3-methyl-aniline, D-10. A-5 (1195 mg, 3.0 mmol) was reacted with 4-bromo-3-methylaniline (837 mg, 4.5 mmol) following General Procedure A, affording a pale brown solid (299 mg, 0.79 mmol, 26%) after purification. LCMS (Method B) $t_R$=0.78 min, m/z=378.13 $[M+H]^+$; $^1H$ NMR (400 MHz, DMSO-$d_6$) δ $^1H$ NMR (400 MHz, $CDCl_3$) δ 8.37 (d, J=5.0 Hz, 1H), 8.22 (d, J=7.3 Hz, 2H), 7.60 (t, J=7.4 Hz, 1H), 7.57-7.47 (m, 2H), 7.03 (s, 1H), 7.02 (d, J=2.5 Hz, 1H), 6.69 (d, J=2.5 Hz, 1H), 6.64 (d, J=8.2 Hz, 1H), 6.16-6.10 (m, 1H), 2.71 (s, 3H), 2.11 (s, 3H).

Scheme 14. Synthesis of intermediate D-11.

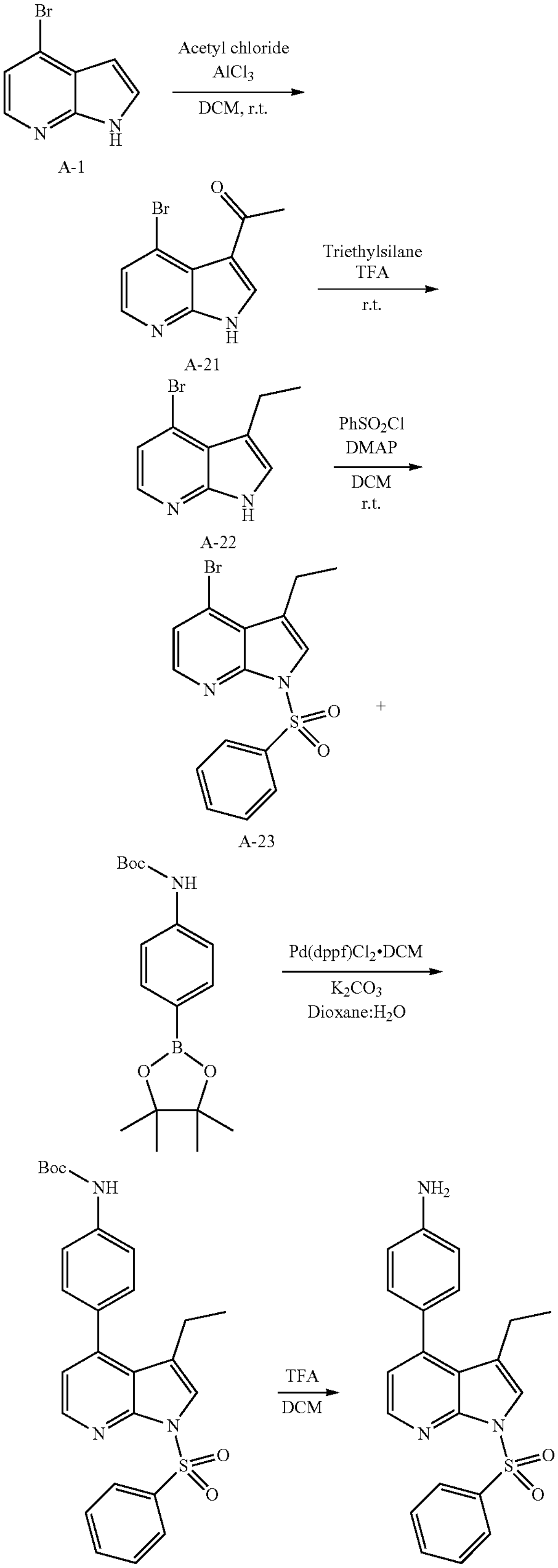

A-1

A-21

A-22

A-23

C-2

D-11

1-(4-Bromo-1H-pyrrolo[2,3-b]pyridin-3-yl)ethanone, A-21. A-1 (591 mg, 3.00 mmol) was added to a suspension of $AlCl_3$ (2.0 g, 15.00 mmol) in DCM (10 mL) and stirred at r.t. for 60 mins before the addition of acetyl chloride (1.07 mL, 15.00 mmol). Reaction was stirred at rt for 2 days before quenching by the careful addition of MeOH then concentrated in vacuo. Sat. aq. $NaHCO_3$ and EtOAc were added to the residue followed by vigorous stirring. The aqueous layer was extracted with EtOAc and the combined organic layers were dried over $Na_2SO_4$ and concentrated in vacuo. Purification by ISCO flash chromatography (0-100% EtOAc in hexanes) affords as a colourless solid (450 mg, 1.88 mmol, 63%). LCMS (Method A) $t_R$=1.22 min, m/z=238.9641 $[M+H]^+$.

4-Bromo-3-ethyl-1H-pyrrolo[2,3-b]pyridine, A-22. To a solution of A-21 (740 mg, 3.10 mmol) in TFA (8.6 mL, 112.44 mmol) was added triethylsilane (3.09 mL, 19.36 mmol) and stirred at r.t. for 24 h. The solution was concentrated, diluted with 2 M aqueous NaOH solution, extracted with DCM, dried over $Na_2SO_4$, filtered and concentrated in vacuo to afford A-22 as a tan solid (695 mg, 3.09 mmol, 99%). LCMS (Method A) $t_R$=1.51 min, m/z=225.0025 $[M+H]^+$.

1-(Benzenesulfonyl)-4-bromo-3-ethyl-pyrrolo[2,3-b]pyridine, A-23. To a suspension of A-22 (400 mg, 1.78 mmol) in DCM (8.88 mL) was added benzenesulfonyl chloride (272 μL, 2.13 mmol), DIPEA (743 μL, 4.26 mmol) and DMAP (11 mg, 0.09 mmol) and stirred at r.t. for 24 h. Diluted with DCM, washed with water, dried over $Na_2SO_4$ and concentrated in vacuo. Purification by ISCO flash chromatography (0-100% EtOAc in hexanes) affords title compound as a cream solid (610 mg, 1.67 mmol, 94%). LCMS (Method B); $t_R$=2.20 min, m/z=366.9948 $[M+H]^+$; $^1H$ NMR (500 MHz, DMSO-$d_6$) δ 7.82 (d, J=5.2 Hz, 1H), 7.74 (d, J=7.3 Hz, 2H), 7.43 (s, 1H), 7.38-7.32 (m, 1H), 7.29-7.23 (m, 2H), 7.18 (d, J=5.2 Hz, 1H), 2.51 (q, J=7.5 Hz, 2H), 0.91 (t, J=7.5 Hz, 3H).

tert-butyl N-[4-[1-(benzenesulfonyl)-3-ethyl-pyrrolo[2,3-b]pyridin-4-yl]phenyl]carbamate, C-2. tert-Butyl N-[4-(4,4,5,5-tetramethyl-1,3,2-dioxaborolan-2-yl)phenyl]carbamate (503 mg, 1.58 mmol) and A-23 (480 mg, 1.31 mmol) were reacted according to General Procedure A. Purification by ISCO flash chromatography (10-100% EtOAc in hexanes) to afford C-2 as a colourless solid (628 mg, 1.31 mmol, quant.). LCMS (Method B); $t_R$=2.31 min, m/z=478-1835 $[M+H]^+$; $^1H$ NMR (500 MHz, DMSO-$d_6$) δ 9.55 (s, 1H), 8.33 (d, J=5.0 Hz, 1H), 8.16-8.10 (m, 2H), 7.75-7.69 (m, 1H), 7.67 (s, 1H), 7.65-7.61 (m, 2H), 7.56 (d, J=8.3 Hz, 2H), 7.33-7.27 (m, 2H), 7.10 (d, J=5.0 Hz, 1H), 2.28 (q, J=7.4, 2H), 1.49 (s, 9H), 0.83 (t, J=7.4 Hz, 3H).

4-[1-(Benzenesulfonyl)-3-ethyl-pyrrolo[2,3-b]pyridin-4-yl]aniline, D-11. TFA (650 μL, 8.49 mmol) was added to a solution of C-2 (620 mg, 1.30 mmol) in DCM (6.5 mL) at stirred at r.t. for 1 h. Reaction was concentrated then purified by ISCO flash chromatography (0-100% EtOAc in hexanes) to afford D-11 as a yellow oil (470 mg, 1.25 mmol, 96%). LCMS (Method A) $t_R$=1.87 min, m/z=378.1254 $[M+H]^+$; $^1H$ NMR (400 MHz, DMSO-$d_6$) δ 8.30 (d, J=4.9 Hz, 1H), 8.13 (d, J=7.7 Hz, 2H), 7.77-7.56 (m, 4H), 7.18 (d, J=8.0 Hz, 2H), 7.07 (d, J=4.9 Hz, 1H), 6.82 (d, J=7.9 Hz, 2H), 2.33 (q, J=7.5 Hz, 2H), 0.84 (t, J=7.5 Hz, 3H).

Scheme 15. Synthesis of thiazole intermediate D-12.

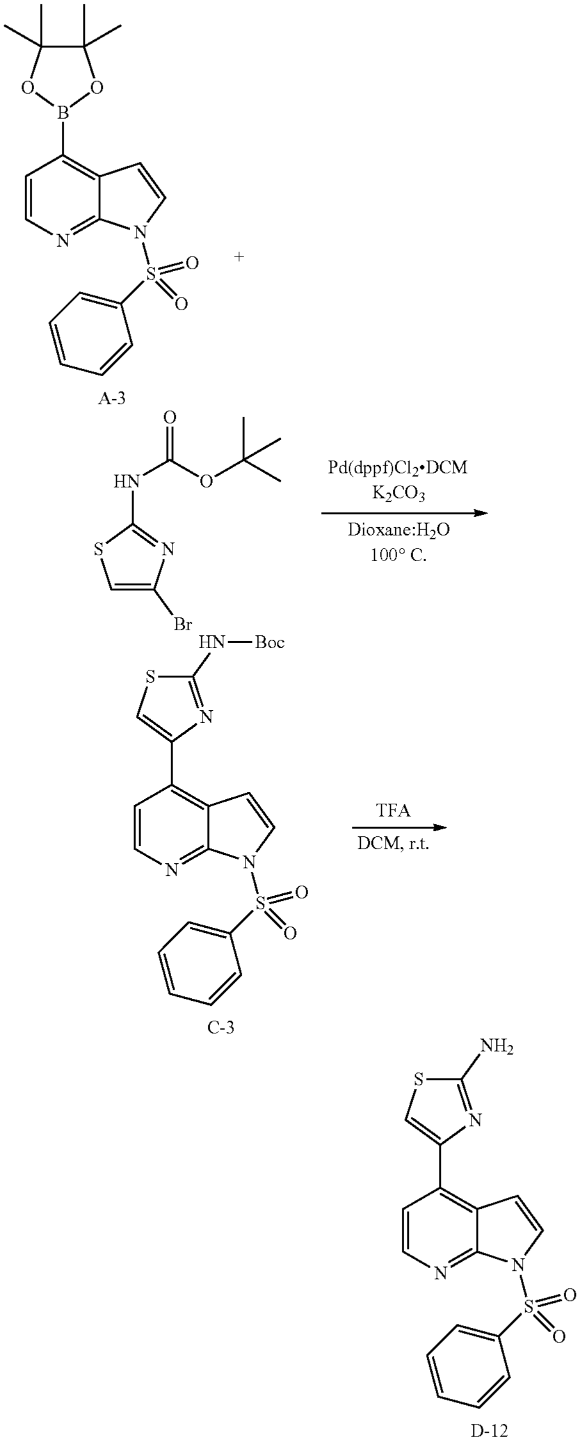

A-3

C-3

D-12

4-[1-(Benzenesulfonyl)pyrrolo[2,3-b]pyridin-4-yl]thiazol-2-amine, D-12. A-3 (384 mg, 1.0 mmol) was reacted with tert-butyl 4-bromothiazol-2-ylcarbamate (419 mg, 1.5 mmol) following General Procedure A, affording a cream solid of Boc-protected intermediate C-3 (450 mg, quant.) that was immediately deprotected by dissolving in DCM (5 mL) and stirring with TFA (0.77 mL, 10 mmol) for 18 h. The mixture was poured into sat. aq. $NaHCO_3$ and stirred for 1 h then extracted with DCM. Concentrated and purified by ISCO flash chromatography (0-5% MeOH in DCM) affording a pale brown solid (340 mg, 0.95 mmol, 95%). LCMS (Method B) $t_R$=0.60 min, m/z=357.05 $[M+H]^+$; $^1H$ NMR (400 MHz, $CDCl_3$) δ 8.50 (d, J=5.1 Hz, 1H), 8.23-8.14 (m, 2H), 7.84 (d, J=4.1 Hz, 1H), 7.59 (t, J=7.6 Hz, 1H), 7.54-7.45 (m, 3H), 6.94 (d, J=4.1 Hz, 1H), 6.89 (s, 1H), 3.49 (s, 2H).

Scheme 16. Synthesis of thiazole intermediate D-13.

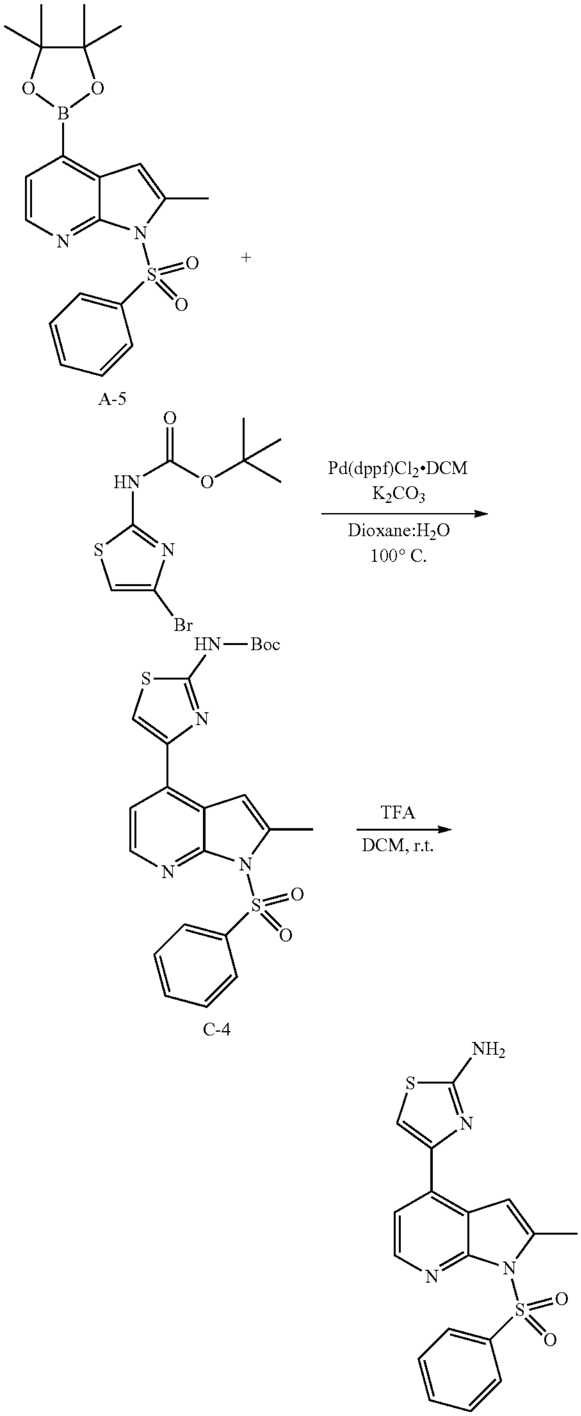

A-5

C-4

D-13 tert-Butyl N-[4-[1-(benzenesulfonyl)-2-methyl-pyrrolo[2,3-b]pyridin-4-yl]thiazol-2-yl]carbamate, C-4. A-5 (796 mg, 2.0 mmol) was reacted with tert-butyl 4-bromothiazol-2-ylcarbamate (670 mg, 2.4 mmol) following General Procedure A, affording a pale brown solid of Boc-protected intermediate, C-4 (823 mg, 1.75 mmol, 87%). LCMS (Method B) $t_R$=1.92 min, m/z=471.13 $[M+H]^+$.

4-[1-(Benzenesulfonyl)-2-methyl-pyrrolo[2,3-b]pyridin-4-yl]thiazol-2-amine, D-13. Intermediate C-4 (823 mg, 1.75 mmol) was deprotected following General Procedure I, affording a crude cream solid (496 mg, 1.34 mmol, 77%) that was used without purification. LCMS (Method A) $t_R$=1.76 min, m/z=371.08 $[M+H]^+$.

Scheme 17. Synthesis of intermediate D-14.

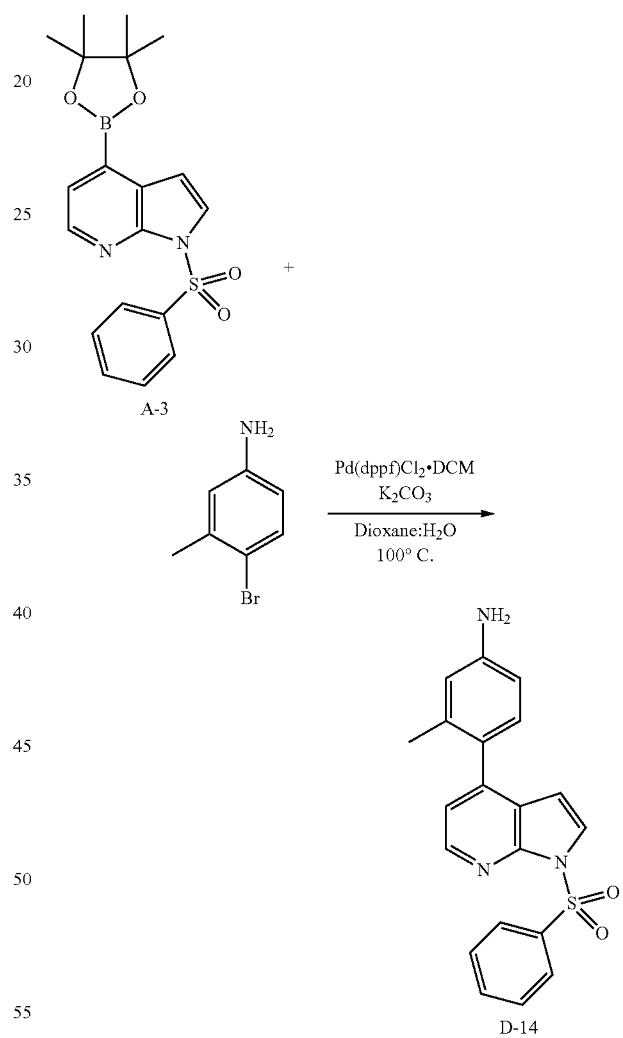

A-3

D-14

4-[1-(Benzenesulfonyl)pyrrolo[2,3-b]pyridin-4-yl]-3-methyl-aniline, D-14. A-3 (231 mg, 0.6 mmol) was reacted with 4-bromo-3-methylaniline (93 mg, 0.5 mmol) following General Procedure A, affording a pale brown solid (62 mg, 0.17 mmol, 34%) after purification. LCMS (Method A) $t_R$=1.79 min, m/z=364.1098 $[M+H]^+$; $^1H$ NMR (400 MHz, Methanol-$d_4$) δ 8.38 (d, J=4.9 Hz, 1H), 8.21-8.14 (m, 2H), 7.86 (d, J=4.0 Hz, 1H), 7.68 (t, J=7.4 Hz, 1H), 7.57 (t, J=7.8 Hz, 2H), 7.28 (d, J=8.2 Hz, 1H), 7.20-7.09 (m, 3H), 6.42 (d, J=4.0 Hz, 1H), 2.14 (s, 3H).

Scheme 18. General synthesis of aromatic amide intermediates by COMU mediated amide coupling

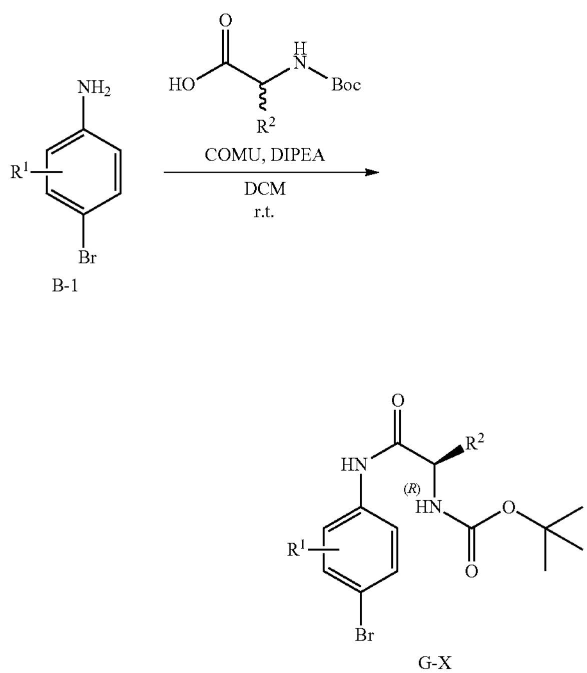

B-1

G-X tert-Butyl N-[(1R)-1-[(4-bromophenyl)carbamoyl]-3-methyl-butyl]carbamate, G-1

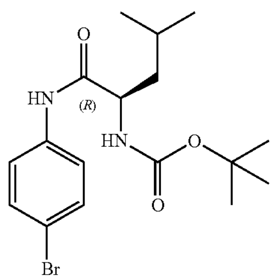

Boc-D-Leu-OH (3.90 g, 16.8 mmol) was reacted with 4-bromoaniline (1.93 mg, 11.2 mmol) following General Procedure E. Purification by ISCO flash chromatography (0-20% EtOAc in hexanes) affords a colourless solid (2.7 g, 7.0 mmol, 62%). LCMS (Method B) $t_R$=1.82 min, m/z=329.05, 331.05 (loss of t-bu) $[M+H]^+$; $^1H$ NMR (400 MHz, DMSO-$d_6$) δ 10.09 (s, 1H), 7.59 (d, J=8.8 Hz, 2H), 7.49 (d, J=8.8 Hz, 2H), 7.06 (d, J=7.9 Hz, 1H), 4.13-4.08 (m, 1H), 1.70-1.60 (m, 1H), 1.60-1.46 (m, 1H), 1.45-1.35 (m, 1H), 1.38 (s, 9H), 0.89 (dd, J=6.7, 3.8 Hz, 6H).

tert-Butyl N-[(1R)-1-[(4-bromophenyl)carbamoyl]-2,2-dimethyl-propyl]carbamate, G2

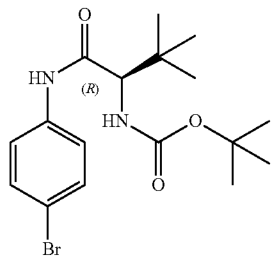

Boc-D-Tle-OH (1.73 g, 7.5 mmol) was reacted with 4-bromoaniline (860 mg, 5.0 mmol) following General Procedure E. Purification by ISCO flash chromatography (0-20% EtOAc in hexanes) affords a colourless solid (1.29 g, 3.4 mmol, 67%). LCMS (Method A) $t_R$=2.44 min, m/z=329.05, 331.05 (loss of t-bu) $[M+H]^+$. tert-Butyl (1R)-(1-((4-bromophenyl)amino)-4,4-dimethyl-1-oxopentan-2-yl)carbamate, G-3

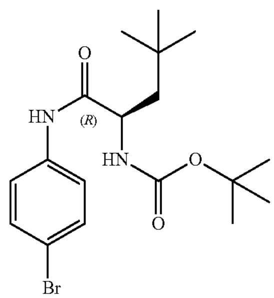

Step 1. (2R)-2-(tert-Butoxycarbonylamino)-4,4-dimethyl-pentanoic acid, Boc-D-Neo-OH. To a rapidly stirring solution of (R)-2-amino-4,4-dimethylpentanoic acid (11.4 g, 78.2 mmol) and sodium hydroxide (3.44 g, 86.1 mmol) in THE (98 mL) and $H_2O$ (98 mL) was added $Boc_2O$ (17.9 g, 82.2 mmol). The mixture was stirred at r.t. for 16 h then acidified by the slow addition of 2M HCl (45 mL) and stirred for 1 h at r.t. then extracted with EtOAc (3×100 mL). Concentrated to afford product as a crude colourless solid that was used without purification (17.7 g, 72.2 mmol, 92%).

Step 2. tert-butyl (R)-(1-((4-bromophenyl)amino)-4,4-dimethyl-1-oxopentan-2-yl)carbamate, G-3. Boc-D-Neo-OH (1.47 g, 6.0 mmol) was reacted with 4-bromoaniline (860 mg, 5.0 mmol) following General Procedure E. Purification by ISCO flash chromatography (0-100% EtOAc in hexanes) affords a colourless solid (1.42 g, 3.6 mmol, 71%). LCMS (Method B) $t_R$=1.96 min, m/z=343.08, 345.08 (loss of t-bu) $[M+H]^+$.

tert-Butyl N-[(1R)-1-[(4-bromo-3-methyl-phenyl) carbamoyl]-3,3-dimethyl-butyl]carbamate, G-4

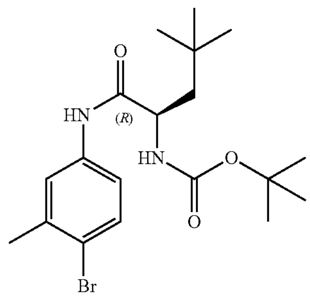

Boc-D-Neo-OH (2.21 g, 9.0 mmol) was reacted with 4-bromo-3-methyloaniline (1.40 g, 7.5 mmol) following General Procedure E. Purification by ISCO flash chromatography (0-100% EtOAc in hexanes) affords a yellow solid (2.18 g, 5.27 mmol, 70%). LCMS (Method B) $t_R$=2.11 min, m/z=357.08, 359.08 (loss of t-bu) $[M+H]^+$.

tert-Butyl N-[(1R)-1-[(6-chloro-3-pyridyl)carbamoyl]-3,3-dimethyl-butyl]carbamate, G-5

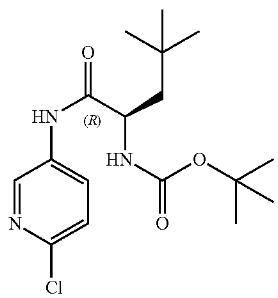

Boc-D-Neo-OH (301 mg, 1.6 mmol) was reacted with 6-chloropyridin-3-amine (140 mg, 1.1 mmol) following General Procedure E. Purification by ISCO flash chromatography (0-100% EtOAc in hexanes) affords a pale brown solid (82 mg, 0.23 mmol, 21%). LCMS (Method B) $t_R$=1.44 min, m/z=356.17 $[M+H]^+$; $^1$H NMR (400 MHz, $CDCl_3$) δ 8.71 (s, 1H), 8.38 (d, J=2.8 Hz, 1H), 8.09 (d, J=8.6 Hz, 1H), 7.29 (br s, 1H), 4.87-4.81 (m, 1H), 4.23 (br s, 1H), 2.11-2.04 (m, 1H), 1.46 (s, 9H), 1.44-1.40 (m, 1H), 0.99 (s, 9H).

tert-Butyl N-[(1R)-1-[(6-chloro-5-methyl-3-pyridyl) carbamoyl]-3,3-dimethyl-butyl]carbamate, G-6

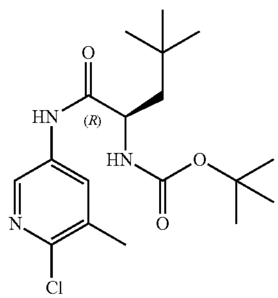

Boc-D-Neo-OH (295 mg, 1.2 mmol) was reacted with 5-amino-2-chloro-3-picoline (142 mg, 1.0 mmol) following General Procedure E. Purification by ISCO flash chromatography (0-100% EtOAc in hexanes) affords an orange-brown solid (199 mg, 0.54 mmol, 54%). LCMS (Method B) $t_R$=1.65 min, m/z=370.21 $[M+H]^+$;

tert-Butyl N-[(1R)-1-[(6-bromo-2-methoxy-3-pyridyl)carbamoyl]-3,3-dimethyl-butyl]carbamate, G-7

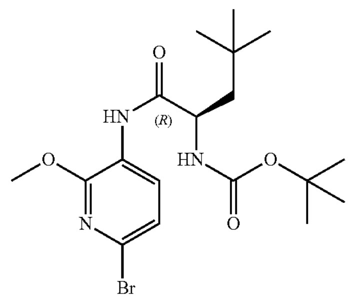

Boc-D-Neo-OH (368 mg, 1.5 mmol) was reacted with 3-amino-6-bromo-2-methoxypyridine (203 mg, 1.0 mmol) following General Procedure E. Purification by ISCO flash chromatography (0-100% EtOAc in hexanes) affords an orange-brown solid (314 mg, 0.73 mmol, 73%). LCMS (Method B) $t_R$=2.13 min, m/z=374.08, 376.08 (loss of t-Bu) $[M+H]^+$;

Scheme 19. Synthesis of intermediate G-8

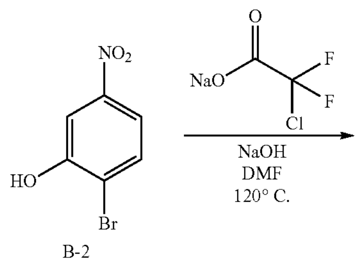

B-2

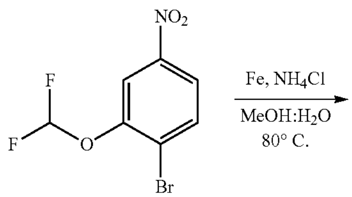

B-3

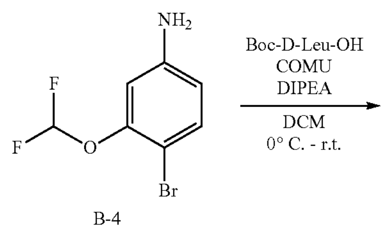

B-4

-continued

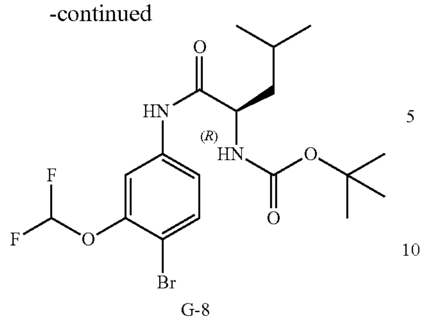

G-8

1-Bromo-2-(difluoromethoxy)-4-nitro-benzene, B-3. To a solution of 2-bromo-5-nitrophenol, B-2 (625 mg, 2.87 mmol) and sodium chlorodifluoroacetate (437 mg, 2.87 mmol) in DMF (15 mL) and water (0.5 mL), was added sodium hydroxide (115 mg, 2.87 mmol). The reaction mixture was heated at 120° C. for 1.5 h. The mixture was diluted with EtOAc and washed with water, then sat. aq. NaCl. Purification by ISCO flash chromatography (5% EtOAc in hexanes) affords a yellow solid (525 mg, 1.96 mmol, 68%). $^1$H NMR (400 MHz, $CDCl_3$) δ 8.10 (dd, J=2.5, 1.1 Hz, 1H), 8.00 (dd, J=8.8, 2.5 Hz, 1H), 7.83 (d, J=8.8 Hz, 1H), 6.66 (t, J=71.9 Hz, 1H); $^{19}$F NMR (376 MHz, $CDCl_3$) δ −82.26.

4-Bromo-3-(difluoromethoxy)aniline, B-4. To a solution of 1-bromo-2-(difluoromethoxy)-4-nitro-benzene (525 mg, 1.96 mmol) in MeOH (7 mL) and water (15 mL) was added Iron (547 mg, 9.79 mmol) and $NH_4Cl$ (524 mg, 9.79 mmol). The reaction mixture was heated to 80° C. for 3 h. The reaction mixture was filtered through celite and concentrated. The filtrate was diluted with EtOAc (15 ml) and washed with water (10 ml). Concentration affords a crude brown solid (370 mg, 1.55 mmol, 79%) that was used without further purification. LCMS (Method A) $t_R$=1.61 min, m/z=237.89, 239.89, bromine split [M+H]$^+$; $^1$H NMR (400 MHz, $CDCl_3$) δ 7.31 (d, J=8.6 Hz, 1H), 6.68-6.26 (m, 3H), 3.79 (s, 2H); $^{19}$F NMR (376 MHz, $CDCl_3$) δ −81.00.

tert-butyl N-[(1R)-1-[[4-bromo-3-(difluoromethoxy)phenyl]carbamoyl]-3-methyl-butyl]carbamate, G-8. 4-Bromo-3-(difluoromethoxy)aniline (357 mg, 1.50 mmol) was reacted with Boc-D-Leu-OH (520 mg, 2.25 mmol) according to General Procedure E, affording a colourless solid (350 mg, 0.78 mmol, 52%). LCMS (Method B) $t_R$=1.926 min, m/z=395.0426 [M-$^t$Bu]f; $^1$H NMR (400 MHz, $CDCl_3$) δ 8.74 (s, 1H), 7.51 (s, 1H), 7.46 (d, J=8.7 Hz, 1H), 7.18 (dd, J=8.8, 2.3 Hz, 1H), 6.55 (t, J=73.3 Hz, 1H), 4.88 (s, 1H), 4.23 (s, 1H), 1.82-1.68 (m, 2H), 1.60 (m, 1H), 1.46 (s, 9H), 0.97 (m, 6H); $^{19}$F NMR (376 MHz, $CDCl_3$) δ −81.34 (d, J=41.4 Hz), −81.54 (d, J=41.4 Hz).

Scheme 20. General synthesis of aromatic amide intermediates by activation of amino acid to acyl fluoride and thermal displacement.

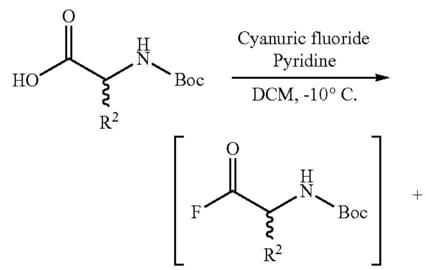

-continued

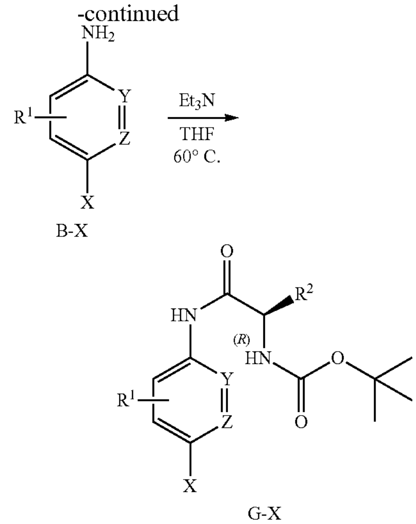

B-X

G-X tert-Butyl N-[(1R)-1-[(5-bromo-6-methoxy-2-pyridyl)carbamoyl]-3-methyl-butyl]carbamate, G-9

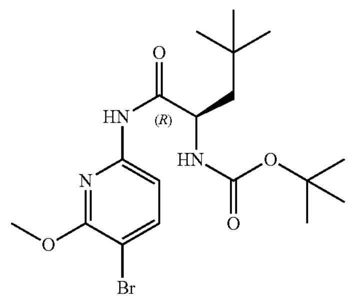

According to General Procedure M, Boc-D-Leu-F (1.16 g, 5 mmol) was prepared from Boc-D-Leu-OH then immediately reacted with bromo-6-methoxypyridin-2-amine (203 mg, 1 mmol). Purification by ISCO flash chromatography (0-50% EtOAc in hexanes) to afford a cream solid (422 mg. 100%). LCMS (Method A) $t_R$=2.47 min, m/z=418.1176 [M+H]$^+$; Purity ≥95% (DAD, 210, 254 nm). 1H NMR (400 MHz, DMSO-$d_6$) δ 10.38 (s, 1H), 7.94 (d, J=8.4 Hz, 1H), 7.61 (d, J=8.4 Hz, 1H), 7.12 (d, J=8.0 Hz, 1H), 4.26 (q, J=10.8, 8.1 Hz, 1H), 3.93 (s, 3H), 1.65 (h, J=6.5 Hz, 1H), 1.59-1.47 (m, 2H), 1.37 (s, 9H), 0.88 (d, J=6.6 Hz, 6H).

tert-Butyl N-[(1R)-1-[(5-bromo-6-methoxy-2-pyridyl)carbamoyl]-3,3-dimethyl-butyl]carbamate, G-10

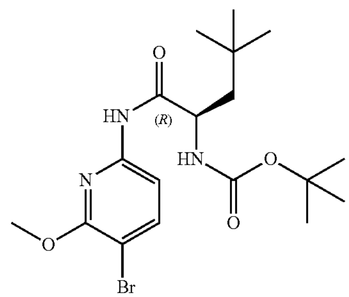

Synthesised in a manner analogous to G-9 forming Boc-D-Neo-F from Boc-D-Neo-OH and subsequent reaction with 5-Bromo-6-methoxypyridin-2-amine. Beige solid. LCMS (Method B) $t_R$=2.06 min, m/z=430.1829 [M+H]$^+$.

tert-Butyl N-[(1R)-1-[(5-chloro-2-pyridyl)carbamoyl]-3,3-dimethyl-butyl]carbamate, G-11

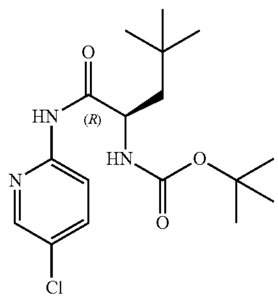

Synthesised in a manner analogous to G-9 forming Boc-D-Neo-F from Boc-D-Neo-OH and subsequent reaction with 5-amino5-chloropyridine. Beige solid. LCMS (Method A) $t_R$=2.39 min, m/z=356.22 [M+H]$^+$.

tert-Butyl N-[(1R)-1-[(5-chloro-6-methyl-2-pyridyl)carbamoyl]-3,3-dimethyl-butyl]carbamate, G-12

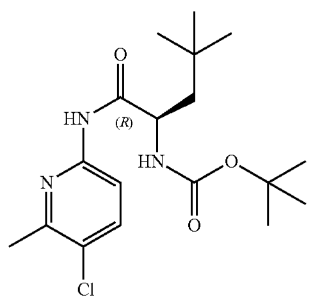

Synthesised in a manner analogous to G-9 forming Boc-D-Neo-F from Boc-D-Neo-OH and subsequent reaction with 5-chloro-6-methylpyridin-2-amine. Beige solid. LCMS (Method B) $t_R$=1.99 min, m/z=370.2360 [M+Na]$^+$.

tert-Butyl N-[(1R)-1-[(4-bromo-2-fluoro-3-methyl-phenyl)carbamoyl]-3,3-dimethyl-butyl]carbamate, G-13

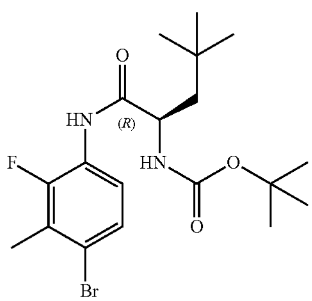

Synthesised in a manner analogous to 7 forming Boc-D-Neo-F from Boc-D-Neo-OH and subsequent reaction with 4-bromo-2-fluoro-3-methyl-aniline. Beige solid. LCMS (Method B) $t_R$=2.23 min, m/z=455.1654 [M+Na]$^+$.

Example 2: Compound Syntheses

2-Amino-N-[4-(1H-pyrrolo[2,3-b]pyridin-4-yl)phenyl]acetamide, F-1

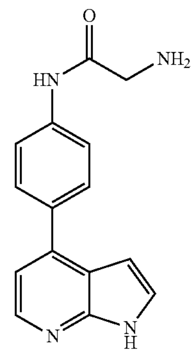 [SMILES: NCC(=O)Nc1ccc(-c2ccnc3[nH]ccc23)cc1]

Step 1. tert-Butyl N-[2-[4-[1-(benzenesulfonyl)pyrrolo[2,3-b]pyridin-4-yl]anilino]-2-oxo-ethyl]carbamate, E-1. Boc-Gly-OH (52 mg, 0.30 mmol) was reacted with C-1 (70 mg, 0.20 mmol) following General Procedure D. Purification by ISCO flash chromatography (0-100% EtOAc in hexanes) affords a colourless gum (55 mg, 0.11 mmol, 55%). LCMS (Method B) $t_R$=1.58 min, m/z=507.17 [M+H]$^+$.

Step 2. 2-Amino-N-[4-(1H-pyrrolo[2,3-b]pyridin-4-yl)phenyl]acetamide, F-1. Intermediate E-1 (53 mg, 0.10 mmol) was deprotected according to General Procedure K, affording title compound as a colourless solid (9 mg, 0.03 mmol, 32%). LCMS (Method A) $t_R$=1.10 min, m/z=267.12 [M+H]$^+$; Purity ≥95% (DAD, 210, 254 nm); HRMS calculated for $C_{15}H_{14}N_4O$=266.1168, observed 266.1166; $^1$H NMR (400 MHz, MeOH-$d_4$) δ 8.24 (d, J=5.1 Hz, 1H), 7.85-7.77 (m, 4H), 7.46 (d, J=3.6 Hz, 1H), 7.22 (d, J=5.1 Hz, 1H), 6.71 (d, J=3.6 Hz, 1H), 3.51 (s, 2H).

N-(4-(1H-pyrrolo[2,3-b]pyridin-4-yl)phenyl)-2-(methylamino)acetamide, F-2

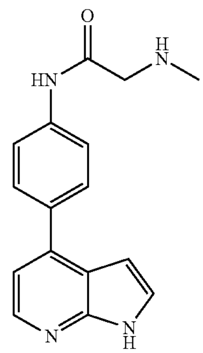 [SMILES: CNCC(=O)Nc1ccc(-c2ccnc3[nH]ccc23)cc1]

Step 1. tert-Butyl N-[2-[4-[1-(benzenesulfonyl)pyrrolo[2,3-b]pyridin-4-yl]anilino]-2-oxo-ethyl]-N-methyl-carbamate, E-2. D-1 (50 mg, 0.14 mmol) and 2-[tert-butoxycarbonyl(methyl)amino]acetic acid (40 mg, 0.21 mmol) were reacted according to General Procedure D. Purification by ISCO flash chromatography (20-100% EtOAc in hexanes) to afford a cream powder (65 mg, 0.12 mmol, 87%). LCMS (Method A) $t_R$=1.70 min, m/z=521.1995 $[M+H]^+$. $^1H$ NMR (400 MHz, DMSO-$d_6$) δ 10.19 (d, J=17.0 Hz, 1H), 8.40 (d, J=5.1 Hz, 1H), 8.18-8.11 (m, 2H), 7.98 (d, J=4.1 Hz, 1H), 7.81-7.59 (m, 7H), 7.40 (d, J=5.1 Hz, 1H), 6.97 (t, J=3.8 Hz, 1H), 4.00 (d, J=15.3 Hz, 2H), 2.88 (d, J=10.3 Hz, 3H), 1.37 (d, J=33.4 Hz, 9H).

Step 2. N-(4-(1H-pyrrolo[2,3-b]pyridin-4-yl)phenyl)-2-(methylamino)acetamide, F-2. Intermediate E-2 was deprotected according to General Procedure K then purified by preparative HPLC (5-40% MeCN in H2O, 0.1% TFA). The free base was obtained after SCX-II chromatography (load/wash MeOH, elution with 2N $NH_3$ in MeOH) to afford the title compound as a colourless solid (0.9 mg, 0.003 mmol, 3%). LCMS (Method A) $t_R$=1.16 min, m/z=281.1394 $[M+H]^+$; Purity ≥95% (DAD, 210, 254 nm). $^1H$ NMR (400 MHz, DMSO-$d_6$) δ 11.76 (s, 1H), 8.26 (d, J=5.0 Hz, 1H), 7.81 (d, J=8.8 Hz, 2H), 7.76 (d, J=8.8 Hz, 2H), 7.53 (t, J=3.0 Hz, 1H), 7.17 (d, J=5.0 Hz, 1H), 6.65-6.62 (m, 1H), 3.53 (s, 2H), 2.45 (s, 3H).

2-(Dimethylamino)-N-[4-(1H-pyrrolo[2,3-b]pyridin-4-yl)phenyl]acetamide, F-3

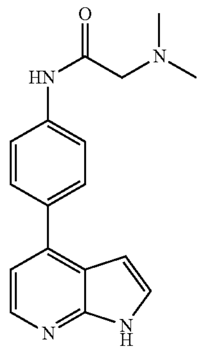 [SMILES: CN(C)CC(=O)Nc1ccc(-c2ccnc3[nH]ccc23)cc1]

Step 1. N-[4-[1-(Benzenesulfonyl)pyrrolo[2,3-b]pyridin-4-yl]phenyl]-2-(dimethylamino)acetamide, E-3. D-1 (50 mg, 0.14 mmol) and 2-(dimethylamino)acetic acid were reacted according to General Procedure D. Purification by ISCO flash chromatography (0-8% MeOH in DCM) to afford a cream powder (51 mg, 0.12 mmol, 82%). LCMS (Method A) $t_R$=1.76 min, m/z=435.2 $[M+H]^+$; $^1H$ NMR (400 MHz, DMSO-$d_6$) δ 9.95 (s, 1H), 8.40 (d, J=5.1 Hz, 1H), 8.19-8.09 (m, 2H), 7.98 (d, J=4.1 Hz, 1H), 7.90-7.82 (m, 2H), 7.78-7.69 (m, 1H), 7.67-7.62 (m, 4H), 7.39 (d, J=5.1 Hz, 1H), 6.97 (d, J=4.1 Hz, 1H), 3.11 (s, 2H), 2.29 (s, 6H).

Step 2. 2-(Dimethylamino)-N-[4-(1H-pyrrolo[2,3-b]pyridin-4-yl)phenyl]acetamide, F-3. Intermediate E-3 (45 mg, 0.10 mmol) was dissolved in MeOH (0.5 mL), NaOH (12.4 mg, 0.52 mmol) was added and the reaction stirred at rt for 1 h. The reaction was filtered and concentrated then purified by preparative HPLC (10-100% MeCN in H2O, 0.1% TFA). The free base was obtained after SCX-II chromatography (load/wash MeOH, elution with 2N $NH_3$ in MeOH) to afford the title compound as a colourless solid (15 mg, 0.05 mmol, 48%). LCMS (Method A) $t_R$=1.14 min, m/z=295.1553 $[M+H]^+$; Purity ≥95% (DAD, 210, 254 nm). 1H NMR (400 MHz, DMSO-$d_6$) δ 11.75 (s, 1H), 9.99 (s, 1H), 8.25 (d, J=4.9 Hz, 1H), 7.88-7.80 (m, 2H), 7.78-7.70 (m, 2H), 7.53 (dd, J=3.5, 2.6 Hz, 1H), 7.16 (d, J=4.9 Hz, 1H), 6.63 (dd, J=3.5, 1.9 Hz, 1H), 3.22 (s, 2H), 2.36 (s, 6H).

(2S)-2-Amino-N-[4-(1H-pyrrolo[2,3-b]pyridin-4-yl)phenyl]propenamide, F-4

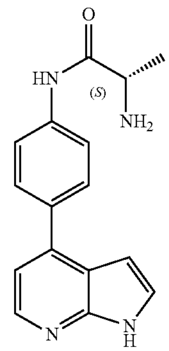

Step 1. tert-butyl N-[(1S)-2-[4-[1-(benzenesulfonyl)pyrrolo[2,3-b]pyridin-4-yl]anilino]-1-methyl-2-oxo-ethyl]carbamate, E-4. Boc-Ala-OH (57 mg, 0.30 mmol) was reacted with D-1 (70 mg, 0.20 mmol) following General Procedure D. Purification by ISCO flash chromatography (0-100% EtOAc in hexanes) affords a colourless gum (95 mg, 0.183 mmol, 91%). LCMS (Method B) $t_R$=1.68 min, m/z=521.19 $[M+H]^+$.

Step 2. (2S)-2-Amino-N-[4-(1H-pyrrolo[2,3-b]pyridin-4-yl)phenyl]propenamide, F-4. Intermediate E-4 (95 mg, 0.18 mmol) was deprotected according to General Procedure K, affording title compound as a colourless solid (11 mg, 0.04 mmol, 21%). LCMS (Method A) $t_R$=1.14 min, m/z=281.14 $[M+H]^+$; Purity ≥95% (DAD, 210, 254 nm); HRMS calculated for $C_{16}H_{16}N_4O$=280.1324, observed 280.1324; $^1H$ NMR (500 MHz, DMSO-$d_6$) δ 11.76 (s, 1H), 8.26 (d, J=5.0 Hz, 1H), 7.87-7.81 (m, 2H), 7.75 (d, J=8.6 Hz, 2H), 7.53 (t, J=3.0 Hz, 1H), 7.17 (d, J=5.0 Hz, 1H), 6.64 (dd, J=3.5, 1.8 Hz, 1H), 3.47 (q, J=6.9 Hz, 1H), 1.25 (d, J=6.9 Hz, 3H).

(2R)-2-Amino-N-[4-(1H-pyrrolo[2,3-b]pyridin-4-yl)phenyl]propenamide, F-5

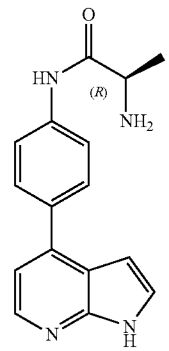

Step 1. tert-butyl N-[(1R)-2-[4-[1-(benzenesulfonyl)pyrrolo[2,3-b]pyridin-4-yl]anilino]-1-methyl-2-oxo-ethyl]carbamate, E-5. Boc-D-Ala-OH (57 mg, 0.30 mmol) was reacted with D-1 (70 mg, 0.20 mmol) following General Procedure D. Purification by ISCO flash chromatography (0-100% EtOAc in hexanes) affords a colourless gum (102 mg, 0.159 mmol, 97%). LCMS (Method B) $t_R$=1.68 min, m/z=521.19 $[M+H]^+$.

Step 2. (2R)-2-Amino-N-[4-(1H-pyrrolo[2,3-b]pyridin-4-yl)phenyl]propenamide, F-5. Intermediate E-5 (102 mg, 0.19 mmol) was deprotected according to General Procedure K, affording title compound as a colourless solid (10 mg, 0.035 mmol, 18%). LCMS (Method A) $t_R$=1.14 min, m/z=281.14 $[M+H]^+$; Purity ≥95% (DAD, 210, 254 nm); HRMS calculated for $C_{16}H_{16}N_4O$=280.1324, observed 280.1329; $^1H$ NMR (500 MHz, DMSO-$d_6$) δ 11.76 (s, 1H), 8.26 (d, J=5.0 Hz, 1H), 7.87-7.81 (m, 2H), 7.75 (d, J=8.6 Hz, 2H), 7.53 (t, J=3.0 Hz, 1H), 7.17 (d, J=5.0 Hz, 1H), 6.64 (dd, J=3.5, 1.8 Hz, 1H), 3.47 (q, J=6.9 Hz, 1H), 1.25 (d, J=6.9 Hz, 3H).

(2S)-2-Amino-3-methyl-N-[4-(1H-pyrrolo[2,3-b]pyridin-4-yl)phenyl]butanamide, F-6

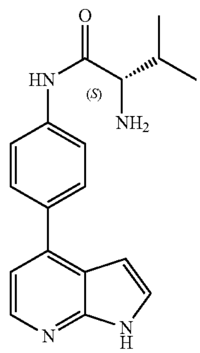

Step 1. tert-Butyl N-[(1S)-1-[[4-[1-(benzenesulfonyl)pyrrolo[2,3-b]pyridin-4-yl]phenyl]carbamoyl]-2-methyl-propyl]carbamate, E-6. Boc-Val-OH (65 mg, 0.30 mmol) was reacted with D-1 (70 mg, 0.20 mmol) following General Procedure D. Purification by ISCO flash chromatography (0-100% EtOAc in hexanes) affords a colourless gum (90 mg, 0.16 mmol, 82%). LCMS (Method B) $t_R$=1.99 min, m/z=549.22 $[M+H]^+$.

Step 2. (2S)-2-Amino-3-methyl-N-[4-(1H-pyrrolo[2,3-b]pyridin-4-yl)phenyl]butanamide, F-6. Intermediate E-6 (90 mg, 0.16 mmol) was deprotected according to General Procedure K, affording title compound as a colourless solid (28 mg, 0.09 mmol, 55%). LCMS (Method A) $t_R$=1.26 min, m/z=309.17 $[M+H]^+$; Purity ≥95% (DAD, 210, 254 nm); HRMS calculated for $C_{18}H_{20}N_4O$=308.1637, observed 308.1630; $^1H$ NMR (500 MHz, DMSO-$d_6$) $\delta_H$ 11.76 (s, 1H), 8.26 (d, J=4.9 Hz, 1H), 7.86-7.81 (m, 2H), 7.77-7.72 (m, 2H), 7.56-7.52 (m, 1H), 7.17 (d, J=5.0 Hz, 1H), 6.64 (dd, J=3.5, 1.8 Hz, 1H), 3.15 (d, J=5.5 Hz, 1H), 1.96 (dq, J=13.3, 6.7 Hz, 1H), 0.96 (d, J=6.8 Hz, 3H), 0.88 (d, J=6.8 Hz, 3H).

(2R)-2-Amino-3-methyl-N-[4-(1H-pyrrolo[2,3-b]pyridin-4-yl)phenyl]butanamide, F-7

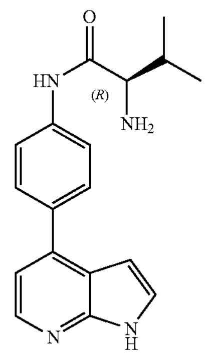

Step 1. tert-Butyl N-[(1R)-1-[[4-[1-(benzenesulfonyl)pyrrolo[2,3-b]pyridin-4-yl]phenyl]carbamoyl]-2-methyl-propyl]carbamate, E-7. D-1 (69 mg, 0.20 mmol) and Boc-D-Val-OH (65 mg, 0.30 mmol) were reacted according to General Procedure D. Purification by ISCO flash chromatography (40-100% EtOAc in hexanes) to afford a colourless solid (101 mg, 0.18 mmol, 92%). LCMS (Method A) $t_R$=2.15 min, m/z=549.2172 $[M+H]^+$.

Step 2. (2R)-2-Amino-3-methyl-N-[4-(1H-pyrrolo[2,3-b]pyridin-4-yl)phenyl]butanamide, F-7. Intermediate E-7 (80 mg, 0.14 mmol) was deprotected according to General Procedure K then purified by preparative HPLC (5-95% MeCN in H2O, 0.1% TFA). The free base was obtained after SCX-II chromatography (load/wash MeOH, elution with 2N $NH_3$ in MeOH) to afford the title compound as a colourless solid (21 mg, 0.07 mmol, 47%). LCMS (Method A) $t_R$=1.38 min, m/z=309.1709 $[M+H]^+$; Purity ≥95% (DAD, 210, 254 nm); $^1H$ NMR (500 MHz, DMSO-$d_6$) δ 11.75 (s, 1H), 8.25 (d, J=4.9 Hz, 1H), 7.87-7.80 (m, 2H), 7.77-7.71 (m, 2H), 7.53 (t, J=3.0 Hz, 1H), 7.16 (d, J=5.0 Hz, 1H), 6.64 (dd, J=3.5, 1.8 Hz, 1H), 3.15 (d, J=5.5 Hz, 1H), 1.96 (dq, J=13.3, 6.7 Hz, 1H), 0.95 (d, J=6.8 Hz, 3H), 0.88 (d, J=6.8 Hz, 3H).

(2S)-2-Amino-4-methyl-N-[4-(1H-pyrrolo[2,3-b]pyridin-4-yl)phenyl]pentanamide, F-8

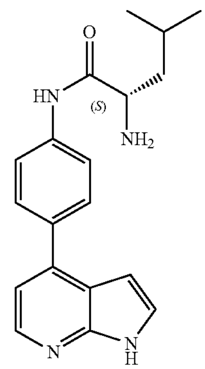

Step 1. tert-Butyl N-[(1S)-1-[[4-[1-(benzenesulfonyl)pyrrolo[2,3-b]pyridin-4-yl]phenyl]carbamoyl]-3-methyl-butyl]carbamate, E-8. D-1 (69 mg, 0.20 mmol) and Boc-Leu-OH (69 mg, 0.30 mmol) were reacted according to General Procedure K. Purification by ISCO flash chromatography (40-100% EtOAc in hexanes) to afford a colourless solid (44 mg, 0.80 mmol, 39%). LCMS (Method A) $t_R$=2.22 min, m/z=563.2329 $[M+H]^+$.

Step 2. (2S)-2-Amino-4-methyl-N-[4-(1H-pyrrolo[2,3-b]pyridin-4-yl)phenyl]pentanamide, F-8. Intermediate E-8 (42 mg, 0.07 mmol) was deprotected according to General Procedure K then purified by preparative HPLC (5-95% MeCN in H2O, 0.1% TFA). The free base was obtained after SCX-II chromatography (load/wash MeOH, elution with 2N $NH_3$ in MeOH) to afford the title compound as a colourless solid (15 mg, 0.05 mmol, 62%). LCMS (Method A) $t_R$=1.06 min, m/z=323.2 $[M+H]^+$; Purity ≥95% (DAD, 210, 254 nm); $^1$H NMR (500 MHz, DMSO-$d_6$) δ 11.89 (s, 1H), 10.71 (s, 1H), 8.29 (d, J=5.0 Hz, 3H), 7.85-7.78 (m, 4H), 7.57 (t, J=3.0 Hz, 1H), 7.22 (d, J=5.0 Hz, 1H), 6.67 (dd, J=3.6, 1.8 Hz, 1H), 4.00-3.94 (m, 1H), 1.74-1.66 (m, 3H), 0.98-0.93 (m, 6H).

(2R)-2-Amino-4-methyl-N-[4-(1H-pyrrolo[2,3-b]pyridin-4-yl)phenyl]pentanamide, F-9

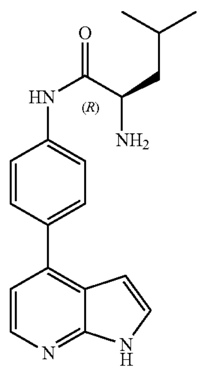

Step 1. tert-Butyl N-[(1R)-1-[[4-[1-(benzenesulfonyl)pyrrolo[2,3-b]pyridin-4-yl]phenyl]carbamoyl]-3-methyl-butyl] carbamate, E-9. D-1 (200 mg, 0.57 mmol) and Boc-D-Leu-OH (199 mg, 0.86 mmol) were reacted according to General Procedure D. Purification by ISCO flash chromatography (40-100% EtOAc in hexanes) to afford a colourless solid (319 mg, 0.57 mmol, 99%). LCMS (Method A) $t_R$=2.22 min, m/z=563.2327 $[M+H]^+$; $^1$H NMR (500 MHz, DMSO-$d_6$) δ 10.19 (s, 1H), 8.40 (d, J=5.0 Hz, 1H), 8.14 (dd, J=8.5, 1.3 Hz, 2H), 7.98 (d, J=4.1 Hz, 1H), 7.82-7.77 (m, 2H), 7.77-7.69 (m, 1H), 7.69-7.60 (m, 4H), 7.39 (d, J=5.1 Hz, 1H), 7.09 (d, J=7.9 Hz, 1H), 6.98 (d, J=4.1 Hz, 1H), 4.15 (td, J=8.8, 5.4 Hz, 1H), 1.70-1.60 (m, 1H), 1.59-1.50 (m, 1H), 1.47-1.41 (m, 1H), 1.38 (s, 9H), 0.90 (dd, J=6.6, 4.6 Hz, 6H).

Step 2. (2R)-2-Amino-4-methyl-N-[4-(1H-pyrrolo[2,3-b]pyridin-4-yl)phenyl]pentanamide, F-9. Intermediate E-9 (200 mg, 0.57 mmol) was deprotected according to General Procedure K then purified by preparative HPLC (5-40% MeCN in H2O, 0.1% TFA). The free base was obtained after SCX-II chromatography (load/wash MeOH, elution with 2N $NH_3$ in MeOH) to afford the title compound as a colourless solid (87 mg, 0.27 mmol, 46%). LCMS (Method A) $t_R$=1.35 min, m/z=323.1856 $[M+H]^+$; Purity ≥95% (DAD, 210, 254 nm); H NMR (500 MHz, DMSO-$d_6$) δ 11.76 (s, 1H), 8.27-8.24 (m, 1H), 7.86-7.79 (m, 2H), 7.77-7.74 (m, 2H), 7.54-7.51 (m, 1H), 7.18-7.15 (m, 1H), 6.65-6.62 (m, 1H), 3.52-3.46 (m, 1H), 1.79-1.72 (m, 1H), 1.58-1.51 (m, 1H), 1.46-1.39 (m, 1H), 0.96-0.89 (m, 6H).

(2S,3S)-2-Amino-3-methyl-N-[4-(1H-pyrrolo[2,3-b]pyridin-4-yl)phenyl]pentanamide, F-10

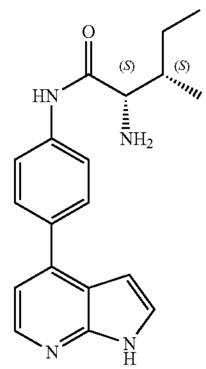

Step 1. tert-Butyl N-[(1S,2S)-1-[[4-[1-(benzenesulfonyl)pyrrolo[2,3-b]pyridin-4-yl]phenyl]carbamoyl]-2-methyl-butyl]carbamate, E-10. D-1 (50 mg, 0.14 mmol) and Boc-Ile-OH (50 mg, 0.21 mmol) were reacted according to General Procedure D. Purification by ISCO flash chromatography (40-100% EtOAc in hexanes) to afford a colourless solid (61 mg, 0.11 mmol, 76%). LCMS (Method B) $t_R$=2.14 min, m/z=563.2329 $[M+H]^+$; $^1$H NMR (500 MHz, DMSO-$d_6$) δ 10.22 (s, 1H), 8.40 (d, J=5.1 Hz, 1H), 8.17-8.12 (m, 2H), 7.98 (d, J=4.1 Hz, 1H), 7.80 (d, J=8.4 Hz, 2H), 7.73 (t, J=7.5 Hz, 1H), 7.69-7.60 (m, 4H), 7.39 (d, J=5.1 Hz, 1H), 7.02-6.96 (m, 2H), 4.05-3.73 (m, 1H), 1.82-1.75 (m, 1H), 1.54-1.46 (m, 1H), 1.38 (s, 9H), 1.16 (dq, J=15.0, 7.6 Hz, 1H), 0.96-0.75 (m, 6H).

Step 2. (2S,3S)-2-Amino-3-methyl-N-[4-(1H-pyrrolo[2,3-b]pyridin-4-yl)phenyl]pentanamide, F-10. Intermediate E-10 (50 mg, 0.09 mmol) was deprotected according to General Procedure K then purified by preparative HPLC (10-100% MeCN in H2O, 0.1% TFA). The product salt was taken in DCM, shaken with 5M $K_2CO_3$ solution, separated using a phase separator and concentrated in vacuo. The resulting gum was dissolved in minimal MeOH, water was added and lyophilized to afford the title compound as a colourless solid (20 mg, 0.06 mmol, 70%). LCMS (Method A) $t_R$=1.33 min, m/z=323.1866 $[M+H]^+$; Purity ≥95% (DAD, 210, 254 nm); $^1$H NMR (500 MHz, DMSO-$d_6$) δ 11.75 (s, 1H), 8.25 (d, J=5.0 Hz, 1H), 7.87-7.80 (m, 2H), 7.77-7.71 (m, 2H), 7.53 (t, J=2.9 Hz, 1H), 7.16 (d, J=5.0 Hz, 1H), 6.64 (dd, J=3.5, 1.7 Hz, 1H), 3.19 (d, J=5.9 Hz, 1H), 1.74-1.66 (m, 1H), 1.57-1.49 (m, 1H), 1.20-1.11 (m, 1H), 0.92 (d, J=6.9 Hz, 3H), 0.86 (t, J=7.4 Hz, 3H).

(2R,3R)-2-Amino-3-methyl-N-[4-(1H-pyrrolo[2,3-b]pyridin-4-yl)phenyl]pentanamide, F-11

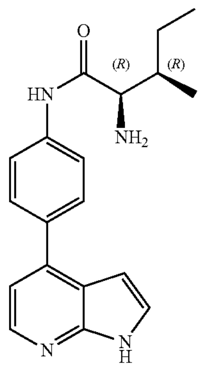

Step 1. tert-butyl N-[(1R,2R)-1-[[4-[1-(benzenesulfonyl)pyrrolo[2,3-b]pyridin-4-yl]phenyl]carbamoyl]-2-methyl-butyl]carbamate, E-11. D-1 (50 mg, 0.14 mmol) and Boc-D-Ile-OH (50 mg, 0.21 mmol) were reacted according to General Procedure D. Purification by ISCO flash chromatography (40-100% EtOAc in hexanes) to afford a colourless oil (74 mg, 0.12 mmol, 85%). LCMS (Method B) $t_R$=2.75 min, m/z=563.3 $[M+H]^+$.

Step 2. (2R,3R)-2-Amino-3-methyl-N-[4-(1H-pyrrolo[2,3-b]pyridin-4-yl)phenyl]pentanamide, F-11. Intermediate E-11 (70 mg, 0.11 mmol) was deprotected according to General Procedure K then purified by ISCO flash chromatography (2-10% MeOH in DCM+0.5% $NH_{40}H$) to afford the title compound as a colourless solid (15 mg, 0.05 mmol, 39%). LCMS (Method A) $t_R$=1.34 min, m/z=323.1858 $[M+H]^+$; Purity ≥95% (DAD, 210, 254 nm); $^1H$ NMR (400 MHz, DMSO-$d_6$) δ 11.78 (s, 1H), 8.27 (d, J=5.0 Hz, 1H), 7.81 (d, J=3.2 Hz, 4H), 7.65-7.28 (m, 2H), 7.18 (d, J=4.9 Hz, 1H), 6.65 (s, 1H), 3.61 (d, J=5.9 Hz, 1H), 1.90 (d, J=14.3 Hz, 1H), 1.57 (s, 1H), 1.21 (s, 1H), 1.03-0.81 (m, 6H).

(2S)-2-Amino-3,3-dimethyl-N-[4-(1H-pyrrolo[2,3-b]pyridin-4-yl)phenyl]butanamide, F-12

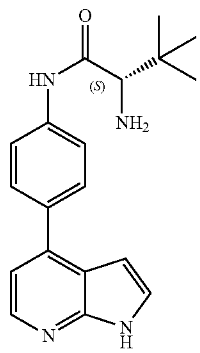

Step 1. tert-Butyl N-[(1S)-1-[[4-[1-(benzenesulfonyl)pyrrolo[2,3-b]pyridin-4-yl]phenyl]carbamoyl]-2,2-dimethyl-propyl]carbamate, E-12. Boc-Tie-OH (69 mg, 0.30 mmol) was reacted with D-1 (70 mg, 0.20 mmol) following General Procedure D. Purification by ISCO flash chromatography (0-100% EtOAc in hexanes) affords a cream solid (108 mg, 0.19 mmol, 96%). LCMS (Method B) $t_R$=2.17 min, m/z=563.23 $[M+H]^+$.

Step 2. (2S)-2-Amino-3,3-dimethyl-N-[4-(1H-pyrrolo[2,3-b]pyridin-4-yl)phenyl]butanamide, F-12. Intermediate E-12 (108 mg, 0.19 mmol) was deprotected according to General Procedure K, affording title compound as a colourless solid (26 mg, 0.08 mmol, 42%). LCMS (Method A) $t_R$=1.34 min, m/z=323.19 $[M+H]^+$; Purity ≥95% (DAD, 210, 254 nm); HRMS calculated for $C_{19}H_{22}N_4O$=322.1794, observed 322.1795; $^1H$ NMR (400 MHz, MeOH-$d_4$) δ 8.13 (d, J=5.1 Hz, 1H), 7.68 (s, 4H), 7.35 (d, J=3.6 Hz, 1H), 7.11 (d, J=5.1 Hz, 1H), 6.60 (d, J=3.6 Hz, 1H), 3.16 (s, 1H), 0.99 (s, 9H).

(2R)-2-Amino-3,3-dimethyl-N-[4-(1H-pyrrolo[2,3-b]pyridin-4-yl)phenyl]butanamide, F-13

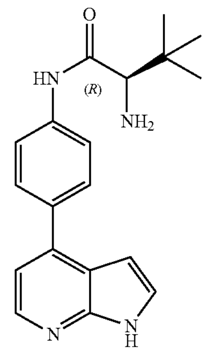

Step 1. tert-Butyl (R)-(3,3-dimethyl-1-oxo-1-((4-(1-(phenylsulfonyl)-1H-pyrrolo[2,3-b]pyridin-4-yl)phenyl)amino)butan-2-yl)carbamate, E-13. Boc-D-Tle-OH (71 mg, 0.30 mmol) was reacted with D-1 (70 mg, 0.20 mmol) following General Procedure D. Purification by ISCO flash chromatography (0-100% EtOAc in hexanes) affords a colourless gum (99 mg, 0.176 mmol, 88%). LCMS (Method B) $t_R$=2.17 min, m/z=563.23 $[M+H]^+$.

Step 2. (2R)-2-Amino-3,3-dimethyl-N-[4-(1H-pyrrolo[2,3-b]pyridin-4-yl)phenyl]butanamide, F-13. Intermediate E-13 (99 mg, 0.18 mmol) was deprotected according to General Procedure K, affording title compound as a colourless solid (37 mg, 0.115 mmol, 65%). LCMS (Method A) $t_R$=1.33 min, m/z=323.19 $[M+H]^+$; Purity ≥95% (DAD, 210, 254 nm); HRMS calculated for $C_{19}H_{22}N_4O$=322.1794, observed 322.1793; $^1H$ NMR (400 MHz, MeOH-$d_4$) $\delta_H$ 8.25 (d, J=5.1 Hz, 1H), 7.79 (s, 4H), 7.46 (d, J=3.6 Hz, 1H), 7.22 (d, J=5.1 Hz, 1H), 6.71 (d, J=3.6 Hz, 1H), 1.10 (s, 9H).

(2R)-2-Amino-N-[4-(1H-pyrrolo[2,3-b]pyridin-4-yl) phenyl]pentanamide, F-14

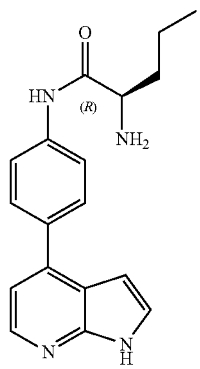

Step 1. tert-Butyl N-[(1R)-1-[[4-[1-(benzenesulfonyl)pyrrolo[2,3-b]pyridin-4-yl]phenyl]carbamoyl]butyl]carbamate, E-14. (2R)-2-(tert-Butoxycarbonylamino)pentanoic acid (65 mg, 0.30 mmol) was reacted with D-1 (70 mg, 0.20 mmol) following General Procedure E. Purification by ISCO flash chromatography (0-100% EtOAc in hexanes) affords a colourless gum (89 mg, 0.16 mmol, 81%). LCMS (Method B) $t_R$=1.95 min, m/z=549.17 $[M+H]^+$.

Step 2. (2R)-2-Amino-N-[4-(1H-pyrrolo[2,3-b]pyridin-4-yl)phenyl]pentanamide, F-14. Intermediate E-14 (89 mg, 0.16 mmol) was deprotected according to General Procedure K, affording title compound as a colourless solid (24 mg, 48%). LCMS (Method A) $t_R$=1.29 min, m/z=309.19 $[M+H]^+$; Purity ≥95% (DAD, 210, 254 nm); $^1$H NMR (400 MHz, MeOH-$d_4$) δ 8.25 (d, J=5.1 Hz, 1H), 7.83-7.75 (m, 4H), 7.46 (d, J=3.6 Hz, 1H), 7.22 (d, J=5.1 Hz, 1H), 6.71 (d, J=3.6 Hz, 1H), 3.51 (t, J=6.6 Hz, 1H), 1.87-1.73 (m, 1H), 1.73-1.60 (m, 1H), 1.60-1.40 (m, 1H), 1.02 (t, J=7.3 Hz, 3H).

2-Amino-4,4-dimethyl-N-[4-(1H-pyrrolo[2,3-b]pyridin-4-yl)phenyl]pentanamide, F-15

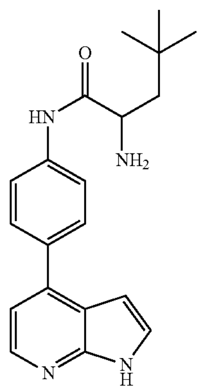

Step 1. tert-Butyl (4,4-dimethyl-1-oxo-1-((4-(1-(phenylsulfonyl)-1H-pyrrolo[2,3-b]pyridin-4-yl)phenyl)amino) pentan-2-yl)carbamate, E-15. 2-(tert-Butoxycarbonylamino)-4,4-dimethyl-pentanoic acid (74 mg, 0.30 mmol) was reacted with 4 (70 mg, 0.20 mmol) following General Procedure E. Purification by ISCO flash chromatography (0-100% EtOAc in hexanes) afforded a colourless solid (112 mg, 0.19 mmol, 97%). LCMS (Method B) $t_R$=2.34 min, m/z=513.32 $[M+H]^+$.

Step 2. 2-Amino-4,4-dimethyl-N-[4-(1H-pyrrolo[2,3-b]pyridin-4-yl)phenyl]pentanamide, F-15. Intermediate E-15 (112 mg, 0.19 mmol) was deprotected according to General Procedure K, affording title compound as a colourless solid (36 mg, 0.107 mmol, 55%). LCMS (Method A) $t_R$=1.42 min, m/z=337.38 $[M+H]^+$; Purity ≥95% (DAD 210, 254 nm); HRMS calculated for $C_{20}H_{24}N_4O$=336.1950, observed 336.1955; $^1$H NMR (400 MHz, DMSO-$d_6$) $\delta_H$ 11.75 (s, 1H), 8.26 (d, J=4.9 Hz, 1H), 7.83 (d, J=8.7 Hz, 2H), 7.78-7.72 (m, 2H), 7.53 (t, J=3.0 Hz, 1H), 7.17 (d, J=4.9 Hz, 1H), 6.64 (dd, J=3.5, 1.8 Hz, 1H), 3.42 (t, J=6.2 Hz, 1H), 1.78 (dd, J=13.8, 6.2 Hz, 1H), 1.35 (dd, J=13.8, 6.2 Hz, 1H), 0.96 (s, 9H).

(2R)-2-Amino-4,4-dimethyl-N-[4-(1H-pyrrolo[2,3-b]pyridin-4-yl)phenyl]pentanamide, F-16

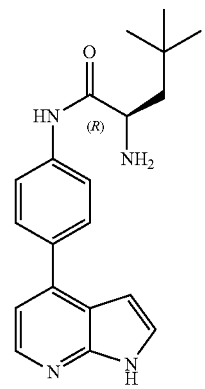

Step 1. tert-Butyl N-[(1R)-1-[[4-[1-(benzenesulfonyl)pyrrolo[2,3-b]pyridin-4-yl]phenyl]carbamoyl]-3,3-dimethyl-butyl]carbamate, E-16. Boc-D-Neo-OH (74 mg, 0.30 mmol) was reacted with D-1 (70 mg, 0.20 mmol) following General Procedure E. Purification by ISCO flash chromatography (0-100% EtOAc in hexanes) affords a colourless solid (88 mg, 0.15 mmol, 75%). LCMS (Method B) $t_R$=2.05 min, m/z=561.22 $[M+H]^+$.

Step 2. (2R)-2-Amino-4,4-dimethyl-N-[4-(1H-pyrrolo[2,3-b]pyridin-4-yl)phenyl]pentanamide, F-16. Intermediate E-16 (88 mg, 0.15 mmol) was deprotected according to General Procedure K, affording title compound as a colourless solid (33 mg, 64%). LCMS (Method A) $t_R$=1.42 min, m/z=337.20 $[M+H]^+$; Purity ≥95% (DAD, 210, 254 nm); $^1$H NMR (400 MHz, MeOH-$d_4$) δ 8.25 (d, J=5.1 Hz, 1H), 7.88-7.74 (m, 4H), 7.46 (d, J=3.5 Hz, 1H), 7.22 (d, J=5.1 Hz, 1H), 6.71 (d, J=3.5 Hz, 1H), 3.56 (dd, J=7.2, 5.3 Hz, 1H), 1.98 (dd, J=14.0, 7.2 Hz, 1H), 1.49 (dd, J=14.0, 5.3 Hz, 1H), 1.04 (s, 9H).

(2R)-2-Amino-5-methyl-N-[4-(1H-pyrrolo[2,3-b]pyridin-4-yl)phenyl]hexanamide, F-17

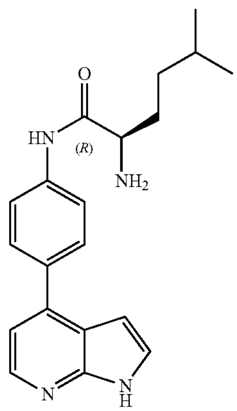

Step 1. tert-Butyl N-[(1R)-1-[[4-[1-(benzenesulfonyl)pyrrolo[2,3-b]pyridin-4-yl]phenyl]carbamoyl]-4-methyl-pentyl]carbamate, E-17. (R)-2-((tert-Butoxycarbonyl)amino)-5-methylhexanoic acid (74 mg, 0.30 mmol) was reacted with D-1 (70 mg, 0.20 mmol) following General Procedure E. Purification by ISCO flash chromatography (0-100% EtOAc in hexanes) affords a cream solid (47 mg, 0.08 mmol, 41%). LCMS (Method B) $t_R$=2.30 min, m/z=577.25 $[M+H]^+$.

Step 2. (2R)-2-Amino-5-methyl-N-[4-(1H-pyrrolo[2,3-b]pyridin-4-yl)phenyl]hexanamide, F-17. Intermediate E-17 (47 mg, 0.08 mmol) was deprotected according to General Procedure K, affording title compound as a colourless solid (16 mg, 0.05 mmol, 58%). LCMS (Method A) $t_R$=1.44 min, m/z=337.20 $[M+H]^+$; Purity ≥95% (DAD, 210, 254 nm); HRMS calculated for $C_{20}H_{24}N_4O$=336.1950, observed 336.1950; $^1H$ NMR (400 MHz, MeOH-$d_4$) δ 8.13 (d, J=5.1 Hz, 1H), 7.73-7.64 (m, 4H), 7.34 (d, J=3.6 Hz, 1H), 7.11 (d, J=5.1 Hz, 1H), 6.60 (d, J=3.6 Hz, 1H), 3.39 (t, J=6.6 Hz, 1H), 1.80-1.66 (m, 1H), 1.66-1.45 (m, 2H), 1.35-1.13 (m, 2H), 0.84 (d, J=6.6 Hz, 6H).

2-Amino-2-cyclopropyl-N-[4-(1H-pyrrolo[2,3-b]pyridine-4-yl)phenyl]acetamide, F-18

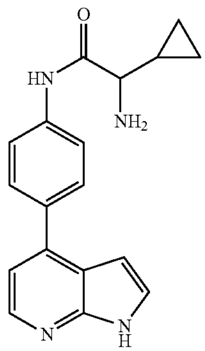

Step 1. tert-Butyl (1-cyclopropyl-2-oxo-2-((4-(1-(phenylsulfonyl)-1H-pyrrolo[2,3-b]pyridine-4-yl)phenyl)amino)ethyl)carbamate, E-18. 2-(tert-Butoxycarbonylamino)-2-cyclopropyl-acetic acid (32 mg, 0.15 mmol) was reacted with D-1 (35 mg, 0.10 mmol) following General Procedure D. Purification by ISCO flash chromatography (20-80% EtOAc in hexanes) affords a colourless gum (52 mg, 0.095 mmol, 95%). LCMS (Method B) $t_R$=2.07 min, m/z=547.20 $[M+H]^+$.

Step 2. 2-Amino-2-cyclopropyl-N-[4-(1H-pyrrolo[2,3-b]-83-pyridine-4-yl)phenyl]acetamide, F-18. Intermediate E-18 (52 mg, 0.095 mmol) was deprotected according to General Procedure K, affording title compound as a colourless solid (6.2 mg, 0.02 mmol, 21%). LCMS (Method A) $t_R$=0.94 min, m/z=307.14 $[M+H]^+$; Purity ≥95% (DAD 210, 254 nm).

(2R)-2-Amino-3-cyclopropyl-N-[4-(1H-pyrrolo[2,3-b]pyridin-4-yl)phenyl]propenamide, F-19

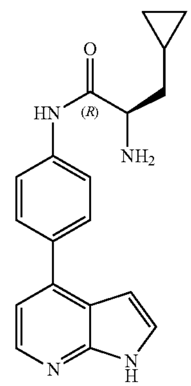

Step 1. tert-Butyl N-[(1R)-2-[4-[1-(benzenesulfonyl)pyrrolo[2,3-b]pyridin-4-yl]anilino]-1-(cyclopropylmethyl)-2-oxo-ethyl]carbamate, E-19. β-Cyclopropyl-D-Ala-OH (26 mg, 0.20 mmol) was reacted with D-1 (70 mg, 0.20 mmol) following General Procedure G. Purification by ISCO flash chromatography affords a colourless gum (107 mg, 95%). LCMS (Method B) $t_R$=2.05 min, m/z=560.66 $[M+H]^+$.

Step 2. (2R)-2-Amino-3-cyclopropyl-N-[4-(1H-pyrrolo[2,3-b]pyridin-4-yl)phenyl]propenamide, F-19. Intermediate E-19 (107 mg, 0.19 mmol) was deprotected according to General Procedure K, affording title compound as a colourless solid (35 mg, 0.11 mmol, 57%). LCMS (Method A); $t_R$=1.29 min, m/z=321.17 $[M+H]^+$; Purity ≥95% (DAD, 210, 254 nm); HRMS calculated for $C_{19}H_{20}N_4O$=320.1637, observed 320.1639; $^1H$ NMR (400 MHz, MeOH-$d_4$) δ 8.23 (d, J=5.1 Hz, 1H), 7.82-7.74 (m, 4H), 7.44 (d, J=3.6 Hz, 1H), 7.21 (d, J=5.1 Hz, 1H), 6.69 (d, J=3.6 Hz, 1H), 3.65 (t, J=6.6 Hz, 1H), 1.74 (dt, J=13.7, 6.6 Hz, 1H), 1.63 (dt, J=13.7, 7.1 Hz, 1H), 0.85 (d, J=8.5 Hz, 1H), 0.52 (p, J=9.6 Hz, 2H), 0.16 (dd, J=4.9, 1.9 Hz, 2H).

(2R)-2-Amino-3-cyclobutyl-N-[4-(1H-pyrrolo[2,3-b]pyridin-4-yl)phenyl]propenamide, F-20

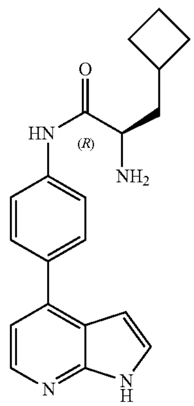

Step 1. tert-Butyl N-[(1R)-2-[4-[1-(benzenesulfonyl)pyrrolo[2,3-b]pyridin-4-yl]anilino]-1-(cyclobutylmethyl)-2-oxo-ethyl]carbamate, E-20. (2R)-2-Amino-3-cyclobutyl-propanoic acid (29 mg, 0.20 mmol) was reacted with D-1 (70 mg, 0.20 mmol) following General Procedure G. Purification by ISCO flash chromatography (0-100% EtOAc in hexanes) affords a colourless gum (76 mg, 0.13 mmol, 66%). LCMS (Method B) $t_R$=2.20 min, m/z=575.24 $[M+H]^+$.

Step 2. (2R)-2-Amino-3-cyclobutyl-N-[4-(1H-pyrrolo[2,3-b]pyridin-4-yl)phenyl]propenamide, F-20. Intermediate E-20 (76 mg, 0.13 mmol) was deprotected according to General Procedure K, affording title compound as a colourless solid (29 mg, 66%. LCMS (Method A) $t_R$=1.41 min, m/z=335.19 $[M+H]^+$; Purity ≥95% (DAD, 210, 254 nm); HRMS calculated for $C_{20}H_{22}N_4O$=334.1794, observed 334.1794; $^1$H NMR (400 MHz, MeOH-$d_4$) δ 8.25 (d, J=5.1 Hz, 1H), 7.83-7.75 (m, 4H), 7.46 (d, J=3.6 Hz, 1H), 7.23 (d, J=5.1 Hz, 1H), 6.72 (d, J=3.6 Hz, 1H), 3.44 (t, J=6.7 Hz, 1H), 2.53 (p, J=7.9 Hz, 1H), 2.23-2.05 (s, 2H), 1.99-1.67 (m, 4H).

(2R)-2-Amino-3-cyclopentyl-N-[4-(1H-pyrrolo[2,3-b]pyridin-4-yl)phenyl]propenamide, F-21

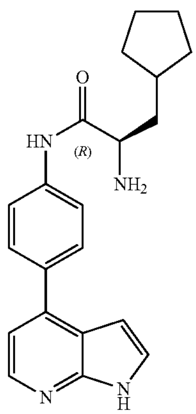

Synthesized in a manner analogous to F-19, using (2R)-2-amino-3-cyclopentyl-propanoic acid in the first step. Deprotection affords title compound as a colourless solid (24 mg, 53%). LCMS (Method A) $t_R$=1.47 min, m/z=349.20 $[M+H]^+$; Purity ≥95% (DAD, 210, 254 nm); $^1$H NMR (400 MHz, MeOH-$d_4$) δ 8.25 (d, J=5.1 Hz, 1H), 7.85-7.75 (m, 4H), 7.46 (d, J=3.5 Hz, 1H), 7.23 (d, J=5.1 Hz, 1H), 6.72 (d, J=3.5 Hz, 1H), 3.53 (t, J=7.1 Hz, 1H), 2.06-1.78 (m, 4H), 1.77-1.64 (m, 2H), 1.64-1.54 (m, 2H), 1.31-1.16 (m, 2H).

2-Amino-4,4,4-trifluoro-N-[4-(1H-pyrrolo[2,3-b]pyridin-4-yl)phenyl]butanamide, F-22

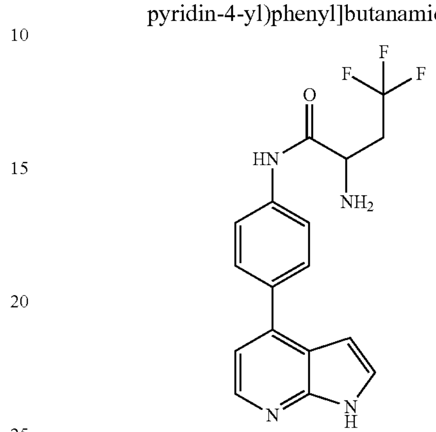

Step 1. tert-Butyl N-[1-[[4-[1-(benzenesulfonyl)pyrrolo[2,3-b]pyridin-4-yl]phenyl]carbamoyl]-3,3,3-trifluoro-propyl]carbamate, E-22. 2-Amino-4,4,4-trifluorobutanoic acid (31 mg, 0.20 mmol) was reacted with D-1 (70 mg, 0.20 mmol) following General Procedure G. Purification by ISCO flash chromatography (0-100% EtOAc in hexanes) affords a colourless gum (40 mg, 0.07 mmol, 34%). LCMS (Method B) $t_R$=1.97 min, m/z=589.1$[M+H]^+$.

Step 2. 2-Amino-4,4,4-trifluoro-N-[4-(1H-pyrrolo[2,3-b]pyridin-4-yl)phenyl]butanamide, F-22. Intermediate E-22 (40 mg, 0.07 mmol) was deprotected according to General Procedure K, affording title compound as a colourless solid (14 mg, 59%). LCMS (Method A) $t_R$=1.29 min, m/z=349.13 $[M+H]^+$; Purity ≥95% (DAD, 210, 254 nm); HRMS calculated for $C_{17}H_{25}F3N_4O$=348.1198, observed 348.1199; $^1$H NMR (400 MHz, MeOH-$d_4$) δ 8.25 (d, J=5.1 Hz, 1H), 7.80 (d, J=2.2 Hz, 4H), 7.46 (d, J=3.6 Hz, 1H), 7.23 (d, J=5.1 Hz, 1H), 6.71 (d, J=3.6 Hz, 1H), 4.60 (s, 1H), 3.83 (dd, J=7.3, 5.8 Hz, 1H), 2.96-2.80 (m, 1H), 2.51 (ddd, J=15.1, 10.9, 7.3 Hz, 1H); $^{19}$F NMR (376 MHz, MeOH-$d_4$) δ −65.29.

2-Amino-N-[4-(1H-pyrrolo[2,3-b]pyridin-4-yl)phenyl]-2-[1-(trifluoromethyl)cyclopropyl]acetamide, F-23

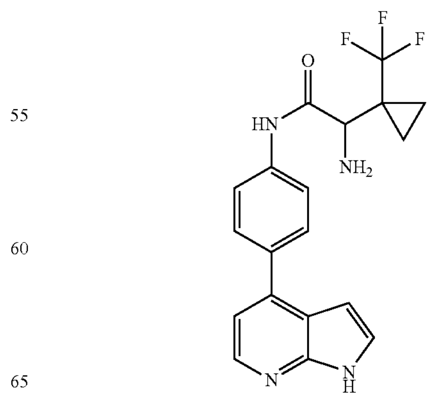

Step 1. tert-Butyl N-[2-[4-[1-(benzenesulfonyl)pyrrolo[2,3-b]pyridin-4-yl]anilino]-2-oxo-1-[1-(trifluoromethyl)cyclopropyl]ethyl]carbamate, E-23. 2-(tert-butoxycarbonylamino)-2-[1-(trifluoromethyl)cyclopropyl]acetic acid (34 mg, 0.12 mmol) was reacted with D-1 (70 mg, 0.20 mmol) following General Procedure E. Purification by ISCO flash chromatography (0-100% EtOAc in hexanes) affords a colourless solid (49 mg, 0.08 mmol, 80%). LCMS (Method B) $t_R$=2.12 min, m/z=615.19 $[M+H]^+$.

Step 2. 2-Amino-N-[4-(1H-pyrrolo[2,3-b]pyridin-4-yl)phenyl]-2-[1-(trifluoromethyl)cyclopropyl]acetamide, F-23. Intermediate E-23 (49 mg, 0.08 mmol) was deprotected according to General Procedure K, affording title compound as a colourless solid (18 mg, 60%). LCMS (Method A) $t_R$=1.37 min, m/z=375.16 $[M+H]^+$; Purity ≥95% (DAD, 210, 254 nm); $^1H$ NMR (400 MHz, MeOH-$d_4$) δ 8.25 (d, J=5.1 Hz, 1H), 7.79 (s, 4H), 7.46 (d, J=3.5 Hz, 1H), 7.23 (d, J=5.1 Hz, 1H), 6.72 (d, J=3.5 Hz, 1H), 3.71 (s, 1H), 1.31-1.22 (m, 1H), 1.17-1.03 (m, 2H), 1.03-0.93 (m, 1H); $^{19}F$ NMR (376 MHz, MeOH-$d_4$) δ −69.14.

(2R)-2-Amino-5,5,5-trifluoro-N-[4-(1H-pyrrolo[2,3-b]pyridin-4-yl)phenyl]pentanamide, F-24

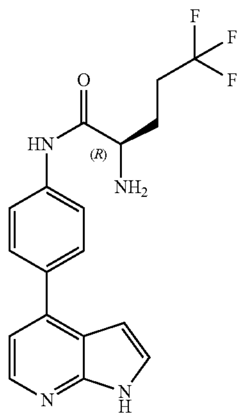

(2R)-2-Amino-5,5,5-trifluoro-pentanoic acid (51 mg, 0.30 mmol) was reacted with D-1 (105 mg, 0.30 mmol) following General Procedure G to afford an impure solid of tert-butyl N-[(1R)-1-[[4-[1-(benzenesulfonyl)pyrrolo[2,3-b]pyridin-4-yl]phenyl]carbamoyl]-4,4,4-trifluoro-butyl]carbamate (88 mg, 0.15 mmol) after purification by ISCO flash chromatography. This material was immediately deprotected following General Procedure K, affording title compound as a colourless solid (3 mg, 3%). LCMS (Method A) $t_R$=1.37 min, m/z=363.16 $[M+H]^+$; Purity ≥95% (DAD, 210, 254 nm); $^1H$ NMR (400 MHz, MeOH-$d_4$) δ 8.25 (d, J=5.1 Hz, 1H), 7.86-7.73 (m, 4H), 7.46 (d, J=3.6 Hz, 1H), 7.23 (d, J=5.1 Hz, 1H), 6.71 (d, J=3.6 Hz, 1H), 3.64-3.56 (m, 1H), 2.50-2.26 (m, 2H), 2.21-2.00 (m, 1H), 1.99-1.85 (m, 1H); $^{19}F$ NMR (376 MHz, MeOH-$d_4$) δ −68.02.

(2S)-2-Amino-3-methoxy-N-[4-(1H-pyrrolo[2,3-b]pyridin-4-yl)phenyl]propenamide, F-25

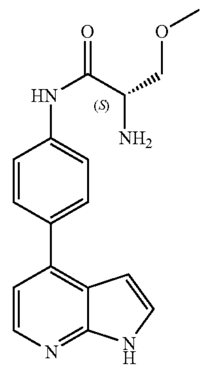

Step 1. tert-butyl (S)-(3-methoxy-1-oxo-1-((4-(1-(phenylsulfonyl)-1H-pyrrolo[2,3-b]pyridin-4-yl)phenyl)amino)propan-2-yl)carbamate, E-25. Boc-Ser(Me)-OH (66 mg, 0.30 mmol) was reacted with D-1 (70 mg, 0.20 mmol) following General Procedure D. Purification by ISCO flash chromatography (20-80% EtOAc in hexanes) affords a colourless gum (96 mg, 0.174 mmol, 87%). LCMS (Method B) $t_R$=1.75 min, m/z=551.19 $[M+H]^+$.

Step 2. (2S)-2-Amino-3-methoxy-N-[4-(1H-pyrrolo[2,3-b]pyridin-4-yl)phenyl]propenamide, F-25. Intermediate E-25 (96 mg, 0.17 mmol) was deprotected according to General Procedure K, affording title compound as a colourless solid (15 mg, 0.05 mmol, 28%). LCMS (Method A) $t_R$=1.18 min, m/z=311.15 $[M+H]^+$; Purity ≥95% (DAD, 210, 254 nm); HRMS calculated for $C_{17}H_{18}N_4O_2$=310.1430, observed 310.1415; $^1H$ NMR (500 MHz, DMSO-$d_6$) δ 8.28-8.25 (m, 1H), 7.87-7.83 (m, 1H), 7.78-7.71 (m, 3H), 7.56-7.51 (m, 1H), 7.17 (dd, J=4.9, 2.1 Hz, 1H), 6.64 (d, J=3.4 Hz, 1H), 3.59-3.55 (m, 1H), 3.53-3.50 (m, 1H), 3.28 (s, 3H).

2-Amino-4-methoxy-N-[4-(1H-pyrrolo[2,3-b]pyridin-4-yl)phenyl]butanamide, F-26

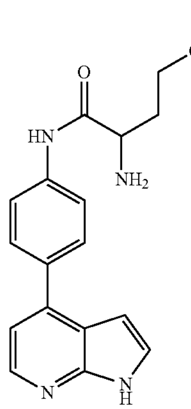

Step 1. tert-Butyl N-[1-[[4-[1-(benzenesulfonyl)pyrrolo[2,3-b]pyridin-4-yl]phenyl]carbamoyl]-3-methoxy-propyl]carbamate, E-26. 2-Amino-4-methoxy-butanoic acid (27 mg, 0.20 mmol) was reacted with D-1 (70 mg, 0.20 mmol)

following General Procedure G. Purification by ISCO flash chromatography (0-100% EtOAc in hexanes) affords a colourless gum (52 mg, 0.09 mmol, 46%). LCMS (Method B) $t_R$=1.72 min, m/z=565.21 $[M+H]^+$.

Step 2. 2-Amino-4-methoxy-N-[4-(1H-pyrrolo[2,3-b]pyridin-4-yl)phenyl]butanamide, F-26. Intermediate E-26 (52 mg, 0.0.09 mmol) was deprotected according to General Procedure K, affording title compound as a colourless solid (13 mg, 43%). LCMS (Method A) $t_R$=1.22 min, m/z=325.17 $[M+H]^+$; Purity ≥95% (DAD, 210, 254 nm); HRMS calculated for $C_{18}H_{20}N_4O_2$=324.1586, observed 324.1591; $^1H$ NMR (400 MHz, MeOH-$d_4$) δ 8.24 (d, J=5.1 Hz, 1H), 7.83-7.76 (m, 4H), 7.46 (d, J=3.6 Hz, 1H), 7.22 (d, J=5.1 Hz, 1H), 6.71 (d, J=3.6 Hz, 1H), 3.69-3.51 (m, 3H), 3.37 (s, 3H), 2.17-2.03 (m, 1H), 1.97-1.84 (m, 1H).

(2S)-2-Amino-3-hydroxy-N-[4-(1H-pyrrolo[2,3]-b pyridin-4-yl)phenyl]propenamide, F-27

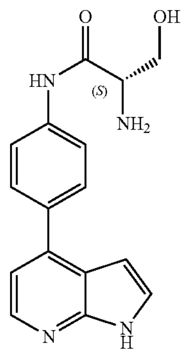

Step 1. tert-Butyl N-[(1S)-2-[4-[1-(benzenesulfonyl)pyrrolo[2,3-b]pyridin-4-yl]anilino]-1-(hydroxymethyl)-2-oxo-ethyl]carbamate, E-27. Boc-Ser-OH (41 mg, 0.20 mmol) was reacted with D-1 (84 mg, 0.24 mmol) following General Procedure F. Purification by ISCO flash chromatography (0-100% EtOAc in hexanes) affords a straw-colored oil (79 mg, 0.15 mmol, 74%). LCMS (Method B) $t_R$=1.38 min, m/z=537.18 $[M+H]^+$.

Step 2. (2S)-2-Amino-3-hydroxy-N-[4-(1H-pyrrolo[2,3-b]pyridin-4-yl)phenyl]propenamide, F-27. Intermediate F-27 (79 mg, 0.15 mmol) was deprotected according to General Procedure K, affording the TFA salt of the title compound as a colourless solid (37 mg, 0.09 mmol, 61%). LCMS (Method A) $t_R$=1.06 min, m/z=297.13 $[M+H]^+$; Purity ≥95% (DAD, 210, 254 nm); HRMS calculated for $C_{16}H_{16}N_4O_2$=296.1273, observed 296.1274; $^1H$ NMR (500 MHz, DMSO-$d_6$) δ 11.86 (s, 1H), 10.61 (s, 1H), 8.30 (d, J=5.0 Hz, 1H), 8.28-8.22 (m, 3H), 7.85-7.78 (m, 4H), 7.57 (t, J=3.0 Hz, 1H), 7.21 (d, J=5.0 Hz, 1H), 6.66 (dd, J=3.5, 1.9 Hz, 1H), 4.03 (dd, J=5.2, 5.1 Hz, 1H), 3.88 (d, J=5.1 Hz, 2H).

(2R)-2-Amino-3-hydroxy-N-[4-(1H-pyrrolo[2,3-b]pyridin-4-yl)phenyl]propenamide, F-28

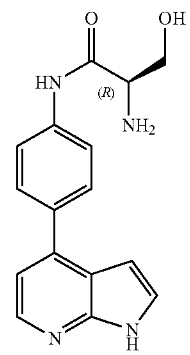

Step 1. tert-Butyl N-[(1R)-2-[4-[1-(benzenesulfonyl)pyrrolo[2,3-b]pyridin-4-yl]anilino]-1-(hydroxymethyl)-2-oxo-ethyl]carbamate, E-27. Boc-D-Ser-OH (41 mg, 0.20 mmol) was reacted with D-1 (84 mg, 0.24 mmol) following General Procedure F. Purification by ISCO flash chromatography (0-100% EtOAc in hexanes) affords a straw-colored gum (98 mg, 0.183 mmol, 91%). LCMS (Method B) $t_R$=1.34 min, m/z=537.18 $[M+H]^+$.

Step 2. (2R)-2-Amino-3-hydroxy-N-[4-(1H-pyrrolo[2,3-b]pyridin-4-yl)phenyl]propenamide, F-28. Intermediate E-28 (98 mg, 0.18 mmol) was deprotected according to General Procedure K, affording title compound as a colourless solid (40 mg, 0.135 mmol, 74%). LCMS (Method A) $t_R$=1.07 min, m/z=297.13 $[M+H]^+$; Purity ≥95% (DAD, 210, 254 nm); HRMS calculated for $C_{16}H_{16}N_4O_2$=297.1273, observed 296.1277; $^1H$ NMR (400 MHz, DMSO-$d_6$) δ 11.75 (s, 1H), 8.30-8.22 (m, 1H), 7.85 (d, J=8.2 Hz, 2H), 7.75 (d, J=8.1 Hz, 2H), 7.53 (s, 1H), 7.21-7.13 (m, 1H), 6.64 (s, 1H), 4.96-4.75 (m, 1H), 3.67-3.51 (m, 2H), 3.46-3.38 (m, 1H).

(2S)-2-Amino-3-hydroxy-N-[4-(1H-pyrrolo[2,3-b]pyridin-4-yl)phenyl]butanamide, F-29

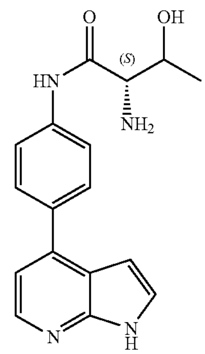

Step 1. tert-Butyl N-[(1S)-1-[[4-[1-(benzenesulfonyl)pyrrolo[2,3-b]pyridin-4-yl]phenyl]carbamoyl]-2-hydroxy-propyl]carbamate, E-29. Boc-Thr-OH (44 mg, 0.20 mmol) was reacted with D-1 (84 mg, 0.24 mmol) following General Procedure F. Purification by ISCO flash chromatography (0-100% EtOAc in hexanes) affords a straw-colored gum (108 mg, 0.196 mmol, 98%). LCMS (Method B) $t_R$=1.52 min, m/z=551.20 $[M+H]^+$.

Step 2. (2S)-2-Amino-3-hydroxy-N-[4-(1H-pyrrolo[2,3-b]pyridin-4-yl)phenyl]butanamide, F-29. Intermediate E-29 (108 mg, 0.20 mmol) was deprotected according to General Procedure K, affording title compound as a colourless solid (35 mg, 0.11 mmol 57%). LCMS (Method A) $t_R$=1.13 min, m/z=311.15 $[M+H]^+$; Purity ≥95% (DAD, 210, 254 nm); HRMS calculated for $C_{17}H_{18}N_4O_2$=310.1430, observed 310.1408; $^1$H NMR (400 MHz, DMSO-$d_6$)[rotamers]δ 11.75 (s, 1H), 8.26 (d, J=4.9 Hz, 1H), 7.85 (d, J=8.4 Hz, 2H), 7.79-7.70 (m, 2H), 7.53 (s, 1H), 7.17 (d, J=3.2 Hz, 1H), 6.64 (s, 1H), [4.80 (d, J=3.7 Hz, 0.3H), 4.74 (d, J=3.7 Hz, 0.7H)], [3.97 (br s, 0.3H), 3.86 (br s, 0.7H)], [1.14 (d, J=6.1 Hz, 2H), 1.09 (d, J=6.1 Hz, 1H)].

(2R)-2-Amino-3-hydroxy-N-[4-(1H-pyrrolo[2,3-b]pyridin-4-yl)phenyl]butanamide, F-30

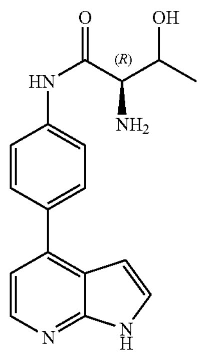

Step 1. tert-butyl N-[(1R)-1-[[4-[1-(benzenesulfonyl)pyrrolo[2,3-b]pyridin-4-yl]phenyl]carbamoyl]-2-hydroxy-propyl]carbamate, E-30. Boc-D-Thr-OH (44 mg, 0.20 mmol) was reacted with D-1 (84 mg, 0.24 mmol) following General Procedure F. Purification by ISCO flash chromatography (0-100% EtOAc in hexanes) affords a straw-colored gum (76 mg, 0.138 mmol, 69%). LCMS (Method B) $t_R$=1.52 min, m/z=551.20 $[M+H]^+$.

Step 2. (2R)-2-Amino-3-hydroxy-N-[4-(1H-pyrrolo[2,3-b]pyridin-4-yl)phenyl]butanamide, F-30. Intermediate E-30 (76 mg, 0.14 mmol) was deprotected according to General Procedure K, affording title compound as a colourless solid (34 mg, 0.11 mmol 79%). LCMS (Method A) $t_R$=1.13 min, m/z=311.15 $[M+H]^+$; Purity ≥95% (DAD, 210, 254 nm); HRMS calculated for $C_{17}H_{18}N_4O_2$=310.1430, observed 310.1401; $^1$H NMR $^1$H NMR (400 MHz, DMSO-$d_6$)[rotamers]δ 11.75 (s, 1H), 8.26 (d, J=4.9 Hz, 1H), 7.85 (d, J=8.4 Hz, 2H), 7.79-7.70 (m, 2H), 7.53 (s, 1H), 7.17 (d, J=3.2 Hz, 1H), 6.64 (s, 1H), [4.80 (d, J=3.7 Hz, 0.3H), 4.74 (d, J=3.7 Hz, 0.7H)], [3.97 (br s, 0.3H), 3.86 (br s, 0.7H)], [1.14 (d, J=6.1 Hz, 2H), 1.09 (d, J=6.1 Hz, 1H)].

(2R)-2-Amino-3-hydroxy-3-methyl-N-[4-(1H-pyrrolo[2,3-b]pyridin-4-yl)phenyl]butanamide, F-31

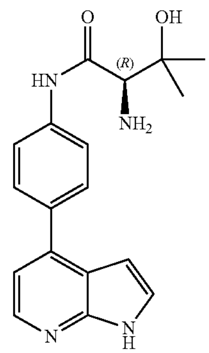

Step 1. tert-Butyl N-[(1R)-1-[[4-[1-(benzenesulfonyl)pyrrolo[2,3-b]pyridin-4-yl]phenyl]carbamoyl]-2-hydroxy-2-methyl-propyl]carbamate, E-31. To an ice-cold solution of (2R)-2-(tert-butoxycarbonylamino)-3-hydroxy-3-methyl-butanoic acid (70 mg, 0.30 mmol) and 4-methylmorpholine (36 μL, 0.33 mmol) in THE (1 mL) was added drop-wise a solution of ethyl chloroformate (31.6 μL, 0.33 mmol) in THE (0.5 mL). Upon complete addition the mixture was stirred for 15 min then D-1 (126 mg, 0.36 mmol) was added and stirred for 16 h at r.t. The mixture was diluted with DCM and washed with water, then concentrated and purified by ISCO flash chromatography (20-100% EtOAc in hexanes) to afford a straw-coloured oil (123 mg 0.22 mmol, 73%). LCMS (Method B) $t_R$=1.60 min, m/z=565.20 $[M+H]^+$.

Step 2. (2R)-2-Amino-3-hydroxy-3-methyl-N-[4-(1H-pyrrolo[2,3-b]pyridin-4-yl)phenyl]butanamide, F-31. Intermediate E-31 (123 mg, 0.22 mmol) was deprotected following General Procedure K, affording title compound as a colourless solid (29 mg, 41%). LCMS (Method A) $t_R$=1.16 min, m/z=325.17 $[M+H]^+$; Purity ≥95% (DAD, 210, 254 nm); $^1$H NMR (400 MHz, MeOH-$d_4$) δ 11.75 (s, 1H), 8.26 (d, J=5.0 Hz, 1H), 7.82 (d, J=8.5 Hz, 2H), 7.75 (d, J=8.5 Hz, 2H), 7.53 (t, J=3.0 Hz, 1H), 7.17 (d, J=5.0 Hz, 1H), 6.64 (d, J=3.0 Hz, 1H), 4.65 (s, 1H), 3.27 (s, 1H), 1.19 (s, 3H), 1.17 (s, 3H).

(S)-N-(4-(1H-pyrrolo[2,3-b]pyridin-4-yl)phenyl)-2-amino-3-phenylpropanamide, F-32

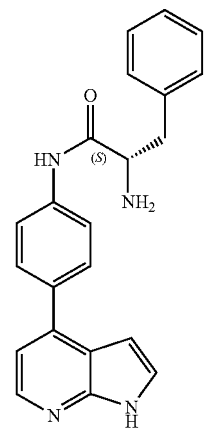

Step 1. (S)-tert-Butyl (1-((4-bromophenyl)amino)-1-oxo-3-phenylpropan-2-yl)carbamate, G-32. Boc-Phe-OH (550 mg, 2.08 mmol) was reacted with 4-bromoaniline (239 mg, 1.39 mmol) following General Procedure D. Purified by flash chromatography (0-50% EtOAc/Petroether) affords a colourless solid (610 mg, 70%). LCMS m/z=419.0 $[M+H]^+$.

Step 2. (S)-tert-Butyl (1-oxo-3-phenyl-1-((4-(1-(phenylsulfonyl)-1H-pyrrolo[2,3-b]pyridin-4-yl)phenyl)amino)propan-2-yl)carbamate, E-32. A mixture of G-32 (350 mg, 0.84 mmol), A-3 (386 mg, 1.00 mmol), tetrakis(triphenylphosphine)palladium (97 mg, 0.084 mmol) and potassium carbonate (232 mg, 1.68 mmol) in 1,4-dioxane (5 mL) & water (0.5 mL) was heated to 80° C. for 16 hrs. Water (40 mL) was added and the solution was extracted with EtOAc (3-20 mL). The combined organics were washed with brine (30 mL), dried over anhydrous sodium sulfate and concentrated. The residue was purified on silica gel column chromatography using 0~30% EtOAc/Petroether to provide a colourless solid (162 mg, 33%). LCMS m/z=597.1 $[M+H]^+$.

Step 3. (S)-tert-Butyl (1-((4-(1H-pyrrolo[2,3-b]pyridin-4-yl)phenyl)amino)-1-oxo-3-phenylpropan-2-yl)carbamate, H-32. To a solution of E-32 (162 mg, 0.27 mmol) in MeOH (5 mL) was added NaOH (54 mg, 1.36 mmol) in $H_2O$ (1 mL) at room temperature. The mixture was heated to 80° C. for 16 hrs. After the reaction was completed, the solvent was removed under reduced pressure and water (20 mL) was added, followed by extracted with EtOAc (3×15 mL). The combined organics were washed with brine (20 mL), dried over anhydrous sodium sulfate and concentrated. The residue was purified on silica gel column chromatography using 0-30% EtOAc/Petroether to provide a colourless solid (115 mg, 93%). LCMS m/z=457.0 $[M+H]^+$.

Step 4. (S)-N-(4-(1H-Pyrrolo[2,3-b]pyridin-4-yl)phenyl)-2-amino-3-phenylpropanamide, F-32. To a solution of H-32 (115 mg, 0.25 mmol) in 1,4-dioxane (1.2 mL) was added 4 M HCl in dioxane (0.6 mL, 2.52 mmol) and the mixture was stirred for 5 h at r.t. then concentrated. The residue was purified by reversed HPLC to provide the title compound (86 mg, 96% yield) as a colourless solid. LCMS m/z=357.2 $[M+H]^+$. $^1H$ NMR (400 MHz, MeOH-$d_4$) δ 8.37 (d, J=6.0 Hz, 1H), 7.87-7.85 (m, 2H), 7.80-7.77 (m, 2H), 7.65 (d, J=3.2 Hz, 1H), 7.51 (d, J=5.6 Hz, 1H), 7.37-7.32 (m, 5H), 6.91 (d, J=3.6 Hz, 1H), 4.25 (t, J=7.6 Hz, 1H), 3.33 (dd, J=14.0, 6.8 Hz, 1H), 3.20 (dd, J=14.0, 8.0 Hz, 1H).

(R)-N-(4-(1H-pyrrolo[2,3-b]pyridin-4-yl)phenyl)-2-amino-3-phenylpropanamide, F-33

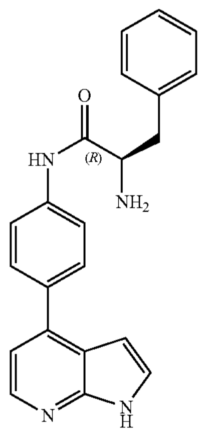

Step 1. (R)-tert-Butyl (1-((4-bromophenyl)amino)-1-oxo-3-phenylpropan-2-yl)carbamate, G-33. Boc-D-Phe-OH (535 mg, 2.02 mmol) was reacted with 4-bromoaniline (232 mg, 1.35 mmol) following General Procedure D. Purified by flash chromatography (0-50% EtOAc/Petroether) affords a colourless solid (582 mg, 69%). LCMS m/z=419.0 $[M+H]^+$.

Step 2. (R)-tert-Butyl (1-oxo-3-phenyl-1-((4-(1-(phenylsulfonyl)-1H-pyrrolo[2,3-b]pyridin-4-yl)phenyl)amino)propan-2-yl)carbamate, E-33. A mixture of G-33 (350 mg, 0.84 mmol), A-3 (386 mg, 1.00 mmol), tetrakis(triphenylphosphine)palladium (97 mg, 0.084 mmol) and potassium carbonate (232 mg, 1.68 mmol) in 1,4-dioxane (5 mL) & water (0.5 mL) was heated to 80° C. for 16 hrs. Water (40 mL) was added and the solution was extracted with EtOAc (3-20 mL). The combined organics were washed with brine (30 mL), dried over anhydrous sodium sulfate and concentrated. The residue was purified on silica gel column chromatography using 0~30% EtOAc/Petroether to provide a colourless solid (141 mg, 28%). LCMS m/z=597.1 $[M+H]^+$.

Step 3. (R)-tert-Butyl (1-((4-(1H-pyrrolo[2,3-b]pyridin-4-yl)phenyl)amino)-1-oxo-3-phenylpropan-2-yl)carbamate, H-33. To a solution of E-33 (141 mg, 0.24 mmol) in MeOH (5 mL) was added NaOH (47 mg, 1.28 mmol) in $H_2O$ (1 mL) at room temperature. The mixture was heated to 80° C. for 16 hrs. After the reaction was completed, the solvent was removed under reduced pressure and water (20 mL) was added, followed by extracted with EtOAc (3×15 mL). The combined organics were washed with brine (20 mL), dried over anhydrous sodium sulfate and concentrated. The residue was purified on silica gel column chromatography using 0-30% EtOAc/Petroether to provide a colourless solid (105 mg, 97%). LCMS m/z=457.0 $[M+H]^+$.

Step 4. (R)-N-(4-(1H-Pyrrolo[2,3-b]pyridin-4-yl)phenyl)-2-amino-3-phenylpropanamide, F-33. To a solution of H-33 (105 mg, 0.23 mmol) in 1,4-dioxane (1.2 mL) was added 4 M HCl in dioxane (0.6 mL, 2.30 mmol) and the mixture was stirred for 5 h at r.t. then concentrated. The residue was purified by reversed HPLC to provide the title compound (65 mg, 79%) as a colourless solid. LCMS m/z=357.2 $[M+H]^+$; Purity ≥95% (DAD, 210, 254 nm); H NMR (400 MHz, MeOH-$d_4$) δ 8.33 (d, J=5.6 Hz, 1H), 7.84 (dd, J=6.8, 2.0 Hz, 2H), 7.76 (dd, J=8.8, 2.0 Hz, 2H), 7.60 (d, J=3.6 Hz, 1H), 7.43 (d, J=6.0 Hz, 1H), 7.38-7.32 (m, 5H), 6.85 (d, J=3.6 Hz, 1H), 4.23 (t, J=7.2 Hz, 1H), 3.33 (dd, J=14.0, 6.8 Hz, 1H), 3.20 (dd, J=14.0, 8.0 Hz, 1H).

(2S)-2-Amino-3-(4-methoxyphenyl)-N-[4-(1H-pyrrolo[2,3-b]pyridin-4-yl)phenyl]propenamide, F-34

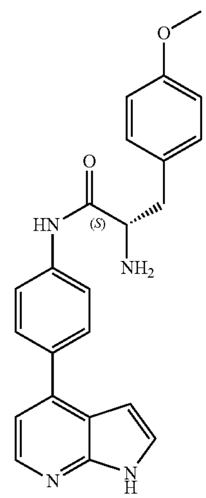

Step 1. tert-Butyl (S)-(3-(4-methoxyphenyl)-1-oxo-1-((4-(1-(phenylsulfonyl)-1H-pyrrolo[2,3-b]pyridin-4-yl)phenyl) amino)propan-2-yl)carbamate, E-34. Boc-Tyr(Me)-OH (89 mg, 0.15 mmol) was reacted with D-1 (70 mg, 0.20 mmol) following General Procedure D. Purification by ISCO flash chromatography (20-100% EtOAc in hexanes) affords a colourless gum (118 mg, 0.188 mmol, 94%). LCMS (Method B) $t_R$=2.07 min, m/z=627.23 $[M+H]^+$.

Step 2. (2S)-2-Amino-3-(4-methoxyphenyl)-N-[4-(1H-pyrrolo[2,3-b]pyridin-4-yl)phenyl]propenamide, F-34. Intermediate E-34 (118 mg, 0.188 mmol) was deprotected according to General Procedure K, affording title compound as a colourless solid (7.6 mg, 0.02 mmol, 10%). LCMS (Method A) $t_R$=1.40 min, m/z=387.17 $[M+H]^+$; Purity ≥95% (DAD, 210, 254 nm); $^1$H NMR (500 MHz, DMSO-$d_6$) $\delta_H$ 11.76 (s, 1H), 8.26 (d, J=5.0 Hz, 1H), 7.81 (d, J=8.7 Hz, 2H), 7.75 (d, J=8.5 Hz, 2H), 7.56-7.51 (m, 1H), 7.21-7.15 (m, 3H), 6.86 (d, J=8.5 Hz, 2H), 6.65 (dd, J=3.5, 1.8 Hz, 1H), 3.72 (s, 3H), 3.57 (t, J=6.7 Hz, 1H), 2.97 (dd, J=13.5, 5.5 Hz, 1H), 2.71 (dd, J=13.5, 7.7 Hz, 1H).

(2R)-2-Amino-3-(4-methoxyphenyl)-N-[4-(1H-pyrrolo[2,3-b]pyridin-4-yl)phenyl]propenamide, F-35

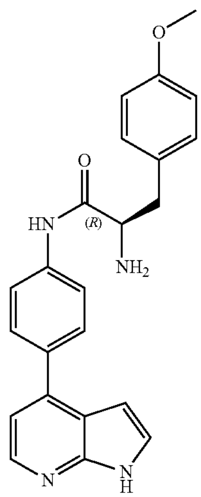

Step 1. tert-Butyl N-[(1R-2-[4-[1-benzenesulfonyl)pyrrolo[2,3-b]pyridin-4-yl]anilino]-1-[(4-methoxyphenyl) methyl]-2-oxo-ethyl]carbamate, E-35. Boc-D-Tyr-OH (89 mg, 0.30 mmol) was reacted with D-1 (70 mg, 0.20 mmol) following General Procedure D. Purification by ISCO flash chromatography (0-100% EtOAc in hexanes) affords a colourless gum (115 mg, 0.184 mmol, 92%). LCMS (Method B) $t_R$=2.05 min, m/z=627.23 $[M+H]^+$.

Step 2. (2R)-2-Amino-3-(4-methoxyphenyl)-N-[4-(1H-pyrrolo[2,3-b]pyridin-4-yl)phenyl]propenamide, F-35. Intermediate E-35 (115 mg, 0.18 mmol) was deprotected according to General Procedure K, affording title compound as a colourless solid (6 mg, 0.015 mmol, 8%). LCMS (Method A) $t_R$=1.38 min, m/z=387.18 $[M+H]^+$; Purity ≥95% (DAD, 210, 254 nm); HRMS calculated for $C_{23}H_{22}N_4O_2$=386.1743, observed 386.1740; $^1$H NMR (500 MHz, DMSO-$d_6$) δ 11.76 (s, 1H), 8.26 (d, J=4.9 Hz, 1H), 7.80 (d, J=8.6 Hz, 2H), 7.75 (d, J=8.7 Hz, 2H), 7.55-7.52 (m, 1H), 7.21-7.16 (m, 3H), 6.88-6.83 (m, 2H), 6.64 (dd, J=3.5, 1.8 Hz, 1H), 3.72 (s, 3H), 3.57 (t, J=6.7 Hz, 1H), 2.97 (dd, J=13.5, 5.6 Hz, 1H), 2.71 (dd, J=13.5, 7.7 Hz, 1H).

(2R)-2-Amino-3-(3-methoxyphenyl)-N-[4-(1H-pyrrolo[2,3-b]pyridin-4-yl)phenyl]propenamide, F-36

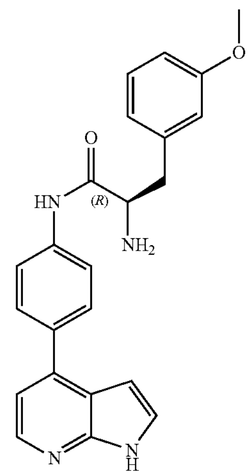

Step 1. tert-Butyl N-[(1R)-2-[4-[1-(Benzenesulfonyl)pyrrolo[2,3-b]pyridin-4-yl]anilino]-1-[(3-methoxyphenyl) methyl]-2-oxo-ethyl]carbamate, E-36. (2R)-2-(tert-Butoxycarbonylamino)-3-(3-methoxyphenyl)propanoic acid (89 mg, 0.30 mmol) was reacted with D-1 (70 mg, 0.20 mmol) following General Procedure D. Purification by ISCO flash chromatography (0-100% EtOAc in hexanes) affords a colourless solid (73 mg, 0.12 mmol, 58%). LCMS (Method B) $t_R$=2.09 min, m/z=627.24 $[M+H]^+$.

Step 2. (2R)-2-Amino-3-(3-methoxyphenyl)-N-[4-(1H-pyrrolo[2,3-b]pyridin-4-yl)phenyl]propenamide, F-36. Intermediate E-36 (73 mg, 0.12 mmol) was deprotected according to General Procedure K, affording title compound as a colourless solid (13 mg, 0.03 mmol, 29%). LCMS (Method A) $t_R$=1.40 min, m/z=387.18 $[M+H]^+$; Purity ≥95% (DAD, 210, 254 nm); $^1$H NMR (400 MHz, MeOH-$d_4$) $\delta_H$ 8.24 (d, J=5.1 Hz, 1H), 7.77 (d, J=8.7 Hz, 2H), 7.71 (d, J=8.7 Hz, 2H), 7.46 (d, J=3.6 Hz, 1H), 7.26-7.20 (m, 2H), 6.91-6.79 (m, 3H), 6.71 (d, J=3.6 Hz, 1H), 3.77 (t, J=6.9 Hz, 1H), 3.75 (s, 3H), 3.11 (dd, J=13.3, 6.9 Hz, 1H), 2.96 (dd, J=13.3, 6.9 Hz, 1H).

(2S)-2-Amino-3-(4-hydroxyphenyl)-N-[4-(1H-pyrrolo[2,3-b]pyridin-4-yl)phenyl]propenamide, F-37

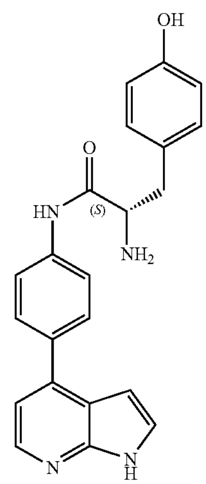

Step 1. tert-Butyl N-[(1S)-2-[4-[1-(benzenesulfonyl)pyrrolo[2,3-b]pyridin-4-yl]anilino]-1-[(4-hydroxyphenyl)methyl]-2-oxo-ethyl]carbamate, E-37. Boc-Tyr-OH (56 mg, 0.20 mmol) was reacted with D-1 (84 mg, 0.24 mmol) following General Procedure F. Purification by ISCO flash chromatography (20-100% EtOAc in hexanes) affords a colourless solid (123 mg, 0.20 mmol, quant.). LCMS (Method B) $t_R$=1.66 min, m/z=613.21 $[M+H]^+$.

Step 2. (2S)-2-Amino-3-(4-hydroxyphenyl)-N-[4-(1H-pyrrolo[2,3-b]pyridin-4-yl)phenyl]propenamide, F-37. Intermediate E-37 (123 mg, 0.0.20 mmol) was deprotected according to General Procedure K, affording title compound as a colourless solid (49 mg, 0.13 mmol, 65%). LCMS (Method A) $t_R$=1.25 min, m/z=373.17 $[M+H]^+$; Purity ≥95% (DAD, 210, 254 nm); HRMS calculated for $C_{22}H_{20}N_4O_2$=372.1586, observed 372.1598; $^1H$ NMR (400 MHz, DMSO-$d_6$) δ 11.75 (s, 1H), 9.17 (s, 1H), 8.26 (d, J=4.8 Hz, 1H), 7.80 (d, J=8.0 Hz, 2H), 7.74 (d, J=8.5 Hz, 3H), 7.53 (s, 1H), 7.17 (d, J=4.9 Hz, 1H), 7.05 (d, J=8.0 Hz, 3H), 6.71-6.61 (m, 3H), 3.59-3.49 (m, 1H), 2.97-2.85 (m, 1H), 2.72-2.65 (m, 1H).

(2R)-2-Amino-3-(4-hydroxyphenyl)-N-[4-(1H-pyrrolo[2,3-b]pyridin-4-yl)phenyl]propenamide, F-38

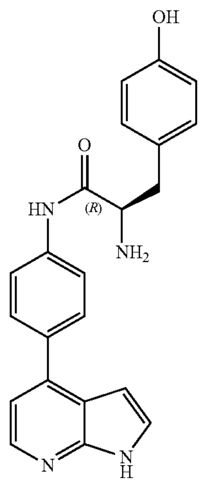

Step 1. tert-Butyl N-[(1R)-2-[4-[1-(benzenesulfonyl)pyrrolo[2,3-b]pyridin-4-yl]anilino]-1-[(4-hydroxyphenyl)methyl]-2-oxo-ethyl]carbamate, E-38. Boc-D-Tyr-OH (56 mg, 0.20 mmol) was reacted with D-1 (84 mg, 0.24 mmol) following General Procedure F. Purification by ISCO flash chromatography (0-100% EtOAc in hexanes) affords a colourless solid (113 mg, 0.184 mmol, 92%). LCMS (Method B) $t_R$=1.66 min, m/z=613.22 $[M+H]^+$.

Step 2. (2R)-2-Amino-3-(4-hydroxyphenyl)-N-[4-(1H-pyrrolo[2,3-b]pyridin-4-yl)phenyl]propenamide, F-38. Intermediate E-38 (113 mg, 0.18 mmol) was deprotected according to General Procedure K, affording title compound as a colourless solid (33 mg, 0.09 mmol, 48%. LCMS (Method A) $t_R$=1.26 min, m/z=373.16 $[M+H]^+$; Purity ≥95% (DAD, 210, 254 nm); HRMS calculated for $C_{22}H_{20}N_4O_2$=372.1586, observed 372.1570; $^1H$ NMR (400 MHz, MeOH-$d_4$) $\delta_H$ 8.13 (d, J=5.1 Hz, 1H), 7.69-7.63 (m, 2H), 7.63-7.56 (m, 2H), 7.35 (d, J=3.5 Hz, 1H), 7.10 (d, J=5.1 Hz, 1H), 7.03-6.98 (m, 2H), 6.67-6.62 (m, 2H), 6.59 (d, J=3.5 Hz, 1H), 3.66 (t, J=7.0 Hz, 1H), 2.95 (dd, J=13.6, 7.0 Hz, 1H), 2.81 (dd, J=13.6, 7.0 Hz, 1H).

(2S)-2-Amino-3-(3-hydroxyphenyl)-N-[4-(1H-pyrrolo[2,3-b]pyridin-4-yl)phenyl]propenamide, F-39

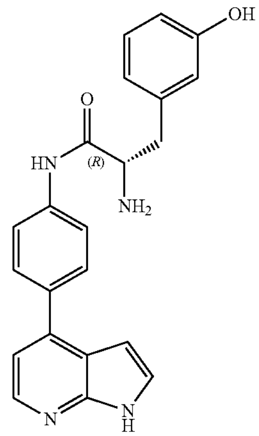

Step 1. tert-Butyl N-[(1S)-2-[4-[1-(benzenesulfonyl)pyrrolo[2,3-b]pyridin-4-yl]anilino]-1-[(3-hydroxyphenyl)methyl]-2-oxo-ethyl]carbamate, E-39. Boc-M-Tyr-OH (56 mg, 0.20 mmol) was reacted with D-1 (84 mg, 0.24 mmol) following General Procedure F. Purification by ISCO flash chromatography (20-100% EtOAc in hexanes) affords a colourless solid (120 mg, 0.20 mmol, quant.). LCMS (Method B) $t_R$=1.70 min, m/z=613.21 $[M+H]^+$.

Step 2. (2S)-2-Amino-3-(3-hydroxyphenyl)-N-[4-(1H-pyrrolo[2,3-b]pyridin-4-yl)phenyl]propenamide, F-39. Intermediate E-39 (125 mg, 0.20 mmol) was deprotected according to General Procedure K, affording title compound as a colourless solid (8 mg, 0.02 mmol, 10%). LCMS (Method A) $t_R$=1.26 min, m/z=373.16 $[M+H]^+$; Purity ≥95% (DAD, 210, 254 nm); HRMS calculated for $C_{22}H_{20}N_4O_2$=372.1586, observed 372.1557; $^1H$ NMR (400 MHz, DMSO-$d_6$) $\delta_H$ 11.76 (s, 1H), 9.29-9.24 (m, 1H), 8.26 (d, J=4.7 Hz, 1H), 7.80 (d, J=7.5 Hz, 2H), 7.75 (d, J=8.1 Hz, 2H), 7.53 (s, 1H), 7.21-7.15 (m, 1H), 7.11-7.04 (m, 1H), 6.72-6.57 (m, 4H), 3.67-3.57 (m, 1H), 3.18 (d, J=5.0 Hz, 1H), 3.01-2.93 (m, 1H), 2.76-2.63 (m, 1H).

(2R)-2-Amino-3-(3-hydroxyphenyl)-N-[4-(1H-pyrrolo[2,3-b]pyridin-4-yl)phenyl]propenamide, F-40

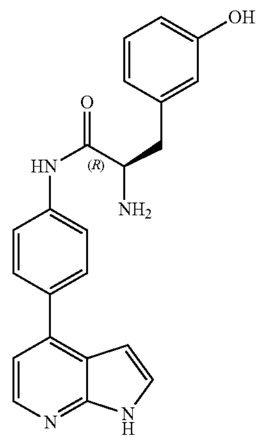

Step 1. tert-Butyl N-[(1R)-2-[4-[1-(benzenesulfonyl)pyrrolo[2,3-b]pyridin-4-yl]anilino]-1-[(3-hydroxyphenyl)

methyl]-2-oxo-ethyl]carbamate, E-40. Boc-M-D-Tyr-OH (56 mg, 0.20 mmol) was reacted with D-1 (84 mg, 0.24 mmol) following General Procedure F. Purification by ISCO flash chromatography (0-100% EtOAc in hexanes) affords a colourless solid (109 mg, 0.18 mmol, 89%). LCMS (Method B) $t_R$=1.70 min, m/z=613.21 $[M+H]^+$.

Step 2. (2R)-2-Amino-3-(3-hydroxyphenyl)-N-[4-(1H-pyrrolo[2,3-b]pyridin-4-yl)phenyl]propenamide, F-40. Intermediate E-40 (109 mg, 0.18 mmol) was deprotected according to General Procedure K, affording title compound as a colourless solid (43 mg, 0.12 mmol, 69%). LCMS (Method A) $t_R$=1.26 min, m/z=373.16 $[M+H]^+$; Purity ≥95% (DAD, 210, 254 nm); HRMS calculated for $C_{22}H_{20}N_4O_2$=372.1586, observed 372.1583; $^1$H NMR (400 MHz, MeOH-$d_4$) $\delta_H$ 8.13 (d, J=5.1 Hz, 1H), 7.65 (d, J=8.8 Hz, 2H), 7.60 (d, J=8.8 Hz, 2H), 7.34 (d, J=3.6 Hz, 1H), 7.10 (d, J=5.1 Hz, 1H), 7.03 (t, J=7.8 Hz, 1H), 6.68-6.62 (m, 2H), 6.62-6.55 (m, 2H), 3.65 (t, J=7.0 Hz, 1H), 2.97 (dd, J=13.3, 7.0 Hz, 1H), 2.78 (dd, J=13.3, 7.0 Hz, 1H).

(2R)-4-Methyl-2-(methylamino)-N-[4-(1H-pyrrolo[2,3-b]pyridin-4-yl)phenyl]pentanamide, F-41

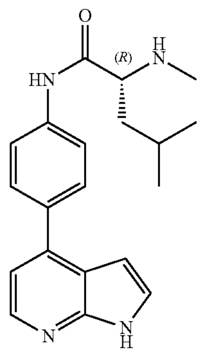

Step 1. tert-Butyl N-[(1R)-1-[[4-[1-(Benzenesulfonyl)pyrrolo[2,3-b]pyridin-4-yl]phenyl]carbamoyl]-3-methyl-butyl]-N-methyl-carbamate, F-41. Boc-N-Me-D-Leu-OH (74 mg, 0.30 mmol) was reacted with D-1 (70 mg, 0.20 mmol) following General Procedure D. Purification by ISCO flash chromatography (0-100% EtOAc in hexanes) affords a colourless gum (90 mg, 0.156 mmol, 78%). LCMS (Method B) $t_R$=2.52 min, m/z=577.25 $[M+H]^+$.

Step 2. (2R)-4-Methyl-2-(methylamino)-N-[4-(1H-pyrrolo[2,3-b]pyridin-4-yl)phenyl]pentanamide, F-41. Intermediate E-41 (90 mg, 0.16 mmol) was deprotected according to General Procedure K, affording title compound as a colourless solid (23 mg, 0.07 mmol, 44%). LCMS (Method A) $t_R$=1.36 min, m/z=337.20 $[M+H]^+$; Purity ≥95% (DAD, 210, 254 nm); HRMS calculated for $C_{20}H_{24}N_4O$=336.1950, observed 336.1957; $^1$H NMR (400 MHz, MeOH-$d_4$) δ 8.13 (d, J=5.1 Hz, 1H), 7.73-7.65 (m, 4H), 7.34 (d, J=3.6 Hz, 1H), 7.11 (d, J=5.1 Hz, 1H), 6.60 (d, J=3.6 Hz, 1H), 3.16 (t, J=7.0 Hz, 1H), 2.31 (s, 3H), 1.65 (dp, J=13.5, 7.0 Hz, 1H), 1.54 (dt, J=13.5, 7.0 Hz, 1H), 1.43 (dt, J=13.5, 7.0 Hz, 1H), 0.92 (d, J=7.0 Hz, 3H), 0.88 (d, J=7.0 Hz, 3H).

(2R)-2-(Dimethylamino)-4-methyl-N-[4-(1H-pyrrolo[2,3-b]pyridin-4-yl)phenyl]pentanamide, F-42

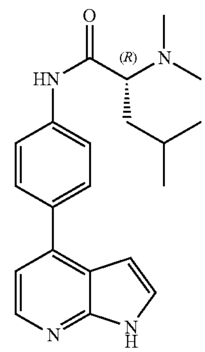

Step 1. (2R)-2-Amino-N-[4-[1-(benzenesulfonyl)pyrrolo[2,3-b]pyridin-4-yl]phenyl]-4-methyl-pentanamide, E-42-1. Intermediate E-9 (275 mg, 0.49 mmol) was dissolved in DCM (3 mL) and TFA (0.37 mL, 10 eq) was added, the mixture was stirred at r.t. for 18 h then poured into sat. aq. $NaHCO_3$ and stirred for 1 h. The solution was extracted with DCM (3×10 mL) and concentrated to afford a colourless solid (207 mg, 0.45 mmol, 91%) which was used without purification. LCMS (Method A) $t_R$=1.92 min, m/z=463.18 $[M+H]^+$.

Step 2. (2R)-N-[4-[1-(Benzenesulfonyl)pyrrolo[2,3-b]pyridin-4-yl]phenyl]-2-(dimethylamino)-4-methyl-pentanamide, E-42-2. To a solution of E-42-1 (23 mg, 0.05 mmol) in THE (0.5 mL) was added formaldehyde (37% aq., 41 μL, 0.50 mmol) and sodium triacetoxyborohydride (15 mg, 0.07 mmol), the mixture was stirred vigorously for 18 h, then diluted with EtOAc and washed with water, brine. Concentrated and purified ISCO flash chromatography (0-100% EtOAc in hexanes) affords a colourless oil (14 mg, 0.03 mmol, 57%). LCMS (Method B) $t_R$=1.10 min, m/z=491.22 $[M+H]^+$.

Step 3. (2R)-2-(Dimethylamino)-4-methyl-N-[4-(1H-pyrrolo[2,3-b]pyridin-4-yl)phenyl]pentanamide, F-42. Intermediate E-42-2 (14 mg, 0.03 mmol) was deprotected according to General Procedure J, affording title compound as a colourless solid (8 mg, 0.02 mmol, 80%). LCMS (Method A) $t_R$=1.44 min, m/z=351.22 $[M+H]^+$; Purity ≥95% (DAD, 210, 254 nm); $^1$H NMR (400 MHz, MeOH-$d_4$) δ 8.25 (d, J=5.1 Hz, 1H), 7.80 (s, 3H), 7.46 (d, J=3.6 Hz, 1H), 7.23 (d, J=5.1 Hz, 1H), 6.72 (d, J=3.6 Hz, 1H), 2.46 (s, 6H), 1.93-1.81 (m, 1H), 1.75-1.61 (m, 1H), 1.60-1.48 (m, 1H), 1.04 (d, J=6.6 Hz, 3H), 1.01 (d, J=6.6 Hz, 3H).

(2R)-2-(Ethylamino)-4-methyl-N-[4-(1H-pyrrolo[2,3-b]pyridin-4-yl)phenyl]pentanamide, F-43

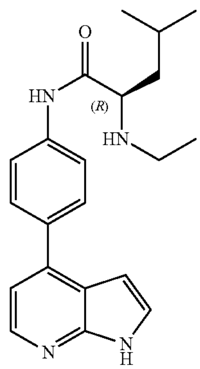

Step 1. (2S)-N-[4-[1-(Benzenesulfonyl)pyrrolo[2,3-b]pyridin-4-yl]phenyl]-2-bromo-4-methyl-pentanamide, J-1. (2S)-2-Bromo-4-methyl-pentanoic acid (293 mg, 1.5 mmol) was reacted with D-1 (349 mg, 1.0 mmol) following General Procedure E. Purification by ISCO flash chromatography (0-100% EtOAc in hexanes) affords a pale-yellow solid (496 mg, 0.94 mmol, 94%). LCMS (Method B) $t_R$=2.17 min, m/z=526.08, 528.07 $[M+H]^+$ (Bromine split clearly visible).

Step 2. (2R)-2-(Ethylamino)-4-methyl-N-[4-(1H-pyrrolo[2,3-b]pyridin-4-yl)phenyl]pentanamide, F-43. Intermediate J-1 (26 mg, 0.05 mmol) was dissolved in MeCN (0.5 mL) and potassium carbonate (35 mg, 0.25 mmol) was added, followed by ethylamine ([2.0 M in THF], 125 μL, 0.25 mmol) and the mixture heated to 60° C. for 20 h. The mixture was filtered, concentrated and redissolved in MeOH (1 mL) and NaOH (20 mg, 0.5 mmol) added, then heated to 60° C. for 30 min. The cooled mixture was filtered and purified by ACCQ-Prep HPLC; free-base obtained by SCX-II chromatography (eluting 2N $NH_3$/MeOH), then lyophilized to afford title compound as a colourless solid (11 mg, 63%). LCMS (Method A) $t_R$=1.41 min, m/z=351.24 $[M+H]^+$; Purity ≥95% (DAD, 210, 254 nm); $^1$H NMR (400 MHz, MeOH-$d_4$) δ 8.25 (d, J=5.1 Hz, 1H), 7.85-7.77 (m, 4H), 7.46 (d, J=3.5 Hz, 1H), 7.23 (d, J=5.1 Hz, 1H), 6.72 (d, J=3.5 Hz, 1H), 2.72 (q, J=7.2 Hz, 2H), 1.86-1.64 (m, 1H), 1.64-1.50 (m, 1H), 1.20 (t, J=7.2 Hz, 3H), 1.05 (d, J=6.5 Hz, 3H), 1.00 (d, J=6.5 Hz, 3H).

(2R)-2-(Cyclopropylamino)-4-methyl-N-[4-(1H-pyrrolo[2,3-b]pyridin-4-yl)phenyl]pentanamide, F-44

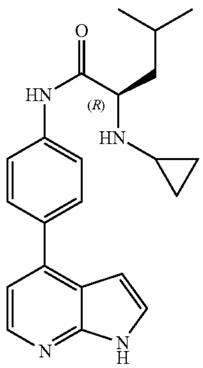

Step 1. (2R)-N-[4-[1-(Benzenesulfonyl)pyrrolo[2,3-b]pyridin-4-yl]phenyl]-2-(cyclopropylamino)-4-methyl-pentanamide, E-44. A solution of J-1 (26 mg, 0.05 mmol), cyclopropylamine (7 μL, 0.10 mmol) and potassium carbonate (14 mg, 0.10 mmol) in MeCN (0.5 mL) was heated to 60° C. for 24 h. Further cyclopropylamine (7 μL, 0.10 mmol) was added and continued at 60° C. for a further 24 h. The mixture was filtered, concentrated and purified by ISCO flash chromatography (0-100% EtOAc in hexanes) affords a colourless oil (21 mg, 0.04 mmol, 84%). LCMS (Method B) $t_R$=1.15 min, m/z=503.21 $[M+H]^+$.

Step 3. (2R)-2-(Cyclopropylamino)-4-methyl-N-[4-(1H-pyrrolo[2,3-b]pyridin-4-yl)phenyl]pentanamide, F-44. Intermediate E-44 (21 mg, 0.04 mmol) was deprotected according to General Procedure J, affording title compound as a colourless solid (10 mg, 66%). LCMS (Method A) $t_R$=1.44 min, m/z=363.24 $[M+H]^+$; Purity ≥95% (DAD, 210, 254 nm); $^1$H NMR (400 MHz, MeOH-$d_4$) δ 8.25 (d, J=5.1 Hz, 1H), 7.85-7.76 (m, 4H), 7.46 (d, J=3.6 Hz, 1H), 7.23 (d, J=5.1 Hz, 1H), 6.72 (d, J=3.6 Hz, 1H), 3.48 (t, J=7.3 Hz, 1H), 2.26-2.15 (m, 1H), 1.77 (dt, J=13.6, 6.6 Hz, 1H), 1.62 (dt, J=13.6, 7.0 Hz, 1H), 1.56-1.47 (m, 1H), 1.03 (d, J=6.6 Hz, 3H), 0.99 (d, J=6.6 Hz, 3H), 0.58-0.37 (m, 4H).

(2R)-2-(Cyclopropymethylamino)-4-methyl-N-[4-[1H-pyrrolo[2,3-b]pyridin-4-yl]phenyl]pentanamide, F-45

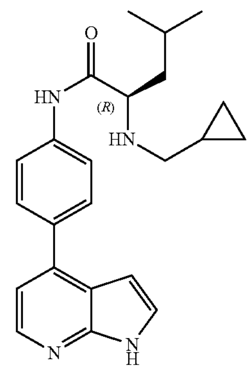

Step 1. (2R)-N-[4-[1-(Benzenesulfonyl)pyrrolo[2,3-b]pyridin-4-yl]phenyl]-2-(cyclopropylmethylamino)-4-methyl-pentanamide, E-45. A solution of J-1 (26 mg, 0.05 mmol), 2-methoxyethylamine (22 μL, 0.25 mmol) and potassium carbonate (35 mg, 0.25 mmol) in MeCN (0.5 mL) was heated to 60° C. for 24 h. The mixture was filtered, concentrated and purified by ISCO flash chromatography (0-100% EtOAc in hexanes) affords a colourless solid (21 mg, 0.04 mmol, 81%). LCMS (Method B) $t_R$=1.13 min, m/z=521.22 $[M+H]^+$.

Step 2. (2R)-2-(Cyclopropylmethylamino)-4-methyl-N-[4-(1H-pyrrolo[2,3-b]pyridin-4-yl)phenyl]pentanamide, F-45. Intermediate E-45 (21 mg, 0.041 mmol) was deprotected according to General Procedure J, affording title compound as a colourless solid (10 mg, 65%). LCMS (Method A) $t_R$=1.50 min, m/z=377.25 $[M+H]^+$; Purity ≥95% (DAD, 210, 254 nm); $^1$H NMR (400 MHz, MeOH-$d_4$) δ 8.25 (d, J=5.1 Hz, 1H), 7.80 (s, 4H), 7.46 (d, J=3.5 Hz, 1H), 7.23 (d, J=5.1 Hz, 1H), 6.72 (d, J=3.5 Hz, 1H), 3.47-3.39 (m, 2H), 2.72-2.63 (m, 1H), 2.42-2.32 (m, 1H), 1.88-1.72 (m, 1H), 1.74-1.63 (m, 1H), 1.63-1.52 (m, 1H), 1.05 (d, J=6.6 Hz, 3H), 1.01 (d, J=6.6 Hz, 3H), 0.60-0.50 (m, 2H), 0.29-0.15 (m, 2H).

(2R)-2-(2-Methoxyethylamino)-4-methyl-N-[4-(1H-pyrrolo[2,3-b]pyridin-4-yl)phenyl]pentanamide, F-46

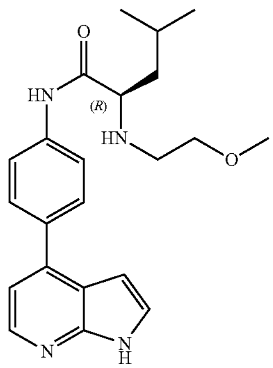

Step 1. (2R)-N-[4-[1-(Benzenesulfonyl)pyrrolo[2,3-b]pyridin-4-yl]phenyl]-2-(2-methoxyethylamino)-4-methyl-pentanamide, E-46. A solution of J-1 (26 mg, 0.05 mmol), 2-methoxyethylamine (22 μL, 0.25 mmol) and potassium carbonate (35 mg, 0.25 mmol) in MeCN (0.5 mL) was heated to 60° C. for 24 h. The mixture was filtered, concentrated and purified by ISCO flash chromatography (0-100% EtOAc in hexanes) affords a colourless solid (21 mg, 0.04 mmol, 81%). LCMS (Method B) $t_R$=1.13 min, m/z=521.22 $[M+H]^+$.

Step 2. (2R)-2-(2-Methoxyethylamino)-4-methyl-N-[4-(1H-pyrrolo[2,3-b]pyridin-4-yl)phenyl]pentanamide, F-46. Intermediate E-46 (23 mg, 0.04 mmol) was deprotected according to General Procedure J, affording title compound as a colourless solid (12 mg, 78%). LCMS (Method A) $t_R$=1.45 min, m/z=381.25 $[M+H]^+$; Purity ≥95% (DAD, 210, 254 nm); $^1$H NMR (400 MHz, MeOH-$d_4$) δ 8.25 (d, J=5.1 Hz, 1H), 7.85-7.76 (m, 4H), 7.46 (d, J=3.5 Hz, 1H), 7.23 (d, J=5.1 Hz, 1H), 6.72 (d, J=3.5 Hz, 1H), 3.59-3.49 (m, 2H), 3.39 (s, 3H), 2.84 (t, J=5.2 Hz, 2H), 1.80 (dt, J=13.4, 6.9 Hz, 1H), 1.67 (dt, J=14.1, 6.8 Hz, 1H), 1.57 (dt, J=13.6, 7.1 Hz, 1H), 1.04 (d, J=6.6 Hz, 2H), 1.01 (d, J=6.6 Hz, 2H).

(2R)-4-Methyl-N-[4-(1H-pyrrolo[2,3-b]pyridin-4-yl)phenyl]-2-(2,2,2-trifluoroethylamino)pentanamide, F-47

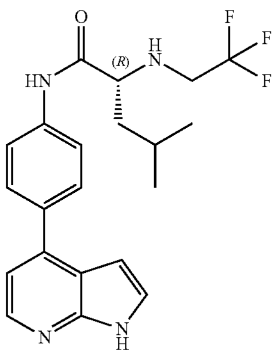

Step 1 (2R)-N-[4-[1-(Benzenesulfonyl)pyrrolo[2,3-b]pyridin-4-yl]phenyl]-4-methyl-2-(2,2,2-trifluoroethyl-amino)pentanamide, E-47. To a solution of E-42-1 (23 mg, 0.05 mmol) in THE (0.5 mL) was added 2,2,2-Trifluoroethyl trifluoromethanesulfonate (14 μL, 0.10 mol) and DIPEA (44 μL, 0.25 mmol). The mixture was heated to 65° C. for 44 h, then concentrated. Purification by ISCO flash chromatography (0-100% EtOAc in hexanes) affords a colourless gum (22 mg, 0.04 mmol, 81%). LCMS (Method B) $t_R$=2.07 min, m/z=545.18 $[M+H]^+$.

Step 2. (2R)-4-Methyl-N-[4-(1H-pyrrolo[2,3-b]pyridin-4-yl)phenyl]-2-(2,2,2-trifluoroethylamino)pentanamide, F-47. Intermediate E-47 (21 mg, 0.04 mmol) was deprotected according to General Procedure J, affording title compound as a colourless solid (9 mg, 58%). LCMS (Method A) $t_R$=1.93 min, m/z=405.19 $[M+H]^+$; Purity ≥95% (DAD, 210, 254 nm); $^1$H NMR (400 MHz, MeOH-$d_4$) δ 8.25 (d, J=5.1 Hz, 1H), 7.80 (s, 4H), 7.46 (d, J=3.6 Hz, 1H), 7.23 (d, J=5.1 Hz, 1H), 6.72 (d, J=3.6 Hz, 1H), 3.53-3.43 (m, 1H), 3.31-3.19 (m, 2H), 1.89 (dt, J=13.4, 6.6 Hz, 1H), 1.66-1.52 (m, 2H), 1.03 (d, J=4.7 Hz, 3H), 1.02 (d, J=4.7 Hz, 4H); $^{19}$F NMR (376 MHz, MeOH-$d_4$) δ −73.70.

(2R)-2-Amino-4-methyl-N-[4-[2-methyl-1H-pyrrolo[2,3-b]pyridin-4-yl]phenyl]pentanamide, F-48

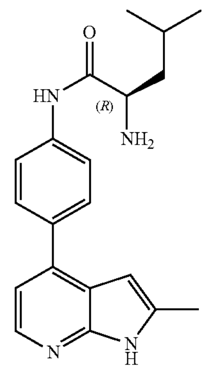

Step 1. tert-Butyl N-[(1R)-1-[[4-[1-(benzenesulfonyl)-2-methyl-pyrrolo[2,3-b]pyridin-4-yl]phenyl]carbamoyl]-3-methyl-butyl]carbamate, E-48. Boc-D-Leu-OH (69 mg, 0.30 mmol) was reacted with D-9 (73 mg, 0.20 mmol) following General Procedure E. Purification by ISCO flash chromatography (0-100% EtOAc in hexanes) affords a pale brown gum (110 mg, 0.19 mmol, 95%). LCMS (Method B) $t_R$=2.23 min, m/z=577.25 $[M+H]^+$.

Step 2. (2R)-2-Amino-4-methyl-N-[4-(2-methyl-1H-pyrrolo[2,3-b]pyridin-4-yl)phenyl]pentanamide, F-48. E-48 (110 mg, 0.19 mmol) was deprotected according to General Procedure K, affording title compound as a colourless solid (16 mg, 0.05 mmol, 25%). LCMS (Method A) $t_R$=1.40 min, m/z=337.20 $[M+H]^+$; Purity ≥95% (DAD, 210, 254 nm); HRMS calculated for $C_{20}H_{24}N_4O$=336.1950, observed 336.1951; $^1$H NMR (400 MHz, DMSO-$d_6$) δ 11.57 (s, 1H), 8.13 (d, J=5.0 Hz, 1H), 7.85-7.78 (m, 2H), 7.76-7.69 (m, 2H), 7.10 (d, J=5.0 Hz, 1H), 6.36 (d, J=1.0 Hz, 1H), 3.39 (dd, J=8.7, 5.6 Hz, 1H), 2.42 (d, J=1.0 Hz, 3H), 1.77 (dq, J=13.6, 6.7 Hz, 1H), 1.52 (ddd, J=13.6, 8.1, 5.6 Hz, 1H), 1.37 (ddd, J=13.6, 8.7, 5.9 Hz, 1H), 0.94 (d, J=6.7 Hz, 3H), 0.91 (d, J=6.7 Hz, 3H).

(2S)-2-Amino-4-methyl-N-[4-(2-methyl-1H-pyrrolo[2,3-b]pyridin-4-yl)phenyl]pentanamide, F-49

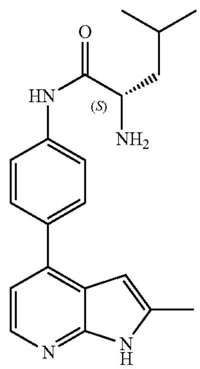

Step 1. tert-Butyl N-[(1S)-1-[[4-[1-(benzenesulfonyl)-2-methyl-pyrrolo[2,3-b]pyridin-4-yl]phenyl]carbamoyl]-3-methyl-butyl]carbamate, E-49. Boc-Leu-OH (69 mg, 0.30 mmol) was reacted with D-9 (73 mg, 0.20 mmol) following General Procedure E. Purification by ISCO flash chromatography (0-100% EtOAc in hexanes) affords an off-white solid (79 mg, 0.14 mmol, 68%). LCMS (Method B) $t_R$=2.17 min, m/z=577.26 $[M+H]^+$.

Step 2. (2S)-2-Amino-4-methyl-N-[4-(2-methyl-1H-pyrrolo[2,3-b]pyridin-4-yl)phenyl]pentanamide, F-49. Intermediate E-49 (79 mg, 0.14 mmol) was deprotected according to General Procedure K, affording title compound as a colourless solid (33 mg, 68%). LCMS (Method A) $t_R$=1.45 min, m/z=337.22 $[M+H]^+$; Purity ≥95% (DAD, 210, 254 nm); $^1$H NMR (400 MHz, MeOH-$d_4$) δ 8.12 (d, J=5.2 Hz, 1H), 7.83-7.72 (m, 4H), 7.15 (d, J=5.2 Hz, 1H), 6.40 (s, 1H), 3.56 (dd, J=8.2, 6.1 Hz, 1H), 2.52-2.48 (m, 3H), 1.88-1.76 (m, 1H), 1.73-1.64 (m, 1H), 1.59-1.49 (m, 1H), 1.04 (d, J=6.7 Hz, 3H), 1.01 (d, J=6.5 Hz, 3H).

(2R)-2-Amino-3,3-dimethyl-N-[4-(2-methyl-1H-pyrrolo[2,3-b]pyridin-4-yl)phenyl]butanamide, F-50

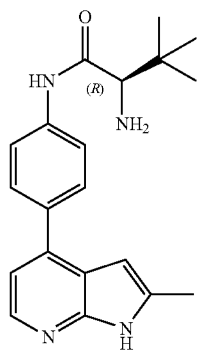

Step 1. tert-Butyl N-[(1R)-1-[[4-[1-(benzenesulfonyl)-2-methyl-pyrrolo[2,3-b]pyridin-4-yl]phenyl]carbamoyl]-2,2-dimethyl-propyl]carbamate, E-50. Boc-D-Tle-OH (69 mg, 0.30 mmol) was reacted with D-9 (73 mg, 0.20 mmol) following General Procedure E. Purification by ISCO flash chromatography (0-100% EtOAc in hexanes) affords a brown solid (110 mg, 0.19 mmol, 95%). LCMS (Method B) $t_R$=2.23 min, m/z=577.24 $[M+H]^+$.

Step 2. (2R)-2-Amino-3,3-dimethyl-N-[4-(2-methyl-1H-pyrrolo[2,3-b]pyridin-4-yl)phenyl]butanamide, F-50. Intermediate E-50 (110 mg, 0.19 mmol) was deprotected according to General Procedure K, affording title compound as a colourless solid (45 mg, 70%). LCMS (Method A) $t_R$=1.44 min, m/z=337.22 $[M+H]^+$; Purity ≥95% (DAD, 210, 254 nm); HRMS calculated for $C_{20}H_{24}N_4O$=336.1950, observed 336.1928; $^1$H NMR (400 MHz, MeOH-$d_4$) δ 8.12 (d, J=5.2 Hz, 1H), 7.76 (s, 4H), 7.15 (d, J=5.2 Hz, 1H), 6.40 (s, 1H), 3.26 (s, 1H), 2.54-2.45 (m, 3H), 1.09 (s, 9H).

(2S)-2-Amino-3,3-dimethyl-N-[4-(2-methyl-1H-pyrrolo[2,3-b]pyridin-4-yl)phenyl]butanamide, F-51

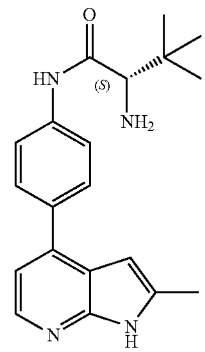

Step 1. tert-Butyl N-[(1S)-1-[[4-[1-(benzenesulfonyl)-2-methyl-pyrrolo[2,3-b]pyridin-4-yl]phenyl]carbamoyl]-2,2-dimethyl-propyl]carbamate, E-51. Boc-Tle-OH (69 mg, 0.30 mmol) was reacted with D-9 (73 mg, 0.20 mmol) following General Procedure E. Purification by ISCO flash chromatography (0-100% EtOAc in hexanes) affords an off-white solid (83 mg, 0.14 mmol, 72%). LCMS (Method B) $t_R$=2.20 min, m/z=577.26 $[M+H]^+$.

Step 2. (2S)-2-Amino-3,3-dimethyl-N-[4-(2-methyl-1H-pyrrolo[2,3-b]pyridin-4-yl)phenyl]butanamide, F-51. Intermediate E-51 (79 mg, 0.14 mmol) was deprotected according to General Procedure K, affording title compound as a colourless solid (34 mg, 74%). LCMS (Method A) $t_R$=1.40 min, m/z=337.20 $[M+H]^+$; Purity ≥95% (DAD, 210, 254 nm); $^1$H NMR (400 MHz, MeOH-$d_4$) δ 8.12 (d, J=5.2 Hz, 1H), 7.82-7.71 (m, 4H), 7.15 (d, J=5.2 Hz, 1H), 6.40 (s, 1H), 3.25 (s, 1H), 2.50 (s, 3H), 1.09 (s, 9H).

(2R)-2-Amino-4,4-dimethyl-N-[4-(2-methyl-1H-pyrrolo[2,3-b]pyridin-4-yl)phenyl]pentanamide, F-52

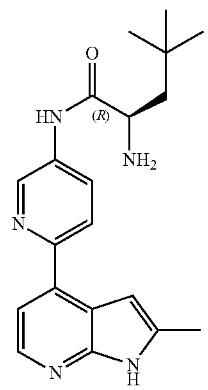

Synthesized in a manner analogous to F-48, using intermediates D-9 and Boc-D-Neo-OH. Colourless solid. LCMS (Method A) $t_R$=1.47 min, m/z=351.22 $[M+H]^+$; Purity ≥95% (DAD, 210, 254 nm); $^1$H NMR (400 MHz, MeOH-$d_4$) δ 8.12 (d, J=5.2 Hz, 1H), 7.83-7.72 (m, 4H), 7.15 (d, J=5.2 Hz, 1H), 6.40 (s, 1H), 3.56 (dd, J=7.2, 5.2 Hz, 1H), 2.50 (s, 3H), 1.98 (dd, J=13.9, 7.2 Hz, 1H), 1.49 (dd, J=13.9, 5.2 Hz, 1H), 1.04 (s, 9H).

(2R)-2-Amino-N-[4-(2-cyclopropyl-1H-pyrrolo[2,3-b]pyridin-4-yl)phenyl]-4-methyl-pentanamide, F-53

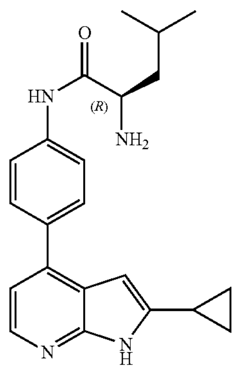

Synthesized in a manner analogous to F-48, using intermediates A-15 and G-1. Colourless solid. LCMS (Method A) $t_R$=1.53 min, m/z=363.24 $[M+H]^+$; Purity ≥95% (DAD, 210, 254 nm); $^1$H NMR (400 MHz, MeOH-$d_4$) δ 8.09 (d, J=5.2 Hz, 1H), 7.81-7.69 (m, 4H), 7.12 (d, J=5.2 Hz, 1H), 6.29 (s, 1H), 3.61-3.54 (m, 1H), 2.12-2.04 (m, 1H), 1.85-1.76 (m, 1H), 1.74-1.64 (m, 1H), 1.59-1.50 (m, 1H), 1.07-1.03 (m, 3H), 0.91-0.85 (m, 2H).

(2R)-2-Amino-N-[4-(2-cyclopropyl-1H-pyrrolo[2,3-b]pyridin-4-yl)phenyl]-3,3-dimethyl-butanamide, F-54

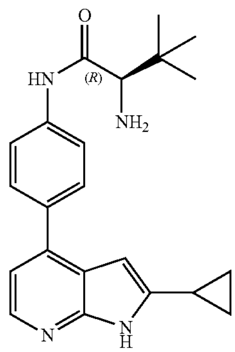

Synthesized in a manner analogous to F-48, using intermediates A-15 and G-2. Colourless solid. LCMS (Method A) $t_R$=1.46 min, m/z=363.24 $[M+H]^+$; Purity ≥95% (DAD, 210, 254 nm); $^1$H NMR (400 MHz, MeOH-$d_4$) δ 7.99 (d, J=5.2 Hz, 1H), 7.68-7.58 (m, 4H), 7.01 (d, J=5.2 Hz, 1H), 6.18 (s, 1H), 3.25 (s, 1H), 2.02-1.93 (m, 1H), 1.00 (s, 9H), 0.97-0.89 (m, 2H), 0.80-0.70 (m, 2H).

(2R)-2-Amino-4-methyl-N-[4-[2-(trifluoromethyl)-1H-pyrrolo[2,3-b]pyridin-4-yl]phenyl]pentanamide, F-55

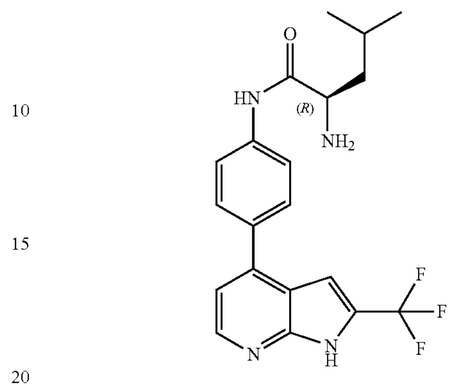

Step 1. tert-Butyl N-[(1R)-3-methyl-1-[[4-[2-(trifluoromethyl)-1H-pyrrolo[2,3-b]pyridin-4-yl]phenyl]carbamoyl]butyl]carbamate, H-55. Intermediate A-12 (219 mg, 0.70 mmol) was reacted with G-1 (180 mg, 0.47 mmol) following General Procedure A, affording a colourless solid (190 mg, 0.39 mmol, 83%). LCMS (Method D) $t_R$=1.58 min, m/z=491.24 $[M+H]^+$; $^1$H NMR (400 MHz, MeOH-$d_4$) δ 8.42 (d, J=5.0 Hz, 1H), 7.80 (d, J=8.5 Hz, 2H), 7.75 (d, J=8.5 Hz, 2H), 7.32 (d, J=5.0 Hz, 1H), 7.12-7.07 (m, 1H), 4.27 (s, 1H), 1.77 (br s, 1H), 1.70-1.60 (m, 2H), 1.47 (s, 9H), 1.02-0.99 (m, 6H); $^{19}$F NMR (376 MHz, MeOH-$d_4$) δ-62.73.

Step 2. (2R)-2-Amino-4-methyl-N-[4-[2-(trifluoromethyl)-1H-pyrrolo[2,3-b]pyridin-4-yl]phenyl]pentanamide, F-55. Intermediate H-55 was deprotected following General Procedure J. Purification by reverse-phase HPLC (5-60% MeCN in $H_2O$, 0.1% TFA) affords title compound as a colourless solid (70 mg, 46%). LCMS (Method A); $t_R$=1.67 min, m/z=391.17 $[M+H]^+$; Purity ≥95% (DAD, 210, 254 nm); $^1$H NMR (400 MHz, MeOH-$d_4$) δ 8.42 (d, J=5.0 Hz, 1H), 7.83 (d, J=8.7 Hz, 2H), 7.76 (d, J=8.7 Hz, 2H), 7.32 (d, J=5.0 Hz, 1H), 7.09 (s, 1H), 3.55 (t, J=7.2 Hz, 1H), 1.84-1.77 (m, 1H), 1.67 (dt, J=13.9, 6.8 Hz, 1H), 1.62-1.45 (m, 1H), 1.05-0.97 (m, 6H); $^{19}$F NMR (376 MHz, MeOH-$d_4$) δ −62.74.

(2R)-2-Amino-3,3-dimethyl-N-[4-[2-(trifluoromethyl)-1H-pyrrolo[2,3-b]pyridin-4-yl]phenyl]butanamide, F-56

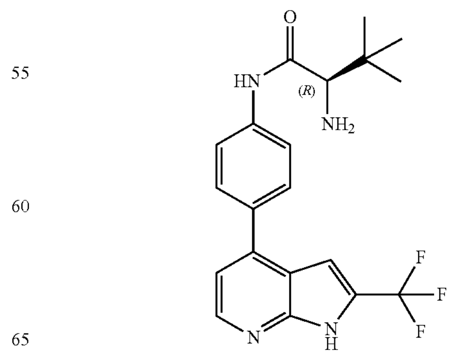

Synthesized in a manner analogous to F-55, using intermediate G-2 in Step 1. Colourless solid. LCMS (Method A) $t_R$=1.66 min, m/z=391.19 $[M+H]^+$; Purity ≥95% (DAD, 210, 254 nm); $^1H$ NMR (400 MHz, MeOH-$d_4$) δ 8.44 (d, J=5.1 Hz, 1H), 7.83 (d, J=8.8 Hz, 2H), 7.78 (d, J=8.8 Hz, 2H), 7.34 (d, J=5.1 Hz, 1H), 7.12 (d, 1H), 3.26 (s, 1H), 1.09 (s, 9H); $^{19}F$ NMR (376 MHz, MeOH-$d_4$) δ −62.74.

(2R)-2-Amino-N-[4-[2-(difluoromethyl)-1H-pyrrolo[2,3-b]pyridin-4-yl]phenyl]-4-methyl-pentanamide, F-57

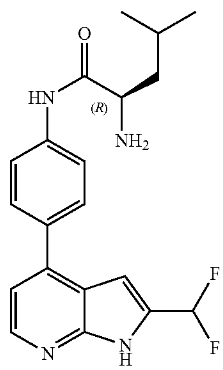

Step 1. tert-Butyl N-[(1R)-1-[[4-[1-(benzenesulfonyl)-2-(difluoromethyl)pyrrolo[2,3-b]pyridin-4-yl]phenyl]carbamoyl]-3-methyl-butyl]carbamate, E-57. Intermediates A-8 (264 mg, 0.61 mmol) and G-1 (180 mg, 0.47 mmol) were reacted following General Procedure B. Purification by ISCO flash chromatography (0-50% EtOAc in hexanes) affords a colourless solid (240 mg, 0.39 mmol, 84%). LCMS (Method B) $t_R$=2.20 min, m/z=613.23 $[M+H]^+$; $^1H$ NMR (400 MHz, $CDCl_3$) δ 8.52 (d, J=5.0 Hz, 1H), 8.37-8.28 (m, 2H), 7.68 (d, J=8.3 Hz, 2H), 7.65-7.58 (m, 1H), 7.58-7.30 (m, 6H), 7.15 (s, 1H), 4.88 (s, 1H), 4.24 (s, 1H), 1.95-1.68 (m, 2H), 1.65-1.55 (m, 1H), 1.48 (s, 9H), 0.99 (t, J=6.6 Hz, 6H); $^{19}F$ NMR (376 MHz, $CDCl_3$) δ −113.06 (d, J=54.8 Hz).

Step 2. (2R)-2-Amino-N-[4-[2-(difluoromethyl)-1H-pyrrolo[2,3-b]pyridin-4-yl]phenyl]-4-methyl-pentanamide, F-57. E-57 (240 mg, 0.39 mmol) was deprotected following General Procedure N. Purified by reverse phase HPLC (5-40% MeCN in $H_2O$, 0.1% TFA) and free base obtained by SCX-II chromatography (load/wash MeOH, elute 2N $NH_3$/MeOH), affording a colourless solid (42 mg, 0.11 mmol, 23%). LCMS (Method A) $t_R$=1.50 min, m/z=373.1849 $[M+H]^+$; Purity ≥95% (DAD, 210, 254 nm); $^1H$ NMR (400 MHz, MeOH-$d_4$) δ 8.35 (d, J=5.1 Hz, 1H), 7.81 (d, J=8.5 Hz, 2H), 7.76 (d, J=8.5 Hz, 2H), 7.27 (d, J=5.1 Hz, 1H), 7.00 (t, J=54.5 Hz, 1H), 6.96 (t, J=2.2 Hz, 1H), 3.55 (dd, J=8.1, 6.1 Hz, 1H), 1.80 (dt, J=13.9, 7.0 Hz, 1H), 1.67 (dt, J=13.9, 7.0 Hz, 1H), 1.52 (dt, J=13.9, 7.5 Hz, 1H), 1.02 (d, J=6.5 Hz, 3H), 1.00 (d, J=6.5 Hz, 3H); $^{19}F$ NMR (376 MHz, MeOH-$d_4$) δ −113.05 (d, J=54.5 Hz).

(2R)-2-Amino-4-methyl-N-[3-methyl-4-(1H-pyrrolo[2,3-b]pyridin-4-yl)phenyl]pentanamide, F-58

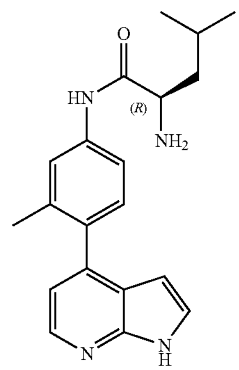

Step 1. 4-[1-(Benzenesulfonyl)pyrrolo[2,3-b]pyridin-4-yl]-3-methyl-aniline, D-58. A-3 (400 mg, 1.04 mmol) and 4-Bromo-3-methylaniline (290 mg, 1.56 mmol) were reacted according to General Procedure B at 70° C. for 18 h. Purification by ISCO flash chromatography (0-10% MeOH in DCM) to afford a beige solid (227 mg, 0.62 mmol, 60%). LCMS (Method A) $t_R$=1.47 min, m/z=364.0954 $[M+H]^+$; $^1H$ NMR (500 MHz, DMSO-$d_6$) δ 8.32 (d, J=5.0 Hz, 1H), 8.18-8.13 (m, 2H), 7.87 (d, J=4.1 Hz, 1H), 7.77-7.65 (m, 1H), 7.64 (t, J=7.8 Hz, 2H), 7.14 (d, J=5.0 Hz, 1H), 6.92 (d, J=8.2 Hz, 1H), 6.52 (d, J=3.6 Hz, 2H), 6.48 (dd, J=8.2, 2.3 Hz, 1H), 5.29 (s, 2H), 2.03 (s, 3H).

Step 2. tert-Butyl N-[(1R)-1-[[4-[1-(Benzenesulfonyl)pyrrolo[2,3-b]pyridin-4-yl]-3-methyl-phenyl]carbamoyl]-3-methyl-butyl]carbamate, E-58. D-58 (50 mg, 0.14 mmol) and Boc-D-Leu-OH (28 mg, 0.21 mmol) were reacted according to General Procedure D. Purification by ISCO flash chromatography (40-100% EtOAc in hexanes) to afford a colourless oil of JJMi92 (66 mg, 0.12 mmol, 84%). LCMS (Method B) $t_R$=2.25 min, m/z=577.2484 $[M+H]^+$; $^1H$ NMR (500 MHz, DMSO-$d_6$) δ 8.32 (d, J=5.0 Hz, 1H), 8.18-8.13 (m, 2H), 7.87 (d, J=4.1 Hz, 1H), 7.77-7.65 (m, 1H), 7.64 (t, J=7.8 Hz, 2H), 7.14 (d, J=5.0 Hz, 1H), 6.92 (d, J=8.2 Hz, 1H), 6.52 (d, J=3.6 Hz, 2H), 6.48 (dd, J=8.2, 2.3 Hz, 1H), 5.29 (s, 2H), 2.03 (s, 3H).

Step 3. (2R)-2-Amino-4-methyl-N-[3-methyl-4-(1H-pyrrolo[2,3-b]pyridin-4-yl)phenyl]pentanamide, F-58. Intermediate E-58 (80 mg, 0.14 mmol) was deprotected according to General Procedure K then purified by preparative HPLC (5-95% MeCN in H2O, 0.1% TFA). The free base was obtained after SCX-II chromatography (load/wash MeOH, elution with 2N $NH_3$ in MeOH) to afford a colourless solid (21 mg, 0.07 mmol, 47%). LCMS (Method A) $t_R$=1.38 min, m/z=309.1709 $[M+H]^+$; Purity ≥95% (DAD, 210, 254 nm); $^1H$ NMR (500 MHz, DMSO-$d_6$) δ 11.71 (s, 1H), 8.24 (d, J=4.8 Hz, 1H), 7.64 (d, J=2.2 Hz, 1H), 7.60 (dd, J=8.3, 2.2 Hz, 1H), 7.46 (t, J=2.9 Hz, 1H), 7.24 (d, J=8.3 Hz, 1H), 6.94 (d, J=4.8 Hz, 1H), 6.14 (dd, J=3.5, 1.8 Hz, 1H), 3.36 (dd, J=8.7, 5.9 Hz, 1H), 2.15 (s, 3H), 1.77 (dq, J=7.8, 6.1 Hz, 1H), 1.50 (ddd, J=13.9, 8.7, 5.9 Hz, 1H), 1.35 (ddd, J=13.9, 8.7, 5.9 Hz, 1H), 0.93 (d, J=6.6 Hz, 3H), 0.90 (d, J=6.6 Hz, 3H).

(2R)-2-Amino-3,3-dimethyl-N-[3-methyl-4-(1H-pyrrolo[2,3-b]pyridin-4-yl)phenyl]butanamide, F-59

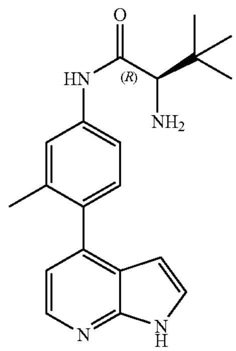

Synthesized in a manner analogous to F-58, using Boc-D-Tle-OH in Step 1. Colourless solid. LCMS (Method A) $t_R$=1.36 min, m/z=337.20 $[M+H]^+$; Purity ≥95% (DAD, 210, 254 nm); HRMS calculated for $C_{20}H_{24}N_4O$=336.1950, observed 336.1949; $^1H$ NMR (400 MHz, MeOH-$d_4$) δ 8.24 (d, J=5.0 Hz, 1H), 7.61 (d, J=2.1 Hz, 1H), 7.55 (dd, J=8.2, 2.1 Hz, 1H), 7.40 (d, J=3.5 Hz, 1H), 7.30 (d, J=8.2 Hz, 1H), 7.01 (d, J=5.0 Hz, 1H), 6.24 (d, J=3.5 Hz, 1H), 3.27 (s, 1H), 2.22 (s, 3H), 1.10 (s, 9H).

(2R)-2-Amino-4,4-dimethyl-N-[3-methyl-4-(1H-pyrrolo[2,3-b]pyridin-4-yl)phenyl]pentanamide, F-60

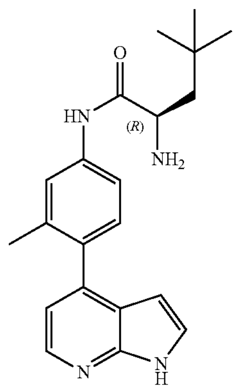

Synthesized in a manner analogous to F-58, using Boc-D-Neo-OH in Step 1. Colourless solid. LCMS (Method A) $t_R$=1.46 min, m/z=351.22 $[M+H]^+$; Purity ≥95% (DAD, 210, 254 nm); $^1H$ NMR (400 MHz, MeOH-$d_4$) δ 8.24 (d, J=5.0 Hz, 1H), 7.62 (s, 1H), 7.57 (d, J=7.8 Hz, 1H), 7.40 (d, J=3.5 Hz, 1H), 7.30 (d, J=8.3 Hz, 1H), 7.01 (d, J=5.0 Hz, 1H), 6.24 (d, J=3.5 Hz, 1H), 3.55 (t, J=7.3 Hz, 1H), 2.22 (s, 3H), 1.98 (dd, J=13.8, 7.3 Hz, 1H), 1.49 (dd, J=13.8, 5.2 Hz, 1H), 1.05 (s, 9H).

(2R)-2-Amino-4-methyl-N-[2-methyl-4-(1H-pyrrolo[2,3-b]pyridin-4-yl)phenyl]pentanamide, F-61

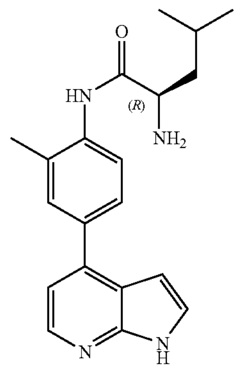

Step 1. 4-[1-(Benzenesulfonyl)pyrrolo[2,3-b]pyridin-4-yl]-2-methyl-aniline, D-61. A-3 (337 mg, 1.0 mmol) and 2-methyl-4-(4,4,5,5-tetramethyl-1,3,2-dioxaborolan-2-yl) aniline (280 mg, 1.0 mmol) were reacted according to General Procedure A at 110° C. for 3 h. Purification by ISCO flash chromatography (0-7% MeOH in DCM) to affords a cream powder (351 mg, 0.97 mmol, 97%). LCMS (Method A) $t_R$=1.90 min, m/z=364.1118 $[M+H]^+$; $^1H$ NMR (400 MHz, DMSO-$d_6$) δ 8.29 (d, J=5.1 Hz, 1H), 8.17-8.07 (m, 2H), 7.90 (d, J=4.1 Hz, 1H), 7.76-7.68 (m, 1H), 7.63 (dd, J=8.6, 7.1 Hz, 2H), 7.33-7.20 (m, 3H), 6.95 (d, J=4.1 Hz, 1H), 6.73 (d, J=8.1 Hz, 1H), 5.30 (s, 2H), 2.12 (s, 3H).

Step 2. tert-Butyl N-[(1R)-1-[[4-[1-(benzenesulfonyl)pyrrolo[2,3-b]pyridin-4-yl]-2-methyl-phenyl]carbamoyl]-3-methyl-butyl]carbamate, E-61. D-61 (55 mg, 0.15 mmol) and Boc-D-Leu-OH (52 mg, 0.22 mmol) were reacted according to General Procedure D. Purification by ISCO flash chromatography (20-100% EtOAc in hexanes) affords a tan powder (66 mg, 0.11 mmol, 76%). LCMS (Method B) $t_R$=2.19 min, m/z=577.2490 $[M+H]^+$.

Step 3. (2R)-2-Amino-4-methyl-N-[2-methyl-4-(1H-pyrrolo[2,3-b]pyridin-4-yl)phenyl]pentanamide, F-61. Intermediate E-61 (55 mg, 0.10 mmol) was deprotected according to General Procedure K, affording the title compound as a colourless solid (20 mg, 0.06 mmol, 62%). LCMS (Method A) $t_R$=1.37 min, m/z=337.2025 $[M+H]^+$; Purity ≥95% (DAD, 210, 254 nm); $^1H$ NMR (400 MHz, MeOH-$d_4$) δ 8.13 (d, J=5.1 Hz, 1H), 7.66 (d, J=8.2 Hz, 1H), 7.56 (s, 1H), 7.52 (dd, J=8.2, 2.1 Hz, 1H), 7.34 (d, J=3.6 Hz, 1H), 7.10 (d, J=5.1 Hz, 1H), 6.58 (d, J=3.6 Hz, 1H), 3.52 (dd, J=8.6, 5.6 Hz, 1H), 2.30 (s, 3H), 1.75 (dq, J=13.2, 6.7 Hz, 1H), 1.63 (ddd, J=13.9, 8.2, 6.0 Hz, 1H), 1.45 (ddd, J=13.9, 8.2, 6.0 Hz, 1H), 0.95 (d, J=6.7 Hz, 3H), 0.92 (d, J=6.7 Hz, 3H).

(2R)-2-Amino-N-[3-ethyl-4-(1H-pyrrolo[2,3-b]pyridin-4-yl)phenyl]-4-methyl-pentanamide, F-62

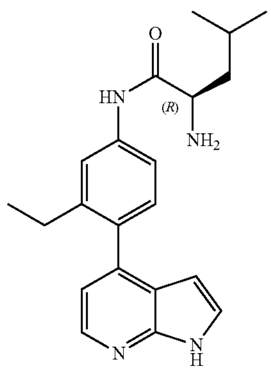

Step 1. 4-[1-(Benzenesulfonyl)pyrrolo[2,3-b]pyridin-4-yl]-3-ethyl-aniline, D-62. 4-bromo-3-ethyl-aniline (240 mg, 1.20 mmol) and A-3 (384 mg, 1 mmol) were reacted according to General Procedure B for 18 h. Purification by ISCO flash chromatography (1-10% MeOH in DCM) to afford a brown powder (300 mg, 0.71 mmol, 72%). LCMS (Method A) $t_R$=1.86 min, m/z=378.1286 $[M+H]^+$; $^1H$ NMR (400 MHz, DMSO-$d_6$) δ 8.34 (d, J=5.0 Hz, 1H), 8.16 (d, J=7.1 Hz, 2H), 7.87 (d, J=4.1 Hz, 1H), 7.75 (dd, J=8.6, 6.3 Hz, 1H), 7.65 (dd, J=8.6, 7.0 Hz, 2H), 7.13 (d, J=5.0 Hz, 1H), 6.87 (d, J=8.2 Hz, 1H), 6.58 (d, J=2.3 Hz, 1H), 6.52-6.45 (m, 2H), 5.28 (s, 2H), 2.35 (q, J=7.5 Hz, 2H), 0.91 (t, J=7.5 Hz, 3H).

Step 2. tert-Butyl N-[(1R)-1-[[4-[1-(benzenesulfonyl)pyrrolo[2,3-b]pyridin-4-yl]-3-ethyl-phenyl]carbamoyl]-3-methyl-butyl]carbamate, E-62. D-62 (94 mg, 0.25 mmol) was reacted with Boc-D-Leu-OH (115 mg, 0.5 mmol) according to General Procedure E. Purification by ISCO flash chromatography (0-100% EtOAc in hexanes) to afford a cream powder (140 mg, 0.24 mmol, 95%). LCMS (Method B) $t_R$=2.27 min, m/z=591.2662 $[M+H]^+$.

Step 3. (2R)-2-Amino-N-[3-ethyl-4-(1H-pyrrolo[2,3-b]pyridin-4-yl)phenyl]-4-methyl-pentanamide, F-62. Intermediate E-62 (140 mg, 0.24 mmol) was deprotected according to General Procedure K, affording the title compound as a colourless solid (42 mg, 0.12 mmol, 51%). LCMS (Method A) $t_R$=1.45 min, m/z=351.2040 $[M+H]^+$; Purity ≥95% (DAD, 210, 254 nm); $^1H$ NMR (400 MHz, MeOH-$d_4$) δ 8.22 (d, J=5.0 Hz, 1H), 7.65 (d, J=2.2 Hz, 1H), 7.55 (dd, J=8.3, 2.2 Hz, 1H), 7.37 (d, J=3.5 Hz, 1H), 7.23 (d, J=8.3 Hz, 1H), 6.99 (d, J=5.0 Hz, 1H), 6.19 (d, J=3.5 Hz, 1H), 3.56 (dd, J=8.2, 6.2 Hz, 1H), 2.55 (q, J=7.6 Hz, 2H), 1.79 (dq, J=13.2, 6.6 Hz, 1H), 1.68 (ddd, J=13.9, 7.8, 6.2 Hz, 1H), 1.54 (ddd, J=13.9, 8.2, 6.2 Hz, 1H), 1.04-0.99 (m, 9H).

(2S)-2-Amino-N-[3-ethyl-4-(1H-pyrrolo[2,3-b]pyridin-4-yl)phenyl]-4-methyl-pentanamide, F-63

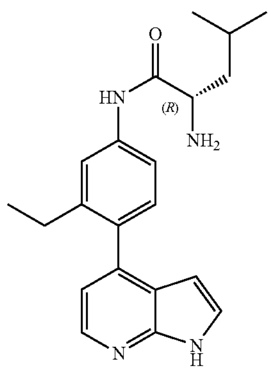

Synthesized in a manner analogous to F-62, using Boc-Leu-OH in Step 1. Colourless solid. LCMS (Method A) $t_R$=1.45 min, m/z=351.2036 $[M+H]^+$; Purity ≥95% (DAD, 210, 254 nm); $^1H$ NMR (400 MHz, MeOH-$d_4$) δ 8.22 (d, J=5.0 Hz, 1H), 7.65 (d, J=2.2 Hz, 1H), 7.55 (dd, J=8.3, 2.2 Hz, 1H), 7.37 (d, J=3.5 Hz, 1H), 7.23 (d, J=8.3 Hz, 1H), 6.99 (d, J=4.9 Hz, 1H), 6.19 (d, J=3.5 Hz, 1H), 3.61 (dd, J=8.2, 6.1 Hz, 1H), 2.55 (q, J=7.6 Hz, 2H), 1.84-1.76 (m, 1H), 1.75-1.66 (m, 1H), 1.61-1.53 (m, 1H), 1.05-0.99 (m, 9H).

(2R)-2-Amino-N-[3,5-dimethyl-4-(1H-pyrrolo[2,3-b]pyridin-4-yl)phenyl]-4-methyl-Pentanamide, F-64

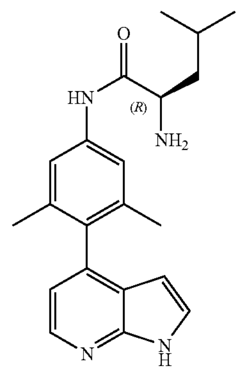

Step 1. tert-Butyl N-[(1R)-1-[(4-bromo-3,5-dimethyl-phenyl)carbamoyl]-3-methyl-butyl]carbamate, G-64. 4-Bromo-3,5-dimethylaniline (180 mg, 0.90 mmol) and Boc-D-Leu-OH (312 mg, 1.35 mmol) were reacted following General Procedure E, affording an off-white powder (362 mg, 0.88 mmol, 97%). LCMS (Method A) $t_R$=2.23 min, m/z=437.1257 $[M+Na]^+$; $^1H$ NMR (400 MHz, MeOH-$d_4$) δ 7.35 (s, 2H), 4.21 (dd, J=9.6, 5.4 Hz, 1H), 2.36 (s, 6H), 1.81-1.68 (m, 1H), 1.66-1.51 (m, 2H), 1.45 (s, 9H), 1.00-0.94 (m, 6H).

Step 2. tert-Butyl N-[(1R)-1-[[4-[1-(benzenesulfonyl)pyrrolo[2,3-b]pyridin-4-yl]-3,5-dimethyl-phenyl]carbamoyl]-3-methyl-butyl]carbamate, E-64. G-64 (193 mg, 0.47 mmol) and A-3 (150 mg, 0.39 mmol) were reacted according to General Procedure B for 18 h. Purification by ISCO flash chromatography (10-80% EtOAc in hexanes) to afford a cream powder (215 mg, 0.36 mmol, 93%). LCMS (Method B) $t_R$=2.20 min, m/z=591.2662 $[M+H]^+$.

Step 3. (2R)-2-Amino-N-[3,5-dimethyl-4-(1H-pyrrolo[2,3-b]pyridin-4-yl)phenyl]-4-methyl-pentanamide, F-64. Intermediate E-64 (210 mg, 0.35 mmol) was deprotected according to General Procedure K, affording the title compound as a colourless solid (69 mg, 0.20 mmol, 55%). LCMS (Method A) $t_R$=1.48 min, m/z=365.2346 $[M+H]^+$; Purity ≥95% (DAD, 210, 254 nm); $^1H$ NMR (400 MHz, MeOH-$d_4$) δ 8.26 (d, J=5.0 Hz, 1H), 7.43 (d, J=3.1 Hz, 2H), 7.38 (d, J=3.5 Hz, 1H), 6.91 (d, J=4.9 Hz, 1H), 6.07 (d, J=3.5 Hz, 1H), 3.64 (t, J=7.2 Hz, 1H), 1.99 (s, 6H), 1.87-1.77 (m, 1H), 1.72 (dt, J=13.8, 6.7 Hz, 1H), 1.59 (dt, J=13.9, 7.3 Hz, 1H), 1.08-1.00 (m, 6H).

(2R)-2-Amino-N-[3-fluoro-4-(1H-pyrrolo[2,3-b]pyridin-4-yl)phenyl]-4-methyl-Pentanamide, F-65

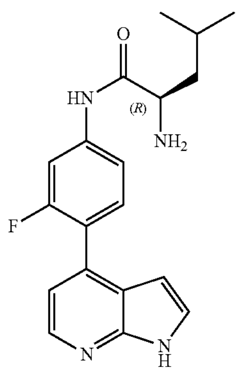

Step 1. 4-[1-(Benzenesulfonyl)pyrrolo[2,3-b]pyridin-4-yl]-3-fluoro-aniline, D-65. A-2 (675 g, 2 mmol) was reacted with 4-amino-2-fluorophenylboronic acid pinacol ester (569 mg, 2.4 mmol) following General Procedure A. Purification by ISCO flash column chromatography (20-80% EtOAc in hexanes) to afford a pale cream solid (690 mg, 1.88 mmol, 94%). LCMS (Method B) $t_R$=1.15 min, m/z=368.1 $[M+H]^+$.

Step 2. 9H-Fluoren-9-ylmethyl N-[(1R)-1-[[4-[1-(benzenesulfonyl)pyrrolo[2,3-b]pyridin-4-yl]-3-fluoro-phenyl]carbamoyl]-3-methyl-butyl]carbamate, E-65. Fmoc-D-Leu-OH (85 mg, 0.24 mmol) was reacted with D-65 (70 mg, 0.20 mmol) following General Procedure H. Purification by ISCO flash chromatography (0-100% EtOAc in hexanes) affords a pale brown solid (121 mg, 0.17 mmol, 86%). LCMS (Method B) $t_R$=2.52 min, m/z=703.25 $[M+H]^+$.

Step 3. (2R)-2-Amino-N-[3-fluoro-4-(1H-pyrrolo[2,3-b]pyridin-4-yl)phenyl]-4-methyl-pentanamide, F-65. Intermediate E-65 (121 mg, 0.17 mmol) was deprotected according to General Procedure L, affording title compound as a colourless solid (16 mg, 27%). LCMS (Method A) $t_R$=1.39 min, m/z=314.19 $[M+H]^+$; Purity ≥95% (DAD, 210, 254 nm); $^1$H NMR (400 MHz, MeOH-$d_4$) δ 8.25 (d, J=5.1 Hz, 1H), 7.81 (dd, J=12.7, 2.1 Hz, 1H), 7.62 (t, J=8.3 Hz, 1H), 7.49 (dd, J=8.4, 2.1 Hz, 1H), 7.45 (d, J=3.5 Hz, 1H), 7.19 (dd, J=5.1, 1.6 Hz, 1H), 6.48 (dd, J=3.6, 2.1 Hz, 1H), 3.55 (dd, J=8.3, 6.0 Hz, 1H), 1.87-1.76 (m, 1H), 1.73-1.62 (m, 1H), 1.59-1.43 (m, 1H), 1.02 (t, J=6.9 Hz, 6H); $^{19}$F NMR (376 MHz, MeOH-$d_4$) δ-114.96.

(2R)-2-Amino-N-[3-fluoro-4-(1H-pyrrolo[2,3-b]pyridin-4-yl)phenyl]-3,3-dimethyl-butanamide, F-66

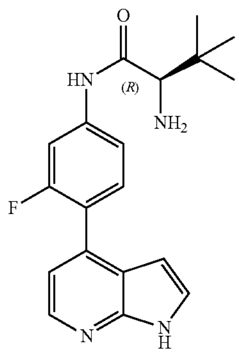

Synthesized via a route analogous to that used to make F-65, reacting Fmoc-D-Tle-OH with D-65. After deprotection, title compound obtained as a colourless solid. LCMS (Method A) $t_R$=1.38 min, m/z=341.19 $[M+H]^+$; Purity ≥95% (DAD, 210, 254 nm); $^1$H NMR (400 MHz, MeOH-$d_4$) δ 8.25 (d, J=5.1 Hz, 1H), 7.79 (d, J=12.8 Hz, 1H), 7.62 (t, J=8.3 Hz, 1H), 7.50-7.42 (m, 1H), 7.19 (d, J=5.0 Hz, 1H), 6.49 (s, 1H), 3.23 (s, 1H), 1.09 (s, 9H); $^{19}$F NMR (376 MHz, MeOH-$d_4$) δ −114.96.

(2R)-2-Amino-N-[3-methoxy-4-(1H-pyrrolo[2,3-b]pyridin-4-yl)phenyl]-4-methyl-pentanamide, F-67

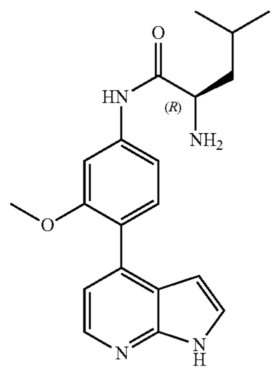

Step 1. 4-[1-(Benzenesulfonyl)pyrrolo[2,3-b]pyridin-4-yl]-3-methoxy-aniline, D-67. A-2 (168 mg, 0.50 mmol) and 3-methoxy-4-(4,4,5,5-tetramethyl-1,3,2-dioxaborolan-2-yl)aniline (150 mg, 0.60 mmol) were reacted according to General Procedure A at 110° C. for 2 h. Purification by ISCO flash chromatography (20-100% EtOAc in hexanes) to afford a brown gum (175 mg, 0.46 mmol, 92%). LCMS (Method A) $t_R$=1.52 min, m/z=380.0901 $[M+H]^+$.

Step 2. tert-Butyl N-[(1R)-1-[[4-[1-(benzenesulfonyl)pyrrolo[2,3-b]pyridin-4-yl]-3-methoxy-phenyl]carbamoyl]-3-methyl-butyl]carbamate, E-67. D-67 (50 mg, 0.13 mmol) and Boc-D-Leu-OH (46 mg, 0.20 mmol) were reacted according to General Procedure D. Purification by ISCO flash chromatography (40-100% EtOAc in hexanes) to afford a colourless oil (65 mg, 0.11 mmol, 83%). LCMS (Method B) $t_R$=2.13 min, m/z=593.2431 $[M+H]^+$; $^1$H NMR (500 MHz, DMSO-$d_6$) δ 10.17 (s, 1H), 8.36 (d, J=5.1 Hz, 1H), 7.88 (d, J=4.1 Hz, 1H), 7.74 (t, J=7.5 Hz, 1H), 7.64 (t, J=7.8 Hz, 2H), 7.52 (d, J=1.9 Hz, 1H), 7.37 (dd, J=8.4, 1.9 Hz, 1H), 7.30-7.24 (m, 2H), 7.08 (d, J=7.9 Hz, 1H), 6.59 (d, J=4.1 Hz, 1H), 4.14 (d, J=8.7 Hz, 1H), 3.71 (s, 3H), 1.66 (dt, J=13.5, 7.1 Hz, 1H), 1.54 (ddd, J=15.1, 10.1, 5.5 Hz, 1H), 1.48-1.40 (m, 1H), 1.39 (s, 9H), 0.93-0.88 m, 6H).

Step 3. (2R)-2-Amino-N-[3-methoxy-4-(1H-pyrrolo[2,3-b]pyridin-4-yl)phenyl]-4-methyl-pentanamide, F-67. Intermediate E-67 (60 mg, 0.10 mmol) was deprotected according to General Procedure K then purified by preparative HPLC (10-100% MeCN in H2O, 0.1% TFA). The free base was obtained after SCX-II chromatography (load/wash MeOH, elution with 2N $NH_3$ in MeOH) to afford the title compound as a colourless solid (21 mg, 0.07 mmol, 47%). LCMS (Method A) $t_R$=1.36 min, m/z=353.1972 $[M+H]^+$; Purity ≥95% (DAD, 210, 254 nm); H NMR (500 MHz, DMSO-$d_6$) δ 11.60 (s, 1H), 8.19 (d, J=4.9 Hz, 1H), 7.59 (d, J=1.9 Hz, 1H), 7.42 (t, J=3.0 Hz, 1H), 7.39 (dd, J=8.2, 1.9 Hz, 1H), 7.34 (d, J=8.2 Hz, 1H), 7.04 (d, J=4.9 Hz, 1H), 6.25 (dd, J=3.5, 1.9 Hz, 1H), 3.73 (s, 3H), 3.37 (dd, J=8.8, 5.5 Hz, 1H), 1.82-1.72 (m, 1H), 1.55-1.48 (m, 1H), 1.39-1.33 (m, 1H), 0.93 (d, J=6.5 Hz, 3H), 0.91 (d, J=6.5 Hz, 3H).

(2R)-2-Amino-N-[3-chloro-4-(1H-pyrrolo[2,3-b]pyridin-4-yl)phenyl]-4-methyl-pentanamide, F-68

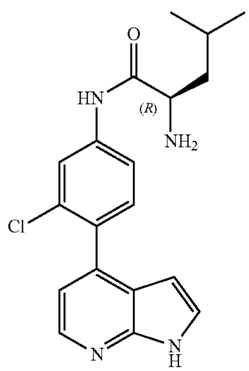

Step 1. 4-[1-(Benzenesulfonyl)pyrrolo[2,3-b]pyridin-4-yl]-3-chloro-aniline, D-68. A-2 (168 mg, 0.50 mmol) and 3-chloro-4-(4,4,5,5-tetramethyl-1,3,2-dioxaborolan-2-yl) aniline (152 mg, 0.60 mmol) were reacted according to General Procedure A at 110° C. for 2 h. Purification by ISCO flash chromatography (20-100% EtOAc in hexanes) to afford a brown gum (162 mg, 0.42 mmol, 84%). LCMS (Method A) $t_R$=1.84 min, m/z=384.0398 $[M+H]^+$.

Step 2. tert-butyl N-[(1R)-1-[[4-[1-(benzenesulfonyl)pyrrolo[2,3-b]pyridin-4-yl]-3-chloro-phenyl]carbamoyl]-3-methyl-butyl]carbamate, E-68. D-68 (50 mg, 0.13 mmol) and Boc-D-Leu-OH (45 mg, 0.20 mmol) were reacted according to General Procedure D. Purification by ISCO flash chromatography (40-100% EtOAc in hexanes) to afford a cream powder (52 mg, 0.09 mmol, 67%). LCMS (Method B) $t_R$=2.30 min, m/z=597.1938 $[M+H]^+$; $^1$H NMR (500 MHz, DMSO-$d_6$) δ 10.34 (s, 1H), 8.44 (d, J=5.0 Hz, 1H), 8.17 (dd, J=7.5, 1.8 Hz, 2H), 8.01 (d, J=2.1 Hz, 1H), 7.96 (d, J=4.1 Hz, 1H), 7.75 (t, J=7.4 Hz, 1H), 7.67-7.62 (m, 3H), 7.42 (d, J=8.4 Hz, 1H), 7.30 (d, J=5.0 Hz, 1H), 7.14 (d, J=7.7 Hz, 1H), 6.57 (d, J=4.1 Hz, 1H), 4.16-4.08 (m, 1H), 1.69-1.61 (m, 1H), 1.59-1.50 (m, 1H), 1.46-1.41 (m, 1H), 1.39 (s, 9H), 0.97-0.87 (m, 6H).

Step 3. (2R)-2-Amino-N-[3-chloro-4-(1H-pyrrolo[2,3-b]pyridin-4-yl)phenyl]-4-methyl-pentanamide, F-68. Intermediate E-68 (45 mg, 0.7 mmol) was deprotected according to General Procedure K then purified by preparative HPLC (10-100% MeCN in H2O, 0.1% TFA). The free base was obtained after SCX-II chromatography (load/wash MeOH, elution with 2N $NH_3$ in MeOH) to afford the title compound as a colourless solid (7 mg, 0.02 mmol, 26%). LCMS (Method A) $t_R$=1.41 min, m/z=357.1479 $[M+H]^+$; Purity ≥95% (DAD, 210, 254 nm); $^1$H NMR (500 MHz, DMSO-$d_6$) δ 11.77 (s, 1H), 8.27 (d, J=4.9 Hz, 1H), 8.05 (d, J=2.0 Hz, 1H), 7.68 (dd, J=8.4, 2.1 Hz, 1H), 7.50 (t, J=3.0 Hz, 1H), 7.46 (d, J=8.4 Hz, 1H), 7.04 (d, J=4.9 Hz, 1H), 6.20 (dd, J=3.5, 1.8 Hz, 1H), 3.42 (dd, J=8.7, 5.7 Hz, 1H), 1.82-1.71 (m, 1H), 1.57-1.48 (m, 1H), 1.43-1.34 (m, 1H), 0.99-0.88 (m, 6H).

(2S)-2-Amino-N-[3-chloro-4-(1H-pyrrolo[2,3-b]pyridin-4-yl)phenyl]-4-methyl-pentanamide, F-69

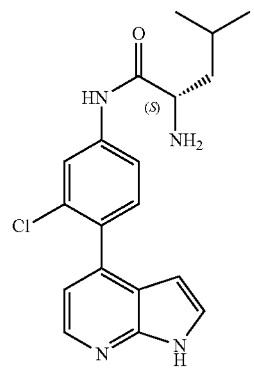

Synthesized via a route analogous to that used to make F-68, reacting Boc-Leu-OH with D-68. Colourless solid (13 mg, 0.04 mmol, 38%). LCMS (Method A) $t_R$=1.41 min, m/z=357.1481 $[M+H]^+$; Purity ≥95% (DAD, 210, 254 nm); $^1$H NMR (500 MHz, DMSO-$d_6$) δ 11.87 (s, 1H), 10.89 (s, 1H), 8.36-8.26 (m, 4H), 7.99 (d, J=2.1 Hz, 1H), 7.67-7.64 (m, 1H), 7.56-7.50 (m, 2H), 7.12-7.05 (m, 1H), 6.23-6.21 (m, 1H), 4.01-3.95 (m, 1H), 1.75-1.66 (m, 3H), 0.97-0.93 (m, 6H).

(2R)-2-Amino-N-[2-fluoro-4-(1H-pyrrolo[2,3-b]pyridin-4-yl)phenyl]-4-methyl-Pentanamide, F-70

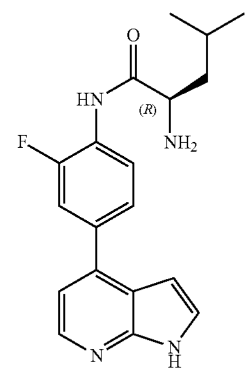

Step 1. tert-Buty N-[(1)-1-[[1-(benzenesulfonyl)pyrrolo[2,3-b]pyridin-4-yl]-2-fluoro-phenyl]carbamoyl]-3-methyl-butyl]carbamate, E-70. D-3 (50 mg, 0.14 mmol) and Boc-D-Leu-OH (47 mg, 0.20 mmol) were reacted according to General Procedure E. Purification by ISCO flash chromatography (40-100% EtOAc in hexanes) to afford a colourless oil (32 mg, 0.06 mmol, 41%). LCMS (Method B) $t_R$=2.28 min, m/z=581.2 $[M+H]^+$.

Step 2: (2R)-2-Amino-N-[2-fluoro-4-(1H-pyrrolo[2,3-b]pyridin-4-yl)phenyl]-4-methyl-pentanamide, F-70. Intermediate E-70 (31 mg, 0.04 mmol) was deprotected according to General Procedure K. Title compound as a colourless solid (4 mg, 0.01 mmol, 28%). LCMS (Method A) $t_R$=1.35 min, m/z=341.1774 $[M+H]^+$; Purity ≥95% (DAD, 210, 254 nm); $^1$H NMR (400 MHz, DMSO-$d_6$) δ 11.82 (s, 1H), 8.35-8.25 (m, 2H), 7.74-7.64 (m, 2H), 7.61-7.53 (m, 1H), 7.29-7.18 (m, 1H), 6.66 (dd, J=3.5, 1.8 Hz, 1H), 3.48 (dd, J=9.3, 4.8

Hz, 1H), 1.81 (ddt, J=15.5, 13.1, 6.6 Hz, 1H), 1.59 (ddd, J=13.6, 8.8, 4.8 Hz, 1H), 1.46-1.32 (m, 1H), 1.00-0.88 (m, 6H).

(2R)-2-Amino-N-[2-fluoro-4-(1H-pyrrolo[2,3-b]pyridin-4-yl)phenyl]-3,3-dimethyl-butanamide, F-71

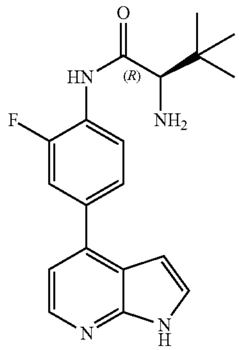

Synthesized via a route analogous to that used to make F-65, reacting Fmoc-D-Tle-OH with D-3. Colourless solid. LCMS (Method A) $t_R$=1.34 min, m/z=341.19 $[M+H]^+$; Purity ≥95% (DAD, 210, 254 nm); $^1$H NMR (400 MHz, MeOH-$d_4$) δ 8.27 (d, J=5.1 Hz, 1H), 8.14 (t, J=8.3 Hz, 1H), 7.64 (s, 1H), 7.63-7.60 (m, 1H), 7.49 (d, J=3.5 Hz, 1H), 7.24 (d, J=5.1 Hz, 1H), 6.72 (d, J=3.6 Hz, 1H), 3.36 (s, 1H), 1.11 (s, 9H); $^{19}$F NMR (376 MHz, MeOH-$d_4$) δ-127.13.

(2R)-2-Amino-N-[2-fluoro-3-methyl-4-(1H-pyrrolo[2,3-b]pyridin-4-yl)phenyl]-4-methyl-pentanamide, F-72

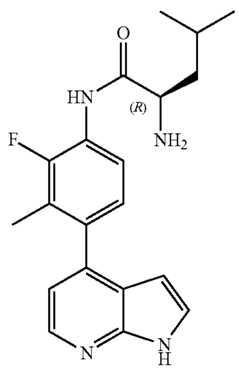

Synthesized via a route analogous to that used to make F-65, using 4-bromo-2-fluoro-3-methyl-aniline as the Step 1 Suzuki coupling partner. After deprotection, title compound obtained as a colourless solid (35 mg, 55%). LCMS (Method A) $t_R$=1.40 min, m/z=355.21 $[M+H]^+$; Purity ≥95% (DAD, 210, 254 nm); $^1$H NMR (400 MHz, MeOH-$d_4$) δ 8.27 (d, J=5.0 Hz, 1H), 8.00 (t, J=8.1 Hz, 1H), 7.43 (d, J=3.5 Hz, 1H), 7.17 (dd, J=8.4, 1.5 Hz, 1H), 7.03 (d, J=5.0 Hz, 1H), 6.25 (d, J=3.5 Hz, 1H), 3.62 (dd, J=8.6, 5.5 Hz, 1H), 2.16 (d, J=2.8 Hz, 3H), 1.92-1.80 (m, 1H), 1.77-1.68 (m, 1H), 1.59-1.49 (m, 1H), 1.04 (d, J=6.7 Hz, 3H), 1.02 (d, J=6.7 Hz, 3H); $^{19}$F NMR (376 MHz, MeOD) δ −131.45.

(2R)-2-Amino-N-[2-fluoro-5-methyl-4-(1H-pyrrolo[2,3-b]pyridin-4-yl)phenyl]-4-methyl-pentanamide, F-73

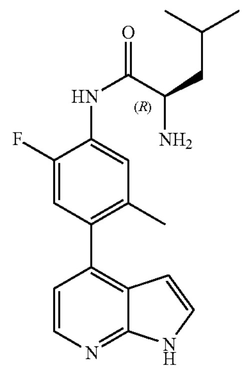

Step 1. tert-Butyl N-[(1R)-1-[(4-bromo-2-fluoro-5-methyl-phenyl)carbamoyl]-3-methyl-butyl]carbamate, G-73. Boc-D-Leu-OH (347 mg, 1.5 mmol) was reacted with 4-bromo-2-fluoro-5-methyl-aniline (204 mg, 1.0 mmol) following General Procedure D. Purification by ISCO flash chromatography (0-50% EtOAc in hexanes) affords a colourless gum (269 mg, 0.64 mmol, 64%). LCMS (Method B) $t_R$=2.17 min, m/z=439.10, 441.10 $[M+Na]^+$.

Step 2. tert-Butyl N-[(1R)-1-[[4-[1-(benzenesulfonyl)pyrrolo[2,3-b]pyridin-4-yl]-2-fluoro-5-methyl-phenyl]carbamoyl]-3-methyl-butyl]carbamate, E-73. Intermediate G-73 (150 mg, 0.36 mmol) was reacted with A-3 (115 mg, 0.30 mmol) following General Procedure A, affording title compound as a straw coloured gum (115 mg, 0.19 mmol, 64%). LCMS (Method B) $t_R$=2.25 min, m/z=595.24 $[M+H]^+$.

Step 3. (2R)-2-Amino-N-[2-fluoro-5-methyl-4-(1H-pyrrolo[2,3-b]pyridin-4-yl)phenyl]-4-methyl-pentanamide, F-73. Intermediate E-73 (114 mg, 0.19 mmol) was deprotected following General Procedure K, affording title compound as a colourless solid (7 mg, 0.02 mmol, 10%). LCMS (Method A) $t_R$=1.40 min, m/z=355.19 $[M+H]^+$; Purity ≥95% (DAD, 210, 254 nm); $^1$H NMR (400 MHz, MeOH-$d_4$) δ 8.26 (d, J=5.0 Hz, 1H), 8.03 (d, J=7.9 Hz, 1H), 7.44 (d, J=3.5 Hz, 1H), 7.16 (d, J=11.1 Hz, 1H), 7.03 (d, J=5.0 Hz, 1H), 6.26 (d, J=3.5 Hz, 1H), 3.71-3.61 (m, 1H), 2.19 (s, 3H), 1.91-1.80 (m, 1H), 1.78-1.68 (m, 1H), 1.63-1.51 (m, 1H), 1.05 (d, J=6.6 Hz, 3H), 1.03 (d, J=6.4 Hz, 3H); $^{19}$F NMR (376 MHz, MeOH-$d_4$) δ −133.35.

(2R)-2-Amino-N-[2-fluoro-5-methyl-4-(1H-pyrrolo[2,3-b]pyridin-4-yl)phenyl]-3,3-dimethyl-butanamide, F-74

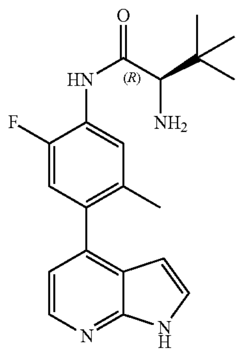

Synthesized via a route analogous to that used to make F-73, using Boc-D-Tle-OH as the Step 1 amide coupling partner. Affords title compound as a colourless solid (23 mg, 71%). LCMS (Method A) $t_R$=1.39 min, m/z=355.19 $[M+H]^+$; Purity ≥95% (DAD, 210, 254 nm); $^1H$ NMR (400 MHz, MeOH-$d_4$) δ 8.26 (d, J=5.0 Hz, 1H), 7.91 (d, J=7.8 Hz, 1H), 7.44 (d, J=3.5 Hz, 1H), 7.15 (d, J=11.1 Hz, 1H), 7.03 (d, J=5.0 Hz, 1H), 6.26 (d, J=3.5 Hz, 1H), 3.35 (s, 1H), 2.19 (s, 3H), 1.11 (s, 9H); $^{19}F$ NMR (376 MHz, MeOH-$d_4$) δ −131.83.

(2R)-2-Amino-N-[2-chloro-4-(1H-pyrrolo[2,3-b]pyridin-4-yl)phenyl]-4-methyl-Pentanamide, F-75

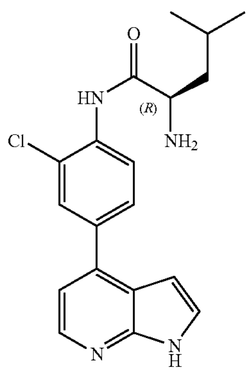

Step 1. 4-[1-(Benzenesulfonyl)pyrrolo[2,3-b]pyridin-4-yl]-2-chloro-aniline, D-75. A-2 (168 mg, 0.5 mmol) was reacted with 4-amino-3-chlorophenylboronic acid pinacol ester (152 mg, 0.6 mmol) following General Procedure A. Purification by ISCO flash column chromatography (0-100% EtOAc in hexanes) to afford a colourless solid (183 mg, 0.48 mmol, 95%). LCMS (Method B) $t_R$=1.55 min, m/z=384.06 $[M+H]^+$.

Step 2. tert-Butyl N-[(1R)-1-[[4-[1-(benzenesulfonyl)pyrrolo[2,3-b]pyridin-4-yl]-2-chloro-phenyl]carbamoyl]-3-methyl-butyl]carbamate, E-75. Intermediate D-75 (77 mg, 0.20 mmol) was reacted with Boc-D-Leu-OH (69 mg, 0.30 mmol) following General Procedure E, affording a colourless gum (98 mg, 0.16 mmol, 82%). LCMS (Method B) $t_R$=2.36 min, m/z=597.19 $[M+H]^+$.

Step 3. (2R)-2-Amino-N-[2-chloro-4-(1H-pyrrolo[2,3-b]pyridin-4-yl)phenyl]-4-methyl-pentanamide, F-75. Intermediate E-75 (98 mg, 0.16 mmol) was deprotected following General Procedure K, affording title compound as a colourless solid (16 mg, 27%). LCMS (Method A) $t_R$=1.41 min, m/z=357.15 $[M+H]^+$; Purity ≥95% (DAD, 210, 254 nm); $^1H$ NMR (400 MHz, MeOH-$d_4$) δ 8.56 (d, J=8.4 Hz, 1H), 8.39 (d, J=5.0 Hz, 1H), 7.98 (d, J=2.1 Hz, 1H), 7.88 (dd, J=8.4, 2.1 Hz, 1H), 7.62 (d, J=3.6 Hz, 1H), 7.33 (d, J=5.1 Hz, 1H), 6.78 (d, J=3.6 Hz, 1H), 3.63 (dd, J=9.4, 4.5 Hz, 1H), 2.02-1.91 (m, 1H), 1.87-1.76 (m, 1H), 1.63-1.52 (m, 1H), 1.09 (d, J=6.6 Hz, 3H), 1.07 (d, J=6.6 Hz, 3H).

(2R)-2-Amino-4-methyl-N-[4-(1H-pyrrolo[2,3-b]pyridin-4-yl)-2-(trifluoromethyl)phenyl]pentanamide, F-76

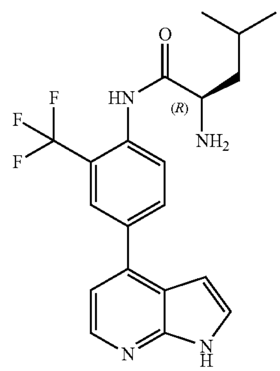

Step 1. 1-(Benzenesulfonyl)-4-[4-nitro-3-(trifluoromethyl)phenyl]pyrrolo[2,3-b]pyridine, D-76-1. A-2 (169 mg, 0.50 mmol) and 4,4,5,5-tetramethyl-2-[4-nitro-3-(trifluoromethyl)phenyl]-1,3,2-dioxaborolane (190 mg, 0.60 mmol) were reacted according to General Procedure A. Purification by ISCO flash chromatography (10-80% EtOAc in hexanes) to afford a yellow powder (100 mg, 0.22 mmol, 47%). LCMS (Method A) $t_R$=2.16 min, m/z=448.0130 $[M+H]^+$ Step 2. 4-[1-(Benzenesulfonyl)pyrrolo[2,3-b]pyridin-4-yl]-2-(trifluoromethyl)aniline, D-76-2. D-76-1 (100 mg, 0.21 mmol), iron (69 mg, 1.23 mmol) and $NH_4Cl$ (8.25 mg, 0.15 mmol) were combined in ethanol (2 mL) and water (0.50 mL) and heated in a sealed tube at 80° C. for 4 h. The reaction mixture was cooled, filtered through celite, washing with EtOAc. The filtrate was dried ($Na_2SO_4$) and concentrated in vacuo. Purification by ISCO flash chromatography (0-10% MeOH in DCM) affords a yellow powder of (79 mg, 0.19 mmol, 92%). LCMS (Method A) $t_R$=1.99 min, m/z=418.0834 $[M+H]^+$.

Step 3. tert-Butyl N-[(1R)-1-[[4-[1-(benzenesulfonyl)pyrrolo[2,3-b]pyridin-4-yl]-2-(trifluoromethyl)phenyl]carbamoyl]-3-methyl-butyl]carbamate, E-76. D-76-2 (50 mg, 0.12 mmol) and Boc-D-Leu-OH (42 mg, 0.18 mmol) were reacted according to General Procedure E. Purification by ISCO flash chromatography (40-100% EtOAc in hexanes) to afford a colourless solid (48 mg, 0.08 mmol, 64%). LCMS (Method B) $t_R$=2.32 min, m/z=631.2200 $[M+H]^+$; $^1H$ NMR (500 MHz, DMSO-$d_6$) δ 10.47 (s, 1H), 8.42 (d, J=5.0 Hz, 1H), 8.23 (s, 1H), 8.22-8.14 (m, 2H), 7.94 (dd, J=13.3, 6.2 Hz, 2H), 7.76 (t, J=7.5 Hz, 1H), 7.66 (t, J=7.8 Hz, 2H), 7.41 (d, J=8.4 Hz, 1H), 7.20 (d, J=5.0 Hz, 1H), 7.16 (d, J=7.6 Hz, 1H), 6.45 (d, J=4.2 Hz, 1H), 4.13 (q, J=8.1, 7.6 Hz, 1H), 1.70-1.64 (m, 1H), 1.56 (td, J=12.0, 10.2, 5.4 Hz, 1H), 1.49-1.41 (m, 1H), 1.39 (s, 9H), 0.93-0.89 (m, 6H).

Step 4: (2R)-2-Amino-4-methyl-N-[4-(1H-pyrrolo[2,3-b]pyridin-4-yl)-2-(trifluoromethyl)phenyl]pentanamide, F-76. Intermediate E-76 (45 mg, 0.07 mmol) was deprotected according to General Procedure K then purified by preparative HPLC (10-100% MeCN in $H_2O$, 0.1% TFA). The free base was obtained after SCX-II chromatography (load/wash MeOH, elution with 2N $NH_3$ in MeOH) to afford the title compound as a colourless solid (17 mg, 0.04 mmol, 61%). LCMS (Method A) $t_R$=1.48 min, m/z=391.1712 $[M+H]^+$; Purity ≥95% (DAD, 210, 254 nm); $^1H$ NMR (400 MHz, DMSO-$d_6$) δ 11.79 (s, 1H), 8.31-8.22 (m, 2H), 7.98 (d, J=8.2 Hz, 1H), 7.45 (t, J=6.9 Hz, 2H), 6.93 (s, 1H), 6.07 (s, 1H), 3.46 (d, J=7.2 Hz, 1H), 1.77 (s, 1H), 1.54 (d, J=8.7 Hz, 1H), 1.48-1.39 (m, 1H), 0.97-0.88 (m, 6H).

(2R)-2-Amino-N-[2-methoxy-4-(1H-pyrrolo[2,3-b]pyridin-4-yl)phenyl]-4-methyl-pentanamide, F-77

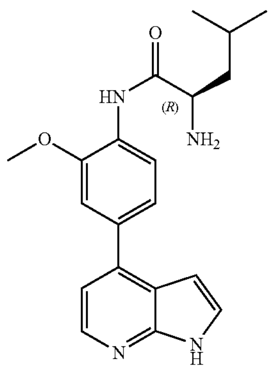

Step 1. 4-[1-(Benzenesulfonyl)pyrrolo[2,3-b]pyridin-4-yl]-2-methoxy-aniline, D-77. A-2 (337 mg, 1.00 mmol) and 2-methoxy-4-(4,4,5,5-tetramethyl-1,3,2-dioxaborolan-2-yl)aniline (299 mg, 1.20 mmol) were reacted according to General Procedure A at 110° C. for 2 h. Purification by ISCO flash chromatography (0-7% MeOH in DCM) to afford a tan powder (367 mg, 0.97 mmol, 97%). LCMS (Method A) $t_R$=1.87 min, m/z=380.1065 $[M+H]^+$; $^1H$ NMR (400 MHz, DMSO-$d_6$) δ 8.32 (d, J=5.1 Hz, 1H), 8.18-8.10 (m, 2H), 7.91 (d, J=4.1 Hz, 1H), 7.77-7.68 (m, 1H), 7.68-7.58 (m, 2H), 7.34 (d, J=5.1 Hz, 1H), 7.11-7.04 (m, 2H), 7.00 (d, J=4.1 Hz, 1H), 6.79-6.73 (m, 1H), 5.17 (s, 2H), 3.84 (s, 3H).

Step 2. tert-Butyl N-[(1R)-1-[[4-[1-(benzenesulfonyl)pyrrolo[2,3-b]pyridin-4-yl]-2-methoxy-phenyl]carbamoyl]-3-methyl-butyl]carbamate, E-77. D-77 (57 mg, 0.15 mmol) and Boc-D-Leu-OH (52 mg, 0.22 mmol) were reacted according to General Procedure E. Purification by ISCO flash chromatography (20-100% EtOAc in hexanes) to afford a tan powder (82 mg, 0.14 mmol, 92%). LCMS (Method B) $t_R$=2.31 min, m/z=593.2436 $[M+H]^+$.

Step 3. (2R)-2-Amino-N-[2-methoxy-4-(1H-pyrrolo[2,3-b]pyridin-4-yl)phenyl]-4-methyl-pentanamide, F-77. Intermediate E-77 (70 mg, 0.12 mmol) was deprotected according to General Procedure K, affording the title compound as a colourless solid (9 mg, 0.03 mmol, 22%). LCMS (Method A) $t_R$=1.37 min, m/z=353.1976 $[M+H]^+$; Purity ≥95% (DAD, 210, 254 nm); $^1H$ NMR (400 MHz, MeOH-$d_4$) δ 8.34 (d, J=8.2 Hz, 1H), 8.23 (d, J=5.1 Hz, 1H), 7.45 (d, J=3.6 Hz, 1H), 7.43-7.35 (m, 2H), 7.24 (d, J=5.1 Hz, 1H), 6.72 (d, J=3.6 Hz, 1H), 4.01 (s, 3H), 3.60-3.56 (m, 1H), 1.89-1.80 (m, 1H), 1.75-1.68 (m, 1H), 1.54-1.46 (m, 1H), 1.04-0.99 (m, 6H).

(2R)-2-Amino-N-[3-cyano-4-(1H-pyrrolo[2,3-b]pyridin-4-yl)phenyl]-4-methyl-pentanamide, F-78

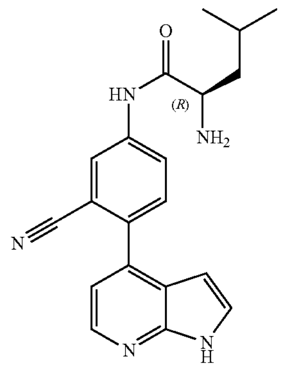

Step 1. 5-Amino-2-[1-(benzenesulfonyl)pyrrolo[2,3-b]pyridin-4-yl]benzonitrile, D-78. A-3 (250 mg, 0.65 mmol) and 5-amino-2-bromo-benzonitrile (192 mg, 0.98 mmol) were reacted according to General Procedure B at 70° C. for 4 h. Purification by ISCO flash chromatography (0-10% MeOH in DCM) affords a beige solid (238 mg, 0.64 mmol, 98%). LCMS (Method B) $t_R$=1.131 min, m/z=375.0801 $[M+H]^+$; $^1H$ NMR (400 MHz, DMSO-$d_6$) δ 8.42 (d, J=5.0 Hz, 1H), 8.16 (dd, J=7.3, 1.8 Hz, 2H), 7.97 (d, J=4.1 Hz, 1H), 7.78-7.70 (m, 1H), 7.65 (dd, J=8.6, 7.3 Hz, 2H), 7.38-7.31 (m, 2H), 7.04 (d, J=2.4 Hz, 1H), 6.96 (dd, J=8.6, 2.4 Hz, 1H), 6.71 (d, J=4.1 Hz, 1H), 5.97 (s, 2H).

Step 2. tert-Butyl N-[(1R)-1-[[4-[1-(benzenesulfonyl)pyrrolo[2,3-b]pyridin-4-yl]-3-cyano-phenyl]carbamoyl]-3-methyl-butyl]carbamate, E-78. D-78 (75 mg, 0.20 mmol) and Boc-D-Leu-OH were reacted according to General Procedure E. Purification by ISCO flash chromatography (0-100% EtOAc in hexanes) to afford a cream powder (47 mg, 0.08 mmol, 40%). LCMS (Method A) $t_R$=2.03 min, m/z=588.2416 $[M+H]^+$.

Step 3. (2R)-2-Amino-N-[3-cyano-4-(1H-pyrrolo[2,3-b]pyridin-4-yl)phenyl]-4-methyl-pentanamide, F-78. Intermediate E-78 (45 mg, 0.08 mmol) was deprotected according to General Procedure K, affording the title compound as a colourless solid (17 mg, 0.05 mmol, 64%). LCMS (Method A) $t_R$=1.40 min, m/z=348.2013 $[M+H]^+$; Purity ≥95% (DAD, 210, 254 nm); $^1H$ NMR (400 MHz, DMSO-$d_6$) δ 8.37-8.30 (m, 2H), 8.05 (dd, J=8.5, 2.3 Hz, 1H), 7.71 (d, J=8.6 Hz, 1H), 7.57 (t, J=2.9 Hz, 1H), 7.17 (d, J=4.9 Hz, 1H), 6.36 (dd, J=3.5, 1.7 Hz, 1H), 3.40 (dd, J=8.7, 5.6 Hz, 1H), 1.84-1.72 (m, 1H), 1.58-1.46 (m, 1H), 1.44-1.32 (m, 1H), 0.92 (dd, J=9.6, 6.6 Hz, 6H).

(2R)-2-Amino-4-methyl-N-[4-(1H-pyrrolo[2,3-b]pyridin-4-yl)-3-(trifluoromethyl)phenyl]pentanamide, F-79

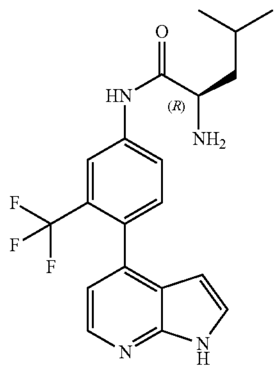

Step 1. tert-Butyl N-[(1R)-1-[[4-[1-(benzenesulfonyl)pyrrolo[2,3-b]pyridin-4-yl]-3-(trifluoromethyl)phenyl]carbamoyl]-3-methyl-butyl]carbamate, E-79. D-8 (100 mg, 0.24 mmol) and Boc-D-Leu-OH (83 mg, 0.36 mmol) were reacted according to General Procedure E. Purification by ISCO flash chromatography (20-80% EtOAc in hexanes) to afford a colourless solid (147 mg, 0.23 mmol, 97%). LCMS (Method B) $t_R$=2.29 min, m/z=631.2207 $[M+H]^+$.

Step 2. (2R)-2-Amino-4-methyl-N-[4-(1H-pyrrolo[2,3-b]pyridin-4-yl)-3-(trifluoromethyl)phenyl]pentanamide, F-79. Intermediate E-79 (140 mg, 0.11 mmol) was deprotected according to General Procedure K, affording a colourless solid (1.6 mg, 0.004 mmol, 4%). LCMS (Method A) $t_R$=1.52 min, m/z=391.1755 $[M+H]^+$; Purity ≥95% (DAD, 210, 254 nm); $^1$H NMR (400 MHz, MeOH-$d_4$) δ 8.24 (s, 1H), 8.21 (d, J=5.1 Hz, 1H), 7.93 (d, J=8.4 Hz, 1H), 7.43 (d, J=8.4 Hz, 1H), 7.38 (d, J=3.5 Hz, 1H), 7.01 (d, J=5.0 Hz, 1H), 6.15 (d, J=3.5 Hz, 1H), 3.66 (t, J=7.3 Hz, 1H), 1.87-1.76 (m, 1H), 1.75-1.66 (m, 1H), 1.65-1.55 (m, 1H), 1.06-0.98 (m, 6H); $^{19}$F NMR (376 MHz, MeOH-$d_4$) δ −59.26.

(2R)-2-Amino-N-[3-(difluoromethyl)-4-(1H-pyrrolo[2,3-b]pyridin-4-yl)phenyl]-4-methyl-pentanamide, F-80

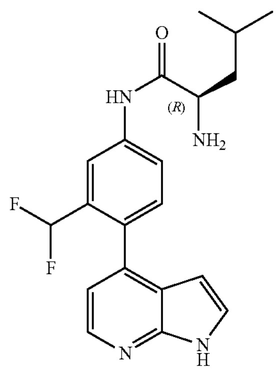

Step 1. tert-Butyl N-[(1R)-1-[[4-[1-(benzenesulfonyl)pyrrolo[2,3-b]pyridin-4-yl]-3-(difluoromethyl)phenyl]carbamoyl]-3-methyl-butyl]carbamate, E-80. D-6 (82 mg, 0.21 mmol) and Boc-D-Leu-OH (71 mg, 0.31 mmol) were reacted according to General Procedure E. Purification by ISCO flash chromatography (0-80% EtOAc in hexanes) to afford a colourless solid (97 mg, 0.16 mmol, 77%). LCMS (Method B) $t_R$=2.13 min, m/z=613.2307 $[M+H]^+$.

Step 2. (2R)-2-Amino-N-[3-(difluoromethyl)-4-(1H-pyrrolo[2,3-b]pyridin-4-yl)phenyl]-4-methyl-pentanamide, F-80. Intermediate E-80 (92 mg, 0.15 mmol) was deprotected according to General Procedure K, affording the title compound as a colourless solid (38 mg, 0.1 mmol, 68%). LCMS (Method A) $t_R$=1.47 min, m/z=373.1866 $[M+H]^+$; Purity ≥95% (DAD, 210, 254 nm); $^1$H NMR (400 MHz, MeOH-$d_4$) δ 8.27 (d, J=4.9 Hz, 1H), 8.15 (d, J=2.3 Hz, 1H), 7.93-7.86 (m, 1H), 7.50-7.41 (m, 2H), 7.03 (d, J=5.0 Hz, 1H), 6.55 (t, J=54.9 Hz, 1H), 6.27 (d, J=3.5 Hz, 1H), 3.63 (dd, J=8.2, 6.1 Hz, 1H), 1.86-1.75 (m, 1H), 1.75-1.65 (m, 1H), 1.62-1.52 (m, 1H), 1.02 (t, J=6.8 Hz, 6H).

(2R)-2-Amino-4-methyl-N-[4-(1H-pyrrolo[2,3-b]pyridin-4-yl)-3 (trifluoromethoxy)phenyl]pentanamide, F-81

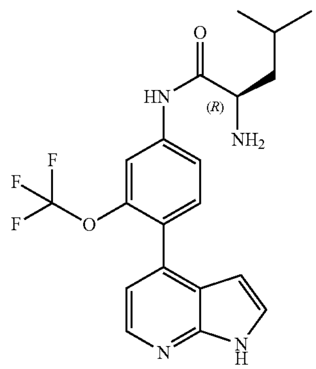

Step 1. tert-Butyl N-[(1R)-1-[[4-bromo-3-(trifluoromethoxy)phenyl]carbamoyl]-3-methyl-butyl]carbamate, G-81. COMU (578 mg, 1.35 mmol) was added to a solution of 4-bromo-3-(trifluoromethoxy)aniline (230 mg, 0.90 mmol), Boc-D-Leu-OH (312 mg, 1.35 mmol) and triethylamine (0.38 mL, 2.70 mmol) in DCM (3 mL) at 0° C. then stirred at 0° C. for 1 h. Reaction was diluted with DCM, washed with water, dried and concentrated in vacuo. Purification by ISCO flash chromatography (0-100% EtOAc in hexanes) affords an off-white solid (227 mg, 0.48 mmol, 54%). LCMS (Method A) $t_R$=2.26 min, m/z=491.0782 $[M+Na]^+$; $^1$H NMR (400 MHz, MeOH-$d_4$) δ 7.90 (s, 1H), 7.63 (d, J=8.8 Hz, 1H), 7.46 (dd, J=8.8, 2.4 Hz, 1H), 4.24-4.16 (m, 1H), 1.80-1.68 (m, 1H), 1.67-1.52 (m, 2H), 1.45 (s, 10H), 1.01-0.92 (m, 6H); $^{19}$F NMR (376 MHz, MeOH-$d_4$) δ −59.14.

Step 2. tert-Butyl N-[(1R)-1-[[4-[1-(benzenesulfonyl)pyrrolo[2,3-b]pyridin-4-yl]-3-(trifluoromethoxy)phenyl]carbamoyl]-3-methyl-butyl]carbamate, E-81. G-81 (220 mg, 0.47 mmol) and A-3 (150 mg, 0.39 mmol) were reacted according to General Procedure B. Purification by ISCO flash chromatography (0-100% EtOAc in hexanes) to afford a yellow gum (244 mg, 0.38 mmol, 97%). LCMS (Method B) $t_R$=2.35 min, m/z=647.2172 $[M+H]^+$.

Step 3. (2R)-2-Amino-4-methyl-N-[4-(1H-pyrrolo[2,3-b]pyridin-4-yl)-3 (trifluoromethoxy)phenyl]pentanamide, F-81. Intermediate E-81 (244 mg, 0.38 mmol) was deprotected according to General Procedure K, affording the title compound as a colourless solid (19 mg, 0.05 mmol, 12%). LCMS (Method A) $t_R$=1.52 min, m/z=407.1700 $[M+H]^+$; Purity ≥95% (DAD, 210, 254 nm); $^1$H NMR (400 MHz, MeOH-$d_4$) δ 8.24 (d, J=5.1 Hz, 1H), 8.02 (t, J=1.8 Hz, 1H), 7.68 (dd, J=8.5, 2.1 Hz, 1H), 7.59 (d, J=8.4 Hz, 1H), 7.43 (d, J=3.5 Hz, 1H), 7.11 (d, J=5.1 Hz, 1H), 6.37 (d, J=3.5 Hz, 1H), 3.57 (dd, J=8.3, 5.9 Hz, 1H), 1.86-1.75 (m, 1H), 1.73-1.62 (m, 1H), 1.60-1.49 (m, 1H), 1.01 (t, J=6.6 Hz, 6H).

(R)-2-Amino-N-(3-(difluoromethoxy)-4-(1H-pyrrolo[2,3-b]pyridin-4-yl)phenyl)-4-methylpentanamide, F-82

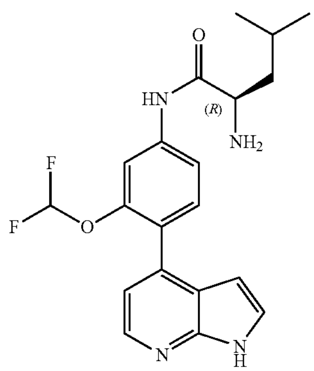

Step 1. tert-Butyl N-[(1R)-1-[[4-[1-(benzenesulfonyl)-2-methyl-pyrrolo[2,3-b]pyridin-4-yl]-3-(difluoromethoxy)phenyl]carbamoyl]-3-methyl-butyl]carbamate, E-82. Intermediate A-5 (136 mg, 0.34 mmol) was reacted with G-8 (110 mg, 0.24 mmol) following General Procedure A, affording a colourless solid (128 mg, 0.20 mmol, 82%). LCMS (Method B) $t_R$=2.133, m/z=643.2410 $[M+H]^+$; $^1$H NMR (400 MHz, $CDCl_3$) δ 8.73 (s, 1H), 8.36 (d, J=5.0 Hz, 1H), 8.19-8.14 (m, 2H), 7.62 (s, 1H), 7.60-7.55 (m, 1H), 7.50 (q, J=7.4, 6.6 Hz, 3H), 7.41-7.34 (m, 1H), 7.30 (d, J=8.3 Hz, 1H), 7.11 (d, J=4.9 Hz, 1H), 6.17 (s, 1H), 4.89 (s, 1H), 4.25 (s, 1H), 2.68 (s, 3H), 1.85-1.74 (m, 2H), 1.63-1.59 (m, 1H), 1.48 (s, 9H), 1.02-0.94 (m, 6H); $^{19}$F NMR (376 MHz, $CDCl_3$) δ −81.24 (d, J=35.4 Hz, 1F), −81.44 (d, J=35.5 Hz, 1F).

Step 2. (R)-2-Amino-N-(3-(difluoromethoxy)-4-(1H-pyrrolo[2,3-b]pyridin-4-yl)phenyl)-4-methylpentanamide, F-82. Intermediate E-82 (120 mg, 0.19 mmol) was deprotected following General Procedure K, affording title compound as a colourless solid (40 mg, 0.10 mmol, 53%). LCMS (Method A) $t_R$=1.49 min, m/z=403.19 $[M+H]^+$; Purity ≥95% (DAD, 210, 254 nm); $^1$H NMR (400 MHz, MeOD-$d_4$) δ 8.09 (d, J=5.2 Hz, 1H), 7.81 (s, 1H), 7.59-7.48 (m, 2H), 7.06 (d, J=5.2 Hz, 1H), 6.63 (t, J=73.9 Hz, 1H), 6.09-6.04 (m, 1H), 3.54 (dd, J=8.2, 6.0 Hz, 1H), 2.45 (s, 3H), 1.79 (dq, J=13.2, 6.6 Hz, 1H), 1.66 (ddd, J=13.8, 7.8, 6.0 Hz, 1H), 1.52 (ddd, J=13.8, 8.2, 6.2 Hz, 1H), 1.05-0.97 (m, 6H); $^{19}$F NMR (376 MHz, MeOD-$d_4$) δ −82.80 (d, J=73.9 Hz).

(2R)-N-(6-(1H-Pyrrolo[2,3-b]pyridin-4-yl)pyridin-3-yl)-2-amino-4-methylpentanamide, F-83

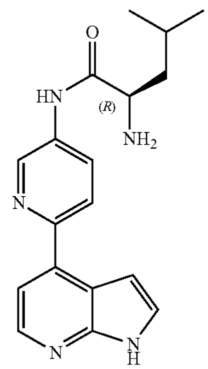

Step 1. tert-Butyl N-[(1R)-1-[(6-chloro-3-pyridyl)carbamoyl]-3-methyl-butyl]carbamate, G-83. 6-Chloropyridin-3-amine (116 mg, 0.90 mmol) was reacted with Boc-D-Leu-OH (312 mg, 1.35 mmol) following General Procedure E. Purification by ISCO flash chromatography (0-100% EtOAc in hexanes) to afford a colourless solid (261 mg, 0.76 mmol, 85%). LCMS (Method A) $t_R$=1.44 min, m/z=342.1769 $[M+H]^+$; $^1$H NMR (400 MHz, DMSO-$d_6$) δ 10.34 (s, 1H), 8.61 (d, J=2.7 Hz, 1H), 8.10 (dd, J=8.7, 2.8 Hz, 1H), 7.46 (d, J=8.7 Hz, 1H), 7.13 (d, J=7.8 Hz, 1H), 4.17-4.07 (m, 1H), 1.71-1.60 (m, 1H), 1.60-1.48 (m, 1H), 1.48-1.42 (m, 1H), 1.38 (s, 9H), 0.92-0.86 (m, 6H).

Step 2. [1-(Benzenesulfonyl)pyrrolo[2,3-b]pyridin-4-yl]-3-pyridyl]carbamoyl]-3-methyl-butyl]carbamate, E-83. A-3 (110 mg, 0.29 mmol), and G-83 (147 mg, 0.43 mmol) were reacted according to General Procedure C, using SPhos Palladacycle G2 at 100° C. for 3 h. Purification by ISCO flash chromatography (20-80% EtOAc in hexanes) affords a colourless solid (155 mg, 0.27 mmol, 96%). LCMS (Method B) $t_R$=1.92 min, m/z=564.2288 $[M+H]^+$.

Step 3. (2R)-2-Amino-4-methyl-N-[6-(1H-pyrrolo[2,3-b]pyridin-4-yl)-3-pyridyl]pentanamide, F-83. Intermediate E-83 was deprotected according to General Procedure K, affording title compound as a colourless solid (27 mg, 0.08 mmol, 33%). LCMS (Method A) $t_R$=1.52 min, m/z=423.1830 $[M+H]^+$; Purity ≥95% (DAD, 210, 254 nm); $^1$H NMR (400 MHz, MeOH-$d_4$) δ 8.97 (d, J=2.5 Hz, 1H), 8.34 (dd, J=8.6, 2.6 Hz, 1H), 8.29 (d, J=5.1 Hz, 1H), 8.02 (d, J=8.7 Hz, 1H), 7.52 (d, J=5.1 Hz, 1H), 7.50 (d, J=3.6 Hz, 1H), 6.93 (d, J=3.5 Hz, 1H), 3.60 (dd, J=8.4, 5.9 Hz, 1H), 1.81 (dp, J=13.2, 6.6 Hz, 1H), 1.69 (ddd, J=13.9, 7.9, 5.9 Hz, 1H), 1.55 (ddd, J=14.0, 8.5, 6.1 Hz, 1H), 1.01 (t, J=6.5 Hz, 6H).

(2R)-2-Amino-4-methyl-N-[5-methyl-6-(1H-pyrrolo[2,3-b]pyridin-4-yl)-3-pyridyl]pentanamide, F-84

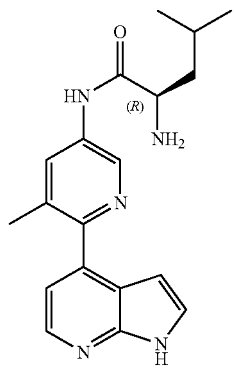

Step 1. tert-Butyl N-[6-[1-(benzenesulfonyl)pyrrolo[2,3-b]pyridin-4-yl]-5-methyl-3-pyridyl]carbamate, C-84. A-3 (250 mg, 0.65 mmol) was reacted with tert-butyl N-(6-chloro-5-methyl-3-pyridyl)carbamate (237 mg, 0.98 mmol) following General Procedure C, using SPhos Palladacyle G2. Purification by ISCO flash chromatography (0-80% EtOAc in hexanes) affords a beige powder (285 mg, 0.61 mmol, 94%). LCMS (Method B) $t_R$=1.26 min, m/z=465.15 $[M+H]^+$.

Step 2. 6-[1-(Benzenesulfonyl)pyrrolo[2,3-b]pyridin-4-yl]-5-methyl-pyridin-3-amine, D-84. C-84 (285 mg, 0.61 mmol) was deprotected according to General Procedure I. Purified by ISCO flash chromatography (0-100% EtOAc in hexanes) affording a tan solid (170 mg, 0.47 mmol, 76%). LCMS (Method A) $t_R$=1.65 min, m/z=365.11 $[M+H]^+$.

Step 3. tert-Butyl N-[(1R)-1-[[6-[1-(benzenesulfonyl)pyrrolo[2,3-b]pyridin-4-yl]-5-methyl-3-pyridyl]carbamoyl]-3-methyl-butyl]carbamate, E-84. D-84 (36 mg, 0.10 mmol) and Boc-D-Leu-OH (35 mg, 0.15 mmol) were reacted according to General Procedure E. Purification by ISCO flash chromatography (0-100% EtOAc in hexanes) to afford a cream solid (30 mg, 0.05 mmol, 52%). LCMS (Method B) $t_R$=1.59 min, m/z=578.2449 $[M+H]^+$.

Step 4. (2R)-2-Amino-4-methyl-N-[5-methyl-6-(1H-pyrrolo[2,3-b]pyridin-4-yl)-3-pyridyl]pentanamide, F-84. Intermediate E-84 (30 mg, 0.05 mmol) was deprotected according to General Procedure K, affording the title compound as a colourless solid (8.2 mg, 0.02 mmol, 47%). LCMS (Method A) $t_R$=1.31 min, m/z=338.1833 $[M+H]^+$; Purity ≥95% (DAD, 210, 254 nm); $^1$H NMR (400 MHz, MeOH-$d_4$) δ 8.74 (d, J=2.4 Hz, 1H), 8.30 (d, J=5.0 Hz, 1H), 8.17 (d, J=2.4 Hz, 1H), 7.44 (d, J=3.5 Hz, 1H), 7.12 (d, J=5.0 Hz, 1H), 6.25 (d, J=3.5 Hz, 1H), 3.64 (dd, J=8.3, 5.9 Hz, 1H), 2.25 (s, 3H), 1.86-1.76 (m, 1H), 1.74-1.66 (m, 1H), 1.54-1.62 (m, 1H), 1.02 (app. t, J=6.4 Hz, 6H).

(2R)-2-Amino-4-methyl-N-[6-methyl-5-(1H-pyrrolo[2,3-b]pyridin-4-yl)-2-pyridyl]pentanamide, F-85

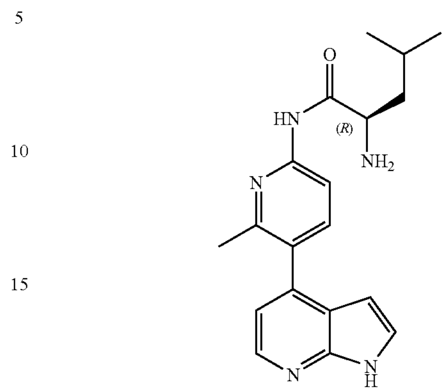

Synthesized following the same synthetic sequence as F-84, using tert-butyl N-(5-chloro-6-methyl-2-pyridyl)carbamate as the Step 1 Suzuki-Miyaura coupling partner. After deprotection, title compound as a colourless solid. LCMS (Method A) $t_R$=1.33 min, m/z=338.2152 $[M+H]^+$; Purity ≥95% (DAD, 210, 254 nm); $^1$H NMR (400 MHz, MeOH-$d_4$) δ 8.16 (d, J=5.0 Hz, 1H), 8.02 (d, J=8.4 Hz, 1H), 7.64 (d, J=8.4 Hz, 1H), 7.33 (d, J=3.5 Hz, 1H), 6.95 (d, J=5.0 Hz, 1H), 6.14 (d, J=3.5 Hz, 1H), 3.56 (t, J=7.5 Hz, 1H), 1.78-1.56 (m, 2H), 1.53-1.41 (m, 1H), 0.97-0.88 (m, 6H).

(2R)-2-Amino-4-methyl-N-[4-methyl-5-(1H-pyrrolo[2,3-b]pyridin-4-yl)-2-pyridyl]pentanamide, F-86

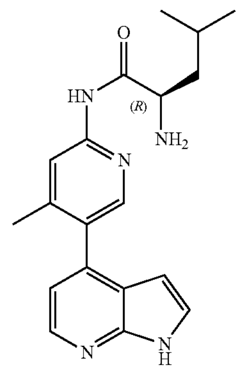

Step 1. 5-[1-(benzenesulfonyl)pyrrolo[2,3-b]pyridin-4-yl]-4-methyl-pyridin-2-amine, D-86. 5-bromo-4-methyl-pyridin-2-amine (112 mg, 0.60 mmol) and A-3 (192 mg, 0.50 mmol) were reacted according to General Procedure B for 18 h. Purification by ISCO flash chromatography (0-10% MeOH in DCM) to afford a brown gum (181 mg, 0.50 mmol, 99%). LCMS (Method A) $t_R$=1.72 min, m/z=365.1043 $[M+H]^+$. ° H NMR (400 MHz, DMSO-$d_6$) δ 8.36 (d, J=5.0 Hz, 1H), 8.20-8.13 (m, 2H), 7.90 (d, J=4.1 Hz, 1H), 7.80-7.70 (m, 2H), 7.8-7.62 (m, 2H), 7.20 (d, J=5.0 Hz, 1H), 6.59 (d, J=4.1 Hz, 1H), 6.41 (s, 1H), 6.11 (s, 2H), 2.02 (s, 3H).

Step 2. tert-Butyl N-[(1R)-1-[[5-[1-(benzenesulfonyl)pyrrolo[2,3-b]pyridin-4-yl]-4-methyl-2-pyridyl]carbamoyl]-3-methyl-butyl]carbamate, E-86. D-86 (181 mg, 0.50 mmol) was reacted with Boc-D-Leu-OH (231 mg, 1.00 mmol) according to General Procedure E. Purification by ISCO flash chromatography (0-100% EtOAc in hexanes) to afford a brown powder (198 mg, 0.34 mmol, 68%). LCMS (Method B); $t_R$=1.85 min, m/z=578.2453 $[M+H]^+$.

Step 3. (2R)-2-Amino-4-methyl-N-[4-methyl-5-(1H-pyrrolo[2,3-b]pyridin-4-yl)-2-pyridyl]pentanamide, F-86. Intermediate E-86 (0.10 g, 0.17 mmol) was deprotected according to General Procedure K, affording the title compound as a colourless solid (12 mg, 0.04 mmol, 21%). LCMS (Method A) $t_R$=1.34 min, m/z=338.1828 $[M+H]^+$; Purity ≥95% (DAD, 210, 254 nm); $^1$H NMR (400 MHz, MeOH-$d_4$) δ 8.27 (d, J=5.0 Hz, 1H), 8.21 (d, J=12.0 Hz, 2H), 7.44 (d, J=3.5 Hz, 1H), 7.05 (d, J=5.0 Hz, 1H), 6.25 (d, J=3.5 Hz, 1H), 3.67 (t, J=7.3 Hz, 1H), 2.27 (s, 3H), 1.87-1.79 (m, 1H), 1.76-1.68 (m, 1H), 1.61-1.52 (m, 1H), 1.01 (t, J=6.2 Hz, 6H).

(2R)-2-Amino-4-methyl-N-[3-(1H-pyrrolo[2,3-b]pyridin-4-yl)phenyl]pentanamide, F-87

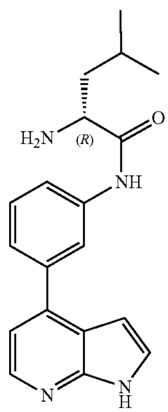

Step 1. 3-[1-(Benzenesulfonyl)pyrrolo[2,3-b]pyridin-4-yl]aniline, D-87. A-2 (337 mg, 1.00 mmol) and 3-(4,4,5,5-Tetramethyl-1,3,2-dioxaborolan-2-yl)aniline (263 mg, 1.20 mmol) were reacted according to General Procedure A. Purification by ISCO flash chromatography 1-10% MeOH in DCM) affords a colourless solid (329 mg, 0.94 mmol, 94%). LCMS (Method A) $t_R$=1.76 min, m/z=350.0959 $[M+H]^+$; $^1$H NMR (400 MHz, DMSO-$d_6$) δ 8.39 (d, J=5.0 Hz, 1H), 8.17-8.10 (m, 2H), 7.98 (d, J=4.1 Hz, 1H), 7.78-7.69 (m, 1H), 7.64 (dd, J=8.4, 7.0 Hz, 2H), 7.32 (d, J=5.1 Hz, 1H), 7.17 (t, J=7.8 Hz, 1H), 6.91 (d, J=4.1 Hz, 1H), 6.87 (t, J=2.0 Hz, 1H), 6.77 (dt, J=7.6, 1.3 Hz, 1H), 6.71-6.63 (m, 1H), 5.30 (s, 2H).

Step 2. tert-Butyl N-[(1R)-1-[[3-[1-(benzenesulfonyl)pyrrolo[2,3-b]pyridin-4-yl]phenyl]carbamoyl]-3-methyl-butyl] carbamate, E-87. D-87 (52 mg, 0.15 mmol) and Boc-D-Leu-OH (52 mg, 0.22 mol) were reacted according to General Procedure D. Purification by ISCO flash chromatography (20-100% EtOAc in hexanes) affords a cream powder (60 mg, 0.11 mmol, 71%). LCMS (Method B) $t_R$=2.17 min, m/z=563.2336 $[M+H]^+$.

Step 3. (2R)-2-Amino-4-methyl-N-[3-(1H-pyrrolo[2,3-b] pyridin-4-yl)phenyl]pentanamide, F-87. Intermediate E-87 (48 mg, 0.09 mmol) was deprotected according to General Procedure K, affording the title compound as a colourless solid (21 mg, 0.07 mmol, 76%). LCMS (Method A) $t_R$=1.40 min, m/z=323.1866 $[M+H]^+$; Purity ≥95% (DAD, 210, 254 nm); $^1$H NMR (400 MHz, MeOH-$d_4$) δ 8.25 (d, J=5.0 Hz, 1H), 8.14 (t, J=1.8 Hz, 1H), 7.64 (dt, J=7.4, 1.9 Hz, 1H), 7.55-7.49 (m, 2H), 7.48-7.43 (m, 1H), 7.23 (d, J=5.1 Hz, 1H), 6.76 (d, J=3.6 Hz, 1H), 3.56 (dd, J=8.2, 6.1 Hz, 1H), 1.79 (dq, J=13.7, 6.7 Hz, 1H), 1.67 (ddd, J=13.7, 7.8, 6.1 Hz, 1H), 1.53 (dt, J=13.7, 7.8 Hz, 1H), 1.00 (dd, J=8.2, 6.7 Hz, 6H).

(2R)-2-Amino-N-[3-ethyl-4-(1H-pyrrolo[2,3-b]pyridin-4-yl)phenyl]-3,3-dimethyl-butanamide, F-88

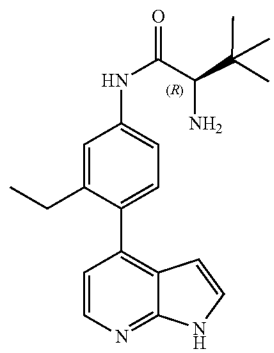

Synthesized in a manner analogous to F-62, using Boc-D-Tle-OH in Step 1. Colourless solid. LCMS (Method A) $t_R$=1.44 min, m/z=351.2186 $[M+H]^+$; Purity ≥95% (DAD, 210, 254 nm); $^1$H NMR (400 MHz, MeOH-$d_4$) δ 8.23 (d, J=5.0 Hz, 1H), 7.65 (d, J=2.2 Hz, 1H), 7.56 (dd, J=8.3, 2.2 Hz, 1H), 7.39 (d, J=3.5 Hz, 1H), 7.25 (d, J=8.3 Hz, 1H), 7.01 (d, J=5.0 Hz, 1H), 6.22 (d, J=3.5 Hz, 1H), 3.31 (s, 1H), 2.57 (q, J=7.6 Hz, 2H), 1.11 (s, 9H), 1.03 (t, J=7.6 Hz, 3H).

(2R)-2-Amino-4-methyl-N-[3-methyl-4-(2-methyl-1H-pyrrolo[2,3-b]pyridin-4-yl)phenyl]pentanamide, F-89

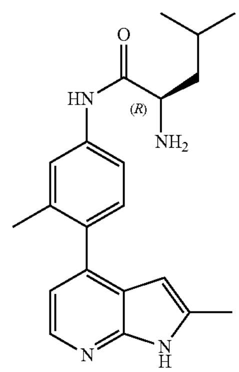

Step 1. tert-Butyl N-[(1R)-1-[[4-[1-(benzenesulfonyl)-2-methyl-pyrrolo[2,3-b]pyridin-4-yl]-3-methyl-phenyl]carbamoyl]-3-methyl-butyl]carbamate, E-89. D-10 (94 mg, 0.25 mmol) and Boc-D-Leu-OH (116 mg, 0.50 mmol) were reacted according to General Procedure E. Purification by ISCO flash chromatography (0-100% EtOAc in hexanes) to afford a cream solid (140 mg, 0.24 mmol). LCMS (Method B) $t_R$=2.23 min, m/z=591.2675 $[M+H]^+$.

Step 2. (2R)-2-Amino-4-methyl-N-[3-methyl-4-(2-methyl-1H-pyrrolo[2,3-b]pyridin-4-yl)phenyl]pentanamide, F-89. Intermediate E-89 (140 mg, 0.24 mmol) was deprotected according to General Procedure K, affording the title compound as a colourless solid (4 mg, 0.01 mmol, 40%). LCMS (Method A) $t_R$=1.45 min, m/z=351.2040 [M+H]$^+$; Purity ≥95% (DAD, 210, 254 nm). 1H NMR (400 MHz, MeOH-$d_4$) δ 8.09 (d, J=5.0 Hz, 1H), 7.59 (d, J=2.2 Hz, 1H), 7.53 (dd, J=8.3, 2.2 Hz, 1H), 7.25 (d, J=8.3 Hz, 1H), 6.91 (d, J=5.1 Hz, 1H), 5.90 (d, J=1.3 Hz, 1H), 3.55 (dd, J=8.1, 6.2 Hz, 1H), 2.43 (d, J=1.0 Hz, 3H), 2.19 (s, 3H), 1.84-1.74 (m, 1H), 1.67 (ddd, J=13.9, 8.1, 6.2 Hz, 1H), 1.52 (ddd, J=13.9, 8.1, 6.2 Hz, 1H), 1.04 (m, 6H).

(2R)-2-Amino-4,4-dimethyl-N-[3-methyl-4-(2-methyl-1H-pyrrolo[2,3-b]pyridin-4-yl)phenyl]pentanamide, F-90

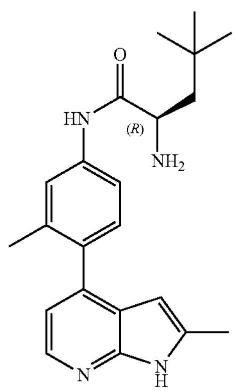

Synthesized in a manner analogous to F-89, reacting intermediate D-10 with Boc-D-Neo-OH in Step 2. Deprotected to affording title compound as a colourless solid. LCMS (Method A) $t_R$=1.50 min, m/z=365.23 [M+H]$^+$; Purity ≥95% (DAD, 210, 254 nm); $^1$H NMR (400 MHz, MeOH-$d_4$) δ 8.11 (d, J=5.1 Hz, 1H), 7.60 (s, 1H), 7.55 (d, J=8.3 Hz, 1H), 7.27 (d, J=8.3 Hz, 1H), 6.94 (d, J=5.1 Hz, 1H), 5.92 (s, 1H), 3.55 (dd, J=7.3, 5.2 Hz, 1H), 2.48-2.42 (m, 3H), 2.21 (s, 3H), 1.98 (dd, J=13.9, 7.3 Hz, 1H), 1.49 (dd, J=13.9, 5.2 Hz, 1H), 1.05 (s, 9H).

(2R)-2-Amino-3,3-dimethyl-N-[3-methyl-4-(2-methyl-1H-pyrrolo[2,3-b]pyridin-4-yl)phenyl]butanamide, F-91

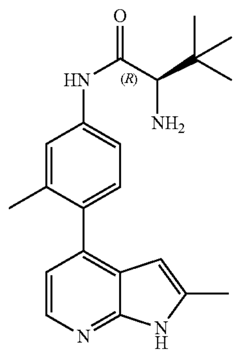

Synthesized in a manner analogous to F-89, reacting intermediate D-89 with Boc-D-Tle-OH in Step 2. Deprotected to affording title compound as a colourless solid.

LCMS (Method A) $t_R$=1.45 min, m/z=351.24 [M+H]$^+$; Purity ≥95% (DAD, 210, 254 nm); $^1$H NMR (400 MHz, MeOH-$d_4$) δ 8.11 (d, J=5.0 Hz, 1H), 7.59 (d, J=2.2 Hz, 1H), 7.53 (dd, J=8.2, 1.4 Hz, 1H), 7.27 (d, J=8.2 Hz, 1H), 6.94 (d, J=5.1 Hz, 1H), 5.92 (d, J=1.4 Hz, 1H), 3.37 (s, 1H), 2.45 (s, 3H), 2.21 (s, 3H), 1.09 (s, 9H).

(2R)-2-Amino-N-[4-(2-methyl-1H-pyrrolo[2,3-b]pyridin-4-yl)phenyl]-3-phenyl-propanamide, F-92

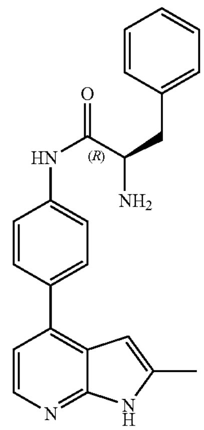

Step 1. tert-Butyl N-[(1R)-2-[4-[1-(benzenesulfonyl)-2-methyl-pyrrolo[2,3-b]pyridin-4-yl]anilino]-1-benzyl-2-oxo-ethyl]carbamate, E-92. Boc-D-Phe-OH (80 mg, 0.30 mmol) was reacted with D-9 (73 mg, 0.20 mmol) following General Procedure D. Purification by ISCO flash chromatography (0-100% EtOAc in hexanes) affords a colourless gum (92 mg, 0.15 mmol, 75%). LCMS (Method B) $t_R$=2.12 min, m/z=611.25 [M+H]$^+$.

Step 2. (2R)-2-Amino-N-[4-(2-methyl-1H-pyrrolo[2,3-b]pyridin-4-yl)phenyl]-3-phenyl-propanamide, F-92. E-92 (92 mg, 0.15 mmol) was deprotected according to General Procedure K, affording title compound as a colourless solid (17 mg, 30%). LCMS (Method A) $t_R$=1.44 min, m/z=371.22 [M+H]$^+$; Purity ≥95% (DAD, 210, 254 nm); $^1$H NMR (400 MHz, DMSO-$d_6$) δ 11.57 (s, 1H), 8.14 (d, J=5.0 Hz, 1H), 7.78 (d, J=8.6 Hz, 2H), 7.72 (d, J=8.6 Hz, 2H), 7.32-7.25 (m, 3H), 7.25-7.18 (m, 1H), 7.10 (d, J=5.0 Hz, 1H), 6.36 (s, 1H), 4.04 (s, 2H), 3.64 (t, J=6.8 Hz, 1H), 3.30 (s, 1H), 3.04 (dd, J=13.5, 5.7 Hz, 1H), 2.78 (dd, J=13.5, 7.9 Hz, 1H), 2.42 (s, 3H).

(2R)-2-Amino-N-[3-ethyl-4-(2-methyl-1H-pyrrolo[2,3-b]pyridin-4-yl)phenyl]-3,3-dimethyl-butanamide, F-93

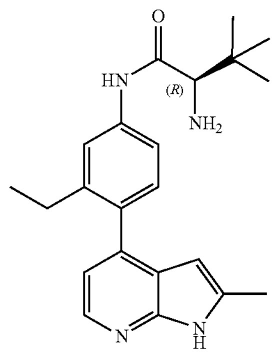

Step 1. tert-Butyl N-[(1R)-1-[(4-bromo-3-ethyl-phenyl)carbamoyl]-2,2-dimethyl-propyl]carbamate, G-93. 4-Bromo-3-ethyl-aniline (100 mg, 0.50 mmol) and Boc-D-Tle-OH (173 mg, 0.75 mmol) were reacted according to General Procedure E. Purification by ISCO flash chromatography (0-100% EtOAc in hexanes) to afford a yellow powder (140 mg, 0.34 mmol, 68%). LCMS (Method A) $t_R$=2.24 min, m/z=435.1264 $[M+Na]^+$.

Step 2. tert-Butyl N-[(1R)-1-[[4-[1-(benzenesulfonyl)-2-methyl-pyrrolo[2,3-b]pyridin-4-yl]-3-ethyl-phenyl]carbamoyl]-2,2-dimethyl-propyl]carbamate, E-93. A-5 (72 mg, 0.18 mmol) and G-93 (62 mg, 0.15 mmol) were reacted according to General Procedure B. Purification by ISCO flash chromatography (10-80% EtOAc in hexanes) affords a colourless solid (59 mg, 0.10 mmol, 65%). LCMS (Method B) $t_R$=2.31 min, m/z=605.2807 $[M+H]^+$.

Step 3. (2R)-2-Amino-N-[3-ethyl-4-(2-methyl-1H-pyrrolo[2,3-b]pyridin-4-yl)phenyl]-3,3-dimethyl-butanamide, F-93. Intermediate E-93 (60 mg, 0.10 mmol) was deprotected according to General Procedure K, affording afford the title compound as a colourless solid (27 mg, 0.07 mmol, 75%). LCMS (Method A) $t_R$=1.48 min, m/z=365.2346 $[M+H]^+$; Purity ≥95% (DAD, 210, 254 nm); $^1$H NMR (400 MHz, MeOH-$d_4$) δ 8.09 (d, J=5.1 Hz, 1H), 7.61 (d, J=2.2 Hz, 1H), 7.52 (dd, J=8.3, 2.2 Hz, 1H), 7.20 (d, J=8.3 Hz, 1H), 6.91 (d, J=5.1 Hz, 1H), 5.90-5.85 (m, 1H), 2.55 (q, J=7.6 Hz, 2H), 2.45-2.40 (m, 3H), 1.09 (s, 9H), 1.00 (t, J=7.6 Hz, 3H).

(2R)-4-Methyl-2-(methylamino)-N-[4-(2-methyl-1H-pyrrolo[2,3-b]pyridin-4-yl)phenyl]pentanamide, F-94

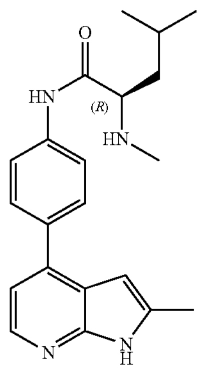

Step 1. tert-Butyl N-[(1R)-1-[[4-[1-(Benzenesulfonyl)-2-methyl-pyrrolo[2,3-b]pyridin-4-yl]phenyl]carbamoyl]-3-methyl-butyl]-N-methyl-carbamate, E-94. Boc-N-Me-D-Leu-OH (74 mg, 0.30 mmol) was reacted with D-9 (73 mg, 0.20 mmol) following General Procedure E. Purification by ISCO flash chromatography (0-100% EtOAc in hexanes) affords a colourless gum (110 mg, 0.18 mmol, 93%). LCMS (Method B) $t_R$=2.53 min, m/z=591.23 $[M+H]^+$.

Step 2. (2R)-4-Methyl-2-(methylamino)-N-[4-(2-methyl-1H-pyrrolo[2,3-b]pyridin-4-yl)phenyl]pentanamide, F-94. Intermediate E-94 (110 mg, 0.18 mmol) was deprotected according to General Procedure K, affording title compound as a colourless solid (19 mg, 29%). LCMS (Method A) $t_R$=1.45 min, m/z=351.24 $[M+H]^+$; Purity ≥95% (DAD, 210, 254 nm); $^1$H NMR (400 MHz, MeOH-$d_4$) δ 8.12 (d, J=5.2 Hz, 1H), 7.84-7.74 (m, 4H), 7.16 (d, J=5.2 Hz, 1H), 6.41 (s, 1H), 3.31-3.26 (m, 1H), 2.50 (s, 3H), 2.43 (s, 3H), 1.83-1.71 (m, 1H), 1.71-1.62 (m, 1H), 1.62-1.51 (m, 1H), 1.04 (d, J=6.5 Hz, 3H), 1.00 (d, J=6.5 Hz, 3H).

(2R)-2-Amino-4-methyl-N-[6-methyl-5-(2-methyl-1H-pyrrolo[2,3-b]pyridin-4-yl)-2-pyridyl]pentanamide, F-95

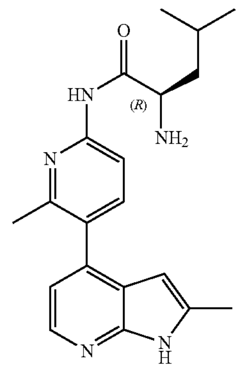

Synthesized following the same synthetic sequence as F-84, using A-5 and tert-butyl N-(5-chloro-6-methyl-2-pyridyl)carbamate as the Step 1 Suzuki-Miyaura coupling partners. After deprotection, title compound as a colourless solid. LCMS (Method A) $t_R$=1.39 min, m/z=352.21 $[M+H]^+$; Purity ≥95% (DAD, 210, 254 nm); $^1$H NMR (400 MHz, MeOH-$d_4$) δ 8.15 (d, J=5.1 Hz, 1H), 8.12 (d, J=8.6 Hz, 1H), 7.74 (d, J=8.6 Hz, 1H), 6.99 (d, J=5.1 Hz, 1H), 5.95 (s, 1H), 3.70 (s, 1H), 2.47 (s, 3H), 2.37 (s, 3H), 1.89-1.69 (m, 2H), 1.67-1.53 (m, 1H), 1.04 (t, J=6.4 Hz, 6H).

(2R)-2-Amino-4,4-dimethyl-N-[5-methyl-6-(2-methyl-1H-pyrrolo[2,3-b]pyridin-4-yl)-3-pyridyl]pentanamide, F-96

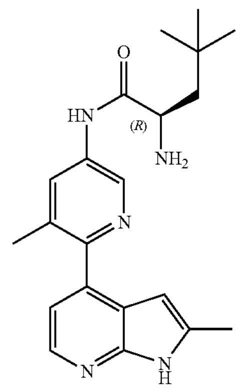

Step 1. tert-Butyl N-[(1R)-1-[(6-chloro-5-methyl-3-pyridyl)carbamoyl]-3,3-dimethyl-butyl]carbamate, G-96. Boc-D-Neo-OH (294.4, 1.2 mmol) and 5-amino-2-chloro-3-picoline were reacted following General Procedure E, affording a yellow-orange gum (199 mg, 0.54 mmol, 54%). LCMS (Method B) $t_R$=1.65 min, m/z=370.21 $[M+H]^+$.

Step 2. tert-butyl N-[(1R)-1-[[6-[1-(benzenesulfonyl)-2-methyl-pyrrolo[2,3-b]pyridin-4-yl]-5-methyl-3-pyridyl]carbamoyl]-3,3-dimethyl-butyl]carbamate, E-96. Intermediate G-96 (160 mg, 0.45 mmol) and A-5 (119 mg, 0.30 mmol) were reacted following General Procedure A, affording a colourless solid (49 mg, 0.08 mmol, 28%). LCMS (Method B) $t_R$=1.93 min, m/z=592.26 $[M+H]^+$.

Step 3. (2R)-2-Amino-4,4-dimethyl-N-[5-methyl-6-(2-methyl-11H-pyrrolo[2,3-b]pyridin-4-yl)-3-pyridyl]pentanamide, F-96. Intermediate E-96 (110 mg, 0.18 mmol) was deprotected following General Procedure K, affording title compound as a colourless solid (37 mg, 0.10 mmol, 56%). LCMS (Method A) $t_R$=1.43 min, m/z=366.23 $[M+H]^+$; Purity ≥95% (DAD, 210, 254 nm); $^1H$ NMR (400 MHz, MeOH-$d_4$) δ 8.73 (s, 1H), 8.19 (d, J=5.1 Hz, 1H), 8.17 (s, 1H), 7.07 (d, J=5.1 Hz, 1H), 5.95 (s, 1H), 3.63-3.54 (m, 1H), 2.47 (s, 3H), 2.26 (s, 3H), 1.99 (dd, J=14.0, 7.1 Hz, 1H), 1.50 (dd, J=14.0, 5.4 Hz, 1H), 1.05 (s, 9H).

(2R)-2-Amino-N-[3-(difluoromethyl)-4-(2-methyl-1H-pyrrolo[2,3-b]pyridin-4-yl)phenyl]-4,4-dimethyl-pentanamide, F-97

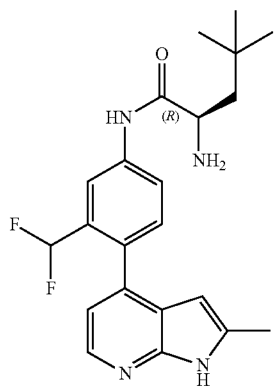

Synthesized following a procedure analogous to the synthesis of F-80, using A-5 as the Suzuki-Miyaura coupling partner with 2-bromo-5-nitro-benzaldehyde, then Boc-D-Neo-OH in the amide coupling. After deprotection, title compound as a colourless solid. LCMS (Method A) $t_R$=1.55 min, m/z=401.22 $[M+H]^+$; Purity ≥95% (DAD, 210, 254 nm); $^1H$ NMR (400 MHz, MeOH-$d_4$) δ 11.68 (s, 1H), 8.21-8.13 (m, 2H), 7.89 (d, J=8.5 Hz, 1H), 7.44 (d, J=8.5 Hz, 1H), 6.89 (d, J=4.9 Hz, 1H), 6.72 (t, J=53.7 Hz, 1H), 5.91 (s, 1H), 3.42 (t, J=6.2 Hz, 1H), 2.38 (s, 3H), 1.79 (dd, J=13.9, 6.2 Hz, 1H), 1.35 (dd, J=13.9, 6.2 Hz, 1H), 0.97 (s, 9H).

(2R)-2-Amino-4-methyl-N-[3-methyl-4-[2-(trifluoromethyl)-1H-pyrrolo[2,3-b]pyridin-4-yl]phenyl]pentanamide, F-98

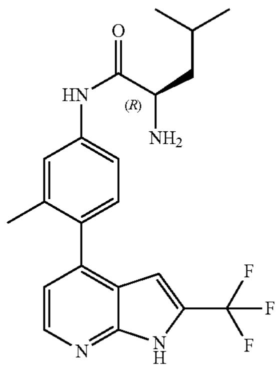

Step 1. tert-Butyl N-[(1R)-1-[(4-bromo-3-methyl-phenyl)carbamoyl]-3-methyl-butyl]carbamate, G-98. 4-Bromo-3-methylaniline (3.72 g, 20 mmol) was reacted with Boc-D-Leu-OH (6.94 g, 30 mmol) following General Procedure E, affording a colourless solid (7.21 g, 18.06 mmol, 90%). LCMS (Method A) $t_R$=2.26 min, m/z=399.04, 401.04, bromine split $[M+H]^+$; $^1H$ NMR (400 MHz, $CDCl_3$) δ 8.44 (s, 1H), 7.44-7.36 (m, 2H), 7.17 (dd, J=8.7, 2.6 Hz, 1H), 4.93 (d, J=8.0 Hz, 1H), 4.23 (br s, 1H), 2.33 (s, 3H), 1.82-1.66 (m, 2H), 1.57-1.53 (m, 1H), 1.45 (s, 9H), 1.04-0.92 (m, 6H).

Step 2. tert-Butyl N-[(1R)-3-methyl-1-[[3-methyl-4-[2-(trifluoromethyl)-1H-pyrrolo[2,3-b]pyridin-4-yl]phenyl]carbamoyl]butyl]carbamate, H-98. Intermediate G-98 (60 mg, 0.15 mmol) was reacted with A-12 (66 mg, 0.21 mmol) according to General Procedure A, affording a colourless powder (35 mg, 0.07 mmol, 46%). LCMS (Method B) $t_R$=1.70 min, m/z=505.2433 $[M+H]^+$; $^1H$ NMR (400 MHz, MeOD-$d_4$) δ 8.42 (d, J=4.9 Hz, 1H), 7.62 (s, 1H), 7.55 (d, J=8.5 Hz, 1H), 7.28 (d, J=8.5 Hz, 1H), 7.13 (d, J=4.9 Hz, 1H), 6.67-6.61 (m, 1H), 4.26 (brs, 1H), 2.20 (s, 3H), 1.83-1.74 (m, 1H), 1.67-1.58 (m, 2H), 1.47 (s, 9H), 1.05-0.99 (m, 6H); $^{19}F$ NMR (376 MHz, MeOD-$d_4$) δ −62.81.

Step 3. (2R)-2-Amino-4-methyl-N-[3-methyl-4-[2-(trifluoromethyl)-1H-pyrrolo[2,3-b]pyridin-4-yl]phenyl]pentanamide, F-98. Intermediate H-98 (34 mg, 0.07 mmol) was deprotected following General Procedure I, affording title compound as a colourless solid (18 mg, 0.04 mmol, 66%). LCMS (Method A) $t_R$=1.71 min, m/z=405.20 $[M+H]^+$; Purity ≥95% (DAD, 210, 254 nm); $^1H$ NMR (400 MHz, MeOD-$d_4$) δ 8.42 (d, J=4.9 Hz, 1H), 7.64 (d, J=2.2 Hz, 1H), 7.58 (dd, J=8.5, 2.2 Hz, 1H), 7.28 (d, J=8.5 Hz, 1H), 7.13 (d, J=4.9 Hz, 1H), 6.66-6.61 (m, 1H), 3.55 (dd, J=8.1, 6.1 Hz, 1H), 2.20 (s, 3H), 1.85-1.75 (m, 1H), 1.67 (dt, J=14.0, 7.0 Hz, 1H), 1.58-1.47 (m, 1H), 1.02 (d, J=6.6 Hz, 3H), 1.00 (d, J=6.6 Hz, 3H); $^{19}F$ NMR (376 MHz, MeOD-$d_4$) δ −62.81.

(2R)-2-Amino-4,4-dimethyl-N-[3-methyl-4-[2-(trifluoromethyl)-1H-pyrrolo[2,3-b]pyridin-4-yl]phenyl]pentanamide, F-99

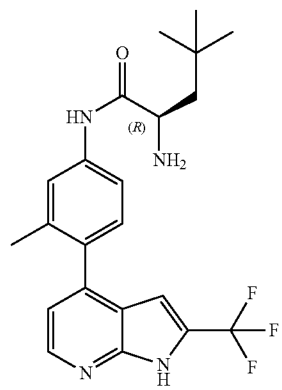

Synthesized following the same synthetic sequence as F-98, using Boc-D-Neo-OH in the Step 1 amide coupling. After deprotection, title compound as a colourless solid. LCMS (Method A) $t_R$=1.76 min, m/z=419.25 $[M+H]^+$; Purity ≥95% (DAD, 210, 254 nm); $^1H$ NMR (400 MHz, MeOD-$d_4$) δ 8.42 (d, J=4.9 Hz, 1H), 7.64 (d, J=2.2 Hz, 1H), 7.58 (dd, J=8.3, 2.2 Hz, 1H), 7.29 (d, J=8.3 Hz, 1H), 7.13 (d, J=4.9 Hz, 1H), 6.66-6.61 (m, 1H), 3.53 (dd, J=7.2, 5.3 Hz, 1H), 2.20 (s, 3H), 1.96 (dd, J=13.9, 7.2 Hz, 1H), 1.47 (dd, J=13.9, 5.3 Hz, 1H), 1.02 (s, 9H); $^{19}$F NMR (376 MHz, MeOD-$d_4$) δ −62.82.

(2R)-2-Amino-3,3-dimethyl-N-[3-methyl-4-[2-(trifluoromethyl)-1H-pyrrolo[2,3-b]pyridin-4-yl]phenyl]butanamide, F-100

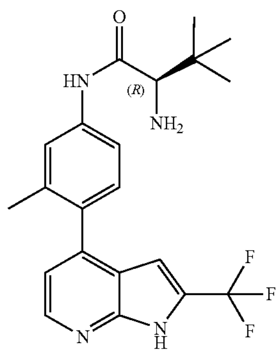

Synthesized following the same synthetic sequence as F-98, using Boc-D-Tle-OH in the Step 1 amide coupling. After deprotection, title compound as a colourless solid. LCMS (Method A) $t_R$=1.69 min, m/z=405.18 [M+H]$^+$; Purity ≥95% (DAD, 210, 254 nm); $^1$H NMR (400 MHz, MeOD-$d_4$) δ 8.42 (d, J=4.9 Hz, 1H), 7.62 (d, J=2.2 Hz, 1H), 7.56 (dd, J=8.3, 2.2 Hz, 1H), 7.28 (d, J=8.3 Hz, 1H), 7.13 (d, J=4.9 Hz, 1H), 6.67-6.62 (m, 1H), 3.22 (s, 1H), 2.20 (s, 3H), 1.07 (s, 9H); $^{19}$F NMR (376 MHz, MeOD-$d_4$) δ −62.82.

(2R)-2-Amino-N-[4-[2-(difluoromethyl)-1H-pyrrolo[2,3-b]pyridin-4-yl]-3-methyl-phenyl]-4-methyl-pentanamide, F-101

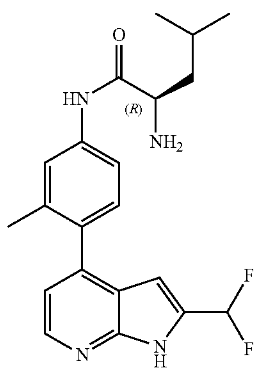

Synthesized in a manner analogous to F-57, reacting intermediate A-8 with G-98 and in Step 1. Colourless solid. LCMS (Method A) $t_R$=1.54 min, m/z=387.21 [M+H]$^+$; Purity ≥95% (DAD, 210, 254 nm); $^1$H NMR (400 MHz, MeOD-$d_4$) δ 8.35 (d, J=4.9 Hz, 1H), 7.63 (d, J=2.1 Hz, 1H), 7.57 (d, J=8.2 Hz, 1H), 7.28 (d, J=8.2 Hz, 1H), 7.10-6.78 (m, 2H), 6.49 (t, J=2.2 Hz, 1H), 3.53 (dd, J=8.1, 6.2 Hz, 1H), 2.20 (s, 3H), 1.80 (dt, J=13.2, 6.5 Hz, 1H), 1.73-1.63 (m, 1H), 1.58-1.46 (m, 1H), 1.02 (d, J=6.6 Hz, 3H), 1.00 (d, J=6.6 Hz, 3H); $^{19}$F NMR (376 MHz, MeOD-$d_4$) δ −113.10 (dd, J=54.6, 2.5 Hz).

(2R)-2-Amino-N-[4-[2-(difluoromethyl)-1H-pyrrolo[2,3-b]pyridin-4-yl]-3-methyl-phenyl]-4,4-dimethyl-pentanamide, F-102

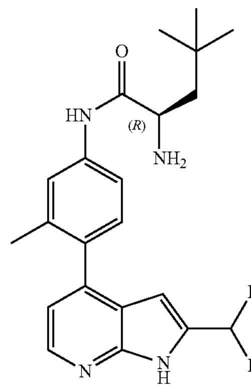

Synthesized in a manner analogous to F-57, using intermediate A-8 in Step 1. Colourless solid. LCMS (Method A) $t_R$=1.60 min, m/z=401.26 [M+H]$^+$; Purity ≥95% (DAD, 210, 254 nm); $^1$H NMR (400 MHz, MeOD-$d_4$) δ 8.35 (d, J=4.9 Hz, 1H), 7.62 (d, J=2.1 Hz, 1H), 7.57 (dd, J=8.3, 2.1 Hz, 1H), 7.28 (d, J=8.3 Hz, 1H), 7.14-6.77 (m, 2H), 6.50 (t, J=2.2 Hz, 1H), 3.53 (dd, J=7.2, 5.3 Hz, 1H), 2.20 (s, 3H), 1.96 (dd, J=13.9, 7.2 Hz, 1H), 1.47 (dd, J=13.9, 5.3 Hz, 1H), 1.03 (s, 9H); $^{19}$F NMR (376 MHz, MeOD-$d_4$) δ −113.09 (dd, J=54.5, 2.2 Hz).

(2R)-2-Amino-N-[4-[2-(difluoromethyl)-1H-pyrrolo[2,3-b]pyridin-4-yl]-3-methyl-phenyl]-3,3-dimethyl-butanamide, F-103

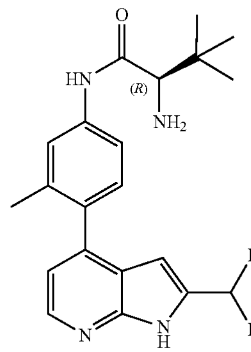

Synthesized in a manner analogous to F-100, using intermediate A-8 in Step 1. Colourless solid. LCMS (Method A) $t_R$=1.54 min, m/z=387.21 [M+H]$^+$; Purity ≥95% (DAD, 210, 254 nm); $^1$H NMR (400 MHz, MeOD-$d_4$) δ 8.35 (d, J=5.0 Hz, 1H), 7.61 (d, J=2.2 Hz, 1H), 7.55 (dd, J=8.3, 2.2 Hz, 1H), 7.28 (d, J=8.3 Hz, 1H), 7.10-6.80 (m, 2H), 6.50 (t, J=2.2 Hz, 1H), 3.22 (s, 1H), 2.20 (s, 3H), 1.07 (s, 9H); $^{19}$F NMR (376 MHz, MeOD-$d_4$) δ −113.07 (dd, J=54.2, 2.2 Hz).

(2R)-2-Amino-4,4-dimethyl-N-[6-[2-(trifluoromethyl)-1H-pyrrolo[2,3-b]pyridin-4-yl]-3-pyridyl]pentanamide, F-104

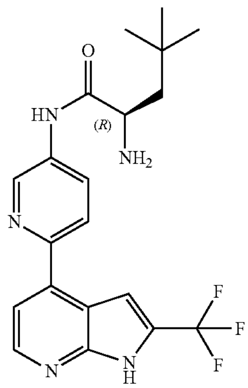

Step 1. tert-Butyl N-[(1R)-1-[(6-chloro-3-pyridyl)carbamoyl]-3,3-dimethyl-butyl]carbamate, G-104. 6-Chloropyridin-3-amine (140 mg, 1.09 mmol) was reacted with Boc-D-Neo-OH (401 mg, 1.63 mmol) following General Procedure E, affording a straw coloured gum (155 mg, 0.44 mmol, 40%). LCMS (Method B) $t_R$=1.50 min, m/z=356.21 $[M+H]^+$; $^1$H NMR (400 MHz, $CDCl_3$) δ 8.71 (s, 1H), 8.38 (d, J=2.8 Hz, 1H), 8.09 (d, J=8.6 Hz, 1H), 7.29 (br s, 1H), 4.87-4.81 (m, 1H), 4.23 (br s, 1H), 2.11-2.04 (m, 1H), 1.46 (s, 9H), 1.44-1.40 (m, 1H), 0.99 (s, 9H).

Step 2. tert-Butyl N-[(1R)-3,3-dimethyl-1-[[6-[2-(trifluoromethyl)-1H-pyrrolo[2,3-b]pyridin-4-yl]-3-pyridyl]carbamoyl]butyl]carbamate, E-104. A-15 (57 mg, 0.18 mmol) and G-104 (54 mg, 0.15 mmol) were reacted following General Procedure C, using X-Phos Palladacycle G2. Purified by ISCO flash chromatography (0-60% EtOAc in hexanes) to afford a yellow solid (63 mg, 0.12 mmol, 82%). LCMS (Method B) $t_R$=1.60 min, m/z=506.23 $[M+H]^+$.

Step 3, (R)-2-Amino-4,4-dimethyl-N-(6-(2-(trifluoromethyl)-1H-pyrrolo[2,3-b]pyridin-4-yl)pyridin-3-yl)pentanamide, F-104. Intermediate E-104 (60 mg, 0.12 mmol) was deprotected according to General Procedure I, affording title compound as a colourless solid (7 mg, 0.02 mmol, 14%). LCMS (Method A) $t_R$=1.69 min, m/z=406.18 $[M+H]^+$; Purity ≥95% (DAD, 210, 254 nm); $^1$H NMR (400 MHz, MeOD-$d_4$) δ 9.01 (d, J=2.5 Hz, 1H), 8.48 (d, J=5.1 Hz, 1H), 8.35 (d, J=7.8 Hz, 1H), 8.05 (d, J=8.7 Hz, 1H), 7.64 (d, J=5.1 Hz, 1H), 7.48 (s, 1H), 3.69 (s, 1H), 2.06-1.98 (m, 1H), 1.59-1.51 (m, 1H), 1.03 (d, J=1.8 Hz, 9H); $^{19}$F NMR (376 MHz, MeOD-$d_4$) δ −62.76.

(2R)-2-Amino-N-[6-[2-(difluoromethyl)-1H-pyrrolo[2,3-b]pyridin-4-yl]-3-pyridyl]-4,4-dimethyl-pentanamide, F-105

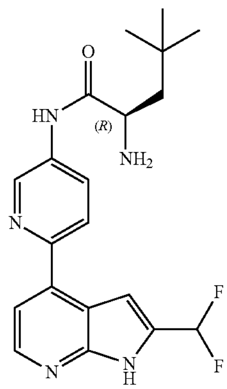

Synthesized in a manner analogous to F-104, using intermediate A-8 in the Step 2 Suzuki-Miyaura coupling. Colourless solid. LCMS (Method A) $t_R$=1.55 min, m/z=388.19 $[M+H]^+$; Purity ≥95% (DAD, 210, 254 nm); $^1$H NMR (400 MHz, MeOD-$d_4$) δ 8.99 (d, J=2.4 Hz, 1H), 8.41 (d, J=5.1 Hz, 1H), 8.37-8.30 (m, 1H), 8.03 (d, J=8.7 Hz, 1H), 7.58 (d, J=5.1 Hz, 1H), 7.28 (d, J=2.4 Hz, 1H), 7.02 (t, J=54.4 Hz, 1H), 3.63 (s, 1H), 1.99 (dd, J=13.9, 7.3 Hz, 1H), 1.56-1.48 (m, 1H), 1.03 (s, 9H); $^{19}$F NMR (376 MHz, MeOD-$d_4$) δ −113.21 (dd, J=54.3, 2.2 Hz).

(2R)-2-Amino-4-methyl-N-[4-(5-methyl-1H-pyrrolo[2,3-b]pyridin-4-yl)phenyl]pentanamide, F-106

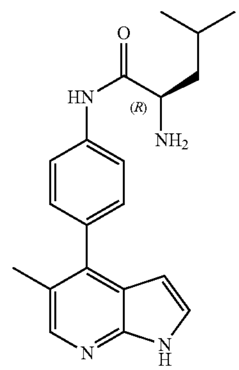

Step 1. tert-Butyl N-[(1R)-3-methyl-1-[[4-(4,4,5,5-tetramethyl-1,3,2-dioxaborolan-2-yl)phenyl]carbamoyl]butyl]carbamate, G-106. 4-Aminophenylboronic acid, pinacol ester (3.29 g, 15 mmol) was reacted with Boc-D-Leu-OH following General Procedure D. Purification by ISCO flash chromatography (0-100% EtOAc in hexanes) affords a cream solid (5.06 g, 11.7 mmol, 78%).

Step 2. tert-Butyl N-[(1R)-1-[[4-[1-(benzenesulfonyl)-5-methyl-pyrrolo[2,3-b]pyridin-4-yl]phenyl]carbamoyl]-3-methyl-butyl]carbamate, E-106. To a vial containing A-18 (31 mg, 0.10 mmol), G-106 (52 mg, 0.12 mmol), PdAmphos (3.6 mg, 0.005 mmol), and $K_2CO_3$ (35 mg, 0.25 mmol) was added dioxane (1 mL) and water (0.2 mL). The mixture was degassed for 10 min then heated to 100° C. for 2 h. The mixture was filtered, concentrated and purified by ISCO flash chromatography (0-100% EtOAc in hexanes) affording a colourless solid (33 mg, 0.06 mmol, 57%). LCMS (Method B) $t_R$=1.77 min, m/z=307.03 $[M+H]^+$.

Step 3. (2R)-2-Amino-4-methyl-N-[4-(5-methyl-1H-pyrrolo[2,3-b]pyridin-4-yl)phenyl]pentanamide, F-106. Intermediate E-106 (33 mg, 0.06 mmol) was deprotected following General Procedure K, affording title compound as a colourless solid (15 mg, 78%). LCMS (Method A) $t_R$=1.39 min, m/z=337.20 $[M+H]^+$; Purity ≥95% (DAD, 210, 254 nm); $^1$H NMR (400 MHz, MeOH-$d_4$) δ 8.13 (s, 1H), 7.78 (d, J=8.4 Hz, 2H), 7.43 (d, J=8.4 Hz, 2H), 7.33 (d, J=3.5 Hz, 1H), 6.22 (d, J=3.5 Hz, 1H), 3.57 (dd, J=8.1, 6.2 Hz, 1H), 2.33 (s, 3H), 1.90-1.77 (m, 1H), 1.77-1.65 (m, 1H), 1.61-1.50 (m, 1H), 1.04 (d, J=6.6 Hz, 3H), 1.02 (d, J=6.6 Hz, 3H).

(2R)-2-Amino-3,3-dimethyl-N-[4-(5-methyl-1H-pyrrolo[2,3-b]pyridin-4-yl)phenyl]butanamide, F-107

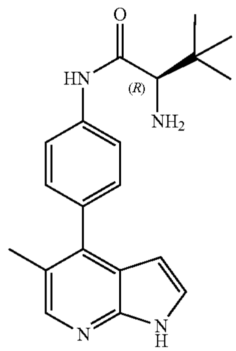

Synthesized in a manner analogous to F-106, using Boc-D-Tle-OH to in the Step 2b amide coupling to generate the require cross-coupling partner. Colourless solid. LCMS (Method A) $t_R$=1.37 min, m/z=337.20 $[M+H]^+$; Purity ≥95% (DAD, 210, 254 nm); $^1H$ NMR (400 MHz, MeOH-$d_4$) δ 8.13 (s, 1H), 7.76 (d, J=8.4 Hz, 2H), 7.43 (d, J=8.4 Hz, 2H), 7.33 (d, J=3.5 Hz, 1H), 6.22 (d, J=3.5 Hz, 1H), 3.26 (s, 1H), 2.33 (s, 3H), 1.10 (s, 9H).

(2R)-2-Amino-4-methyl-N-[4-(1H-pyrrolo[2,3-b]pyridin-4-yl)thiazol-2-yl]pentanamide, NH

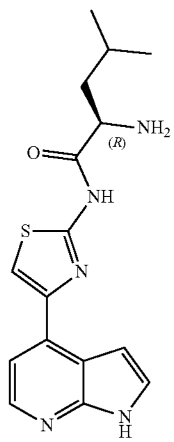

Step 1. tert-Butyl N-[(1R)-1-[[4-[1-(benzenesulfonyl)pyrrolo[2,3-b]pyridin-4-yl]thiazol-2-yl]carbamoyl]-3-methyl-butyl]carbamate, E-110. Boc-D-Leu-OH (69 mg, 0.30 mmol) was reacted with D-12 (71 mg, 0.20 mmol) following General Procedure E. Purification by ISCO flash chromatography (0-100% EtOAc in hexanes) affords a yellow-brown gum (105 mg, 0.18 mmol, 92%). LCMS (Method B) $t_R$=2.06 min, m/z=570.19 $[M+H]^+$.

Step 2. (2R)-2-Amino-4-methyl-N-[4-(1H-pyrrolo[2,3-b]pyridin-4-yl)thiazol-2-yl]pentanamide, F-110. Intermediate E-110 (105 mg, 0.18 mmol) was deprotected according to General Procedure K, affording title compound as a colourless solid (26 mg, 44%). LCMS (Method A) $t_R$=1.33 min, m/z=330.14 $[M+H]^+$; Purity ≥95% (DAD, 210, 254 nm); $^1H$ NMR (400 MHz, DMSO-$d_6$) δ 8.18 (d, J=5.1 Hz, 1H), 7.75 (s, 1H), 7.55 (d, J=5.0 Hz, 1H), 7.42 (d, J=3.5 Hz, 1H), 7.01 (d, J=3.5 Hz, 1H), 3.55 (dd, J=8.4, 6.0 Hz, 1H), 1.77-1.63 (m, 1H), 1.61-1.49 (m, 1H), 1.48-1.35 (m, 1H), 0.89 (t, J=7.2 Hz, 6H).

(2R)-2-Amino-3,3-dimethyl-N-[4-(1H-pyrrolo[2,3-b]pyridin-4-yl)thiazol-2-yl]butanamide, F-111

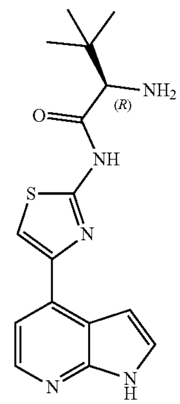

Step 1. tert-Butyl N-[(1R)-1-[[4-[1-(benzenesulfonyl)pyrrolo[2,3-b]pyridin-4-yl]thiazol-2-yl]carbamoyl]-2,2-dimethyl-propyl]carbamate, E-111. Boc-D-Tle-OH (69 mg, 0.30 mmol) was reacted with D-12 (71 mg, 0.20 mmol) following General Procedure E. Purification by ISCO flash chromatography (0-100% EtOAc in hexanes) affords a colourless gum (92 mg, 0.16 mmol, 81%). LCMS (Method B) $t_R$=2.07 min, m/z=570.19 $[M+H]^+$.

Step 2. (2R)-2-Amino-3,3-dimethyl-N-[4-(1H-pyrrolo[2,3-b]pyridin-4-yl)thiazol-2-yl]butanamide, F-111. Intermediate E-111 (92 mg, 0.16 mmol) was deprotected according to General Procedure K, affording title compound as a colourless solid (22 mg, 41%). LCMS (Method A) $t_R$=1.33 min, m/z=330.14 $[M+H]^+$; Purity ≥95% (DAD, 210, 254 nm); $^1H$ NMR (400 MHz, DMSO-$d_6$) δ 8.18 (d, J=5.1 Hz, 1H), 7.75 (s, 1H), 7.55 (d, J=5.1 Hz, 1H), 7.43 (d, J=3.5 Hz, 1H), 7.01 (d, J=3.5 Hz, 1H), 3.27 (s, 1H), 0.95 (s, 9H).

(2R)-2-Amino-3,3-dimethyl-N-[4-(2-methyl-1H-pyrrolo[2,3-b]pyridin-4-yl)thiazol-2-yl]butanamide, F-112

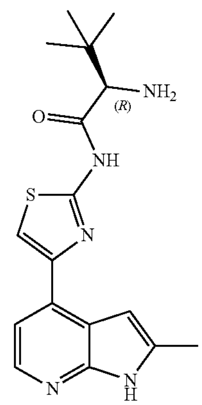

Step 1. tert-Butyl N-[(1R)-1-[[4-[1-(benzenesulfonyl)-2-methyl-pyrrolo[2,3-b]pyridin-4-yl]thiazol-2-yl]carbamoyl]-2,2-dimethyl-propyl]carbamate, E-112. Boc-D-Tle-OH (87 mg, 0.38 mmol) was reacted with D-13 (93 mg, 0.25 mmol) following General Procedure E. Purification by ISCO flash chromatography (0-100% EtOAc in hexanes) affords a brown gum (112 mg, 0.19 mmol, 77%). LCMS (Method B) $t_R$=2.05 min, m/z=584.21 $[M+H]^+$.

Step 2. (2R)-2-Amino-3,3-dimethyl-N-[4-(2-methyl-1H-pyrrolo[2,3-b]pyridin-4-yl)thiazol-2-yl]butanamide, F-112. Intermediate E-112 (112 mg, 0.19 mmol) was deprotected according to General Procedure K, affording title compound as a colourless solid (29 mg, 44%). LCMS (Method A) $t_R$=1.40 min, m/z=344.16 $[M+H]^+$; Purity ≥95% (DAD, 210, 254 nm); HRMS calculated for $C_{17}H_{22}N_5OS$=344.1540, observed 344.1561 $[M+H]^+$; Purity ≥95% (DAD, 210, 254 nm); $^1H$ NMR (400 MHz, DMSO-$d_6$) δ 11.57 (s, 1H), 8.13 (d, J=5.1 Hz, 1H), 7.84 (s, 1H), 7.50 (d, J=5.1 Hz, 1H), 6.75 (s, 1H), 5.32 (s, 2H), 3.32 (s, 1H), 3.27 (s, 1H), 2.45 (s, 3H), 0.96 (s, 9H).

(2S)-2-Amino-3,3-dimethyl-N-[4-(2-methyl-1H-pyrrolo[2,3-b]pyridin-4-yl)thiazol-2-yl]butanamide, F-113

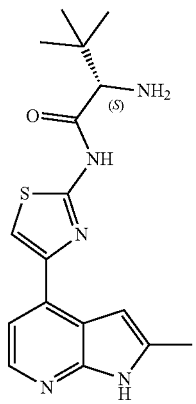

Step 1. tert-Butyl N-[(1S)-1-[[4-[1-(benzenesulfonyl)-2-methyl-pyrrolo[2,3-b]pyridin-4-yl]thiazol-2-yl]carbamoyl]-2,2-dimethyl-propyl]carbamate, E-113. Boc-Tle-OH (69 mg, 0.30 mmol) was reacted with D-13 (74 mg, 0.20 mmol) following General Procedure E. Purification by ISCO flash chromatography (0-100% EtOAc in hexanes) affords a brown solid (85 mg, 0.15 mmol, 73%). LCMS (Method B) $t_R$=2.05 min, m/z=584.21 $[M+H]^+$.

Step 2. (2S)-2-Amino-3,3-dimethyl-N-[4-(2-methyl-1H-pyrrolo[2,3-b]pyridin-4-yl)thiazol-2-yl]butanamide, F-113. Intermediate E-113 (85 mg, 0.15 mmol) was deprotected according to General Procedure K, affording title compound as a colourless solid (20 mg, 40%). LCMS (Method A) $t_R$=1.40 min, m/z=344.17 $[M+H]^+$; Purity ≥95% (DAD, 210, 254 nm); $^1H$ NMR (400 MHz, MeOH-$d_4$) δ 8.10 (d, J=5.2 Hz, 1H), 7.73 (s, 1H), 7.60 (d, J=5.2 Hz, 1H), 6.79 (s, 1H), 3.36 (s, 1H), 2.55-2.49 (m, 3H), 1.08 (s, 9H).

(2R)-2-Amino-3-methyl-N-[4-(2-methyl-1H-pyrrolo[2,3-b]pyridin-4-yl)thiazol-2-yl]butanamide, F-114

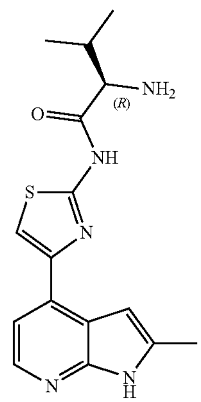

Step 1. tert-Butyl N-[(1R)-1-[[4-[1-(benzenesulfonyl)-2-methyl-pyrrolo[2,3-b]pyridin-4-yl]thiazol-2-yl]carbamoyl]-2-methyl-propyl]carbamate, E-114. Boc-D-Val-OH (65 mg, 0.30 mmol) was reacted with D-13 (74 mg, 0.20 mmol) following General Procedure E. Purification by ISCO flash chromatography (0-100% EtOAc in hexanes) affords a brown solid (91 mg, 0.16 mmol, 80%). LCMS (Method B) $t_R$=1.91 min, m/z=570.20 $[M+H]^+$.

Step 2. (2R)-2-Amino-3-methyl-N-[4-(2-methyl-1H-pyrrolo[2,3-b]pyridin-4-yl)thiazol-2-yl]butanamide, F-114. Intermediate E-114 (91 mg, 0.16 mmol) was deprotected according to General Procedure K, affording title compound as a colourless solid (21 mg, 40%). LCMS (Method A) $t_R$=1.34 min, m/z=330.15 $[M+H]^+$; Purity ≥95% (DAD, 210, 254 nm); $^1H$ NMR (400 MHz, MeOH-$d_4$) δ 8.10 (d, J=5.2 Hz, 1H), 7.73 (s, 1H), 7.60 (d, J=5.2 Hz, 1H), 6.79 (s, 1H), 3.36 (s, 1H), 2.55-2.49 (m, 3H), 1.08 (s, 9H).

2-Amino-N-[4-(2-methyl-1H-pyrrolo[2,3-b]pyridin-4-yl)thiazol-2-yl]-2-[1-(trifluoromethyl)cyclopropyl]acetamide, F-115

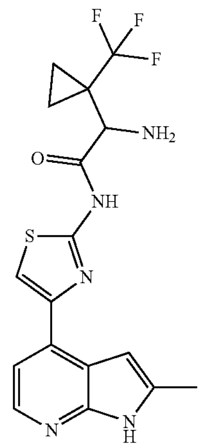 [SMILES: Cc1cc2c(-c3csc(NC(=O)C(N)C4(C(F)(F)F)CC4)n3)ccnc2[nH]1]

Step 1. tert-Butyl N-[2-[[4-[1-(benzenesulfonyl)-2-methyl-pyrrolo[2,3-b]pyridin-4-yl]thiazol-2-yl]amino]-2-oxo-1-[1-(trifluoromethyl)cyclopropyl]ethyl]carbamate, E-115. N-Boc-2-(1-trifluoromethylcyclopropyl)-DL-glycine (68 mg, 0.24 mmol) was reacted with D-13 (74 mg, 0.20 mmol) following General Procedure D. Purification by ISCO flash chromatography (0-100% EtOAc in hexanes) affords a colourless gum (37 mg, 0.06 mmol, 29%). LCMS (Method B) $t_R$=2.00 min, m/z=636.17 $[M+H]^+$.

Step 2. 2-Amino-N-[4-(2-methyl-1H-pyrrolo[2,3-b]pyridin-4-yl)thiazol-2-yl]-2-[1-(trifluoromethyl)cyclopropyl]acetamide, F-115. Intermediate E-115 (37 mg, 0.06 mmol) was deprotected according to General Procedure K, affording title compound as a colourless solid (5 mg, 22%). LCMS (Method A) $t_R$=1.40 min, m/z=396.15 $[M+H]^+$; Purity ≥95% (DAD, 210, 254 nm); $^1H$ NMR (400 MHz, MeOH-$d_4$) δ 8.11 (d, J=5.3 Hz, 1H), 7.76 (s, 1H), 7.60 (d, J=5.3 Hz, 1H), 6.79 (s, 1H), 3.77 (s, 1H), 2.57-2.47 (m, 3H), 1.35-1.25 (m, 1H), 1.20-1.04 (m, 2H), 1.04-0.93 (m, 1H); $^{19}F$ NMR (376 MHz, MeOH-$d_4$) δ −68.93.

(2R)-2-Amino-4-methyl-N-[4-(2-methyl-1H-pyrrolo[2,3-b]pyridin-4-yl)thiazol-2-yl]pentanamide, F-116

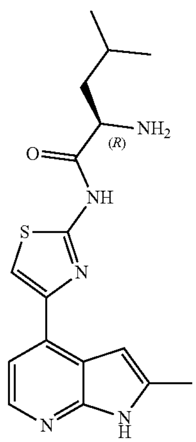

Step 1. tert-Butyl N-[(1R)-1-[[4-[1-(benzenesulfonyl)-2-methyl-pyrrolo[2,3-b]pyridin-4-yl]thiazol-2-yl]carbamoyl]-3-methyl-butyl]carbamate, E-116. Boc-D-Leu-OH (69 mg, 0.24 mmol) was reacted with D-13 (74 mg, 0.20 mmol) following General Procedure D. Purification by ISCO flash chromatography (0-100% EtOAc in hexanes) affords a colourless gum (37 mg, 0.06 mmol, 29%). LCMS (Method B) $t_R$=2.06 min, m/z=584.21 $[M+H]^+$.

Step 2. (2R)-2-Amino-4-methyl-N-[4-(2-methyl-1H-pyrrolo[2,3-b]pyridin-4-yl)thiazol-2-yl]pentanamide, F-116. Intermediate E-116 (92 mg, 0.16 mmol) was deprotected according to General Procedure K, affording title compound as a colourless solid (13 mg, 24%). LCMS (Method A) $t_R$=1.40 min, m/z=396.15 $[M+H]^+$; Purity ≥95% (DAD, 210, 254 nm); $^1H$ NMR (400 MHz, MeOH-$d_4$) δ 8.11 (d, J=5.2 Hz, 1H), 7.73 (s, 1H), 7.59 (d, J=5.2 Hz, 1H), 6.79 (s, 1H), 3.75-3.60 (m, 1H), 2.53 (s, 3H), 1.87-1.76 (m, 1H), 1.75-1.65 (m, 1H), 1.62-1.51 (m, 1H), 1.02 (t, J=6.7 Hz, 6H).

(2R)-2-Amino-3,3-dimethyl-N-[5-methyl-4-(2-methyl-1H-pyrrolo[2,3-b]pyridin-4-yl)thiazol-2-yl]butanamide, F-117

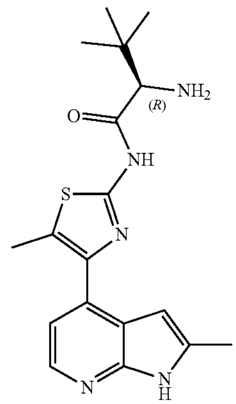

Prepared by a procedure analogous to F-112, using 4-bromo-5-methyl-thiazol-2-amine as the Suzuki-Miyaura coupling partner. Title compound as a colourless solid. LCMS (Method A) $t_R$=1.40 min, m/z=396.15 $[M+H]^+$; Purity ≥95% (DAD, 210, 254 nm); $^1H$ NMR (400 MHz, MeOH-$d_4$) δ 8.13 (d, J=5.2 Hz, 1H), 7.15 (d, J=5.2 Hz, 1H), 6.33 (s, 1H), 3.32 (s, 1H), 2.49 (s, 3H), 2.48 (s, 3H), 1.07 (s, 9H).

N-(4-(1H-Pyrrolo[2,3-b]pyridin-4-yl)phenyl)-2-amino-3-(tetrahydro-2H-pyran-4-yl)propenamide, F-120

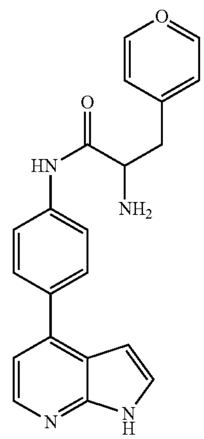

Step 1. tert-Butyl N-[2-[4-[1-(benzenesulfonyl)pyrrolo[2,3-b]pyridin-4-yl]anilino]-2-oxo-ethyl]carbamate, G-120. 2-((tert-Butoxycarbonyl)amino)-3-(tetrahydro-2H-pyran-4-yl)propanoic acid (400 mg, 1.46 mmol) was reacted with 4-bromoaniline (167 mg, 0.97 mmol) following General Procedure D. Purification by silica gel chromatography (0-35% EtOAc in hexanes) affords a colourless solid (398 mg, 96%). LCMS m/z=427.0 $[M+H]^+$.

Step 2. tert-Butyl(1-oxo-1-((4-(1-(phenylsulfonyl)-1H-pyrrolo[2,3-b]pyridin-4-yl)phenyl)amino)-3-(tetrahydro-2H-pyran-4-yl)propan-2-yl)carbamate, E-120. A mixture of G-120 (200 mg, 0.47 mmol), A-3 (216 mg, 0.0.56 mmol), tetrakis(triphenylphosphine)palladium (54 mg, 0.047 mmol) and potassium carbonate (130 mg, 0.94 mmol) in 1,4-dioxane (4 mL) and water (0.4 mL) was heated to 80° C. for 16 hrs. Water (40 mL) was added and the solution was extracted with EtOAc (3×20 mL). The combined organics were washed with brine (30 mL), dried over anhydrous sodium sulfate and concentrated. The residue was purified on silica gel column chromatography (0-30% EtOAc/Petroether) to provide a colourless solid (182 mg, 64%). LCMS m/z=605.1 $[M+H]^+$.

Step 3. N-(4-(1H-Pyrrolo[2,3-b]pyridin-4-yl)phenyl)-2-amino-3-(tetrahydro-2H-pyran-4-yl)propenamide, F-120. E-120 (182 mg, 0.30 mmol) was deprotected following General Procedure K, affording title compound as a colourless solid (72 mg, 0.20 mmol, 65%). LCMS m/z=365.1 $[M+H]^+$; Purity ≥95% (DAD, 210, 254 nm); $^1$H NMR (400 MHz, MeOH-$d_4$) δ 8.22 (d, J=4.8 Hz, 1H), 7.80-7.75 (m, 4H), 7.44 (d, J=3.6 Hz, 1H), 7.20 (d, J=5.2 Hz, 1H), 6.69 (d, J=3.6 Hz, 1H), 3.95-3.92 (m, 2H), 3.56 (dd, J=8.4, 5.6 Hz, 1H), 3.46-3.40 (m, 2H), 1.76-1.69 (m, 4H), 1.58-1.56 (m, 1H), 1.37-1.31 (m, 2H).

2-(Methylamino)-3-phenyl-N-[4-(1H-pyrrolo[2,3-b]pyridin-4-yl)phenyl]propenamide, F-121

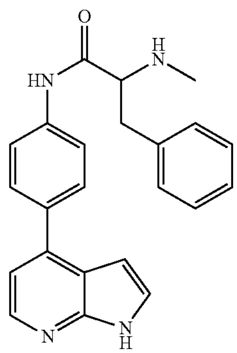 [SMILES: CNC(Cc1ccccc1)C(=O)Nc1ccc(-c2ccnc3[nH]ccc23)cc1]

Step 1. 2-((tert-Butoxycarbonyl)(methyl)amino)-3-phenylpropanoic acid. To a solution of 2-((tert-butoxycarbonyl)amino)-3-phenylpropanoic acid (450 mg, 1.70 mmol) in THE (15 mL) at 0° C. was added sodium hydride (60 wt. % in oil, 204 mg, 5.09 mmol), and stirred for 30 min. Then iodomethane (965 mg, 6.80 mmol) was added to the solution and stirred for 16 h at r.t. The reaction was acidified to pH=5-6 with 1 M HCl then extracted with EtOAc (3×20 mL). The combined organics were washed with brine (20 mL), dried over anhydrous sodium sulfate and concentrated to provide a colourless solid (280 mg, 59%). LCMS m/z=280.0 $[M+H]^+$.

Step 2. tert-Butyl(1-((4-bromophenyl)amino)-1-oxo-3-phenylpropan-2-yl)(methyl)carbamate, G-121. 2-((tert-Butoxycarbonyl)(methyl)amino)-3-phenylpropanoic acid (280 mg, 1.00 mmol) was reacted with 4-bromoaniline (116 mg, 0.67 mmol) following General Procedure D. Purification by silica gel column chromatography (0-50% EtOAc in petroleum ether) affords a yellow solid (280 mg, 96%). LCMS m/z=433.0 $[M+H]^+$.

Step 3. tert-Butyl methyl(1-oxo-3-phenyl-1-((4-(1-(phenylsulfonyl)-1H-pyrrolo[2,3-b]pyridin-4-yl)phenyl)amino)propan-2-yl)carbamate, E-121. A mixture of G-121 (280 mg, 0.65 mmol), A-3 (300 mg, 0.78 mmol), tetrakis(triphenylphosphine)palladium (75 mg, 0.065 mmol) and potassium carbonate (179 mg, 1.30 mmol) in 1,4-dioxane (5 mL) and water (0.5 mL) was heated to 80° C. for 16 hrs. Water (40 mL) was added and the solution was extracted with EtOAc (3×20 mL). The combined organics were washed with brine (30 mL), dried over anhydrous sodium sulfate and concentrated. The residue was purified on silica gel column chromatography (0-30% EtOAc/Petroether) to provide a colourless solid (167 mg, 0.27 mmol, 42%). LCMS m/z=611.1 $[M+H]^+$.

Step 4. 2-(Methylamino)-3-phenyl-N-[4-(1H-pyrrolo[2,3-b]pyridin-4-yl)phenyl]propenamide, F-121. E-121 (167 mg, 0.27 mmol) was deprotected following General Procedure K, affording title compound as a colourless solid (48 mg, 0.12 mmol, 48%). LCMS m/z=365.1 $[M+H]^+$; Purity ≥95% (DAD, 210, 254 nm); $^1$H NMR (400 MHz, MeOH-$d_4$) δ 8.21 (d, J=4.8 Hz, 1H), 7.72 (dd, J=8.4, 2.0 Hz, 2H), 7.63 (dd, J=6.8, 2.4 Hz, 2H), 7.43 (d, J=3.6 Hz, 1H), 7.28-7.20 (m, 5H), 7.19 (d, J=5.2 Hz, 1H), 6.68 (d, J=3.6 Hz, 1H), 3.44 (t, J=7.2 Hz, 1H), 3.01 (dd, J=7.2, 2.4 Hz, 2H), 2.39 (s, 3H).

2-(Dimethylamino)-3-phenyl-N-[4-(1H-pyrrolo[2,3-b]pyridin-4-yl)phenyl]propenamide, F-122

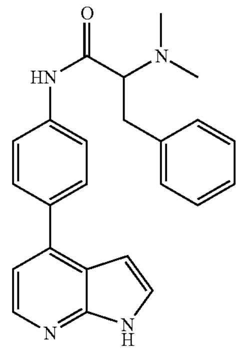 [SMILES: CN(C)C(Cc1ccccc1)C(=O)Nc1ccc(-c2ccnc3[nH]ccc23)cc1]

Step 1. 2-Amino-N-(4-bromophenyl)-3-phenylpropanamide, G-122-1. To a solution of tert-butyl (1-((4-bromophenyl)amino)-1-oxo-3-phenylpropan-2-yl)carbamate (400 mg, 0.96 mmol) in 1,4-dioxane (10 mL) was added a HCl (4.0 M in dioxane, 4.8 mL, 4.78 mmol) at room temperature. The mixture was stirred for 4 h then concentrated to provide a colourless solid (280 mg, 92%). LCMS m/z=319.1 $[M+H]^+$.

Step 2. N-(4-Bromophenyl)-2-(dimethylamino)-3-phenylpropanamide, G-122-2. To a solution of G-122-1 (280 mg, 0.88 mmol) in MeOH (8 mL) was added glacial acetic acid (158 mg, 2.64 mmol), formaldehyde (37 wt. % aq., 357 mg, 4.40 mmol) and sodium cyanoborohydride (276 mg, 4.40 mmol) and the mixture stirred for 1 h at r.t. Upon completion, the mixture was quenched with water (40 mL) and extracted with EtOAc (3×20 mL). The combined organics were washed with brine (30 mL), dried over anhydrous sodium sulfate and concentrated. The residue was purified on silica gel column chromatography (0-35% EtOAc/Petroether) to provide a colourless solid (192 mg, 63%). LCMS m/z=347.0 $[M+H]^+$.

Step 3. 2-(Dimethylamino)-3-phenyl-N-(4-(1-(phenylsulfonyl)-1H-pyrrolo[2,3-b]pyridin-4-yl)phenyl)propenamide, E-122. A mixture of G-122-2 (192 mg, 0.55 mmol), A-3 (256 mg, 0.67 mmol), tetrakis(triphenylphosphine)palladium (64 mg, 0.055 mmol) and potassium carbonate (152 mg, 1.10 mmol) in 1,4-dioxane (4 mL)/water (0.4 mL) was heated to 80° C. for 16 hrs. Water (40 mL) was added and the solution was extracted with EtOAc (3×20 mL). The combined organics were washed with brine (30 mL), dried over anhydrous sodium sulfate and concentrated. The residue was purified on silica gel column chromatography (0-35% EtOAc/Petroether) to provide a colourless solid (142 mg, 49%). LCMS m/z=525.1 $[M+H]^+$.

Step 4. 2-(Dimethylamino)-3-phenyl-N-[4-(1H-pyrrolo[2,3-b]pyridin-4-yl)phenyl]propenamide, F-122. E-122 (142 mg, 0.27 mmol) was deprotected following General Procedure J, affording title compound as a colourless solid (42 mg, 0.11 mmol, 40%). LCMS m/z=385.4 $[M+H]^+$; Purity ≥95% (DAD, 210, 254 nm); $^1H$ NMR (400 MHz, MeOH-$d_4$) δ 8.35 (d, J=6.0 Hz, 1H), 7.80 (dd, J=9.2, 4.4 Hz, 2H), 7.64 (d, J=3.6 Hz, 1H), 7.61 (dd, J=9.2, 2.0 Hz, 2H), 7.47 (d, J=5.6 Hz, 1H), 7.32-7.24 (m, 5H), 6.87 (d, J=3.6 Hz, 1H), 4.14 (dd, J=10.8, 4.8 Hz, 1H), 3.54 (dd, J=12.7, 4.8 Hz, 1H), 3.21 (dd, J=12.7, 10.8 Hz, 1H), 3.09 (s, 6H).

2-Amino-3-(4-chlorophenyl)-N-[4-(1H-pyrrolo[2,3-b]pyridin-4-yl)phenyl]propenamide, F-123

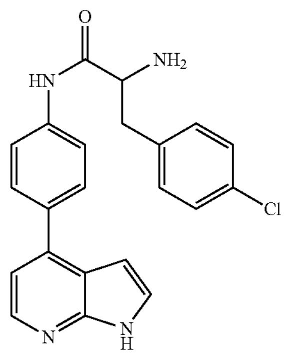 [SMILES: NC(Cc1ccc(Cl)cc1)C(=O)Nc1ccc(-c2ccnc3[nH]ccc23)cc1]

Step 1. tert-Butyl (1-((4-bromophenyl)amino)-3-(4-chlorophenyl)-1-oxopropan-2-yl)carbamate, G-123. 2-((tert-Butoxycarbonyl)amino)-3-(4-chlorophenyl)propanoic acid (415 mg, 2.27 mmol) was reacted with 4-bromoaniline (259 mg, 1.51 mmol) following General Procedure D. Purification by silica gel column chromatography (0-50% EtOAc in petroleum ether) affords a yellow solid (432 mg, 69%). LCMS m/z=455.0 $[M+H]^+$.

Step 2. tert-Butyl (3-(4-chlorophenyl)-1-oxo-1-((4-(1-(phenylsulfonyl)-1H-pyrrolo[2,3-b]pyridin-4-yl)phenyl)amino)propan-2-yl)carbamate, E-123. A mixture of G-123 (300 mg, 0.66 mmol), A-3 (304 mg, 0.79 mmol), tetrakis(triphenylphosphine)palladium (76 mg, 0.066 mmol) and potassium carbonate (182 mg, 1.32 mmol) in 1,4-dioxane (5 mL)/water (0.5 mL) was heated to 80° C. for 16 h. Water (40 mL) was added and the solution was extracted with EtOAc (3×20 mL). The combined organics were washed with brine (30 mL), dried over anhydrous sodium sulfate and concentrated. The residue was purified on silica gel column chromatography (0-30% EtOAc/Petroether) to afford a colourless solid (166 mg, 40%). LCMS m/z=631.1 $[M+H]^+$.

Step 3. 2-Amino-3-(4-chlorophenyl)-N-[4-(1H-pyrrolo[2,3-b]pyridin-4-yl)phenyl]propenamide, F-123. E-123 (166 mg, 0.26 mmol) was deprotected following General Procedure K, affording title compound as a colourless solid (14 mg, 0.04 mmol, 14%). LCMS m/z=391.1 $[M+H]^+$; Purity ≥95% (DAD, 210, 254 nm); $^1H$ NMR (400 MHz, MeOH-$d_4$) δ 8.34 (d, J=6.0 Hz, 1H), 7.85 (dd, J=8.4, 2.0 Hz, 2H), 7.77 (dd, J=8.8, 2.0 Hz, 2H), 7.60 (d, J=3.6 Hz, 1H), 7.44 (d, J=5.6 Hz, 1H), 7.38 (dd, J=8.8, 2.0 Hz, 2H), 7.32 (dd, J=8.8, 2.0 Hz, 2H), 6.86 (d, J=3.6 Hz, 1H), 4.23 (dd, J=10.8, 4.8 Hz, 1H), 3.34 (dd, J=12.7, 4.8 Hz, 1H), 3.22 (dd, J=12.7, 10.8 Hz, 1H).

2-Amino-3-(3-chlorophenyl)-N-[4-(1H-pyrrolo[2,3-b]pyridin-4-yl)phenyl]propenamide, F-124

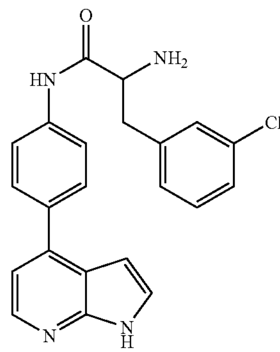 [SMILES: NC(Cc1cccc(Cl)c1)C(=O)Nc1ccc(-c2ccnc3[nH]ccc23)cc1]

Step 1. tert-Butyl (1-((4-bromophenyl)amino)-3-(3-chlorophenyl)-1-oxopropan-2-yl)carbamate, G-124. 2-((tert-Butoxycarbonyl)amino)-3-(3-chlorophenyl)propanoic acid (395 mg, 0.99 mmol) was reacted with 4-bromoaniline (133 mg, 0.66 mmol) following General Procedure D. Purification by silica gel column chromatography (0-50% EtOAc in petroleum ether) affords a yellow solid (422 mg, 70%). LCMS m/z=455.0 $[M+H]^+$.

Step 2. tert-Butyl (3-(3-chlorophenyl)-1-oxo-1-((4-(1-(phenylsulfonyl)-1H-pyrrolo[2,3-b]pyridin-4-yl)phenyl)amino)propan-2-yl)carbamate, E-124. A mixture of G-124 (300 mg, 0.66 mmol), A-3 (304 mg, 0.79 mmol), tetrakis(triphenylphosphine)palladium (76 mg, 0.066 mmol) and potassium carbonate (182 mg, 1.32 mmol) in 1,4-dioxane (5 mL)/water (0.5 mL) was heated to 80° C. for 16 h. Water (40 mL) was added and the solution was extracted with EtOAc (3×20 mL). The combined organics were washed with brine (30 mL), dried over anhydrous sodium sulfate and concentrated. The residue was purified on silica gel column chromatography (0-30% EtOAc/Petroether) to afford a colourless solid (186 mg, 45%). LCMS m/z=631.1 $[M+H]^+$.

Step 3. 2-Amino-3-(3-chlorophenyl)-N-[4-(1H-pyrrolo[2,3-b]pyridin-4-yl)phenyl]propenamide, F-124. E-124 (186 mg, 0.30 mmol) was deprotected following General Procedure K, affording title compound as a colourless solid (81 mg, 0.21 mmol, 69%). LCMS m/z=391.1 $[M+H]^+$; Purity ≥95% (DAD, 210, 254 nm); $^1H$ NMR (400 MHz, MeOH-$d_4$)

δ 8.36 (d, J=5.6 Hz, 1H), 7.87 (dd, J=8.8, 2.0 Hz, 2H), 7.79 (dd, J=8.8, 2.0 Hz, 2H), 7.64 (d, J=3.6 Hz, 1H), 7.50 (d, J=5.6 Hz, 1H), 7.38-7.34 (m, 3H), 7.28-7.24 (m, 1H), 6.90 (d, J=3.6 Hz, 1H), 4.25 (t, J=7.6 Hz, 1H), 3.33 (dd, J=13.8, 6.8 Hz, 1H), 3.20 (dd, J=13.8, 7.6 Hz, 1H).

2-Amino-3-(2-chlorophenyl)-N-[4-(1H-pyrrolo[2,3-b]pyridin-4-yl)phenyl]propenamide, F-125

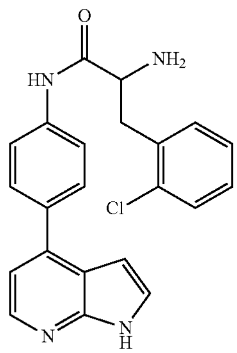 [SMILES: NC(Cc1ccccc1Cl)C(=O)Nc1ccc(-c2ccnc3[nH]ccc23)cc1]

Step 1. tert-Butyl (1-((4-bromophenyl)amino)-3-(2-chlorophenyl)-1-oxopropan-2-yl)carbamate, G-125. 2-((tert-Butoxycarbonyl)amino)-3-(2-chlorophenyl)propanoic acid (405 mg, 1.35 mmol) was reacted with 4-bromoaniline (113 mg, 0.90 mmol) following General Procedure D. Purification by silica gel column chromatography (0-50% EtOAc in petroleum ether) affords a yellow solid (445 mg, 72%). LCMS m/z=455.0 $[M+H]^+$.

Step 2. tert-Butyl (3-(2-chlorophenyl)-1-oxo-1-((4-(1-(phenylsulfonyl)-1H-pyrrolo[2,3-b]pyridin-4-yl)phenyl)amino)propan-2-yl)carbamate, E-125. A mixture of G-125 (300 mg, 0.66 mmol), A-3 (304 mg, 0.79 mmol), tetrakis(triphenylphosphine)palladium (76 mg, 0.066 mmol) and potassium carbonate (182 mg, 1.32 mmol) in 1,4-dioxane (5 mL)/water (0.5 mL) was heated to 80° C. for 16 h. Water (40 mL) was added and the solution was extracted with EtOAc (3×20 mL). The combined organics were washed with brine (30 mL), dried over anhydrous sodium sulfate and concentrated. The residue was purified on silica gel column chromatography (0-30% EtOAc/Petroether) to afford a colourless solid (172 mg, 41%). LCMS m/z=631.1 $[M+H]^+$.

Step 3. 2-Amino-3-(2-chlorophenyl)-N-[4-(1H-pyrrolo[2,3-b]pyridin-4-yl)phenyl]propenamide, F-125. E-125 (172 mg, 0.27 mmol) was deprotected following General Procedure K, affording title compound as a colourless solid (41 mg, 0.11 mmol, 39%). LCMS m/z=391.1 $[M+H]^+$; Purity ≥95% (DAD, 210, 254 nm); $^1$H NMR (400 MHz, MeOH-$d_4$) δ 8.22 (d, J=5.2 Hz, 1H), 7.73 (dd, J=8.8, 2.0 Hz, 2H), 7.67 (dd, J=6.4, 2.0 Hz, 2H), 7.43 (d, J=3.6 Hz, 1H), 7.42-7.40 (m, 1H), 7.35-7.32 (m, 1H), 7.25-7.21 (m, 2H), 7.19 (d, J=5.2 Hz, 1H), 6.68 (d, J=3.2 Hz, 1H), 3.81 (t, J=7.2 Hz, 1H), 3.23 (dd, J=13.6, 7.6 Hz, 1H), 3.14 (dd, J=13.6, 7.2 Hz, 1H).

(2R)-2-Amino-N-[3-methyl-4-(1H-pyrrolo[2,3-b]pyridin-4-yl)phenyl]-3-phenyl-propanamide, F-127

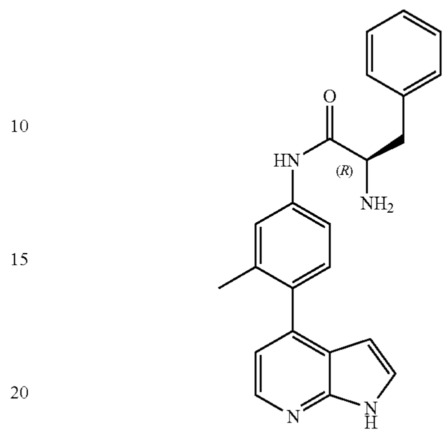

Synthesized in a manner analogous to F-58, using Boc-D-Phe-OH in Step 1. Colourless solid. LCMS (Method A) $t_R$=1.39 min, m/z=371.1873 $[M+H]^+$; Purity ≥95% (DAD, 210, 254 nm); $^1$H NMR (500 MHz, DMSO-$d_6$) δ 11.72 (s, 1H), 8.24 (d, J=4.8 Hz, 1H), 7.64-7.53 (m, 2H), 7.31-7.19 (m, 6H), 6.94 (d, J=4.8 Hz, 1H), 6.15 (dd, J=3.5, 1.8 Hz, 1H), 3.61 (dd, J=7.9, 5.5 Hz, 1H), 3.03 (dd, J=13.4, 5.5 Hz, 1H), 2.75 (dd, J=13.4, 7.9 Hz, 1H), 2.15 (s, 3H).

(2R)-2-Amino-N-[3-methoxy-4-(1H-pyrrolo[2,3-b]pyridin-4-yl)phenyl]-3-phenyl-propanamide, F-128

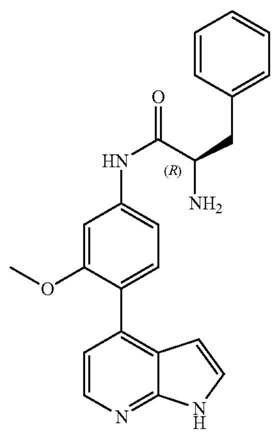

Synthesized in a manner analogous to F-67, reacting Boc-D-Phe-OH with D-67 in Step 2. Cream powder LCMS (Method A) $t_R$=1.38 min, m/z=387.1822 $[M+H]^+$; Purity ≥95% (DAD, 210, 254 nm); $^1$H NMR (500 MHz, DMSO-$d_6$) δ 11.60 (s, 1H), 8.20 (d, J=4.9 Hz, 1H), 7.55-7.52 (m, 1H), 7.43 (t, J=2.9 Hz, 1H), 7.39-7.31 (m, 2H), 7.31-7.25 (m, 4H), 7.23-7.19 (m, 1H), 7.04 (d, J=4.9 Hz, 1H), 6.26-6.24 (m, 1H), 3.73 (s, 3H), 3.62 (dd, J=8.0, 5.5 Hz, 1H), 3.05 (dd, J=13.4, 5.5 Hz, 1H), 2.76 (dd, J=13.4, 8.0 Hz, 1H).

(2S)-2-Amino-3-phenyl-N-[4-(1H-pyrrolo[2,3-b]pyridin-4-yl)-3-(trifluoromethyl)phenyl]propanamide, F-129

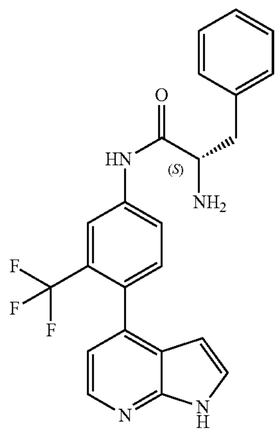

Synthesized in a manner analogous to F-79, reacting Boc-Phe-OH with D-8. Colourless solid. LCMS (Method A) $t_R$=1.49 min, m/z=425.1866 $[M+H]^+$; Purity ≥95% (DAD, 210, 254 nm); $^1H$ NMR (400 MHz, DMSO-$d_6$) δ 11.79 (s, 1H), 8.25 (d, J=5.2 Hz, 2H), 7.94 (d, J=8.2 Hz, 1H), 7.45 (dd, J=12.0, 5.9 Hz, 2H), 7.31-7.15 (m, 5H), 6.93 (d, J=4.7 Hz, 1H), 6.07 (s, 1H), 3.63 (d, J=6.9 Hz, 1H), 3.05 (dd, J=13.7, 5.4 Hz, 1H), 2.78 (dd, J=13.2, 8.0 Hz, 1H).

(2R)-2-Amino-3-phenyl-N-[4-(1H-pyrrolo[2,3-b]pyridin-4-yl)-3-(trifluoromethyl)phenyl]propanamide, F-130

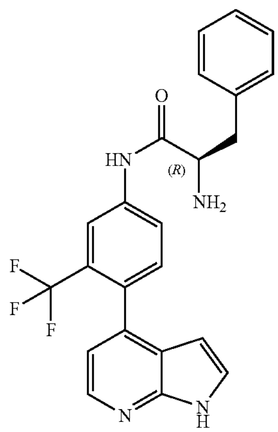

Synthesized in a manner analogous to F-79, reacting Boc-D-Phe-OH with D-8. Colourless solid. LCMS (Method A) $t_R$=2.27 min, m/z=425.1572 $[M+H]^+$; Purity ≥95% (DAD, 210, 254 nm); $^1H$ NMR (400 MHz, DMSO-$d_6$) δ 11.86 (s, 1H), 10.86 (s, 1H), 8.39 (s, 2H), 8.27 (d, J=4.9 Hz, 1H), 8.09 (d, J=2.2 Hz, 1H), 7.87 (dd, J=8.4, 2.2 Hz, 1H), 7.55-7.46 (m, 2H), 7.40-7.35 (m, 2H), 7.33-7.28 (m, 3H), 6.96 (d, J=4.9 Hz, 1H), 6.08 (dd, J=3.5, 1.9 Hz, 1H), 4.23 (s, 1H), 3.24 (dd, J=13.9, 6.5 Hz, 1H), 3.14 (dd, J=13.9, 7.5 Hz, 1H).

(2R)-2-Amino-N-[2-methoxy-4-(1H-pyrrolo[2,3-b]pyridin-4-yl)phenyl]-3-phenyl-propanamide, F-131

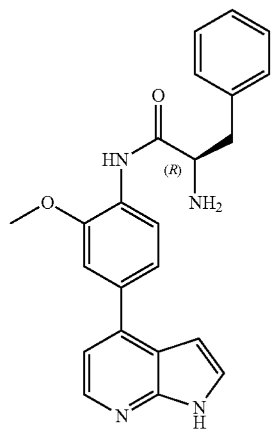

Synthesized in a manner analogous to F-77, reacting Boc-D-Phe-OH with D-77 in Step 2. Colourless solid (17 mg, 0.04 mmol, 34%). LCMS (Method A) $t_R$=1.44 min, m/z=387.1814 $[M+H]^+$; Purity ≥95% (DAD, 210, 254 nm); $^1H$ NMR (400 MHz, MeOH-$d_4$) δ 8.36 (d, J=8.7 Hz, 1H), 8.23 (d, J=5.1 Hz, 1H), 7.46-7.44 (m, 1H), 7.40-7.37 (m, 2H), 7.33-7.28 (m, 4H), 7.25-7.22 (m, 2H), 6.72 (d, J=3.6 Hz, 1H), 3.95 (s, 3H), 3.80 (dd, J=8.2, 5.3 Hz, 1H), 3.21 (dd, J=13.6, 5.3 Hz, 1H), 2.90 (dd, J=13.5, 8.2 Hz, 1H).

(2R)-2-Amino-N-[2-methyl-4-(1H-pyrrolo[2,3-b]pyridin-4-yl)phenyl]-3-phenyl-propanamide, F-132

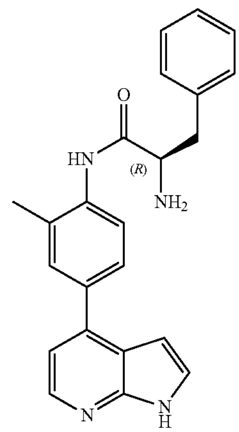

Synthesized in a manner analogous to F-61, reacting Boc-D-Phe-OH with D-61 in Step 2. Colourless solid. LCMS (Method A) $t_R$=1.42 min, m/z=371.1844 $[M+H]^+$; Purity ≥95% (DAD, 210, 254 nm); $^1H$ NMR (400 MHz, MeOH-$d_4$) δ 8.22 (d, J=5.1 Hz, 1H), 7.69 (d, J=8.7 Hz, 1H), 7.60 (br. s, 2H), 7.44 (d, J=3.5 Hz, 1H), 7.37-7.29 (m, 4H), 7.28-7.23 (m, 1H), 7.18 (d, J=5.1 Hz, 1H), 6.67 (d, J=3.5 Hz, 1H), 3.84-3.80 (m, 1H), 3.14 (dd, J=13.4, 6.5 Hz, 1H), 2.99 (dd, J=13.4, 7.2 Hz, 1H), 2.18 (s, 3H).

(2R)-2-Amino-N-[2-chloro-4-(1H-pyrrolo[2,3-b]pyridin-4-yl)phenyl]-3-phenyl-propanamide, F-133

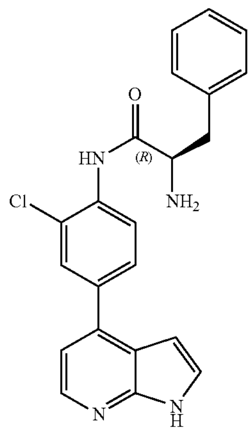

Synthesized in a manner analogous to F-75, reacting Boc-D-Phe-OH with D-75 in Step 2. Colourless solid. LCMS (Method A) $t_R$=1.43 min, m/z=391.1334 $[M+H]^+$; Purity ≥95% (DAD, 210, 254 nm); $^1$H NMR (400 MHz, DMSO-$d_6$) δ 11.91 (s, 1H), 10.20 (s, 1H), 8.41-8.36 (m, 2H), 8.32-8.29 (m, 1H), 7.90-7.75 (m, 2H), 7.59 (t, J=3.0 Hz, 1H), 7.42-7.19 (m, 7H), 6.64-6.60 (m, 1H), 4.46-4.42 (m, 1H), 3.36-3.07 (m, 2H).

(2R)-2-Amino-3-phenyl-N-[3-(1H-pyrrolo[2,3-b]pyridin-4-yl)phenyl]propanamide, F-134

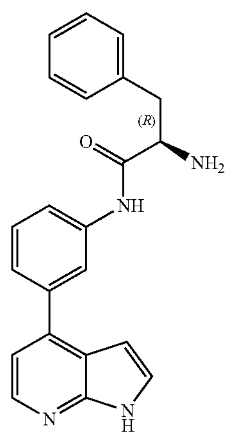

Synthesized in a manner analogous to F-87, reacting Boc-D-Phe-OH with D-87 in Step 2. Colourless solid. LCMS (Method A) $t_R$=1.41 min, m/z=357.1687 $[M+H]^+$; Purity ≥95% (DAD, 210, 254 nm); $^1$H NMR (400 MHz, MeOH-$d_4$) δ 8.25 (d, J=5.1 Hz, 1H), 8.01 (t, J=1.9 Hz, 1H), 7.56-7.43 (m, 4H), 7.34-7.18 (m, 6H), 6.74 (d, J=3.5 Hz, 1H), 3.75 (t, J=7.0 Hz, 1H), 3.11 (dd, J=13.4, 7.0 Hz, 1H), 2.96 (dd, J=13.4, 7.0 Hz, 1H).

2-Amino-N-[4-(3-methyl-1H-pyrrolo[2,3-b]pyridin-4-yl)phenyl]-3-phenyl-propanamide, F-135

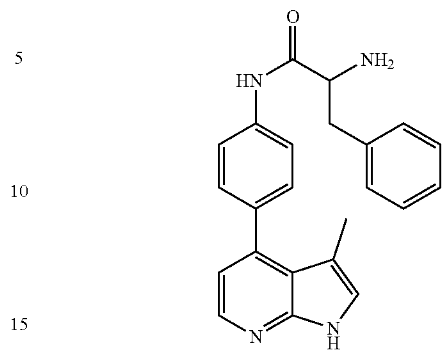

Step 1. tert-Butyl(1-((4-(3-methyl-1-((2-(trimethylsilyl)ethoxy)methyl)-1H-pyrrolo[2,3-b]pyridin-4-yl)phenyl)amino)-1-oxo-3-phenylpropan-2-yl)carbamate, E-135. A mixture of A-20 (200 mg, 0.52 mmol), tert-butyl (1-((4-bromophenyl)amino)-1-oxo-3-phenylpropan-2-yl)carbamate (180 mg, 0.43 mmol), tetrakis(triphenylphosphine)palladium (50 mg, 0.043 mmol) and potassium carbonate (119 mg, 0.86 mmol) in 1,4-dioxane (4 mL)/water (0.4 mL) was heated to 80° C. for 16 h. Water (40 mL) was added and the solution was extracted with EtOAc (3×20 mL). The combined organics were washed with brine (30 mL), dried over anhydrous sodium sulfate and concentrated. The residue was purified on silica gel column chromatography (0-30% EtOAc/Petroether) to provide a colourless solid (98 mg, 38%). LCMS m/z=601.1 $[M+H]^+$.

Step 2. 2-Amino-N-[4-(3-methyl-1H-pyrrolo[2,3-b]pyridin-4-yl)phenyl]-3-phenyl-propanamide, F-135. To a solution of E-135 (98 mg, 0.16 mmol) in 1,4-dioxane (2.0 mL) was added a 4 M solution of HCl (0.4 mL, 1.63 mmol) at r.t. and the mixture stirred for 5 h. Concentrated to provide the title compound hydrochloride salt as a colourless solid (22 mg, 36%). LCMS m/z=371.1 $[M+H]^+$; Purity ≥95% (DAD, 210, 254 nm); $^1$H NMR (400 MHz, $CD_3OD$) δ 8.18 (d, J=5.2 Hz, 1H), 7.63 (dd, J=10.8, 2.4 Hz, 2H), 7.41 (dd, J=8.8, 2.0 Hz, 2H), 7.32-7.14 (m, 6H), 6.93 (d, J=4.8 Hz, 1H), 3.73 (t, J=7.2 Hz, 1H), 3.11 (dd, J=9.2, 6.4 Hz, 1H), 2.94 (dd, J=13.2, 7.2 Hz, 1H), 1.94 (s, 3H).

(2R)-2-Amino-N-[4-(3-ethyl-1H-pyrrolo[2,3-b]pyridin-4-yl)phenyl]-3-phenyl-propanamide, F-136

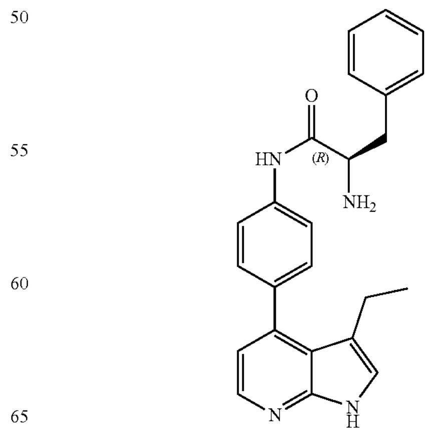

Step 1. tert-butyl N-[(1-R)-2-[4-[1-benzenesulfonyl)-3-ethyl-pyrrolo[2,3-b]pyridin-4-yl]anilino]-1-benzyl-2-oxo-ethyl]carbamate, E-136. Boc-D-Phe-OH (53 mg, 0.20 mmol) was reacted with D-11 (50 mg, 0.13 mmol) according to general procedure D. Purification by ISCO flash chromatography (10-80% EtOAc in hexanes) to afford a white powder (55 mg, 0.09 mmol, 83%). LCMS (Method B) $t_R$=2.29 min, m/z 625.2489 $[M+H]^+$; H NMR (400 MHz, DMSO-$d_6$) δ 10.21 (s, 1H), 8.35 (d, J=5.0 Hz, 1H), 8.14 (d, J=7.6 Hz, 2H), 7.77-7.59 (m, 6H), 7.41-7.24 (m, 6H), 7.24-7.09 (m, 3H), 4.36 (d, J=11.3 Hz, 1H), 3.01 (dd, J=14.3, 4.6 Hz, 1H), 2.86 (t, J=12.2 Hz, 1H), 2.29 (q, J=7.5 Hz, 2H), 1.32 (s, 9H), 0.84 (br. s, 3H).

Step 2. (2R)-2-amino-N-[4-(3-ethyl-1H-pyrrolo[2,3-b]pyridin-4-yl)phenyl]-3-phenyl-propanamide, F-136. Intermediate E-136 (50 mg, 0.08 mmol) was deprotected according to General Procedure K affording the title compound as a white powder (12 mg, 0.03 mmol, 39%). LCMS (Method A) $t_R$=1.47 min, m/z=385.2011 $[M+H]^+$; Purity ≥95% (DAD, 210, 254 nm); $^1$H NMR (400 MHz, DMSO-$d_6$) δ 11.59 (s, 1H), 10.52 (s, 1H), 8.35 (s, 2H), 8.22 (d, J=4.8 Hz, 1H), 7.65 (d, J=7.8 Hz, 1H), 7.45 (d, J=7.8 Hz, 2H), 7.32 (dd, J=18.2, 5.9 Hz, 6H), 6.90 (s, 1H), 4.18 (s, 1H), 3.26-3.04 (m, 2H), 2.32 (q, J=6.0 Hz, 2H), 0.80 (t, J=6.0 Hz, 3H).

(2R)-2-Amino-N-[2-fluoro-3-methyl-4-(1H-pyrrolo[2,3-b]pyridin-4-yl)phenyl]-3,3-dimethyl-butanamide, F-137

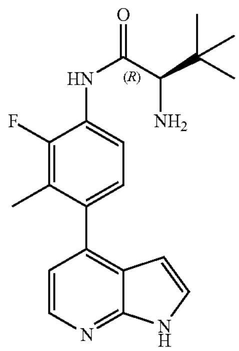

Synthesized via a route analogous to that used to make F-65, using 4-bromo-2-fluoro-3-methyl-aniline as the Step 1 Suzuki coupling partner, and Boc-D-Tle-OH as the amino acid partner. After deprotection, title compound obtained as a colourless solid (35 mg, 55%). LCMS (Method A) $t_R$=1.39 min, m/z=355.21 $[M+H]^+$; Purity ≥95% (DAD, 210, 254 nm); $^1$H NMR (400 MHz, MeOH-$d_4$) δ 8.27 (d, J=5.0 Hz, 1H), 7.87 (t, J=8.2 Hz, 1H), 7.43 (d, J=3.5 Hz, 1H), 7.17 (dd, J=8.2, 1.5 Hz, 1H), 7.03 (d, J=5.0 Hz, 1H), 6.26 (d, J=3.5 Hz, 1H), 3.35 (s, 1H), 2.15 (d, J=2.7 Hz, 3H), 1.11 (s, 9H); $^{19}$F NMR (376 MHz, MeOD) δ −129.66.

(2R)-2-Amino-N-[3,5-dimethyl-4-(1H-pyrrolo[2,3-b]pyridin-4-yl)phenyl]-3,3-dimethyl-butanamide, F-138

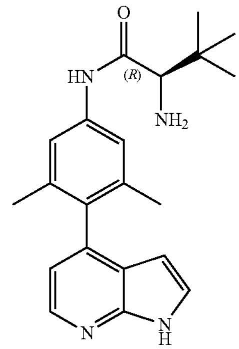

Synthesized in a manner analogous to F-64, using Boc-D-Tle-OH in Step 1. Colourless solid. LCMS (Method A) $t_R$=1.45 min, m/z=351.2041 $[M+H]^+$; Purity ≥95% (DAD, 210, 254 nm); $^1$H NMR (400 MHz, Methanol-$d_4$) δ 8.24 (d, J=5.0 Hz, 1H), 7.41-7.37 (m, 2H), 7.36 (d, J=3.5 Hz, 1H), 6.89 (d, J=5.0 Hz, 1H), 6.06 (d, J=3.5 Hz, 1H), 3.23 (s, 1H), 1.96 (s, 6H), 1.07 (s, 9H).

(2R)-2-Amino-N-[4-[2-(difluoromethyl)-1H-pyrrolo[2,3-b]pyridin-4-yl]-3-methyl-phenyl]-3-hydroxy-3-methyl-butanamide, F-139

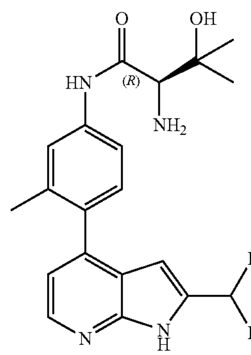

Step 1. tert-Butyl N-[(1R)-1-[(4-bromo-3-methyl-phenyl)carbamoyl]-2-hydroxy-2-methyl-propyl]carbamate, G-139. (2R)-2-(tert-Butoxycarbonylamino)-3-hydroxy-3-methyl-butanoic acid (85 mg, 0.36 mmol) was reacted with 4-bromo-3-methylaniline (95 mg, 0.51 mmol) following General Procedure G. Purification by ISCO flash chromatography (0-100% EtOAc in hexanes) affords a colourless solid (92 mg, 0.23 mmol, 63%). LCMS (Method A) $t_R$=2.17 min, m/z=423.06, 425.06 $[M+Na]^+$.

Step 2. tert-Butyl N-[(1R)-1-[[4-[1-(benzenesulfonyl)-2-(difluoromethyl)pyrrolo[2,3-b]pyridin-4-yl]-3-methyl-phenyl]carbamoyl]-2-hydroxy-2-methyl-propyl]carbamate, E-139. G-139 (92 mg, 0.23 mmol) was reacted with A-8 (87 mg, 0.20 mmol) following General Procedure B. Purification by ISCO flash chromatography (0-100% EtOAc in hexanes) affords a straw-coloured gum (101 mg, 0.16 mmol, 80%). LCMS (Method B) $t_R$=1.79 min, m/z=629.23 $[M+H]^+$.

Step 3. (2R)-2-Amino-N-[4-[2-(difluoromethyl)-1H-pyrrolo[2,3-b]pyridin-4-yl]-3-methyl-phenyl]-3-hydroxy-3-methyl-butanamide, F-139. E-139 (101 mg, 0.16 mmol) was deprotected following General Procedure N. Purified by reverse phase HPLC (5-40% MeCN in $H_2O$, 0.1% TFA) and free base obtained by SCX-II chromatography (load/wash MeOH, elute 2N $NH_3$/MeOH), affording a colourless solid (33 mg, 0.09 mmol, 53%). LCMS (Method A) $t_R$=1.40 min, m/z=389.1801 $[M+H]^+$; Purity ≥95% (DAD, 210, 254 nm); $^1$H NMR (400 MHz, MeOH-$d_4$) δ 8.37 (d, J=5.0 Hz, 1H), 7.64 (d, J=2.2 Hz, 1H), 7.58 (dd, J=8.3, 2.2 Hz, 1H), 7.30 (d, J=8.3 Hz, 1H), 7.11-7.09 (m, 1H), 6.96 (t, J=55.0 Hz, 1H), 6.51 (t, J=2.3 Hz, 1H), 3.41 (s, 1H), 2.22 (s, 3H), 1.34 (s, 3H), 1.32 (s, 3H); $^{19}$F NMR (376 MHz, MeOH-$d_4$) δ −113.10.

(2R)-2-Amino-3-hydroxy-3-methyl-N-[3-methyl-4-(2-methyl-1H-pyrrolo[2,3-b]pyridin-4-yl)phenyl]butanamide, F-140

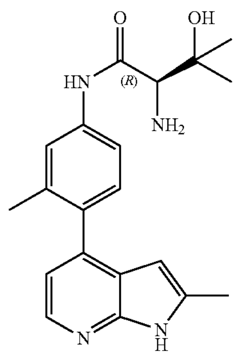

Synthesized in a manner analogous to F-139, using A-5 in Step 2. Colourless solid. LCMS (Method A) $t_R$=1.28 min, m/z=353.1796 $[M+H]^+$; Purity ≥95% (DAD, 210, 254 nm); $^1$H NMR (400 MHz, MeOH-$d_4$) δ 8.11 (d, J=5.0 Hz, 1H), 7.60 (d, J=2.2 Hz, 1H), 7.54 (dd, J=8.3, 2.2 Hz, 1H), 7.27 (d, J=8.3 Hz, 1H), 6.93 (d, J=5.0 Hz, 1H), 5.93-5.88 (m, 1H), 3.40 (s, 1H), 2.45 (s, 3H), 2.21 (s, 3H), 1.34 (s, 3H), 1.32 (s, 3H).

(2R)-2-Amino-N-[4-(2-cyclopropyl-1H-pyrrolo[2,3-b]pyridin-4-yl)phenyl]-4,4-dimethyl-pentanamide, F-141

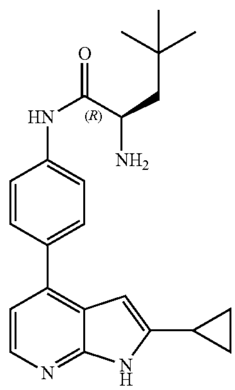

Synthesized in a sequence following General Scheme 3, reacting A-15 and G-3 in Step 1. Colourless solid. LCMS (Method A) $t_R$=1.59 min, m/z=378.24 $[M+H]^+$; Purity ≥95% (DAD 210, 254 nm); $^1$H NMR (400 MHz, DMSO-$d_6$) δ 11.54 (s, 1H), 8.11 (d, J=5.0 Hz, 1H), 7.80 (d, J=8.6 Hz, 2H), 7.70 (d, J=8.6 Hz, 2H), 7.08 (d, J=5.0 Hz, 1H), 6.31 (s, 1H), 3.40 (t, J=6.3 Hz, 1H), 2.05 (ddd, J=13.8, 8.5, 5.2 Hz, 1H), 1.77 (dd, J=13.8, 6.0 Hz, 1H), 1.33 (dd, J=xh 13.8, 6.0 Hz, 1H), 0.95 (s, 9H), 0.88 (dt, J=5.2, 2.9 Hz, 2H).

(2R)-2-Amino-N-[4-(2-cyclopropyl-1H-pyrrolo[2,3-b]pyridin-4-yl)-3-methyl-phenyl]-4,4-dimethyl-pentanamide, F-142

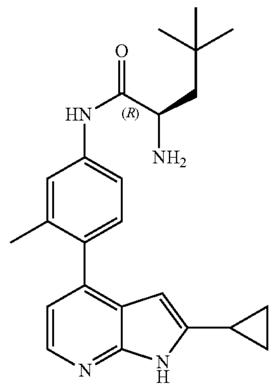

Synthesized in a sequence following General Scheme 3, reacting A-15 and G-4 in Step 1. LCMS (Method A) $t_R$=1.61 min, m/z=391.2302 $[M+H]^+$; Purity ≥95% (DAD 210, 254 nm); $^1$H NMR (400 MHz, DMSO-$d_6$) δ 11.51 (s, 1H), 9.97 (br s, 1H), 8.10 (d, J=4.9 Hz, 1H), 7.62 (d, J=2.0 Hz, 1H), 7.61-7.54 (m, 1H), 7.21 (d, J=8.3 Hz, 1H), 6.85 (d, J=4.9 Hz, 1H), 5.80 (d, J=2.0 Hz, 1H), 3.38 (t, J=6.2 Hz, 1H), 2.14 (s, 3H), 1.77 (dd, J=13.9, 5.9 Hz, 1H), 1.32 (dd, J=13.8, 6.3 Hz, 1H), 0.99-0.93 (m, 11H), 0.82 (dt, J=5.2, 2.9 Hz, 2H).

(2R)-2-Amino-N-[4-[2-(difluoromethyl)-1H-pyrrolo[2,3-b]pyridin-4-yl]phenyl]-4,4-dimethyl-pentanamide, F-143

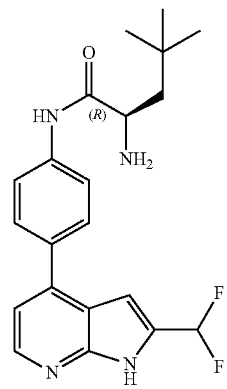

Synthesized in a manner analogous to F-57, reacting A-8 with G-3 in Step 1. Colourless solid. LCMS (Method A) $t_R$=1.53 min, m/z=387.2011 $[M+H]^+$; Purity ≥95% (DAD, 210, 254 nm); $^1$H NMR (400 MHz, MeOH-$d_4$) δ 8.35 (d, J=5.1 Hz, 1H), 7.81 (d, J=8.7 Hz, 2H), 7.78-7.73 (m, 2H), 7.27 (d, J=5.1 Hz, 1H), 7.00 (t, J=54.5 Hz, 1H), 6.96 (t, J=2.3 Hz, 1H), 3.56 (dd, J=7.2, 5.3 Hz, 1H), 1.97 (dd, J=13.9, 7.2 Hz, 1H), 1.48 (dd, J=13.9, 5.3 Hz, 1H), 1.02 (s, 9H); $^{19}$F NMR (376 MHz, MeOH-$d_4$) δ −113.04.

(2R)-2-amino-4,4-dimethyl-N-[4-[2-(trifluoromethyl)-1H-pyrrolo[2,3-b]pyridin-4-yl]phenyl]pentanamide, F-144

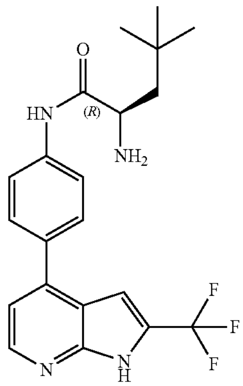

Step 1. tert-Butyl N-[(1R)-3,3-dimethyl-1-[[4-[2-(trifluoromethyl)-1H-pyrrolo[2,3-b]pyridin-4-yl]phenyl]carbamoyl]butyl]carbamate, H-144. Intermediate G-3 (120 mg, 0.30 mmol) was reacted with A-12 (112 mg, 0.36 mmol) according to General Procedure A affording a beige solid (109 mg, 0.22 mmol, 72%). LCMS (Method B) $t_R$=1.68 min, m/z=505.2289 [M+H]$^+$; $^1$H NMR (400 MHz, $CDCl_3$) δ 9.58 (s, 1H), 8.17 (s, 1H), 7.58 (d, J=7.9 Hz, 2H), 7.43 (d, J=8.1 Hz, 2H), 6.97 (s, 1H), 6.76 (s, 1H), 5.44 (s, 1H), 4.57 (d, J=9.8 Hz, 1H), 1.92 (dd, J=14.5, 3.4 Hz, 1H), 1.75-1.61 (m, 1H), 1.47 (s, 9H), 1.06 (s, 9H).

Step 2. (2R)-2-Amino-4,4-dimethyl-N-[4-[2-(trifluoromethyl)-1H-pyrrolo[2,3-b]pyridin-4-yl]phenyl]pentanamide, F-144. Intermediate H-144 (100 mg, 0.20 mmol) was deprotected according to General Procedure I affording the title compound as a colourless solid (32 mg, 0.08 mmol, 40%). LCMS (Method A) $t_R$=1.73 min, m/z=405.1930 [M+H]$^+$; Purity ≥95% (DAD, 210, 254 nm); $^1$H NMR (400 MHz, DMSO-$d_6$) δ 8.47 (d, J=4.9 Hz, 1H), 7.85 (d, J=8.5 Hz, 2H), 7.77 (d, J=8.7 Hz, 2H), 7.33 (d, J=4.9 Hz, 1H), 7.18 (s, 1H), 3.42 (t, J=6.2 Hz, 1H), 1.77 (dd, J=13.8, 6.2 Hz, 1H), 1.34 (dd, J=13.8, 6.1 Hz, 1H), 0.95 (s, 9H); $^{19}$F NMR (376 MHz, DMSO-$d_6$) δ −59.49.

(2R)-2-Amino-4,4-dimethyl-N-(6-(2-methyl-1H-pyrrolo[2,3-b]pyridin-4-yl)pyridin-3-yl)pentanamide, F-145

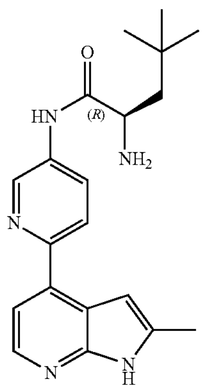

Synthesized in a sequence following General Scheme 2, reacting A-5 and G-5 in Step 1. LCMS (Method A) $t_R$=1.44 min, m/z=352.2143 [M+H]$^+$; Purity ≥95% (DAD, 210, 254 nm); $^1$H NMR (400 MHz, MeOH-$d_4$) δ 8.84 (d, J=2.5 Hz, 1H), 8.21 (dd, J=8.6, 2.5 Hz, 1H), 8.06 (d, J=5.2 Hz, 1H), 7.88 (d, J=8.6 Hz, 1H), 7.35 (d, J=5.2 Hz, 1H), 6.51 (s, 1H), 3.46 (dd, J=7.0, 5.4 Hz, 1H), 2.40 (s, 3H), 1.87 (dd, J=14.0, 7.0 Hz, 1H), 1.38 (dd, J=14.0, 5.4 Hz, 1H), 0.93 (s, 9H).

(2R)-2-Amino-4,4-dimethyl-N-[5-[2-(trifluoromethyl)-1H-pyrrolo[2,3-b]pyridin-4-yl]-2-pyridyl]pentanamide, F-146

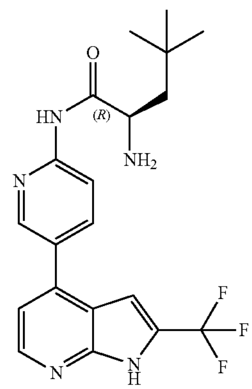

Synthesized in a sequence following General Scheme 3, reacting A-12 and G-11 in Step 1. LCMS (Method A) $t_R$=1.72 min, m/z=406.1867 [M+H]$^+$; Purity ≥95% (DAD, 210, 254 nm); $^1$H NMR (400 MHz, MeOH-$d_4$) δ 8.73 (d, J=2.4 Hz, 1H), 8.47 (d, J=5.0 Hz, 1H), 8.37 (d, J=8.8 Hz, 1H), 8.22 (dd, J=8.7, 2.4 Hz, 1H), 7.37 (d, J=5.0 Hz, 1H), 7.12 (s, 1H), 3.64 (t, J=6.1 Hz, 1H), 1.99 (dd, J=14.1, 6.0 Hz, 1H), 1.47 (dd, J=14.1, 6.1 Hz, 1H), 1.03 (s, 9H); $^{19}$F NMR (376 MHz, MeOH-$d_4$) δ −62.77.

(2R)-2-Amino-N-[2-fluoro-3-methyl-4-[2-(trifluoromethyl)-1H-pyrrolo[2,3-b]pyridin-4-yl]phenyl]-4,4-dimethyl-pentanamide, F-147

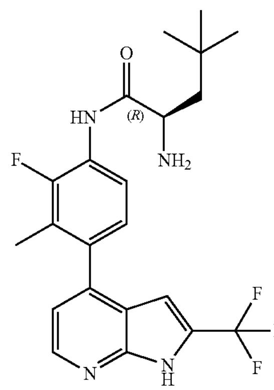

Synthesized in a sequence following General Scheme 3, reacting A-12 and G-13 in Step 1. LCMS (Method A) $t_R$=1.83 min, m/z=437.1983 [M+H]$^+$; Purity ≥95% (DAD, 210, 254 nm); $^1$H NMR (400 MHz, MeOH-$d_4$) δ 8.35 (d, J=4.9 Hz, 1H), 7.93 (t, J=8.1 Hz, 1H), 7.09-7.01 (m, 2H), 6.56 (s, 1H), 3.54 (t, J=6.0 Hz, 1H), 2.04 (d, J=2.7 Hz, 3H), 1.90 (dd, J=14.1, 5.7 Hz, 1H), 1.36 (dd, J=14.1, 6.3 Hz, 1H), 0.95 (s, 9H); $^{19}$F NMR (376 MHz, MeOH-$d_4$) δ-62.84, −131.17.

(2R)-2-Amino-N-[2-methoxy-6-(2-methyl-1H-pyrrolo[2,3-b]pyridin-4-yl)-3-pyridyl]-4,4-dimethyl-pentanamide, F-148

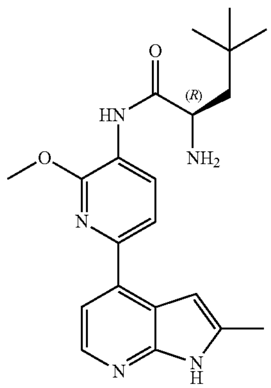

Synthesized in a sequence following General Scheme 2, reacting A-5 and G-9 in Step 1. LCMS (Method A) $t_R$=1.57 min, m/z=382.2024 [M+H]$^+$; Purity ≥95% (DAD 210, 254 nm); $^1$H NMR (400 MHz, DMSO-$d_6$) δ 11.59 (s, 1H), 8.66 (d, J=8.3 Hz, 1H), 8.17 (d, J=5.1 Hz, 1H), 7.73 (d, J=8.3 Hz, 1H), 7.55 (d, J=5.1 Hz, 1H), 6.80 (s, 1H), 4.13 (s, 3H), 3.32-3.28 (m, 1H), 2.45 (s, 3H), 1.89 (d, J=14.1 Hz, 1H), 1.36 (dd, J=14.1, 7.3 Hz, 1H), 0.99 (s, 9H).

(2R)-2-Amino-N-[2-methoxy-6-[2-(trifluoromethyl)-1H-pyrrolo[2,3-b]pyridin-4-yl]-3-pyridyl]-4,4-dimethyl-pentanamide, F-149

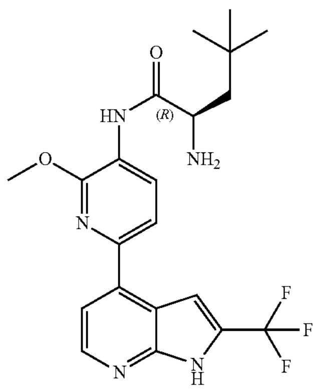

Synthesized in a sequence following General Scheme 3, reacting A-12 and G-9 in Step 1. LCMS (Method A) $t_R$=1.84 min, m/z=436.1777 [M+H]$^+$; Purity ≥95% (DAD 210, 254 nm); $^1$H NMR (400 MHz, MeOH-$d_4$) δ 8.67 (d, J=8.2 Hz, 1H), 8.49 (d, J=5.2 Hz, 1H), 7.79 (d, J=8.2 Hz, 1H), 7.76 (d, J=5.1 Hz, 1H), 7.66 (s, 1H), 4.34 (dd, J=8.6, 4.6 Hz, 1H), 2.15 (dd, J=14.1, 8.7 Hz, 1H), 1.72 (dd, J=14.1, 4.5 Hz, 1H), 1.09 (s, 9H); $^{19}$F NMR (376 MHz, MeOH-$d_4$) δ −62.84.

(2R)-2-Amino-N-[6-[2-(difluoromethyl)-1H-pyrrolo[2,3-b]pyridin-4-yl]-2-methoxy-3-pyridyl]-4,4-dimethyl-pentanamide, F-150

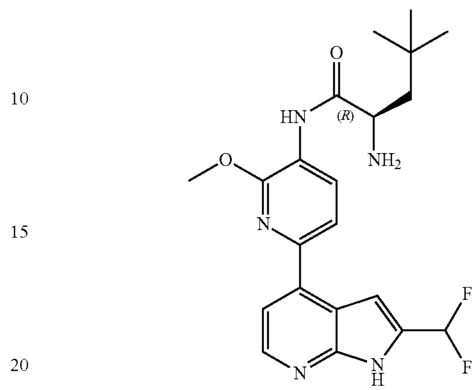

Synthesized in a manner analogous to F-57, reacting A-8 with G-9 in Step 1. LCMS (Method A) $t_R$=1.66 min, m/z=418.2068 [M+H]$^+$; Purity ≥95% (DAD, 210, 254 nm); $^1$H NMR (400 MHz, DMSO-$d_6$) δ 12.51 (s, 1H), 8.70 (d, J=8.2 Hz, 1H), 8.43 (d, J=5.0 Hz, 1H), 7.82 (d, J=8.2 Hz, 1H), 7.69 (d, J=5.0 Hz, 1H), 7.49 (s, 1H), 7.29 (t, J=54.3 Hz, 1H), 4.15 (s, 3H), 3.30 (dd, J=7.8, 5.3 Hz, 1H), 1.89 (dd, J=14.1, 5.3 Hz, 1H), 1.36 (dd, J=14.1, 7.8 Hz, 1H), 0.99 (s, 9H); $^{19}$F NMR (376 MHz, DMSO-$d_6$) δ −110.53.

(2R)-2-Amino-4,4-dimethyl-N-[6-methyl-5-(2-methyl-1H-pyrrolo[2,3-b]pyridin-4-yl)-2-pyridyl]pentanamide, F-151

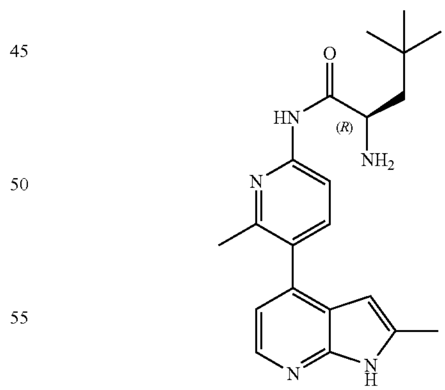

Synthesized in a sequence following General Scheme 2, reacting A-5 and G-12 in Step 1. LCMS (Method A) $t_R$=1.45 min, m/z=366.2307 [M+H]$^+$; Purity ≥95% (DAD, 210, 254 nm); $^1$H NMR (400 MHz, DMSO-$d_6$) δ 11.54 (s, 1H), 8.08 (d, J=4.9 Hz, 1H), 7.99 (d, J=8.5 Hz, 1H), 7.64 (d, J=8.4 Hz, 1H), 6.87 (d, J=4.9 Hz, 1H), 5.83 (s, 1H), 3.43 (t, J=6.0 Hz, 1H), 2.31 (s, 3H), 2.24 (s, 3H), 1.73 (dd, J=13.9, 5.2 Hz, 1H), 1.26 (dd, J=13.8, 6.8 Hz, 1H), 0.89 (s, 9H).

(2R)-2-Amino-N-[5-[2-(difluoromethyl)-1H-pyrrolo[2,3-b]pyridin-4-yl]-6-methyl-2-pyridyl]-4,4-dimethyl-pentanamide, F-152

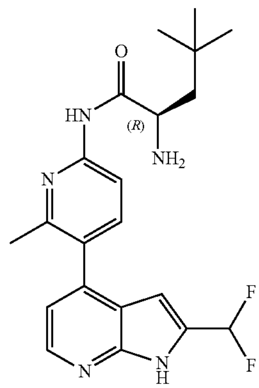

Synthesized in a manner analogous to F-57, reacting A-8 with G-12 in Step 1. LCMS (Method A) $t_R$=1.60 min, m/z=402.2117 $[M+H]^+$; Purity ≥95% (DAD, 210, 254 nm); $^1$H NMR (400 MHz, MeOH-$d_4$) δ 8.41 (d, J=5.0 Hz, 1H), 8.14 (d, J=8.4 Hz, 1H), 7.78 (d, J=8.4 Hz, 1H), 7.17 (d, J=5.0 Hz, 1H), 6.97 (t, J=54.4 Hz, 1H), 6.55 (t, J=2.2 Hz, 1H), 4.16-4.12 (m, 1H), 2.38 (s, 3H), 2.14 (dd, J=14.1, 8.5 Hz, 1H), 1.72 (dd, J=14.1, 4.8 Hz, 1H), 1.07 (s, 9H); $^{19}$F NMR (376 MHz, MeOH-$d_4$) δ −113.44.

(2R)-2-Amino-N-[6-methoxy-5-(2-methyl-1H-pyrrolo[2,3-b]pyridin-4-yl)-2-pyridyl]-4,4-dimethyl-pentanamide, F-153

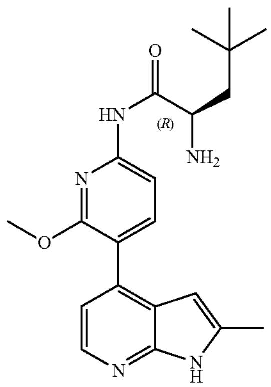

Synthesized in a sequence following General Scheme 2, reacting A-5 and G-10 in Step 1. LCMS (Method A) $t_R$=1.49 min, m/z=382.2254 $[M+H]^+$; Purity ≥95% (DAD, 210, 254 nm); $^1$H NMR (400 MHz, DMSO-$d_6$) δ 11.49 (s, 1H), 8.09 (d, J=5.0 Hz, 1H), 7.84 (s, 2H), 7.04 (d, J=5.0 Hz, 1H), 6.01

(s, 1H), 3.87 (s, 3H), 3.48 (dd, J=7.2, 4.6 Hz, 1H), 2.38 (s, 3H), 1.81 (dd, J=13.9, 4.5 Hz, 1H), 1.32 (dd, J=13.9, 7.2 Hz, 1H), 0.97 (s, 9H).

(2R)-2-Amino-N-[6-methoxy-5-[2-(trifluoromethyl)-1H-pyrrolo[2,3-b]pyridin-4-yl]-2-pyridyl]-4,4-dimethyl-pentanamide, F-154

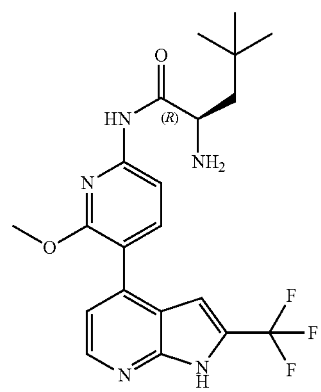

Synthesized in a sequence following General Scheme 3, reacting A-12 and G-10 in Step 1. LCMS (Method A) $t_R$=1.49 min, m/z=436.1980 $[M+H]^+$; Purity ≥95% (DAD, 210, 254 nm); $^1$H NMR (400 MHz, MeOH-$d_4$) δ 8.39 (d, J=5.0 Hz, 1H), 7.91 (d, J=8.1 Hz, 1H), 7.87 (d, J=8.1 Hz, 1H), 7.30 (d, J=5.0 Hz, 1H), 6.81 (s, 1H), 3.95 (s, 3H), 3.64 (t, J=6.2 Hz, 1H), 1.98 (dd, J=14.1, 6.4 Hz, 1H), 1.47 (dd, J=14.1, 5.8 Hz, 1H), 1.03 (s, 9H); $^{19}$F NMR (376 MHz, MeOH-$d_4$) δ −62.77.

(2R)-2-Amino-N-[6-methoxy-5-[2-(trifluoromethyl)-1H-pyrrolo[2,3-b]pyridin-4-yl]-2-pyridyl]-4-methyl-pentanamide, F-155

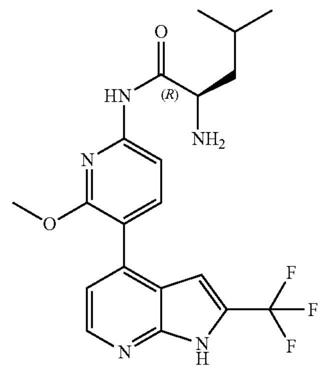

Synthesized in a sequence following General Scheme 3, reacting A-12 and G-9 in Step 1. LCMS (Method A) $t_R$=1.73 min, m/z=422.1822 $[M+H]^+$; Purity ≥95% (DAD, 210, 254 nm); $^1$H NMR (400 MHz, MeOH-$d_4$) δ 8.39 (d, J=5.0 Hz, 1H), 7.92 (d, J=8.1 Hz, 1H), 7.87 (d, J=8.1 Hz, 1H), 7.29 (d, J=5.0 Hz, 1H), 6.80 (d, J=1.8 Hz, 1H), 3.95 (s, 3H), 3.66 (dd, J=8.6, 5.6 Hz, 1H), 1.82 (dp, J=13.0, 6.9, 6.2 Hz, 1H), 1.69 (ddd, J=13.7, 8.1, 5.6 Hz, 1H), 1.54 (ddd, J=13.9, 8.5, 5.9 Hz, 1H), 1.01 (t, J=6.4 Hz, 6H); $^{19}$F NMR (376 MHz, MeOH-$d_4$) δ-62.77.

(2R)-2-Amino-N-[2-fluoro-3-methyl-4-(2-methyl-1H-pyrrolo[2,3-b]pyridin-4-yl)phenyl]-4,4-dimethyl-pentanamide, F-156

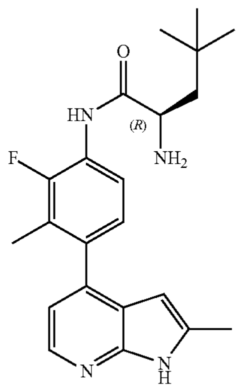

Synthesized in a sequence following General Scheme 2, reacting A-5 and G-13 in Step 1. LCMS (Method A) $t_R$=1.52 min, m/z=383.2261 $[M+H]^+$; Purity ≥95% (DAD, 210, 254 nm); $^1H$ NMR (400 MHz, DMSO-$d_6$) δ 11.59 (s, 1H), 8.14 (d, J=4.9 Hz, 1H), 8.06 (t, J=8.2 Hz, 1H), 6.89 (d, J=4.9 Hz, 1H), 5.88 (s, 1H), 3.47 (dd, J=7.4, 4.1 Hz, 1H), 2.37 (s, 3H), 2.09 (d, J=2.7 Hz, 3H), 1.84 (dd, J=13.9, 4.1 Hz, 1H), 1.33 (dd, J=14.0, 7.4 Hz, 1H), 0.98 (s, 9H); $^{19}F$ NMR (376 MHz, DMSO-$d_6$) δ −130.57.

(2R)-2-Amino-3-(3-methoxyphenyl)-N-[3-methyl-4-(2-methyl-1H-pyrrolo[2,3-b]pyridin-4-yl)phenyl]propenamide, F-157

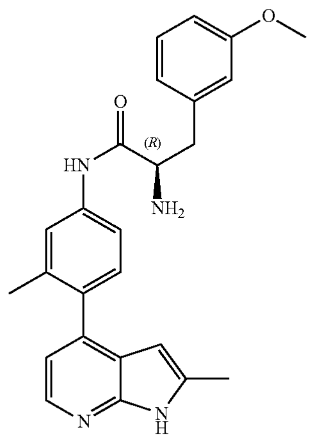

Synthesized in a manner analogous to F-89, reacting intermediate D-10 with (R)-2-((tert-butoxycarbonyl)amino)-3-(3-methoxyphenyl)propanoic acid in Step 2. Deprotected to afford title compound as a colourless solid. LCMS (Method A) $t_R$=1.42 min, m/z=415.21 $[M+H]^+$; Purity ≥95% (DAD, 210, 254 nm); $^1H$ NMR (400 MHz, MeOH-$d_4$) δ 8.11 (d, J=4.9 Hz, 1H), 7.50 (s, 1H), 7.45 (d, J=8.1 Hz, 1H), 7.29-7.19 (m, 2H), 6.93 (d, J=5.0 Hz, 1H), 6.90-6.77 (m, 3H), 5.91 (s, 1H), 3.76 (s, 3H), 3.73 (dd, J=7.0, 6.7 Hz, 1H), 3.09 (dd, J=13.3, 6.7 Hz, 1H), 2.94 (dd, J=13.3, 7.0 Hz, 1H), 2.45 (s, 3H), 2.19 (s, 3H).

(2S)-2-Amino-4,4-dimethyl-N-[3-methyl-4-(2-methyl-1H-pyrrolo[2,3-b]pyridin-4-yl)phenyl]pentanamide, F-158

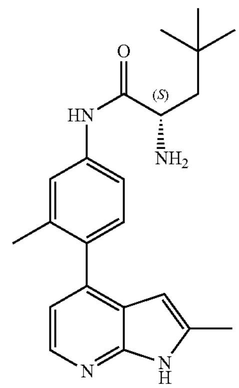

Synthesized in a manner analogous to F-89, reacting intermediate D-10 with Boc-Neo-OH in Step 2. Deprotected to afford title compound as a colourless solid. LCMS (Method A) $t_R$=1.50 min, m/z=365.23 $[M+H]^+$; Purity ≥95% (DAD, 210, 254 nm); $^1H$ NMR (400 MHz, MeOH-$d_4$) δ 8.11 (d, J=5.0 Hz, 1H), 7.60 (s, 1H), 7.54 (d, J=8.3 Hz, 1H), 7.27 (d, J=8.3 Hz, 1H), 6.93 (d, J=5.0 Hz, 1H), 5.92 (s, 1H), 3.54 (dd, J=7.2, 5.2 Hz, 1H), 2.45 (s, 3H), 2.21 (s, 3H), 1.97 (dd, J=14.0, 7.2 Hz, 1H), 1.48 (dd, J=14.0, 5.2 Hz, 1H), 1.04 (s, 9H).

(2S)-2-Amino-3-hydroxy-3-methyl-N-[3-methyl-4-(2-methyl-1H-pyrrolo[2,3-b]pyridin-4-yl)phenyl]butanamide, F-159

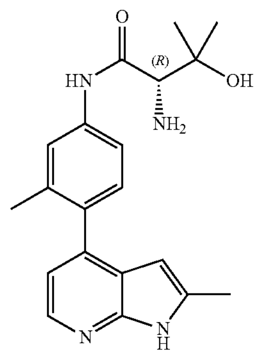

Synthesized in a manner analogous to F-139, reacting intermediate D-10 with N-Boc-(S)-2-amino-3-hydroxy-3-methylbutanoic acid. Deprotected to afford title compound as a colourless solid. LCMS (Method A) $t_R$=1.27 min, m/z=395.19 $[M+H]^+$; Purity ≥95% (DAD, 210, 254 nm); $^1H$ NMR (400 MHz, MeOH-$d_4$) δ 8.09 (d, J=5.0 Hz, 1H), 7.58 (s, 1H), 7.55-7.44 (m, 1H), 7.25 (d, J=8.3 Hz, 1H), 6.91 (d, J=5.0 Hz, 1H), 5.89 (s, 1H), 3.41 (s, 1H), 2.43 (s, 3H), 2.19 (s, 3H), 1.32 (d, J=10.4 Hz, 6H).

2-Amino-3-hydroxy-4,4-dimethyl-N-[3-methyl-4-(2-methyl-1H-pyrrolo[2,3-b]pyridin-4-yl)phenyl]pentanamide, F-160

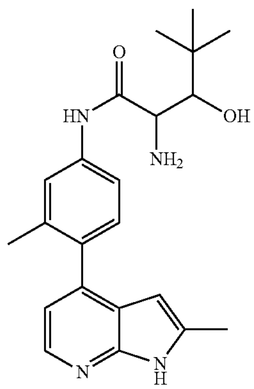 [SMILES: Cc1cc2c(-c3ccc(NC(=O)C(N)C(O)C(C)(C)C)cc3C)ccnc2[nH]1]

Step 1. tert-Butyl N-[1-[[4-[1-(benzenesulfonyl)-2-methyl-pyrrolo[2,3-b]pyridin-4-yl]-3-methyl-phenyl]carbamoyl]-2-hydroxy-3,3-dimethyl-butyl]carbamate, E-160. 2-(tert-butoxycarbonylamino)-3-hydroxy-4,4-dimethyl-pentanoic acid (45 mg, 0.17 mmol) was reacted with intermediate D-10 (72 mg, 0.19 mmol) according to General Procedure F. Purification by preparative HPLC (5-95% MeCN in $H_2O$, 0.1% TFA) affords a cream powder (21 mg, 20%). LCMS (Method B) $t_R$=2.10 min, m/z=621.2728 $[M+H]^+$.

Step 2. 2-Amino-3-hydroxy-4,4-dimethyl-N-[3-methyl-4-(2-methyl-1H-pyrrolo[2,3-b]pyridin-4-yl)phenyl]pentanamide, F-160. Intermediate E-160 (11 mg, 0.018 mmol) was deprotected according to General Procedure K, affording title compound as a colourless solid (3.4 mg, 50%). LCMS (Method A) $t_R$=1.42 min, m/z=381.23 $[M+H]^+$; Purity ≥95% (DAD, 210, 254 nm); $^1$H NMR (400 MHz, MeOH-$d_4$) δ 8.25 (d, J=5.9 Hz, 1H), 7.69 (s, 1H), 7.66-7.61 (m, 1H), 7.36 (d, J=8.4 Hz, 1H), 7.29 (d, J=5.9 Hz, 1H), 6.18 (s, 1H), 3.99 (d, J=6.1 Hz, 1H), 3.79 (d, J=6.1 Hz, 1H), 2.52 (s, 3H), 2.24 (s, 3H), 1.05 (s, 9H).

(2S,3R)-2-Amino-3-hydroxy-4-methyl-N-[3-methyl-4-(2-methyl-1H-pyrrolo[2,3-b]pyridin-4-yl)phenyl]pentanamide, F-161

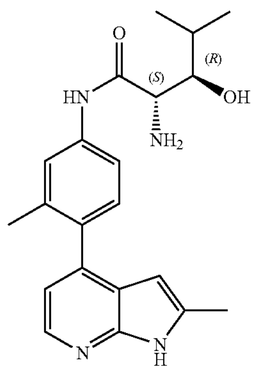

Synthesized in a manner analogous to F-160, reacting intermediate D-10 with (2S,3R)-2-(tert-butoxycarbonylamino)-3-hydroxy-4-methyl-pentanoic acid in Step 1. Deprotected to afford title compound as a colourless solid. LCMS (Method A) $t_R$=1.35 min, m/z=367.22 $[M+H]^+$; Purity ≥95% (DAD, 210, 254 nm); $^1$H NMR (400 MHz, MeOH-$d_4$) δ 8.09 (d, J=4.9 Hz, 1H), 7.61 (s, 1H), 7.55 (d, J=8.3 Hz, 1H), 7.25 (d, J=8.3 Hz, 1H), 6.91 (d, J=5.0 Hz, 1H), 5.89 (s, 1H), 3.67 (dd, J=7.7, 3.5 Hz, 1H), 3.55 (d, J=3.5 Hz, 1H), 2.43 (s, 3H), 2.19 (s, 3H), 1.83 (q, J=6.9 Hz, 1H), 1.06 (d, J=6.7 Hz, 3H), 1.01 (d, J=6.7 Hz, 3H).

(2R,3S)-2-Amino-3-hydroxy-4-methyl-N-[3-methyl-4-(2-methyl-1H-pyrrolo[2,3-b]pyridin-4-yl)phenyl]pentanamide, F-162

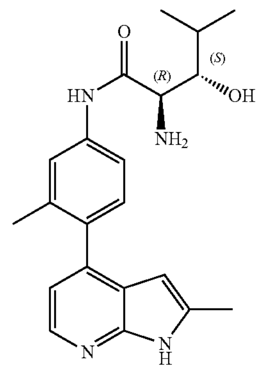

Synthesized in a manner analogous to F-160, reacting intermediate D-10 with (2R,3S)-2-(tert-butoxycarbonylamino)-3-hydroxy-4-methyl-pentanoic acid in Step 1. Deprotected to afford title compound as a colourless solid. LCMS (Method A) $t_R$=1.36 min, m/z=367.21 $[M+H]^+$; Purity ≥95% (DAD, 210, 254 nm); $^1$H NMR (400 MHz, MeOH-$d_4$) δ 8.09 (d, J=5.0 Hz, 1H), 7.61 (d, J=2.3 Hz, 1H), 7.58-7.51 (m, 1H), 7.25 (d, J=8.3 Hz, 1H), 6.91 (d, J=5.0 Hz, 1H), 5.89 (s, 1H), 3.67 (dd, J=7.7, 3.5 Hz, 1H), 3.54 (d, J=3.5 Hz, 1H), 2.43 (s, 3H), 2.19 (s, 3H), 1.83 (h, J=6.9 Hz, 1H), 1.06 (d, J=6.7 Hz, 3H), 1.01 (d, J=6.8 Hz, 3H).

(2R)-2-Amino-3-hydroxy-3-methyl-N-[3-methyl-4-(1H-pyrrolo[2,3-b]pyridin-4-yl)phenyl]butanamide, F-163

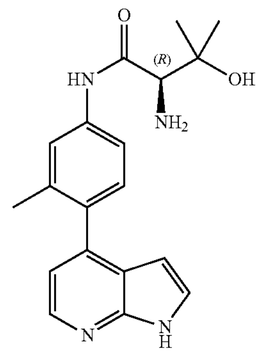

Synthesized in a manner analogous to F-160, reacting intermediate D-14 with (R)-2-((tert-butoxycarbonyl)amino)-3-hydroxy-3-methylbutanoic acid. Deprotected to afford title compound as a colourless solid. LCMS (Method A) $t_R$=1.22 min, m/z=339.1840 [M+H]$^+$; Purity ≥95% (DAD, 210, 254 nm); $^1$H NMR (400 MHz, Methanol-$d_4$) δ 8.22 (d, J=4.9 Hz, 1H), 7.59 (s, 1H), 7.57-7.50 (m, 1H), 7.38 (d, J=3.5 Hz, 1H), 7.27 (d, J=8.3 Hz, 1H), 6.99 (d, J=4.9 Hz, 1H), 6.21 (d, J=3.5 Hz, 1H), 3.38 (s, 1H), 2.19 (s, 3H), 1.31 (d, J=8.1 Hz, 6H).

(2R,3S)-2-Amino-3-hydroxy-4-methyl-N-[3-methyl-4-(1H-pyrrolo[2,3-b]pyridin-4-yl)phenyl]pentanamide, F-164

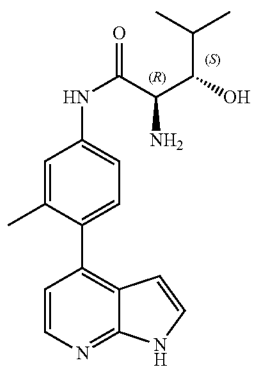

Synthesized in a manner analogous to F-160, reacting intermediate D-14 with (2R,3S)-2-(tert-butoxycarbonylamino)-3-hydroxy-4-methyl-pentanoic acid. Deprotected to afford title compound as a colourless solid. LCMS (Method A) $t_R$=1.31 min, m/z=353.1971 [M+H]$^+$; Purity ≥95% (DAD, 210, 254 nm); $^1$H NMR (400 MHz, Methanol-$d_4$) δ 8.22 (d, J=4.9 Hz, 1H), 7.63 (d, J=2.3 Hz, 1H), 7.57 (d, J=8.4 Hz, 1H), 7.38 (d, J=3.4 Hz, 1H), 7.28 (d, J=8.3 Hz, 1H), 6.99 (d, J=4.9 Hz, 1H), 6.21 (d, J=3.5 Hz, 1H), 3.67 (dd, J=7.6, 3.5 Hz, 1H), 3.56 (d, J=3.5 Hz, 1H), 2.20 (s, 3H), 1.88-1.78 (m, 1H), 1.06 (d, J=6.7 Hz, 3H), 1.01 (d, J=6.7 Hz, 3H).

(2S,3R)-2-Amino-3-hydroxy-4-methyl-N-[3-methyl-4-(1H-pyrrolo[2,3-b]pyridin-4-yl)phenyl]pentanamide, F-165

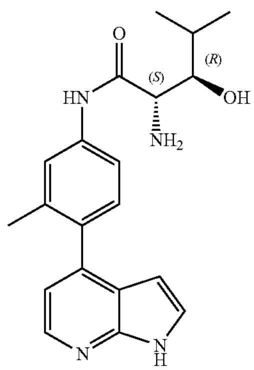

Synthesized in a manner analogous to F-160, reacting intermediate D-14 with (2S,3R)-2-(tert-butoxycarbonylamino)-3-hydroxy-4-methyl-pentanoic acid. Deprotected to afford title compound as a colourless solid. LCMS (Method A) $t_R$=1.31 min, m/z=353.1978 [M+H]$^+$; Purity ≥95% (DAD, 210, 254 nm); $^1$H NMR (400 MHz, Methanol-$d_4$) δ 8.22 (d, J=4.9 Hz, 1H), 7.63 (d, J=2.3 Hz, 1H), 7.60-7.53 (m, 1H), 7.38 (d, J=3.5 Hz, 1H), 7.28 (d, J=8.3 Hz, 1H), 6.99 (d, J=4.9 Hz, 1H), 6.21 (d, J=3.5 Hz, 1H), 3.66 (dd, J=7.8, 3.5 Hz, 1H), 3.53 (d, J=3.4 Hz, 1H), 2.20 (s, 3H), 1.83 (h, J=6.8 Hz, 1H), 1.06 (d, J=6.8 Hz, 3H), 1.01 (d, J=6.8 Hz, 3H).

(2R)-2-Amino-N-[3-methoxy-4-(1H-pyrrolo[2,3-b]pyridin-4-yl)phenyl]-4,4-dimethyl-Pentanamide, F-166

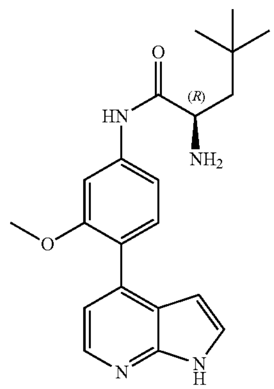

Synthesized in a manner analogous to F-67, reacting intermediate D-67 with Boc-D-Neo-OH in Step 2. Deprotected to afford title compound as a colourless solid. LCMS (Method A) $t_R$=1.43 min, m/z=367.2130 [M+H]$^+$; Purity ≥95% (DAD, 210, 254 nm); $^1$H NMR (400 MHz, MeOH-$d_4$) δ 8.31 (d, J=5.8 Hz, 1H), 7.67 (d, J=2.0 Hz, 1H), 7.57 (d, J=3.4 Hz, 1H), 7.53 (d, J=8.3 Hz, 1H), 7.47 (d, J=5.8 Hz, 1H), 7.38 (dd, J=8.3, 1.9 Hz, 1H), 6.60 (d, J=3.5 Hz, 1H), 4.04 (dd, J=8.7, 4.7 Hz, 1H), 3.85 (s, 3H), 2.14 (dd, J=14.1, 8.8 Hz, 1H), 1.72 (dd, J=14.1, 4.6 Hz, 1H), 1.07 (s, 9H).

(2R)-2-Amino-N-[3-methoxy-4-(2-methyl-1H-pyrrolo[2,3-b]pyridin-4-yl)phenyl]-4,4-dimethyl-pentanamide, F-167

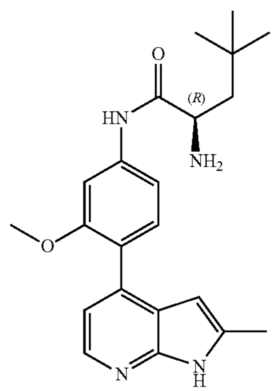

Synthesized in a manner analogous to F-67, using A-5 in Step 1, and Boc-D-Neo-OH in Step 2. Colourless solid. LCMS (Method A) $t_R$=1.49 min, m/z=381.2285 [M+H]$^+$;

Purity ≥95% (DAD, 210, 254 nm); $^{1}H$ NMR (400 MHz, MeOH-$d_4$) δ 8.04 (d, J=5.1 Hz, 1H), 7.59 (d, J=2.1 Hz, 1H), 7.38 (d, J=8.2 Hz, 1H), 7.24 (dd, J=8.2, 1.9 Hz, 1H), 7.06 (d, J=5.1 Hz, 1H), 6.03 (s, 1H), 3.80 (s, 3H), 3.64-3.57 (m, 1H), 2.43 (s, 3H), 1.99 (dd, J=14.0, 7.3 Hz, 1H), 1.50 (dd, J=14.0, 5.1 Hz, 1H), 1.03 (s, 9H).

(2R)-2-Amino-3-hydroxy-N-[3-methoxy-4-(2-methyl-1H-pyrrolo[2,3-b]pyridin-4-yl)phenyl]-3-methyl-butanamide, F-168

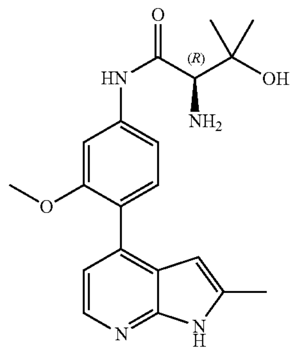

Synthesized in a manner analogous to F-67, using A-5 in Step 1, and (2R)-2-(tert-butoxycarbonylamino)-3-hydroxy-3-methyl-butanoic acid in Step 2. Colourless solid. LCMS (Method A) $t_R$=1.27 min, m/z=369.1925 [M+H]$^+$; Purity ≥95% (DAD, 210, 254 nm); $^{1}H$ NMR (400 MHz, MeOH-$d_4$) δ 8.21 (d, J=6.2 Hz, 1H), 7.68 (d, J=2.0 Hz, 1H), 7.56-7.48 (m, 2H), 7.37 (dd, J=8.4, 1.9 Hz, 1H), 6.38 (s, 1H), 3.90 (s, 1H), 3.85 (s, 3H), 2.53 (s, 3H), 1.46 (s, 3H), 1.38 (s, 3H).

(2R)-2-Amino-N-[3-(difluoromethoxy)-4-(2-methyl-1H-pyrrolo[2,3-b]pyridin-4-yl)phenyl]-4,4-dimethyl-pentanamide, F-169

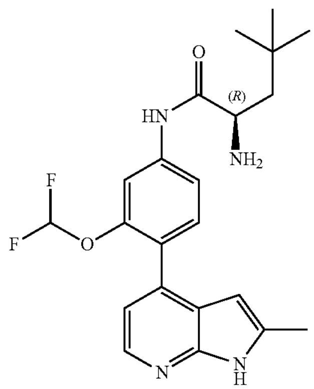

Synthesized in a manner analogous to F-82, reacting intermediate B-4 with Boc-D-Neo-OH. Colourless solid. LCMS (Method A) $t_R$=1.51 min, m/z=417.19 [M+H]$^+$; Purity ≥95% (DAD, 210, 254 nm); $^{1}H$ NMR (400 MHz, MeOH-$d_4$) δ 8.11 (d, J=5.0 Hz, 1H), 7.82 (s, 1H), 7.61-7.49 (m, 2H), 7.08 (d, J=5.1 Hz, 1H), 6.65 (t, J=74.0 Hz, 1H), 6.09 (s, 1H), 3.55 (dd, J=7.1, 5.3 Hz, 1H), 2.47 (s, 3H), 1.98 (dd, J=14.0, 7.1 Hz, 1H), 1.49 (dd, J=14.0, 5.3 Hz, 1H), 1.04 (s, 9H); $^{19}F$ NMR (376 MHz, MeOH-$d_4$) δ −82.79.

(2R)-2-Amino-N-[3-(difluoromethoxy)-4-(2-methyl-1H-pyrrolo[2,3-b]pyridin-4-yl)phenyl]-3-hydroxy-3-methyl-butanamide, F-170

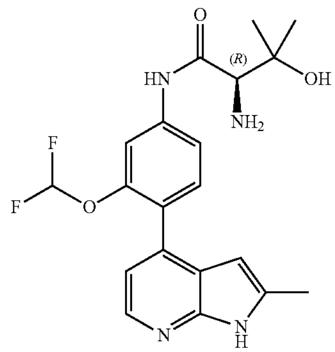

Synthesized in a manner analogous to F-82, reacting intermediate B-4 with (2R)-2-(tert-butoxycarbonylamino)-3-hydroxy-3-methyl-butanoic acid. Colourless solid. LCMS (Method A) $t_R$=1.31 min, m/z=405.16 [M+H]$^+$; Purity ≥95% (DAD, 210, 254 nm); $^{1}H$ NMR (400 MHz, MeOH-$d_4$) δ 8.11 (d, J=5.2 Hz, 1H), 7.82 (s, 1H), 7.60-7.49 (m, 2H), 7.08 (d, J=5.2 Hz, 1H), 6.88-6.43 (m, 1H), 6.09 (s, 1H), 3.41 (s, 1H), 2.47 (s, 3H), 1.34 (s, 3H), 1.32 (s, 3H); $^{19}F$ NMR (376 MHz, MeOH-$d_4$) δ −82.82.

(2R)-2-Amino-N-[4-methoxy-6-(2-methyl-1H-pyrrolo[2,3-b]pyridin-4-yl)-3-pyridyl]-4,4-dimethyl-pentanamide, F-171

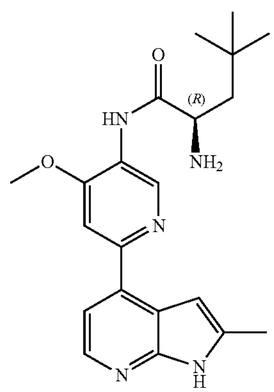

Synthesized in a manner analogous to F-148. Colourless solid. LCMS (Method A) $t_R$=1.39 min, m/z=382.22 [M+H]$^+$; Purity ≥95% (DAD, 210, 254 nm); $^{1}H$ NMR (400 MHz, MeOH-$d_4$) δ 9.41 (s, 1H), 8.19 (d, J=5.2 Hz, 1H), 7.60 (s, 1H), 7.45 (d, J=5.2 Hz, 1H), 6.60 (s, 1H), 4.12 (s, 3H), 3.64 (dd, J=6.8, 4.6 Hz, 1H), 2.52 (s, 3H), 2.01 (dd, J=14.1, 4.7 Hz, 1H), 1.44 (dd, J=14.1, 6.9 Hz, 1H), 1.06 (s, 9H).

(2R)-2-Amino-N-[5-methoxy-6-(2-methyl-1H-pyrrolo[2,3-b]pyridin-4-yl)-3-pyridyl]-4,4-dimethyl-pentanamide, F-172

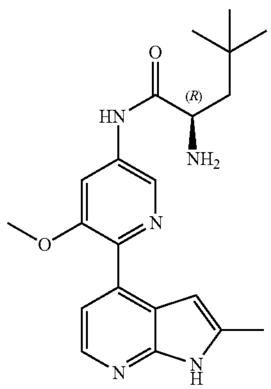

Synthesized in a manner analogous to F-148. Colourless solid. LCMS (Method A) $t_R$=1.43 min, m/z=382.22 $[M+H]^+$; Purity ≥95% (DAD, 210, 254 nm); $^1H$ NMR (400 MHz, MeOH-$d_4$) δ 8.47 (d, J=2.0 Hz, 1H), 8.19-8.08 (m, 2H), 7.27 (d, J=5.1 Hz, 1H), 6.16 (s, 1H), 4.60 (s, 1H), 3.90 (s, 3H), 3.58 (t, J=6.2 Hz, 1H), 2.47 (s, 3H), 1.99 (dd, J=14.0, 6.9 Hz, 1H), 1.50 (dd, J=14.0, 5.4 Hz, 1H), 1.05 (s, 9H).

(2S)-2-Amino-3-fluoro-3-methyl-N-[3-methyl-4-(2-methyl-1H-pyrrolo[2,3-b]pyridin-4-yl)phenyl]butanamide, F-173

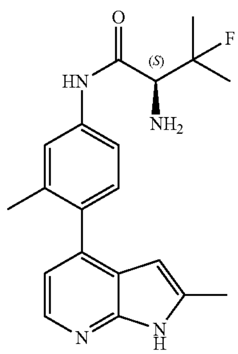

Step 1. tert-butyl N-[(1R)-1-[[4-[1-(benzenesulfonyl)-2-methyl-pyrrolo[2,3-b]pyridin-4-yl]-3-methyl-phenyl]carbamoyl]-2-hydroxy-2-methyl-propyl]carbamate, E-173-1. (2R)-2-(tert-butoxycarbonylamino)-3-hydroxy-3-methyl-butanoic acid (116 mg, 0.50 mmol) was reacted with intermediate D-10 (208 mg, 0.55 mmol) following General Procedure F. Purification by ISCO flash chromatography (0-100% EtOAc in hexanes) affords a yellow solid (270 mg, 0.46 mmol, 91%). LCMS (Method B) $t_R$=1.82, m/z=593.25 $[M+H]^+$.; $^1H$ NMR (400 MHz, DMSO-$d_6$) δ 9.87 (s, 1H), 8.30 (d, J=5.0 Hz, 1H), 8.19-8.12 (m, 2H), 7.72 (t, J=7.4 Hz, 1H), 7.67-7.60 (m, 3H), 7.55 (d, J=8.4, 2.2 Hz, 1H), 7.19-7.11 (m, 2H), 6.59 (d, J=9.0 Hz, 1H), 6.30 (s, 1H), 5.75 (s, 1H), 4.09 (d, J=9.1 Hz, 1H), 2.68 (s, 3H), 2.08 (s, 3H), 1.40 (s, 9H), 1.25-1.13 (m, 6H).

Step 2. tert-butyl N-[(1S)-1-[[4-[1-(benzenesulfonyl)-2-methyl-pyrrolo[2,3-b]pyridin-4-yl]-3-methyl-phenyl]carbamoyl]-2-fluoro-2-methyl-propyl]carbamate, E-173-2. Diethylaminosulfur trifluoride (67 μL, 0.51 mmol) was added to a cooled solution of intermediate E-173-1 (100 mg, 0.17 mmol) in THE (0.84 mL) at 0° C. and stirred for 1.5 h. Water was added and the reaction was extracted with DCM. The extracts were dried over $Na_2SO_4$ and concentrated in vacuo. Purification by ISCO flash chromatography (0-100% EtOAc in hexanes) affords a cream powder (36 mg, 0.06 mmol, 36%). LCMS (Method B) $t_R$=2.12, m/z=595.36 $[M+H]^+$.

Step 3. (2S)-2-amino-3-fluoro-3-methyl-N-[3-methyl-4-(2-methyl-11H-pyrrolo[2,3-b]pyridin-4-yl)phenyl]butanamide, F-173. Intermediate E-173-2 (34 mg, 0.06 mmol) was deprotected according to General Procedure K affording the title compound as a colourless solid (3.9 mg, 0.01 mmol, 19%). LCMS (Method A) $t_R$=1.31, m/z=355.1779 $[M+H]^+$. $^1H$ NMR (400 MHz, Methanol-$d_4$) δ 8.09 (d, J=5.0 Hz, 1H), 7.59 (s, 1H), 7.53 (d, J=8.3 Hz, 1H), 7.26 (d, J=8.3 Hz, 1H), 6.91 (d, J=5.0 Hz, 1H), 5.89 (s, 1H), 3.76 (d, J=10.6 Hz, 1H), 2.43 (s, 3H), 2.19 (s, 3H), 1.54 (s, 3H), 1.48 (s, 3H). $^{19}F$ NMR (376 MHz, MeOH-$d_4$) δ −143.34.

Example 3: Biological Activity

Inhibition of Citron kinase by various compounds has been determined. $IC_{50}$ values are reported in Table 1. Compounds were screened for biochemical kinase activity (Eurofins Discovery, France) using one of two assays. The TR-FRET based assay was available as Cat #2628; and the radiometric binding assay was available as Cat #16-040KP. All values in Table 1 are the mean of at least two independent assays.

TABLE 1

Biochemical inhibition of Citron kinase by disclosed compounds

| Compound | Name | Radiometric CitK $IC_{50}$ (nM) | TR-FRET CitK $IC_{50}$ (nM) |
|---|---|---|---|
| F-1 | 2-Amino-N-[4-(1H-pyrrolo[2,3-b]pyridin-4-yl)phenyl]acetamide | 3000 | — |
| F-2 | N-(4-(1H-pyrrolo[2,3-b]pyridin-4-yl)phenyl)-2-(methylamino)acetamide | 728 | — |
| F-3 | 2-(Dimethylamino)-N-[4-(1H-pyrrolo[2,3-b]pyridin-4-yl)phenyl]acetamide | 1059 | — |
| F-4 | (2S)-2-Amino-N-[4-(1H-pyrrolo[2,3-b]pyridin-4-yl)phenyl]propenamide | 3000 | — |
| F-5 | (2R)-2-Amino-N-[4-(1H-pyrrolo[2,3-b]pyridin-4-yl)phenyl]propenamide | 806 | — |

TABLE 1-continued

| Compound | Name | Radiometric CitK $IC_{50}$ (nM) | TR-FRET CitK $IC_{50}$ (nM) |
|---|---|---|---|
| F-6 | (2S)-2-Amino-3-methyl-N-[4-(1H-pyrrolo[2,3-b]pyridin-4-yl)phenyl]butanamide | 183 | — |
| F-7 | (2R)-2-Amino-3-methyl-N-[4-(1H-pyrrolo[2,3-b]pyridin-4-yl)phenyl]butanamide | 65.8 | — |
| F-8 | (2S)-2-Amino-4-methyl-N-[4-(1H-pyrrolo[2,3-b]pyridin-4-yl)phenyl]pentanamide | 54.1 | 29.9 |
| F-9 | (2R)-2-Amino-4-methyl-N-[4-(1H-pyrrolo[2,3-b]pyridin-4-yl)phenyl]pentanamide | 12.5 | 4.9 |
| F-10 | (2S,3S)-2-Amino-3-methyl-N-[4-(1H-pyrrolo[2,3-b]pyridin-4-yl)phenyl]pentanamide | 91.9 | — |
| F-11 | (2R,3R)-2-Amino-3-methyl-N-[4-(1H-pyrrolo[2,3-b]pyridin-4-yl)phenyl]pentanamide | 315 | — |
| F-12 | (2S)-2-Amino-3,3-dimethyl-N-[4-(1H-pyrrolo[2,3-b]pyridin-4-yl)phenyl]butanamide | 49.1 | — |
| F-13 | (2R)-2-Amino-3,3-dimethyl-N-[4-(1H-pyrrolo[2,3-b]pyridin-4-yl)phenyl]butanamide | 19.6 | 16.6 |
| F-14 | (2R)-2-Amino-N-[4-(1H-pyrrolo[2,3-b]pyridin-4-yl)phenyl]pentanamide | 69.6 | — |
| F-15 | 2-Amino-4,4-dimethyl-N-[4-(1H-pyrrolo[2,3-b]pyridin-4-yl)phenyl]pentanamide | 14.1 | — |
| F-16 | (2R)-2-Amino-4,4-dimethyl-N-[4-(1H-pyrrolo[2,3-b]pyridin-4-yl)phenyl]pentanamide | 13.8 | — |
| F-17 | (2R)-2-Amino-5-methyl-N-[4-(1H-pyrrolo[2,3-b]pyridin-4-yl)phenyl]hexanamide | 30.6 | — |
| F-18 | 2-Amino-2-cyclopropyl-N-[4-(1H-pyrrolo[2,3-b]pyridine-4-yl)phenyl]acetamide | — | 120 |
| F-19 | (2R)-2-Amino-3-cyclopropyl-N-[4-(1H-pyrrolo[2,3-b]pyridin-4-yl)phenyl]propenamide | 157 | — |
| F-20 | (2R)-2-Amino-3-cyclobutyl-N-[4-(1H-pyrrolo[2,3-b]pyridin-4-yl)phenyl]propenamide | 61.4 | — |
| F-21 | (2R)-2-Amino-3-cyclopentyl-N-[4-(1H-pyrrolo[2,3-b]pyridin-4-yl)phenyl]propenamide | 10.4 | — |
| F-22 | 2-Amino-4,4,4-trifluoro-N-[4-(1H-pyrrolo[2,3-b]pyridin-4-yl)phenyl]butanamide | 554 | — |
| F-23 | 2-Amino-N-[4-(1H-pyrrolo[2,3-b]pyridin-4-yl)phenyl]-2-[1-(trifluoromethyl)cyclopropyl]acetamide | 172 | — |
| F-24 | (2R)-2-Amino-5,5,5-trifluoro-N-[4-(1H-pyrrolo[2,3-b]pyridin-4-yl)phenyl]pentanamide | 66.7 | — |
| F-25 | (2S)-2-Amino-3-methoxy-N-[4-(1H-pyrrolo[2,3-b]pyridin-4-yl)phenyl]propenamide | 3000 | — |
| F-26 | 2-Amino-4-methoxy-N-[4-(1H-pyrrolo[2,3-b]pyridin-4-yl)phenyl]butanamide | 2467 | — |
| F-27 | (2S)-2-Amino-3-hydroxy-N-[4-(1H-pyrrolo[2,3-b]pyridin-4-yl)phenyl]propenamide | 2089 | — |
| F-28 | (2R)-2-Amino-3-hydroxy-N-[4-(1H-pyrrolo[2,3-b]pyridin-4-yl)phenyl]propenamide | 702 | — |
| F-29 | (2S)-2-Amino-3-hydroxy-N-[4-(1H-pyrrolo[2,3-b]pyridin-4-yl)phenyl]butanamide | 778 | — |
| F-30 | (2R)-2-Amino-3-hydroxy-N-[4-(1H-pyrrolo[2,3-b]pyridin-4-yl)phenyl]butanamide | 218 | — |

Biochemical inhibition of Citron kinase by disclosed compounds

TABLE 1-continued

| Compound | Name | Radiometric CitK $IC_{50}$ (nM) | TR-FRET CitK $IC_{50}$ (nM) |
|---|---|---|---|
| Biochemical inhibition of Citron kinase by disclosed compounds | | | |
| F-31 | (2R)-2-Amino-3-hydroxy-3-methyl-N-[4-(1H-pyrrolo[2,3-b]pyridin-4-yl)phenyl]butanamide | 52.4 | — |
| F-32 | (S)-N-(4-(1H-Pyrrolo[2,3-b]pyridin-4-yl)phenyl)-2-amino-3-phenylpropanamide | 130 | 164 |
| F-33 | (R)-N-(4-(1H-Pyrrolo[2,3-b]pyridin-4-yl)phenyl)-2-amino-3-phenylpropanamide | 56.4 | 23.8 |
| F-34 | (2S)-2-Amino-3-(4-methoxyphenyl)-N-[4-(1H-pyrrolo[2,3-b]pyridin-4-yl)phenyl]propenamide | 898 | — |
| F-35 | (2R)-2-Amino-3-(4-methoxyphenyl)-N-[4-(1H-pyrrolo[2,3-b]pyridin-4-yl)phenyl]propenamide | 1458 | — |
| F-36 | (2R)-2-Amino-3-(3-methoxyphenyl)-N-[4-(1H-pyrrolo[2,3-b]pyridin-4-yl)phenyl]propenamide | 89.7 | — |
| F-37 | (2S)-2-Amino-3-(4-hydroxyphenyl)-N-[4-(1H-pyrrolo[2,3-b]pyridin-4-yl)phenyl]propenamide | 647 | — |
| F-38 | (2R)-2-Amino-3-(4-hydroxyphenyl)-N-[4-(1H-pyrrolo[2,3-b]pyridin-4-yl)phenyl]propenamide | 325 | — |
| F-39 | (2S)-2-Amino-3-(3-hydroxyphenyl)-N-[4-(1H-pyrrolo[2,3-b]pyridin-4-yl)phenyl]propenamide | 305 | — |
| F-40 | (2R)-2-Amino-3-(3-hydroxyphenyl)-N-[4-(1H-pyrrolo[2,3-b]pyridin-4-yl)phenyl]propenamide | 39.6 | — |
| F-41 | (2R)-4-Methyl-2-(methylamino)-N-[4-(1H-pyrrolo[2,3-b]pyridin-4-yl)phenyl]pentanamide | 22.1 | — |
| F-42 | (2R)-2-(Dimethylamino)-4-methyl-N-[4-(1H-pyrrolo[2,3-b]pyridin-4-yl)phenyl]pentanamide | 277 | — |
| F-43 | (2R)-2-(Ethylamino)-4-methyl-N-[4-(1H-pyrrolo[2,3-b]pyridin-4-yl)phenyl]pentanamide | 209 | — |
| F-44 | (2R)-2-(Cyclopropylamino)-4-methyl-N-[4-(1H-pyrrolo[2,3-b]pyridin-4-yl)phenyl]pentanamide | 555 | — |
| F-45 | (2R)-2-(Cyclopropylmethylamino)-4-methyl-N-[4-(1H-pyrrolo[2,3-b]pyridin-4-yl)phenyl]pentanamide | 683 | — |
| F-46 | (2R)-2-(2-Methoxyethylamino)-4-methyl-N-[4-(1H-pyrrolo[2,3-b]pyridin-4-yl)phenyl]pentanamide | 1262 | — |
| F-47 | (2R)-4-Methyl-N-[4-(1H-pyrrolo[2,3-b]pyridin-4-yl)phenyl]-2-(2,2,2-trifluoroethylamino)pentanamide | 3000 | — |
| F-48 | (2R)-2-Amino-4-methyl-N-[4-(2-methyl-1H-pyrrolo[2,3-b]pyridin-4-yl)phenyl]pentanamide | 21.9 | — |
| F-49 | (2S)-2-Amino-4-methyl-N-[4-(2-methyl-1H-pyrrolo[2,3-b]pyridin-4-yl)phenyl]pentanamide | 286 | — |
| F-50 | (2R)-2-Amino-3,3-dimethyl-N-[4-(2-methyl-1H-pyrrolo[2,3-b]pyridin-4-yl)phenyl]butanamide | 59.0 | — |
| F-51 | (2S)-2-Amino-3,3-dimethyl-N-[4-(2-methyl-1H-pyrrolo[2,3-b]pyridin-4-yl)phenyl]butanamide | 366 | — |
| F-52 | (2R)-2-Amino-4,4-dimethyl-N-[4-(2-methyl-1H-pyrrolo[2,3-b]pyridin-4-yl)phenyl]pentanamide | 9.1 | — |
| F-53 | (2R)-2-Amino-N-[4-(2-cyclopropyl-1H-pyrrolo[2,3-b]pyridin-4-yl)phenyl]-4-methyl-pentanamide | 47.8 | — |
| F-54 | (2R)-2-Amino-N-[4-(2-cyclopropyl-1H-pyrrolo[2,3-b]pyridin-4-yl)phenyl]-3,3-dimethyl-butanamide | 35.1 | — |
| F-55 | (2R)-2-Amino-4-methyl-N-[4-[2-(trifluoromethyl)-1H-pyrrolo[2,3-b]pyridin-4-yl]phenyl]pentanamide | 87.3 | — |

TABLE 1-continued

| Biochemical inhibition of Citron kinase by disclosed compounds | | | |
|---|---|---|---|
| Compound | Name | Radiometric CitK $IC_{50}$ (nM) | TR-FRET CitK $IC_{50}$ (nM) |
| F-56 | (2R)-2-Amino-3,3-dimethyl-N-[4-[2-(trifluoromethyl)-1H-pyrrolo[2,3-b]pyridin-4-yl]phenyl]butanamide | 108 | — |
| F-57 | (2R)-2-Amino-N-[4-[2-(difluoromethyl)-1H-pyrrolo[2,3-b]pyridin-4-yl]phenyl]-4-methyl-pentanamide | 16.8 | — |
| F-58 | (2R)-2-Amino-4-methyl-N-[3-methyl-4-(1H-pyrrolo[2,3-b]pyridin-4-yl)phenyl]pentanamide | 8.1 | — |
| F-59 | (2R)-2-Amino-3,3-dimethyl-N-[3-methyl-4-(1H-pyrrolo[2,3-b]pyridin-4-yl)phenyl]butanamide | 49.1 | — |
| F-60 | (2R)-2-Amino-4,4-dimethyl-N-[3-methyl-4-(1H-pyrrolo[2,3-b]pyridin-4-yl)phenyl]pentanamide | 7.8 | — |
| F-61 | (2R)-2-Amino-4-methyl-N-[2-methyl-4-(1H-pyrrolo[2,3-b]pyridin-4-yl)phenyl]pentanamide | 134 | — |
| F-62 | (2R)-2-Amino-N-[3-ethyl-4-(1H-pyrrolo[2,3-b]pyridin-4-yl)phenyl]-4-methyl-pentanamide | 17.1 | — |
| F-63 | (2S)-2-Amino-N-[3-ethyl-4-(1H-pyrrolo[2,3-b]pyridin-4-yl)phenyl]-4-methyl-pentanamide | 829 | — |
| F-64 | (2R)-2-Amino-N-[3,5-dimethyl-4-(1H-pyrrolo[2,3-b]pyridin-4-yl)phenyl]-4-methyl-pentanamide | 3000 | — |
| F-65 | (2R)-2-Amino-N-[3-fluoro-4-(1H-pyrrolo[2,3-b]pyridin-4-yl)phenyl]-4-methyl-pentanamide | 37.5 | — |
| F-66 | (2R)-2-Amino-N-[3-fluoro-4-(1H-pyrrolo[2,3-b]pyridin-4-yl)phenyl]-3,3-dimethyl-butanamide | 57.7 | — |
| F-67 | (2R)-2-Amino-N-[3-methoxy-4-(1H-pyrrolo[2,3-b]pyridin-4-yl)phenyl]-4-methyl-pentanamide | 69.3 | — |
| F-68 | (2R)-2-Amino-N-[3-chloro-4-(1H-pyrrolo[2,3-b]pyridin-4-yl)phenyl]-4-methyl-pentanamide | 172 | — |
| F-69 | (2S)-2-Amino-N-[3-chloro-4-(1H-pyrrolo[2,3-b]pyridin-4-yl)phenyl]-4-methyl-pentanamide | 533 | — |
| F-70 | (2R)-2-Amino-N-[2-fluoro-4-(1H-pyrrolo[2,3-b]pyridin-4-yl)phenyl]-4-methyl-pentanamide | 36.9 | — |
| F-71 | (2R)-2-Amino-N-[2-fluoro-4-(1H-pyrrolo[2,3-b]pyridin-4-yl)phenyl]-3,3-dimethyl-butanamide | 64.6 | — |
| F-72 | (2R)-2-Amino-N-[2-fluoro-3-methyl-4-(1H-pyrrolo[2,3-b]pyridin-4-yl)phenyl]-4-methyl-pentanamide | 17.0 | — |
| F-73 | (2R)-2-Amino-N-[2-fluoro-5-methyl-4-(1H-pyrrolo[2,3-b]pyridin-4-yl)phenyl]-4-methyl-pentanamide | 694 | — |
| F-74 | (2R)-2-Amino-N-[2-fluoro-5-methyl-4-(1H-pyrrolo[2,3-b]pyridin-4-yl)phenyl]-3,3-dimethyl-butanamide | 1058 | — |
| F-75 | (2R)-2-Amino-N-[2-chloro-4-(1H-pyrrolo[2,3-b]pyridin-4-yl)phenyl]-4-methyl-pentanamide | 80 | — |
| F-76 | (2R)-2-Amino-4-methyl-N-[4-(1H-pyrrolo[2,3-b]pyridin-4-yl)-2-(trifluoromethyl)phenyl]pentanamide | 316 | — |
| F-77 | (2R)-2-Amino-N-[2-methoxy-4-(1H]-pyrrolo[2,3-b]pyridin-4-yl)phenyl]-4-methyl-pentanamide | 39.3 | — |
| F-78 | (2R)-2-Amino-N-[3-cyano-4-(1H-pyrrolo[2,3-b]pyridin-4-yl)phenyl]-4-methyl-pentanamide | 88.7 | — |
| F-79 | (2R)-2-Amino-4-methyl-N-[4-(1H-pyrrolo[2,3-b]pyridin-4-yl)-3-(trifluoromethyl)phenyl]pentanamide | 207 | — |

TABLE 1-continued

| Compound | Name | Radiometric CitK $IC_{50}$ (nM) | TR-FRET CitK $IC_{50}$ (nM) |
|---|---|---|---|
| | Biochemical inhibition of Citron kinase by disclosed compounds | | |
| F-80 | (2R)-2-Amino-N-[3-(difluoromethyl)-4-(1H-pyrrolo[2,3-b]pyridin-4-yl)phenyl]-4-methyl-pentanamide | 31.3 | — |
| F-81 | (2R)-2-Amino-4-methyl-N-[4-(1H-pyrrolo[2,3-b]pyridin-4-yl)-3 (trifluoromethoxy)phenyl]pentanamide | 36.9 | — |
| F-82 | (R)-2-Amino-N-(3-(difluoromethoxy)-4-(1H-pyrrolo[2,3-b]pyridin-4-yl)phenyl)-4-methylpentanamide | 21.5 | — |
| F-83 | (2R)-N-(6-(1H-Pyrrolo[2,3-b]pyridin-4-yl)pyridin-3-yl)-2-amino-4-methylpentanamide | 39.8 | — |
| F-84 | (2R)-2-Amino-4-methyl-N-[5-methyl-6-(1H-pyrrolo[2,3-b]pyridin-4-yl)-3-pyridyl]pentanamide | 161.3 | — |
| F-85 | (2R)-2-Amino-4-methyl-N-[6-methyl-5-(1H-pyrrolo[2,3-b]pyridin-4-yl)-2-pyridyl]pentanamide | 111 | — |
| F-86 | (2R)-2-Amino-4-methyl-N-[4-methyl-5-(1H-pyrrolo[2,3-b]pyridin-4-yl)-2-pyridyl]pentanamide | 340 | — |
| F-87 | (2R)-2-Amino-4-methyl-N-[3-(1H-pyrrolo[2,3-b]pyridin-4-yl)phenyl]pentanamide | 245 | — |
| F-88 | (2R)-2-Amino-N-[3-ethyl-4-(1H-pyrrolo[2,3-b]pyridin-4-yl)phenyl]-3,3-dimethyl-butanamide | 57.5 | — |
| F-89 | (2R)-2-Amino-4-methyl-N-[3-methyl-4-(2-methyl-1H-pyrrolo[2,3-b]pyridin-4-yl)phenyl]pentanamide | 18.8 | — |
| F-90 | (2R)-2-Amino-4,4-dimethyl-N-[3-methyl-4-(2-methyl-1H-pyrrolo[2,3-b]pyridin-4-yl)phenyl]pentanamide | 12.0 | — |
| F-91 | (2R)-2-Amino-3,3-dimethyl-N-[3-methyl-4-(2-methyl-1H-pyrrolo[2,3-b]pyridin-4-yl)phenyl]butanamide | 48.8 | — |
| F-92 | (2R)-2-Amino-N-[4-(2-methyl-1H-pyrrolo[2,3-b]pyridin-4-yl)phenyl]-3-phenyl-propanamide | 415 | — |
| F-93 | (2R)-2-Amino-N-[3-ethyl-4-(2-methyl-1H-pyrrolo[2,3-b]pyridin-4-yl)phenyl]-3,3-dimethyl-butanamide | 121 | — |
| F-94 | (2R)-4-Methyl-2-(methylamino)-N-[4-(2-methyl-1H-pyrrolo[2,3-b]pyridin-4-yl)phenyl]pentanamide | 43.7 | — |
| F-95 | (2R)-2-Amino-4-methyl-N-[6-methyl-5-(2-methyl-1H-pyrrolo[2,3-b]pyridin-4-yl)-2-pyridyl]pentanamide | 240 | — |
| F-96 | (2R)-2-Amino-4,4-dimethyl-N-[5-methyl-6-(2-methyl-1H-pyrrolo[2,3-b]pyridin-4-yl)-3-pyridyl]pentanamide | 96.9 | — |
| F-97 | (2R)-2-Amino-N-[3-(difluoromethyl)-4-(2-methyl-1H-pyrrolo[2,3-b]pyridin-4-yl)phenyl]-4,4-dimethyl-pentanamide | 29.3 | — |
| F-98 | (2R)-2-Amino-4-methyl-N-[3-methyl-4-[2-(trifluoromethyl)-1H-pyrrolo[2,3-b]pyridin-4-yl]phenyl]pentanamide | 30.4 | — |
| F-99 | (2R)-2-Amino-4,4-dimethyl-N-[3-methyl-4-[2-(trifluoromethyl)-1H-pyrrolo[2,3-b]pyridin-4-yl]phenyl]pentanamide | 102.8 | — |
| F-100 | (2R)-2-Amino-3,3-dimethyl-N-[3-methyl-4-[2-(trifluoromethyl)-1H-pyrrolo[2,3-b]pyridin-4-yl]phenyl]butanamide | 380 | — |
| F-101 | (2R)-2-Amino-N-[4-[2-(difluoromethyl)-1H-pyrrolo[2,3-b]pyridin-4-yl]-3-methyl-phenyl]-4-methyl-pentanamide | 18.1 | — |
| F-102 | (2R)-2-Amino-N-[4-[2-(difluoromethyl)-1H-pyrrolo[2,3-b]pyridin-4-yl]-3-methyl-phenyl]-4,4-dimethyl-pentanamide | 11.7 | — |
| F-103 | (2R)-2-Amino-N-[4-[2-(difluoromethyl)-1H-pyrrolo[2,3-b]pyridin-4-yl]-3-methyl-phenyl]-3,3-dimethyl-butanamide | 68.1 | — |

TABLE 1-continued

| Biochemical inhibition of Citron kinase by disclosed compounds | | | |
|---|---|---|---|
| Compound | Name | Radiometric CitK $IC_{50}$ (nM) | TR-FRET CitK $IC_{50}$ (nM) |
| F-104 | (2R)-2-Amino-4,4-dimethyl-N-[6-[2-(trifluoromethyl)-1H-pyrrolo[2,3-b]pyridin-4-yl]-3-pyridyl]pentanamide | 418 | — |
| F-105 | (2R)-2-Amino-N-[6-[2-(difluoromethyl)-1H-pyrrolo[2,3-b]pyridin-4-yl]-3-pyridyl]-4,4-dimethyl-pentanamide | 266 | — |
| F-106 | (2R)-2-Amino-4-methyl-N-[4-(5-methyl-1H-pyrrolo[2,3-b]pyridin-4-yl)phenyl]pentanamide | 66.5 | — |
| F-107 | (2R)-2-Amino-3,3-dimethyl-N-[4-(5-methyl-1H-pyrrolo[2,3-b]pyridin-4-yl)phenyl]butanamide | 371 | — |
| F-110 | (2R)-2-Amino-4-methyl-N-[4-(1H-pyrrolo[2,3-b]pyridin-4-yl)thiazol-2-yl]pentanamide | 92.4 | — |
| F-111 | (2R)-2-Amino-3,3-dimethyl-N-[4-(1H-pyrrolo[2,3-b]pyridin-4-yl)thiazol-2-yl]butanamide | 29.6 | — |
| F-112 | (2R)-2-Amino-3,3-dimethyl-N-[4-(2-methyl-1H-pyrrolo[2,3-b]pyridin-4-yl)thiazol-2-yl]butanamide | 122 | — |
| F-113 | (2S)-2-Amino-3,3-dimethyl-N-[4-(2-methyl-1H-pyrrolo[2,3-b]pyridin-4-yl)thiazol-2-yl]butanamide | 111 | — |
| F-114 | (2R)-2-Amino-3-methyl-N-[4-(2-methyl-1H-pyrrolo[2,3-b]pyridin-4-yl)thiazol-2-yl]butanamide | 244 | — |
| F-115 | 2-Amino-N-[4-(2-methyl-1H-pyrrolo[2,3-b]pyridin-4-yl)thiazol-2-yl]-2-[1-(trifluoromethyl)cyclopropyl]acetamide | 129 | — |
| F-116 | (2R)-2-Amino-4-methyl-N-[4-(2-methyl-1H-pyrrolo[2,3-b]pyridin-4-yl)thiazol-2-yl]pentanamide | 368 | — |
| F-117 | (2R)-2-Amino-3,3-dimethyl-N-[5-methyl-4-(2-methyl-1H-pyrrolo[2,3-b]pyridin-4-yl)thiazol-2-yl]butanamide | 3000 | — |
| F-120 | N-(4-(1H-Pyrrolo[2,3-b]pyridin-4-yl)phenyl)-2-amino-3-(tetrahydro-2H-pyran-4-yl)propenamide | — | 153 |
| F-121 | 2-(Methylamino)-3-phenyl-N-[4-(1H-pyrrolo[2,3-b]pyridin-4-yl)phenyl]propenamide, | — | 3000 |
| F-122 | 2-(Dimethylamino)-3-phenyl-N-[4-(1H-pyrrolo[2,3-b]pyridin-4-yl)phenyl]propenamide | — | 1500 |
| F-123 | 2-Amino-3-(4-chlorophenyl)-N-[4-(1H-pyrrolo[2,3-b]pyridin-4-yl)phenyl]propenamide | — | 1291 |
| F-124 | 2-Amino-3-(3-chlorophenyl)-N-[4-(1H-pyrrolo[2,3-b]pyridin-4-yl)phenyl]propenamide | — | 536 |
| F-125 | 2-Amino-3-(2-chlorophenyl)-N-[4-(1H-pyrrolo[2,3-b]pyridin-4-yl)phenyl]propenamide | — | 1771 |
| F-127 | (2R)-2-Amino-N-[3-methyl-4-(1H-pyrrolo[2,3-b]pyridin-4-yl)phenyl]-3-phenyl-propanamide | 144 | — |
| F-128 | (2R)-2-Amino-N-[3-methoxy-4-(1H]-pyrrolo[2,3-b]pyridin-4-yl)phenyl]-3-phenyl-propanamide | 598 | — |
| F-129 | (2S)-2-Amino-3-phenyl-N-[4-(1H-pyrrolo[2,3-b]pyridin-4-yl)-3-(trifluoromethyl)phenyl]propanamide | 3000 | — |
| F-130 | (2R)-2-Amino-3-phenyl-N-[4-(1H-pyrrolo[2,3-b]pyridin-4-yl)-3-(trifluoromethyl)phenyl]propanamide | 1416 | — |
| F-131 | (2R)-2-Amino-N-[2-methoxy-4-(1H-pyrrolo[2,3-b]pyridin-4-yl)phenyl]-3-phenyl-propanamide | 301 | — |
| F-132 | (2R)-2-Amino-N-[2-methyl-4-(1H-pyrrolo[2,3-b]pyridin-4-yl)phenyl]-3-phenyl-propanamide | 237 | — |

TABLE 1-continued

| Compound | Name | Radiometric CitK $IC_{50}$ (nM) | TR-FRET CitK $IC_{50}$ (nM) |
|---|---|---|---|
| Biochemical inhibition of Citron kinase by disclosed compounds | | | |
| F-133 | (2R)-2-Amino-N-[2-chloro-4-(1H-pyrrolo[2,3-b]pyridin-4-yl)phenyl]-3-phenyl-propanamide | 557 | — |
| F-134 | (2R)-2-Amino-3-phenyl-N-[3-(1H-pyrrolo[2,3-b]pyridin-4-yl)phenyl]propanamide | 64.1 | — |
| F-135 | 2-Amino-N-[4-(3-methyl-1H-pyrrolo[2,3-b]pyridin-4-yl)phenyl]-3-phenyl-propanamide | — | 392 |
| F-136 | (2R)-2-Amino-N-[4-(3-ethyl-1H-pyrrolo[2,3-b]pyridin-4-yl)phenyl]-3-phenyl-propanamide | 1256 | — |
| F-137 | (2R)-2-Amino-N-[2-fluoro-3-methyl-4-(1H-pyrrolo[2,3-b]pyridin-4-yl)phenyl]-3,3-dimethyl-butanamide | 23.1 | — |
| F-138 | (2R)-2-Amino-N-[3,5-dimethyl-4-(1H-pyrrolo[2,3-b]pyridin-4-yl)phenyl]-3,3-dimethyl-butanamide | 3000 | — |
| F-139 | (2R)-2-Amino-3-hydroxy-3-methyl-N-[3-methyl-4-(2-methyl-1H-pyrrolo[2,3-b]pyridin-4-yl)phenyl]butanamide | 151 | — |
| F-140 | (2R)-2-Amino-N-[4-[2-(difluoromethyl)-1H-pyrrolo[2,3-b]pyridin-4-yl]-3-methyl-phenyl]-3-hydroxy-3-methyl-butanamide | 40 | — |
| F-141 | (2R)-2-Amino-N-[4-(2-cyclopropyl-1H-pyrrolo[2,3-b]pyridin-4-yl)phenyl]-4,4-dimethyl-pentanamide | 10 | — |
| F-142 | (2R)-2-Amino-N-[4-(2-cyclopropyl-1H-pyrrolo[2,3-b]pyridin-4-yl)-3-methyl-phenyl]-4,4-dimethyl-pentanamide | 18 | — |
| F-143 | (2R)-2-Amino-N-[4-[2-(difluoromethyl)-1H-pyrrolo[2,3-b]pyridin-4-yl]phenyl]-4,4-dimethyl-pentanamide | 4 | — |
| F-144 | (2R)-2-amino-4,4-dimethyl-N-[4-[2-(trifluoromethyl)-1H-pyrrolo[2,3-b]pyridin-4-yl]phenyl]pentanamide | 22 | — |
| F-145 | (2R)-2-Amino-4,4-dimethyl-N-(6-(2-methyl-1H-pyrrolo[2,3-b]pyridin-4-yl)pyridin-3-yl)pentanamide | 26 | — |
| F-146 | (2R)-2-Amino-4,4-dimethyl-N-[5-[2-(trifluoromethyl)-1H-pyrrolo[2,3-b]pyridin-4-yl]-2-pyridyl]pentanamide | 307 | — |
| F-147 | (2R)-2-Amino-N-[2-fluoro-3-methyl-4-[2-(trifluoromethyl)-1H-pyrrolo[2,3-b]pyridin-4-yl]phenyl]-4,4-dimethyl-pentanamide | 24 | — |
| F-148 | (2R)-2-Amino-N-[2-methoxy-6-(2-methyl-1H-pyrrolo[2,3-b]pyridin-4-yl)-3-pyridyl]-4,4-dimethyl-pentanamide | 18 | — |
| F-149 | (2R)-2-Amino-N-[2-methoxy-6-[2-(trifluoromethyl)-1H-pyrrolo[2,3-b]pyridin-4-yl]-3-pyridyl]-4,4-dimethyl-pentanamide | 38 | — |
| F-150 | (2R)-2-Amino-N-[6-[2-(difluoromethyl)-1H-pyrrolo[2,3-b]pyridin-4-yl]-2-methoxy-3-pyridyl]-4,4-dimethyl-pentanamide | 9 | — |
| F-151 | (2R)-2-Amino-4,4-dimethyl-N-[6-methyl-5-(2-methyl-1H-pyrrolo[2,3-b]pyridin-4-yl)-2-pyridyl]pentanamide | 91 | — |
| F-152 | (2R)-2-Amino-N-[5-[2-(difluoromethyl)-1H-pyrrolo[2,3-b]pyridin-4-yl]-6-methyl-2-pyridyl]-4,4-dimethyl-pentanamide | 120 | — |
| F-153 | (2R)-2-Amino-N-[6-methoxy-5-(2-methyl-1H-pyrrolo[2,3-b]pyridin-4-yl)-2-pyridyl]-4,4-dimethyl-pentanamide | 35 | — |
| F-154 | (2R)-2-Amino-N-[6-methoxy-5-[2-(trifluoromethyl)-1H-pyrrolo[2,3-b]pyridin-4-yl]-2-pyridyl]-4,4-dimethyl-pentanamide | 59 | — |
| F-155 | (2R)-2-Amino-N-[6-methoxy-5-[2-(trifluoromethyl)-1H-pyrrolo[2,3-b]pyridin-4-yl]-2-pyridyl]-4-methyl-pentanamide | 113 | — |

TABLE 1-continued

Biochemical inhibition of Citron kinase by disclosed compounds

| Compound | Name | Radiometric CitK $IC_{50}$ (nM) | TR-FRET CitK $IC_{50}$ (nM) |
|---|---|---|---|
| F-156 | (2R)-2-Amino-N-[2-fluoro-3-methyl-4-(2-methyl-1H-pyrrolo[2,3-b]pyridin-4-yl)phenyl]-4,4-dimethyl-pentanamide | 10 | — |
| F-157 | (2R)-2-Amino-3-(3-methoxyphenyl)-N-[3-methyl-4-(2-methyl-1H-pyrrolo[2,3-b]pyridin-4-yl)phenyl]propenamide | 519 | — |
| F-158 | (2S)-2-Amino-4,4-dimethyl-N-[3-methyl-4-(2-methyl-1H-pyrrolo[2,3-b]pyridin-4-yl)phenyl]pentanamide | 126 | — |
| F-159 | (2S)-2-Amino-3-hydroxy-3-methyl-N-[3-methyl-4-(2-methyl-1H-pyrrolo[2,3-b]pyridin-4-yl)phenyl]butanamide | 852 | — |
| F-160 | 2-Amino-3-hydroxy-4,4-dimethyl-N-[3-methyl-4-(2-methyl-1H-pyrrolo[2,3-b]pyridin-4-yl)phenyl]pentanamide | 29 | |
| F-161 | (2S,3R)-2-Amino-3-hydroxy-4-methyl-N-[3-methyl-4-(2-methyl-1H-pyrrolo[2,3-b]pyridin-4-yl)phenyl]pentanamide | 19 | |
| F-162 | (2R,3S)-2-Amino-3-hydroxy-4-methyl-N-[3-methyl-4-(2-methyl-1H-pyrrolo[2,3-b]pyridin-4-yl)phenyl]pentanamide | 5 | |
| F-163 | (2R)-2-Amino-3-hydroxy-3-methyl-N-[3-methyl-4-(1H-pyrrolo[2,3-b]pyridin-4-yl)phenyl]butanamide | ND | |
| F-164 | (2R,3S)-2-Amino-3-hydroxy-4-methyl-N-[3-methyl-4-(1H-pyrrolo[2,3-b]pyridin-4-yl)phenyl]pentanamide | ND | |
| F-165 | (2S,3R)-2-Amino-3-hydroxy-4-methyl-N-[3-methyl-4-(1H-pyrrolo[2,3-b]pyridin-4-yl)phenyl]pentanamide | ND | |
| F-166 | (2R)-2-Amino-N-[3-methoxy-4-(1H-pyrrolo[2,3-b]pyridin-4-yl)phenyl]-4,4-dimethyl-pentanamide | 37 | |
| F-167 | (2R)-2-Amino-N-[3-methoxy-4-(2-methyl-1H-pyrrolo[2,3-b]pyridin-4-yl)phenyl]-4,4-dimethyl-pentanamide | 50 | |
| F-168 | (2R)-2-Amino-3-hydroxy-N-[3-methoxy-4-(2-methyl-1H-pyrrolo[2,3-b]pyridin-4-yl)phenyl]-3-methyl-butanamide | 1529 | |
| F-169 | (2R)-2-Amino-N-[3-(difluoromethoxy)-4-(2-methyl-1H-pyrrolo[2,3-b]pyridin-4-yl)phenyl]-4,4-dimethyl-pentanamide | 53 | |
| F-170 | (2R)-2-Amino-N-[3-(difluoromethoxy)-4-(2-methyl-1H-pyrrolo[2,3-b]pyridin-4-yl)phenyl]-3-hydroxy-3-methyl-butanamide | 315 | |
| F-171 | (2R)-2-Amino-N-[4-methoxy-6-(2-methyl-1H-pyrrolo[2,3-b]pyridin-4-yl)-3-pyridyl]-4,4-dimethyl-pentanamide | 232 | |
| F-172 | (2R)-2-Amino-N-[5-methoxy-6-(2-methyl-1H-pyrrolo[2,3-b]pyridin-4-yl)-3-pyridyl]-4,4-dimethyl-pentanamide | 3000 | |
| F-173 | (2S)-2-Amino-3-fluoro-3-methyl-N-[3-methyl-4-(2-methyl-1H-pyrrolo[2,3-b]pyridin-4-yl)phenyl]butanamide | 461 | |

The effect of various compounds on the inhibition of other kinases has also been determined. Table 2 reports measured $IC_{50}$ values; value units are nanomolar inhibition. Compounds were screened for biochemical kinase activity (Eurofins Discovery, France) using their commercial radiometric KinaseProfiler™ binding assays with the following catalog numbers: AAK (16-043KP), ACK1 (14-756KP), AKT-1 (14-276KP), AUR-B (14-835KP), BIKE (16-044KP), DRAK2 (16-003KP), HTPK4 (15-003KP), IKKP3 (14-485KP), Mnk2 (14-664KP), PKAα (14-440KP), ROCK-1 (14-601KP), ROCK-2 (14-451KP), and TRK-B (14-507KP).

TABLE 2

Biochemical inhibition of compounds against a panel of kinases. Values are nanomolar, and the mean of at least two independent experiments.

| Compound | AAK1 | ACK1 | AKT-1 | AUR-B | BIKE | DRAK2 | HIPK4 |
|---|---|---|---|---|---|---|---|
| F-9 | — | — | 761 | 230 | — | — | — |
| F-13 | — | — | — | — | — | — | — |
| F-32 | — | — | 1104 | 156 | — | — | — |
| F-33 | — | — | 436 | 104 | — | — | — |
| F-41 | — | — | — | — | — | — | — |
| F-48 | — | — | — | — | — | — | — |
| F-58 | — | — | — | — | — | — | — |
| F-59 | — | — | — | — | — | — | — |
| F-70 | — | — | — | — | — | — | — |
| F-77 | — | — | — | — | — | — | — |
| F-90 | 212 | >3000 | — | — | 902 | >3000 | 2275 |
| F-140 | 1908 | >3000 | — | — | >3000 | >3000 | >3000 |

| Compound | HIPK4 | IKKβ | Mnk2 | PKAα | ROCK-1 | ROCK-2 | TRK-B |
|---|---|---|---|---|---|---|---|
| F-9 | — | 111 | — | 7 | 230 | 18 | >3000 |
| F-13 | — | 234 | — | 1 | — | 64 | — |
| F-32 | — | — | — | 7 | 119 | — | 469 |
| F-33 | — | — | — | 3 | 107 | — | 332 |
| F-41 | — | 345 | — | 6 | — | 11 | — |
| F-48 | — | 122 | — | >3000 | — | >3000 | — |
| F-58 | — | >3000 | — | 82 | — | 104 | — |
| F-59 | — | >3000 | — | 319 | — | 546 | — |
| F-70 | — | 2295 | — | 43 | — | 49 | — |
| F-77 | — | 829 | — | 26 | — | 12 | — |
| F-90 | 2275 | >3000 | 2180 | >3000 | — | >3000 | — |
| F-140 | >3000 | >3000 | 1989 | >3000 | — | >3000 | — |

Table 3 reports a biochemical kinase activity against 373 WT kinases (Eurofins Discovery, France) using their commercial radiometric KinaseProfiler™ binding assays. In this experiment, compound F-90 was screened at 1 M. The reported numbers are 00 Activity remaining, and are an average of two independent experiments.

TABLE 3

Biochemical Kinase Activity for Compound F-90

| Kinase | % Activity |
|---|---|
| CRIK(h) | 0 |
| A-Raf(h) | 97 |
| AAK1(h) | 13 |
| Abl(h) | 99 |
| ACK1(h) | 39 |
| ACTR2(h) | 96 |
| ALK(h) | 77 |
| ALK1(h) | 94 |
| ALK2(h) | 122 |
| ALK4(h) | 94 |
| ALK6(h) | 74 |
| AMPKα1(h) | 120 |
| AMPKα2(h) | 117 |
| Arg(h) | 72 |
| ARK5(h) | 85 |
| ASK1(h) | 100 |
| ATM(h) | 103 |
| ATR/ATRIP(h) | 110 |
| Aurora-A(h) | 97 |
| Aurora-B(h) | 109 |
| Aurora-C(h) | 94 |
| Axl(h) | 91 |
| B-Raf(h) | 110 |
| BIKE(h) | 50 |
| Blk(h) | 88 |
| BMPR2(h) | 85 |
| Bmx(h) | 97 |
| BRK(h) | 83 |
| BrSK1(h) | 96 |
| BrSK2(h) | 83 |

TABLE 3-continued

Biochemical Kinase Activity for Compound F-90

| Kinase | % Activity |
|---|---|
| BTK(h) | 122 |
| c-RAF(h) | 106 |
| CaMKI(h) | 104 |
| CaMKIIα(h) | 88 |
| CaMKIIβ(h) | 93 |
| CaMKIIγ(h) | 106 |
| CaMKIIδ(h) | 96 |
| CaMKIβ(h) | 85 |
| CaMKIV(h) | 99 |
| CaMKIγ(h) | 110 |
| CaMKIδ(h) | 89 |
| CaMKK1(h) | 89 |
| CaMKK2(h) | 96 |
| Cdc7/cyclinB1(h) | 75 |
| CDK1/cyclinB(h) | 94 |
| CDK12/cyclinK(h) | 89 |
| CDK13/cyclinK(h) | 99 |
| CDK14/cyclinY(h) | 91 |
| CDK16/cyclinY(h) | 98 |
| CDK17/cyclinY(h) | 108 |
| CDK18/cyclinY(h) | 94 |
| CDK2/cyclinA(h) | 87 |
| CDK2/cyclinE(h) | 92 |
| CDK3/cyclinE(h) | 102 |
| CDK4/cyclinD3(h) | 74 |
| CDK5/p25(h) | 72 |
| CDK5/p35(h) | 79 |
| CDK6/cyclinD3(h) | 90 |
| CDK7/cyclinH/MAT1(h) | 95 |
| CDK9/cyclin T1(h) | 81 |
| CDKL1(h) | 99 |
| CDKL2(h) | 80 |
| CDKL3(h) | 79 |
| CDKL4(h) | 104 |
| ChaK1(h) | 106 |
| CHK1(h) | 108 |
| CHK2(h) | 95 |
| CK1α(h) | 97 |

TABLE 3-continued

Biochemical Kinase Activity for Compound F-90

| Kinase | % Activity |
| --- | --- |
| CK1γ1(h) | 101 |
| CK1γ2(h) | 97 |
| CK1γ3(h) | 84 |
| CK1δ(h) | 96 |
| CK1ε(h) | 96 |
| CK2(h) | 112 |
| CK2α1(h) | 112 |
| CK2α2(h) | 115 |
| cKit(h) | 85 |
| CLIK1(h) | 97 |
| CLK1(h) | 88 |
| CLK2(h) | 106 |
| CLK3(h) | 107 |
| CLK4(h) | 85 |
| CSK(h) | 92 |
| cSRC(h) | 93 |
| DAPK1(h) | 82 |
| DAPK2(h) | 109 |
| DCAMKL1(h) | 95 |
| DCAMKL2(h) | 104 |
| DCAMKL3(h) | 86 |
| DDR1(h) | 98 |
| DDR2(h) | 85 |
| DMPK(h) | 93 |
| DNA-PK(h) | 107 |
| DRAK1(h) | 80 |
| DRAK2(h) | 50 |
| DYRK1A(h) | 112 |
| DYRK1B(h) | 108 |
| DYRK2(h) | 101 |
| DYRK3(h) | 99 |
| eEF-2K(h) | 92 |
| EGFR(h) | 107 |
| EphA1(h) | 92 |
| EphA2(h) | 95 |
| EphA3(h) | 79 |
| EphA4(h) | 92 |
| EphA5(h) | 89 |
| EphA7(h) | 114 |
| EphA8(h) | 115 |
| EphB1(h) | 83 |
| EphB2(h) | 96 |
| EphB3(h) | 79 |
| EphB4(h) | 107 |
| ErbB2(h) | 97 |
| ErbB4(h) | 94 |
| FAK(h) | 96 |
| Fer(h) | 103 |
| Fes(h) | 111 |
| FGFR1(h) | 100 |
| FGFR2(h) | 89 |
| FGFR3(h) | 86 |
| FGFR4(h) | 114 |
| Fgr(h) | 97 |
| Flt1(h) | 125 |
| Flt3(h) | 84 |
| Flt4(h) | 96 |
| Fms(h) | 115 |
| Fyn(h) | 100 |
| GCK(h) | 118 |
| GCN2(h) | 101 |
| GRK1(h) | 86 |
| GRK2(h) | 95 |
| GRK3(h) | 81 |
| GRK5(h) | 97 |
| GRK6(h) | 95 |
| GRK7(h) | 98 |
| GSK3α(h) | 87 |
| GSK3β(h) | 93 |
| Haspin(h) | 140 |
| Hck(h) | 99 |
| Hck(h) activated | 111 |
| HIPK1(h) | 100 |
| HIPK2(h) | 105 |
| HIPK3(h) | 85 |
| HIPK4(h) | 52 |

TABLE 3-continued

Biochemical Kinase Activity for Compound F-90

| Kinase | % Activity |
| --- | --- |
| HPK1(h) | 73 |
| HRI(h) | 80 |
| ICK(h) | 99 |
| IGF-1R(h) | 98 |
| IGF-1R(h), activated | 93 |
| IKKα(h) | 98 |
| IKKβ(h) | 99 |
| IKKε(h) | 87 |
| IR(h) | 94 |
| IR(h), activated | 92 |
| IRAK1(h) | 95 |
| IRAK4(h) | 90 |
| IRE1(h) | 99 |
| IRR(h) | 110 |
| Itk(h) | 86 |
| JAK1(h) | 85 |
| JAK2(h) | 104 |
| JAK3(h) | 106 |
| JNK1α1(h) | 110 |
| JNK2α2(h) | 99 |
| JNK3(h) | 88 |
| KDR(h) | 78 |
| LATS1(h) | 90 |
| LATS2(h) | 102 |
| Lck(h) | 86 |
| Lck(h) activated | 119 |
| LIMK1(h) | 70 |
| LIMK2(h) | 72 |
| LKB1(h) | 99 |
| LOK(h) | 96 |
| LRRK2(h) | 100 |
| LTK(h) | 97 |
| Lyn(h) | 80 |
| MAK(h) | 120 |
| MAP4K3(h) | 109 |
| MAP4K4(h) | 101 |
| MAP4K5(h) | 92 |
| MAPK1(h) | 95 |
| MAPK2(h) | 109 |
| MAPKAP-K2(h) | 72 |
| MAPKAP-K3(h) | 125 |
| MARK1(h) | 106 |
| MARK3(h) | 90 |
| MARK4(h) | 92 |
| MEK1(h) | 101 |
| MEK2(h) | 92 |
| MEKK2(h) | 122 |
| MEKK3(h) | 107 |
| MELK(h) | 82 |
| Mer(h) | 105 |
| Met(h) | 90 |
| MINK(h) | 89 |
| MKK3(h) | 97 |
| MKK6(h) | 101 |
| MLCK(h) | 98 |
| MLK1(h) | 103 |
| MLK2(h) | 77 |
| MLK3(h) | 91 |
| MLK4(h) | 112 |
| Mnk2(h) | 35 |
| MOK(h) | 90 |
| MRCKα(h) | 94 |
| MRCKβ(h) | 100 |
| MRCKγ(h) | 98 |
| MSK1(h) | 111 |
| MSK2(h) | 88 |
| MSSK1(h) | 134 |
| MST1(h) | 76 |
| MST2(h) | 106 |
| MST3(h) | 85 |
| MST4(h) | 106 |
| mTOR(h) | 95 |
| mTOR/FKBP12(h) | 120 |
| MuSK(h) | 96 |
| MYLK2(h) | 76 |
| MYO3B(h) | 79 |

TABLE 3-continued

| Biochemical Kinase Activity for Compound F-90 | |
|---|---|
| Kinase | % Activity |
| NDR1(h) | 100 |
| NDR2(h) | 107 |
| NEK1(h) | 94 |
| NEK11(h) | 97 |
| NEK2(h) | 118 |
| NEK3(h) | 110 |
| NEK4(h) | 90 |
| NEK6(h) | 86 |
| NEK7(h) | 88 |
| NEK9(h) | 79 |
| NIM1(h) | 112 |
| NLK(h) | 98 |
| NUAK2(h) | 72 |
| OSR1(h) | 80 |
| p70S6K(h) | 93 |
| PAK1(h) | 95 |
| PAK2(h) | 95 |
| PAK3(h) | 89 |
| PAK4(h) | 83 |
| PAK5(h) | 87 |
| PAK6(h) | 101 |
| PAR-1Bα(h) | 88 |
| PASK(h) | 72 |
| PDGFRα(h) | 116 |
| PDGFRβ(h) | 105 |
| PDHK2(h) | 87 |
| PDHK4(h) | 101 |
| PDK1(h) | 105 |
| PEK(h) | 91 |
| PhKγ1(h) | 101 |
| PhKγ2(h) | 98 |
| PI3 Kinase (p110a/p85a)(h) | 96 |
| PI3 Kinase (p110b/p85a)(h) | 102 |
| PI3 Kinase (p110d/p85a)(h) | 110 |
| PI3 Kinase (p120g)(h) | 105 |
| PI3KC2a(h) | 102 |
| PI3KC2g(h) | 103 |
| Pim-1(h) | 95 |
| Pim-2(h) | 117 |
| Pim-3(h) | 103 |
| PIP4K2a(h) | 100 |
| PIP5K1a(h) | 103 |
| PIP5K1g(h) | 102 |
| PKA(h) | 109 |
| PKAcβ(h) | 12 |
| PKBα(h) | 87 |
| PKBβ(h) | 109 |
| PKBγ(h) | 101 |
| PKCα(h) | 92 |
| PKCβI(h) | 90 |
| PKCβII(h) | 87 |
| PKCγ(h) | 97 |
| PKCδ(h) | 93 |
| PKCε(h) | 97 |
| PKCζ(h) | 88 |
| PKCη(h) | 118 |
| PKCθ(h) | 103 |
| PKCι(h) | 110 |
| PKCμ(h) | 109 |
| PKD2(h) | 95 |
| PKD3(h) | 97 |
| PKG1α(h) | 118 |
| PKG1β(h) | 92 |
| PKR(h) | 85 |
| Plk1(h) | 111 |
| Plk3(h) | 100 |
| Plk4(h) | 92 |
| PRAK(h) | 107 |
| PRK1(h) | 91 |
| PRK2(h) | 92 |
| PRKG2(h) | 110 |
| PrKX(h) | 101 |
| PRP4(h) | 100 |
| PTK5(h) | 90 |
| Pyk2(h) | 76 |
| Ret(h) | 97 |

TABLE 3-continued

| Biochemical Kinase Activity for Compound F-90 | |
|---|---|
| Kinase | % Activity |
| RIPK1(h) | 84 |
| RIPK2(h) | 97 |
| ROCK-I(h) | 96 |
| ROCK-II(h) | 96 |
| Ron(h) | 111 |
| Ros(h) | 97 |
| Rse(h) | 129 |
| Rsk1(h) | 99 |
| Rsk2(h) | 88 |
| Rsk3(h) | 112 |
| Rsk4(h) | 101 |
| SAPK2a(h) | 94 |
| SAPK2b(h) | 90 |
| SAPK3(h) | 113 |
| SAPK4(h) | 94 |
| SBK1(h) | 97 |
| SGK(h) | 113 |
| SGK2(h) | 82 |
| SGK3(h) | 102 |
| SIK(h) | 105 |
| SIK2(h) | 109 |
| SIK3(h) | 105 |
| SLK(h) | 109 |
| Snk(h) | 94 |
| SNRK(h) | 111 |
| SRMS(h) | 86 |
| SRPK1(h) | 95 |
| SRPK2(h) | 93 |
| STK16(h) | 94 |
| STK25(h) | 92 |
| STK32A(h) | 90 |
| STK32B(h) | 115 |
| STK32C(h) | 85 |
| STK33(h) | 98 |
| STK39(h) | 102 |
| Syk(h) | 66 |
| TAF1L(h) | 101 |
| TAK1(h) | 91 |
| TAO1(h) | 83 |
| TAO2(h) | 90 |
| TAO3(h) | 100 |
| TBK1(h) | 100 |
| Tec(h) activated | 126 |
| TGFBR1(h) | 103 |
| TGFBR2(h) | 96 |
| Tie2 (h) | 99 |
| TLK1(h) | 82 |
| TLK2(h) | 92 |
| TNIK(h) | 93 |
| TRB2(h) | 104 |
| TrkA(h) | 105 |
| TrkB(h) | 84 |
| TrkC(h) | 86 |
| TSSK1(h) | 116 |
| TSSK2(h) | 113 |
| TSSK3(h) | 96 |
| TSSK4(h) | 117 |
| TTBK1(h) | 96 |
| TTBK2(h) | 94 |
| TTK(h) | 102 |
| Txk(h) | 110 |
| TYK2(h) | 103 |
| ULK1(h) | 95 |
| ULK2(h) | 98 |
| ULK3(h) | 95 |
| VRK1(h) | 99 |
| VRK2(h) | 100 |
| Wee1(h) | 94 |
| Wee1B(h) | 88 |
| WNK1(h) | 109 |
| WNK2(h) | 94 |
| WNK3(h) | 85 |
| WNK4(h) | 97 |
| Yes(h) | 87 |

TABLE 3-continued

| Biochemical Kinase Activity for Compound F-90 | |
|---|---|
| Kinase | % Activity |
| ZAK(h) | 83 |
| ZAP-70(h) | 71 |
| ZIPK(h) | 94 |

Example 4: NanoBRET Intracellular Target Engagement Assay

In-cell $K_d$ values were evaluated with a NanoBRET Target Engagement Assay essentially as recommended by the manufacturer (Promega Corporation—for details see https://www.promega.com/resources/technologies/nanoluc-luciferase-enzyme/cellular-target-engagement/).

Full-length human CITK (UniProt: 014578, Met1-Val2069) was amplified from cDNA (NCBI: NG_029792.1) and cloned into pNLF1-N (Promega) using a HiFi® Assembly (NEB) to generate an N-terminal NanoLuc® fusion construct referred to as NanoLuc-CITK (FIG. 6A). HEK293T cells were transfected with 5.0 μg/mL sterile NanoLuc-CITK DNA, 5.0 μg/mL Transfection Carrier DNA, and 30 μL/mL FugeneHD® (Promega) in Opti-Mem™ (Thermo) media at a cell density of 250,000 cells/mL. After transfection, 100 μL of cells (25,000 cells/well) were seeded into 96-well, TC-treated, black, clear-bottom CellCarrier™ Ultra plates (Perkin Elmer 6055302) and rested overnight at 37° C., 5% $CO_2$. The next morning, Kinase Tracer K10 (Promega) was prepared at 100× (100 μM) and then diluted to 25× (25 μM) with Tracer Dilution Buffer. 5 μL of the 25× Tracer K10 solution was added to each well. Next, designated inhibitors were prepared from powder as 10 mM DMSO stocks and then further diluted to 10× the final assay concentration in Opti-Mem™. 12-pt dose-response curves were prepared by 3×-serial dilution. 10 μL/well of 10× compounds were added to the corresponding wells, resulting in a final [inhibitor] ranging from 10 μM to 57 μM, and the plate(s) were incubated for 2 hours at 37° C., 5% $CO_2$. A 3× Complete Substrate+Inhibitor solution, containing 6 mL of Opti-Mem™, 36 μL of NanoBRET Nano-Glo Substrate, and 12 μL Extracellular NanoLuc Inhibitor was freshly prepared for each plate. 50 μL of the 3× Complete Substrate+Inhibitor solution was added to all wells and the plate was incubated for 2 min with 500 RPM shaking. The bottom of the plates were covered with black plate seals and then measured on a Cytation 5 plate reader (Biotek) with a NanoBRET Filter Cube (Biotek; 450/50 emission & 610LP emission). Background corrected BRET ratios (in mBU) were calculated in Excel and IC50's were subsequently extracted using four-parameter non-linear regression in GraphPad Prism 8. IC50s were converted to $K_d$ values using the Cheng-Prussoff relationship based on the measured $K_d$=0.23 M for Tracer K10. Over the course of multiple assays, Z' values ranged from 0.4-0.7 with a signal window of ~1.5 mBU.

Assay verification was conducted using a control compound having the structure shown below; note this compound differs from example compound F-90 only in that it has a 6-azaindole moiety compared to a 7-azaindole moiety. Using the biochemical assay described in Example 3, the $IC_{50}$ for this compound was greater than 3 μM, where as the $IC_{50}$ for compound F-90 was 12 nM (see Table 1). Data for this control compound and compound F-90 using the NanoBRET assay is shown in FIG. 6B, and validates the utility of this assay for target engagement of citron kinase.

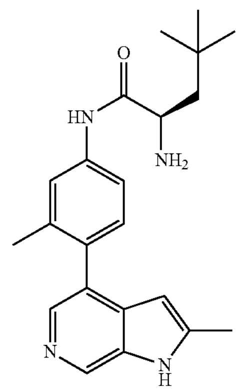 [SMILES: Cc1cc2c(-c3ccc(NC(=O)[C@H](N)CC(C)(C)C)cc3C)cncc2[nH]1]

Figure 7:
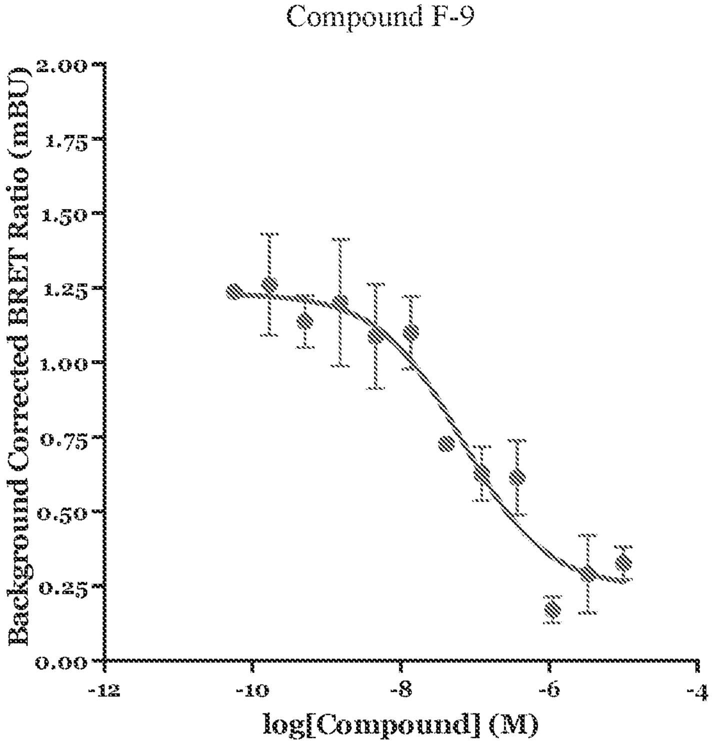
FIG. 7 shows representative dose-response curves for compounds F-9, F-140, F-161, and F-162 using the NanoBRET target engagement assay.
Figure 7:
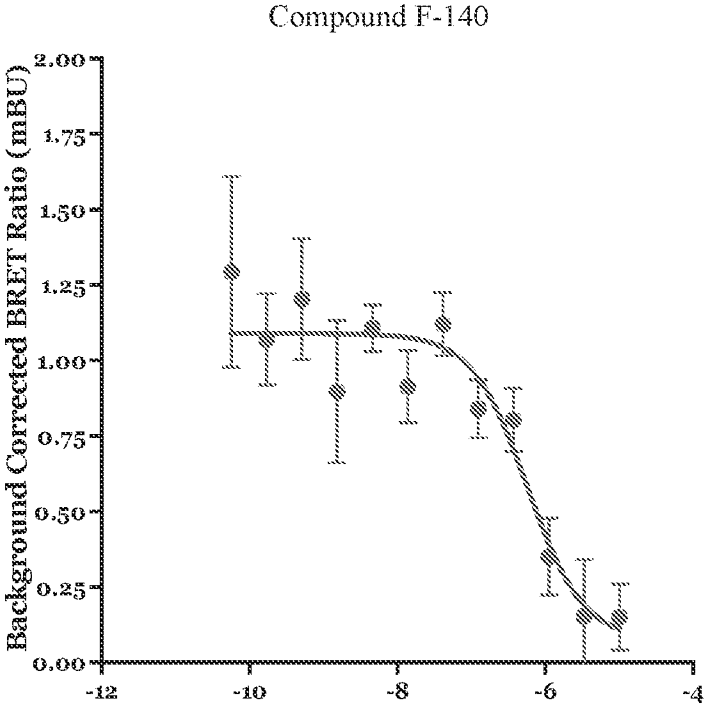
Figure 7:
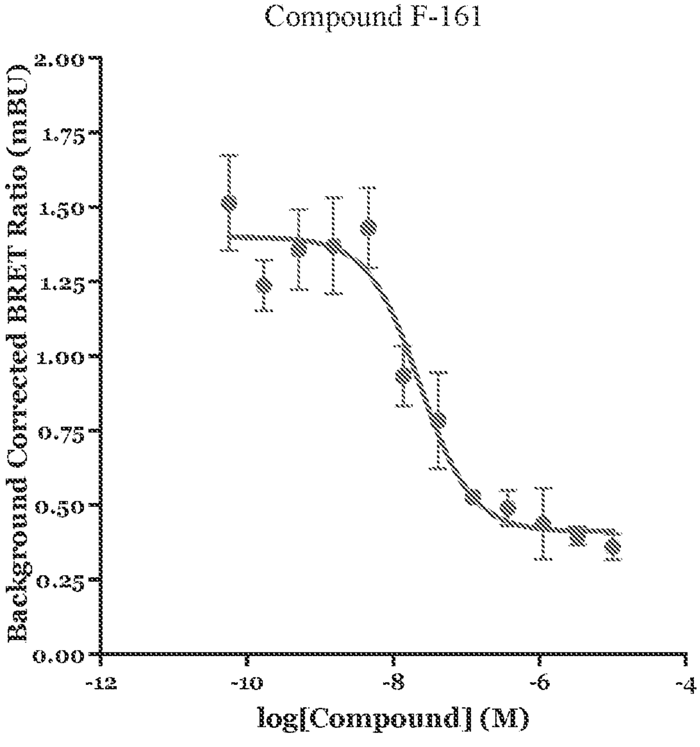
Figure 7:
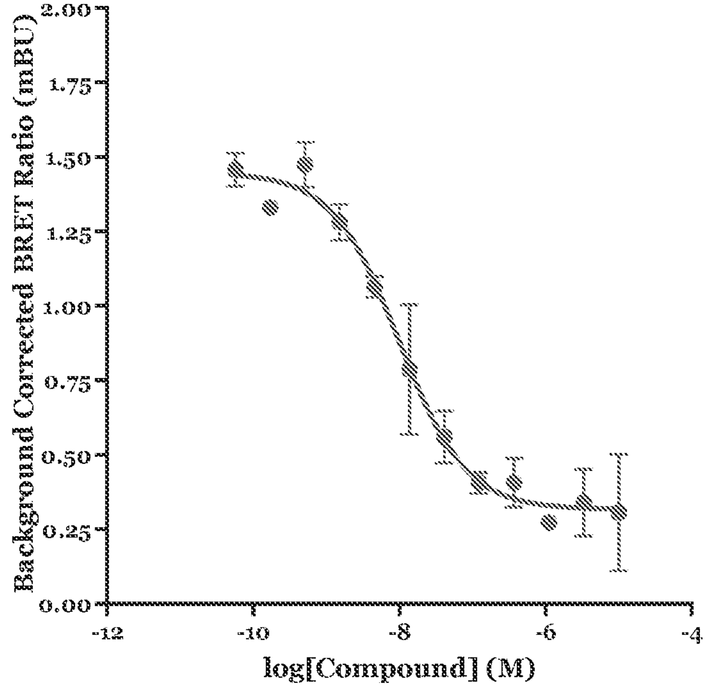

Compounds F-9, F-140, F-161, and F-162 were additionally evaluated using this NanoBRET assay. Representative dose-response curves for these compounds are shown in FIG. 7 and the corresponding $IC_{50}$ and $K_D$ values in Table 4.

TABLE 4

| $IC_{50}$ values and in-cell $K_D$ values derived from the NanoBRET assay | | |
|---|---|---|
| Compound | NanoBRET $IC_{50}$ (nM) | $K_D$ (nM)* |
| 6-Azaindole Control | No binding (n = 2) | No binding |
| F-9 | 67 (n = 1) | 13 |
| F-90 | 53 (n = 2) | 9.9 |
| F-140 | 580 (n = 2) | 108 |
| F-161 | 23 (n = 2) | 4.3 |
| F-162 | 10 (n = 2) | 1.9 |

*At [Tracer K10] = 1 μM and $K_D$ Tracer K10 vs. NanoLuc ®-CITK = 0.23 μM

Example 5: Identification of Citron Kinase as a Druggable Target for Prostate Cancer A significant increase in citron kinase expression was noted in two independent prostate cancer cell lines, LNCaP and VCaP, after stimulation with low doses of the synthetic androgen R1881 (FIG. 1A). This finding is consistent with the well-known biphasic growth response of prostate cancer cells to androgens, in which doses of androgens <1 nM stimulate and doses ~1 nM restrict cell proliferation. Similar results were obtained when cells were treated with different doses of the natural androgen dihydrotestosterone (DHT) (FIG. 1).

Silencing of citron kinase in LNCaP and VCaP cells led to a marked decrease in the number of Ki67-positive cells (FIGS. 2A-B), and delayed cell cycle progression (FIG. 2C), indicating that changes in citron kinase levels affect prostate cancer cell proliferation. Similar effects of citron kinase silencing were seen in the castration-resistant LNCaP subline C4-2 (FIG. 2D). That these results were due to effects on cell division was supported by an increase in the number of multinucleated cells after knock-down of citron kinase (FIG. 3, arrows).

The effects of citron kinase on prostate cancer proliferation require its kinase moiety. Citron kinase is 1 of 2 isoforms. The second isoform, known as citron, does not contain a kinase domain. Only the larger kinase isoform (230 kDa) was detected in lysates of prostate cancer cells using Western blot. Prostate cancer cells' reliance on citron kinase's kinase activity was evident also in several failed attempts to establish a cell line that stably overexpresses a kinase-dead version (K126A). Even transient overexpression of the K126A mutant led to severe decreases in prostate cancer cell numbers, whereas overexpression of wild-type citron kinase stimulated prostate cancer cell growth (FIG. 4).

To assess its clinical relevance, CIT expression was quantitated in CaP tissue microarrays (TMAs) containing 149 localized treatment-naïve CaP cores and, for 121 of these CaPs, the matching benign prostate tissue cores. Of the CaP cores, 136 were positive for CIT, compared to 105 benign prostate tissues, and more CaP cores showed stronger (i.e. moderate or marked) CIT expression than benign tissue (FIG. 5A). Consistent with this observation, overall CIT expression was higher ($p<0.001$) in CaP (average score/core=1.449) compared to adjacent non-neoplastic prostate tissues (average score/core=1.099) (FIG. 5B). Western blotting on frozen tissue cores from treatment-naïve CaPs localized treatment-naive CaPs with ≥90% neoplastic content and adjacent benign prostate tissue detected only the 230 kD CIT isoform (FIG. 5C), confirming kinase-competent CIT is expressed in clinical CaP. CIT expression on the TMA tended to increase with higher Gleason scores (FIG. 5D). Gene Set Enrichment Analysis (GSEA) on CIT-dependent gene sets obtained in RNA-Seq studies showed that genes that rely on CIT to maintain basal expression (down regulated after CIT loss) were significantly positively enriched in CRPC compared to localized untreated CaP, confirming relevance of CIT action to lethal CaP progression (FIG. 5E). No enrichment of CIT growth-dependent gene signatures was observed between localized and metastatic CaP, indicating their expression is maintained in CRPC. This finding is in stark contrast to the behavior of genes controlled directly by AR, the target for default treatment of metastatic CaP, which show decreased expression in metastatic CRPC, indicating that growth-regulated CIT-dependent genes are (more) strongly associated with poor CaP outcome.

The association between citron kinase overexpression and prostate cancer outcome was examined using the cBIO database. Two independent gene expression profiles from localized prostate cancer specimens from patients with follow-up data were analyzed. The dataset (Taylor et al.) contains expression profiles from 216 treatment-naïve localized prostate cancers from patients for whom information on disease-free survival (biochemical recurrence, AUA definition) was available. The second study (TCGA dataset) expression profiled 499 localized prostate cancer tissues from patients for whom information on disease-free as well as overall survival is available. In both studies, overexpression of citron kinase correlated significantly ($p<0.05$) with shorter disease-free survival. Overexpression also correlated inversely ($p=0.00937$) with overall survival in the TCGA dataset (FIG. 5). In both studies, expression of citron kinase significantly correlated with that of the proliferation marker Ki67 ($p<0.001$, log odds ratio >3). These data underscore the importance of citron kinase action for aggressive prostate cancer progression, and validate it as a valuable novel target for therapy.

Example 6: Activity in Cancer Cell Lines

The NCI-60 human tumor cell line panel was screened with Compound F-90. $GI_{50}$ data are presented in Table 5.

TABLE 5

| Tumor Type | Cell Line | $GI_{50}$ (Log(M)) | $GI_{50}$ (μM) |
|---|---|---|---|
| Breast Cancer | HS 578T | −5.849 | 1.4 |
| Renal Cancer | 786-0 | −5.744 | 1.8 |
| Colon Cancer | COLO 205 | −5.741 | 1.8 |
| Leukemia | SR | −5.682 | 2.1 |
| Renal Cancer | A498 | −5.657 | 2.2 |
| Melanoma | SK-MEL-5 | −5.609 | 2.5 |
| Non-Small Cell Lung Cancer | HOP-92 | −5.574 | 2.7 |
| Colon Cancer | HT29 | −5.565 | 2.7 |
| Breast Cancer | MDA-MB-468 | −5.564 | 2.7 |
| Leukemia | RPMI-8226 | −5.557 | 2.8 |
| Leukemia | K-562 | −5.551 | 2.8 |
| Leukemia | HL-60(TB) | −5.539 | 2.9 |
| Renal Cancer | RXF 393 | −5.434 | 3.7 |
| Renal Cancer | CAKI-1 | −5.347 | 4.5 |
| Colon Cancer | HCT-15 | −5.345 | 4.5 |
| Renal Cancer | UO-31 | −5.335 | 4.6 |
| Leukemia | MOLT-4 | −5.329 | 4.7 |
| CNS Cancer | SNB-75 | −5.326 | 4.7 |
| Colon Cancer | HCT-116 | −5.314 | 4.9 |
| Leukemia | CCRF-CEM | −5.267 | 5.4 |
| Breast Cancer | MCF7 | −5.256 | 5.5 |
| Colon Cancer | SW-620 | −5.250 | 5.6 |
| Non-Small Cell Lung Cancer | NCI-H460 | −5.245 | 5.7 |
| Colon Cancer | HCC-2998 | −5.236 | 5.8 |
| CNS Cancer | U251 | −5.222 | 6.0 |
| Colon Cancer | KM12 | −5.215 | 6.1 |
| Melanoma | LOX IMVI | −5.211 | 6.2 |
| Breast Cancer | BT-549 | −5.200 | 6.3 |
| Breast Cancer | T-47D | −5.174 | 6.7 |
| Ovarian Cancer | OVCAR-4 | −5.158 | 7.0 |
| Breast Cancer | MDA-MB-435 | −5.155 | 7.0 |
| Breast Cancer | MDA-MB-231/ATCC | −5.129 | 7.4 |
| Prostate Cancer | PC-3 | −5.102 | 7.9 |
| CNS Cancer | SF-539 | −5.098 | 8.0 |
| CNS Cancer | SF-295 | −5.079 | 8.3 |
| Melanoma | SK-MEL-28 | −5.072 | 8.5 |
| Melanoma | UACC-62 | −5.066 | 8.6 |
| Melanoma | MALME-3M | −4.992 | 10.2 |
| Non-Small Cell Lung Cancer | A549/ATCC | −4.985 | 10.3 |
| Ovarian Cancer | OVCAR-5 | −4.982 | 10.4 |
| Renal Cancer | ACHN | −4.978 | 10.5 |
| Melanoma | UACC-257 | −4.977 | 10.5 |
| Non-Small Cell Lung Cancer | NCI-H226 | −4.971 | 10.7 |
| Melanoma | M14 | −4.959 | 11.0 |
| Renal Cancer | SN12C | −4.953 | 11.1 |
| CNS Cancer | SF-268 | −4.953 | 11.1 |
| Non-Small Cell Lung Cancer | EKVX | −4.950 | 11.2 |
| CNS Cancer | SNB-19 | −4.945 | 11.3 |
| Non-Small Cell Lung Cancer | HOP-62 | −4.941 | 11.4 |
| Ovarian Cancer | OVCAR-3 | −4.937 | 11.6 |
| Ovarian Cancer | IGROV1 | −4.915 | 12.2 |
| Non-Small Cell Lung Cancer | NCI-H23 | −4.915 | 12.2 |
| Prostate Cancer | DU-145 | −4.905 | 12.4 |
| Ovarian Cancer | SK-OV-3 | −4.905 | 12.4 |
| Renal Cancer | TK-10 | −4.901 | 12.6 |
| Non-Small Cell Lung Cancer | NCI-H522 | −4.887 | 13.0 |
| Breast Cancer | NCI/ADR-RES | −4.873 | 13.4 |
| Ovarian Cancer | OVCAR-8 | −4.867 | 13.6 |
| Melanoma | SK-MEL-2 | −4.853 | 14.0 |
| Non-Small Cell Lung Cancer | NCI-H322M | −4.845 | 14.3 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

(I)

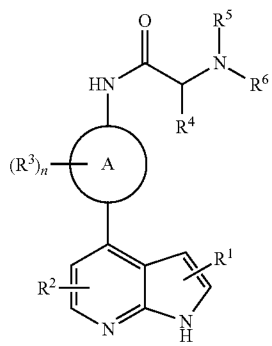

or a pharmaceutically acceptable salt thereof, wherein:

A is phenyl or a monocyclic 5- or 6-membered heteroaryl;

$R^1$ is selected from hydrogen, $C_1$-$C_3$ alkyl, $C_1$-$C_3$ haloalkyl, and $C_3$-$C_5$ cycloalkyl;

$R^2$ is selected from hydrogen, $C_1$-$C_3$ alkyl, $C_1$-$C_3$ haloalkyl, and $C_3$-$C_5$ cycloalkyl;

n is 0, 1, or 2;

each $R^3$ is independently selected from $C_1$-$C_3$ alkyl, $C_1$-$C_3$ haloalkyl, $C_3$-$C_5$ cycloalkyl, $C_1$-$C_3$ alkoxy, $C_1$-$C_3$ haloalkoxy, halo, and cyano;

$R^4$ is selected from hydrogen, $C_1$-$C_6$ alkyl, $C_1$-$C_6$ haloalkyl, $C_3$-$C_6$ cycloalkyl, aryl-$C_1$-$C_3$-alkyl, $C_3$-$C_6$ cycloalkyl-$C_1$-$C_3$-alkyl, hydroxy-$C_1$-$C_6$-alkyl, $C_1$-$C_3$-alkoxy-$C_1$-$C_6$-alkyl, and heterocyclyl-$C_1$-$C_3$-alkyl, wherein each cycloalkyl, aryl, and heterocyclyl is independently unsubstituted or substituted with 1-2 substituents independently selected from $C_1$-$C_3$ alkyl, $C_1$-$C_3$ haloalkyl, $C_1$-$C_3$ alkoxy, hydroxy, and halo; and $R^5$ and $R^6$ are each independently selected from hydrogen, $C_1$-$C_3$ alkyl, $C_1$-$C_3$ haloalkyl, $C_3$-$C_5$ cycloalkyl, $C_1$-$C_3$-alkoxy-$C_1$-$C_3$-alkyl, and $C_3$-$C_6$ cycloalkyl-$C_1$-$C_3$-alkyl.

2. The compound of claim 1, or a pharmaceutically acceptable salt thereof, wherein A is selected from phenyl, pyridyl, and thiazolyl.

3. The compound of claim 1, or a pharmaceutically acceptable salt thereof, wherein A is phenyl.

4. The compound of claim 1, or a pharmaceutically acceptable salt thereof, wherein the compound has formula (Ia):

(Ia)

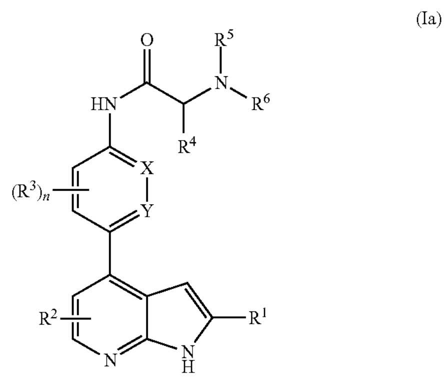

wherein:

X and Y are each independently selected from CH and N.

5. The compound of claim 1, or a pharmaceutically acceptable salt thereof, wherein the compound has formula (Ib):

(Ib)

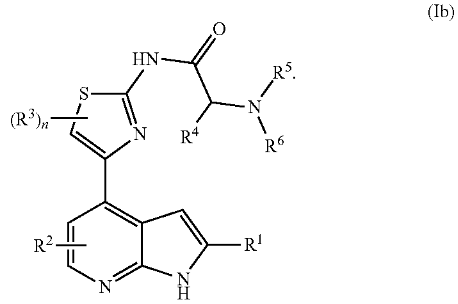

6. The compound of claim 1, or a pharmaceutically acceptable salt thereof, wherein $R^1$ is selected from hydrogen, $C_1$-$C_2$ alkyl, $C_1$-$C_2$ fluoroalkyl, and $C_3$-$C_4$ cycloalkyl.

7. The compound of claim 1, or a pharmaceutically acceptable salt thereof, wherein $R^1$ is selected from hydrogen, methyl, ethyl, difluoromethyl, trifluoromethyl, and cyclopropyl.

8. The compound of claim 1, or a pharmaceutically acceptable salt thereof, wherein $R^2$ is selected from hydrogen and $C_1$-$C_3$ alkyl.

9. The compound of claim 1, or a pharmaceutically acceptable salt thereof, wherein $R^2$ is selected from hydrogen and methyl.

10. The compound of claim 1, or a pharmaceutically acceptable salt thereof, wherein n is 0.

11. The compound of claim 1, or a pharmaceutically acceptable salt thereof, wherein n is 1 or 2.

12. The compound of claim 11, or a pharmaceutically acceptable salt thereof, wherein each $R^3$ is independently selected from $C_1$-$C_2$ alkyl, $C_1$-$C_2$ haloalkyl, $C_1$-$C_2$ alkoxy, $C_1$-$C_2$ haloalkoxy, halo, and cyano.

13. The compound of claim 11, or a pharmaceutically acceptable salt thereof, wherein each $R^3$ is independently selected from methyl, ethyl, difluoromethyl, trifluoromethyl, methoxy, trifluoromethoxy, fluoro, chloro, and cyano.

14. The compound of claim 1, or a pharmaceutically acceptable salt thereof, wherein $R^4$ is selected from hydrogen, $C_1$-$C_5$alkyl, $C_1$-$C_3$ haloalkyl, $C_3$-$C_4$ cycloalkyl, aryl-$C_1$-$C_2$-alkyl, $C_3$-$C_5$ cycloalkylmethyl, hydroxy-$C_1$-$C_4$-alkyl, and methoxy-$C_1$-$C_2$-alkyl.

15. The compound of claim 1, or a pharmaceutically acceptable salt thereof, wherein $R^4$ is selected from hydrogen, methyl, ethyl, n-propyl, iso-propyl, n-butyl, sec-butyl, iso-butyl, tert-butyl, iso-pentyl, neo-pentyl, trifluoromethyl, 1-fluoro-1-methylethyl, 2,2,2-trifluoroethyl, 3,3,3-trifluoropropyl, cyclopropyl, benzyl, 3-chlorobenzyl, 4-chlorobenzyl, 3-hydroxybenzyl, 4-hydroxybenzyl, 3-methoxybenzyl, 4-methoxybenzyl, hydroxymethyl, 1-hydroxyethyl, 2-hydroxyisopropyl, 1-hydroxy-2-methylpropyl, 1-hydroxy-2,2-dimethylpropyl, methoxymethyl, 2-methoxyethyl, cyclopropylmethyl, cyclobutylmethyl, cyclopentylmethyl, and tetrahydro-2H-pyran-4-ylmethyl.

16. The compound of claim 1, or a pharmaceutically acceptable salt thereof, wherein $R^5$ and $R^6$ are each independently selected from hydrogen, $C_1$-$C_2$ alkyl, $C_1$-$C_2$ haloalkyl, $C_3$-$C_4$ cycloalkyl, methoxy-$C_1$-$C_2$-alkyl, and $C_3$-$C_4$-cycloalkylmethyl.

17. The compound of claim 1, or a pharmaceutically acceptable salt thereof, wherein $R^5$ and $R^6$ are each independently selected from hydrogen, methyl, ethyl, 2,2,2-trifluoroethyl, cyclopropyl, 2-methoxyethyl, and cyclopropylmethyl.

18. The compound of claim 1, or a pharmaceutically acceptable salt thereof, wherein $R^5$ and $R^6$ are each hydrogen.

19. A compound selected from:

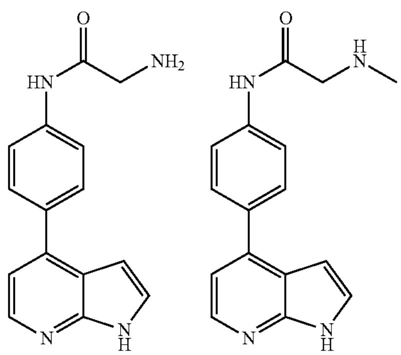

-continued

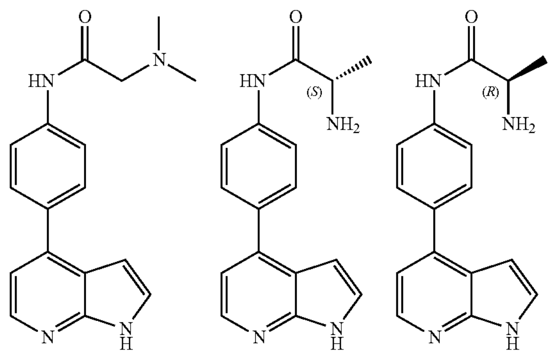

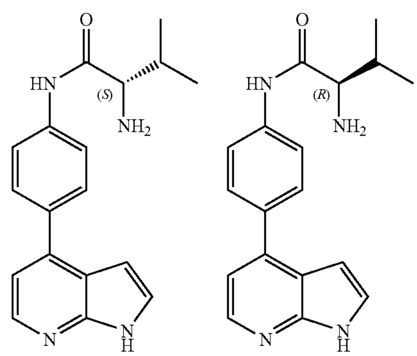

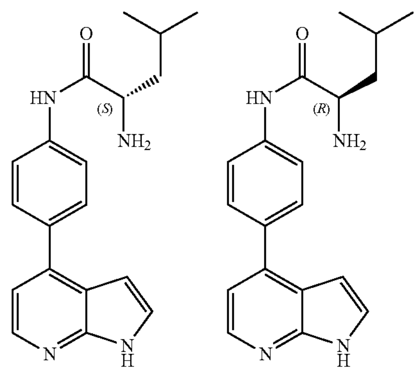

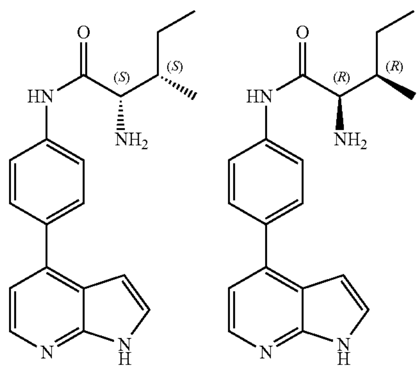

-continued
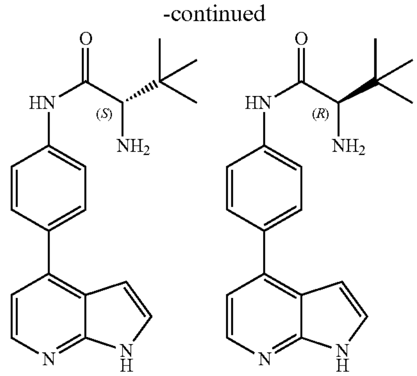
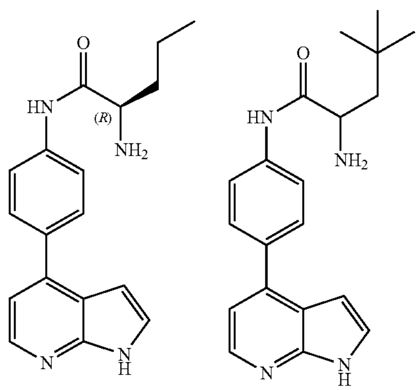
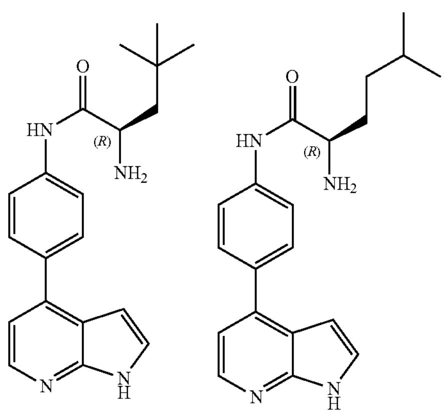
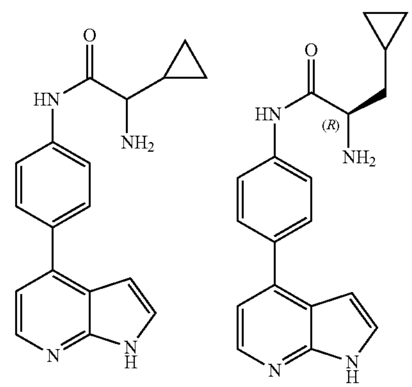
-continued
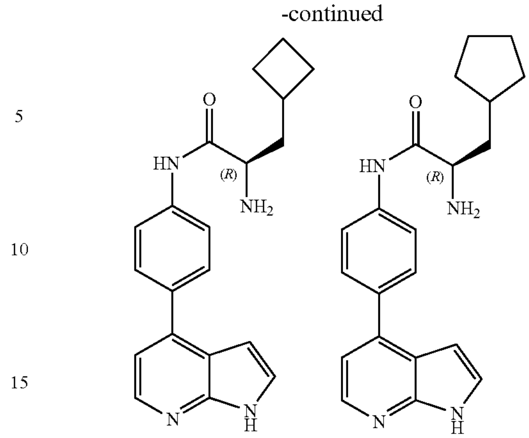
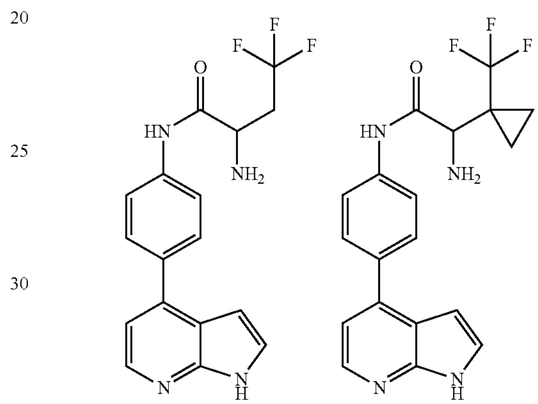
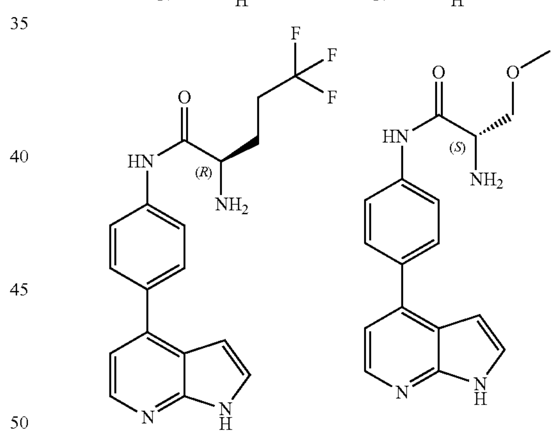
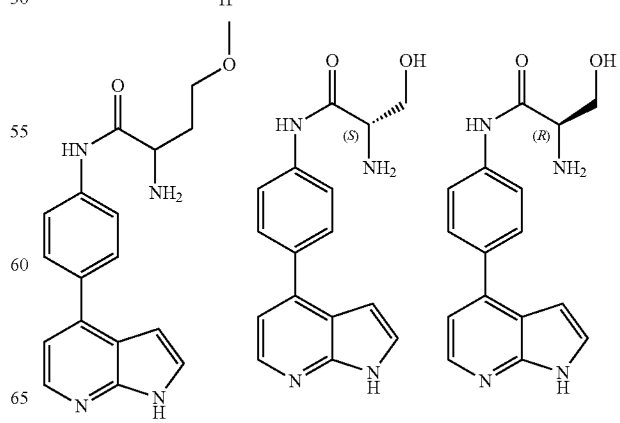

-continued
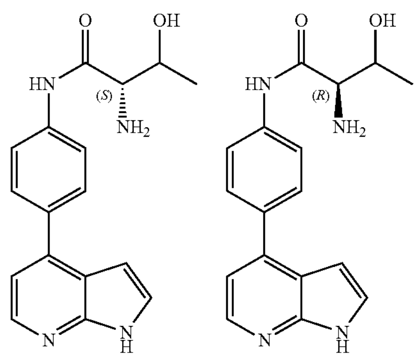
-continued
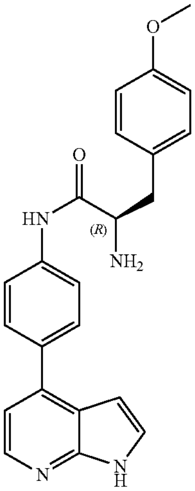
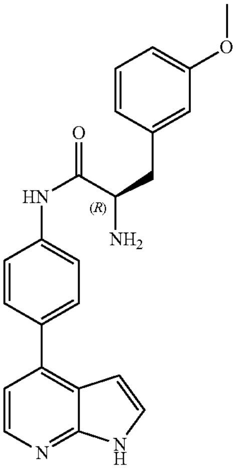
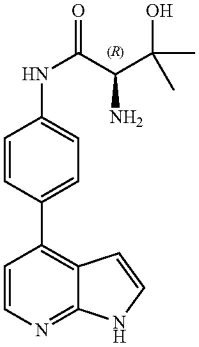
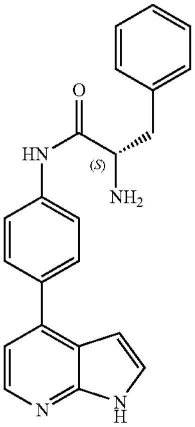
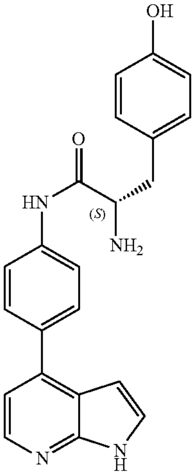
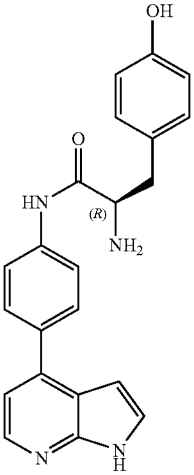
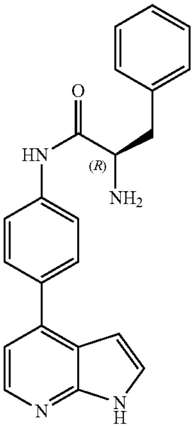
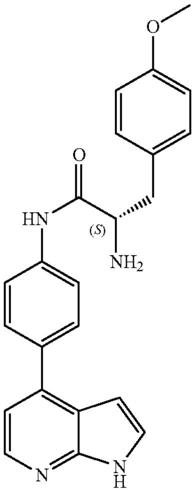
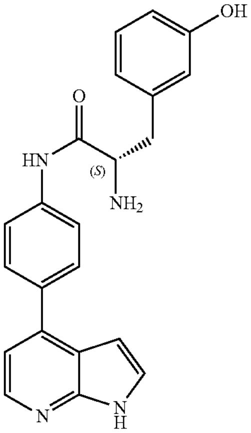
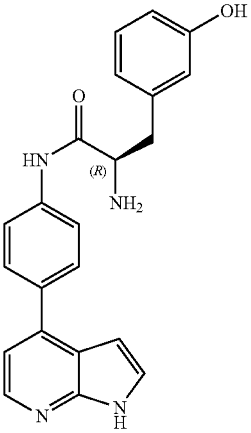

-continued
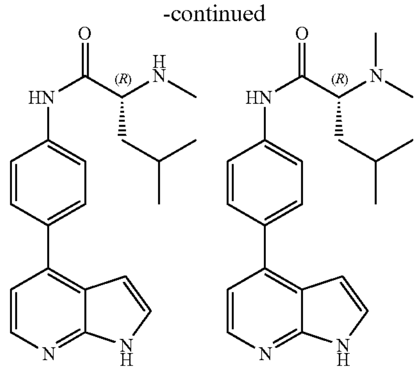
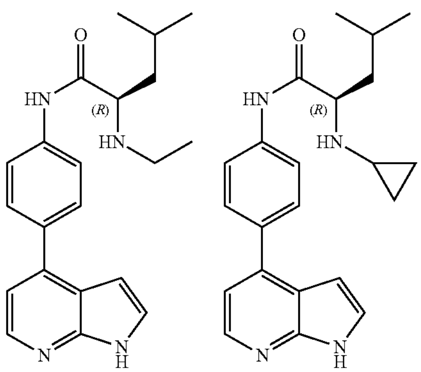
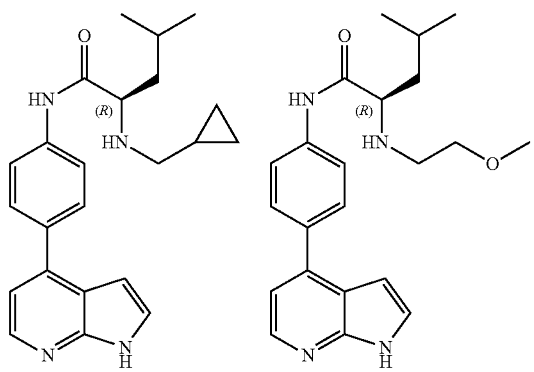
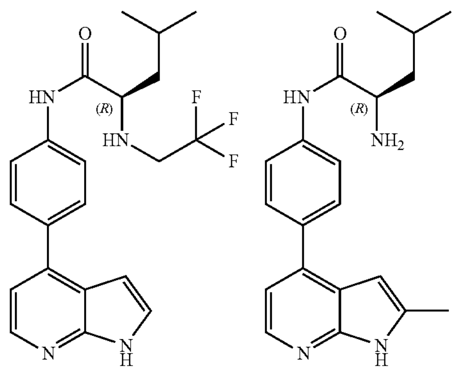
-continued
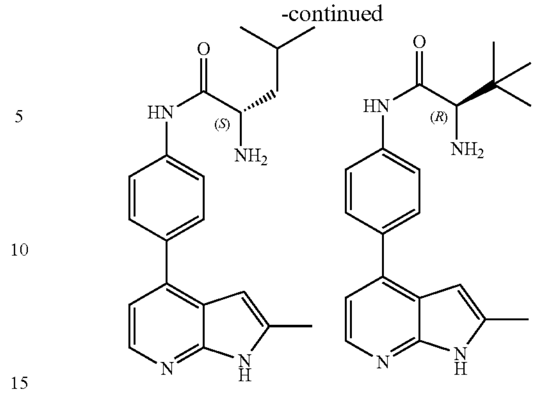
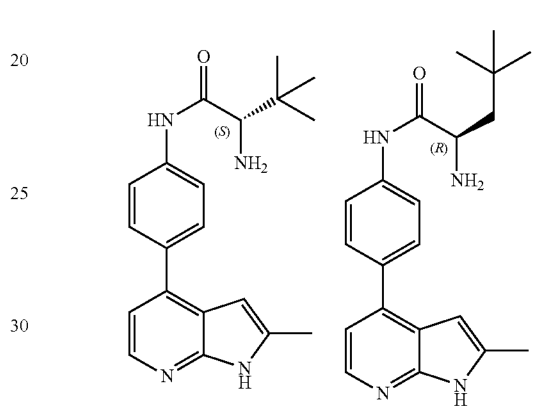
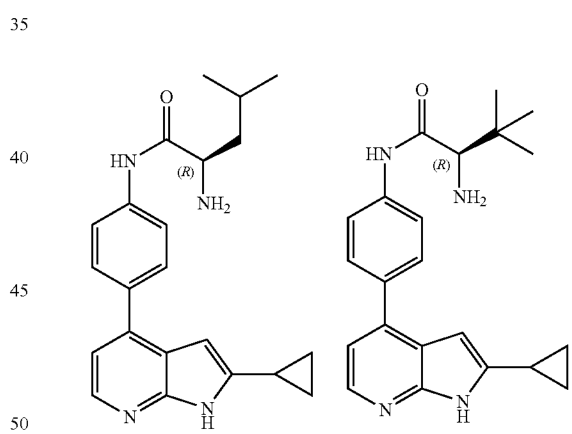
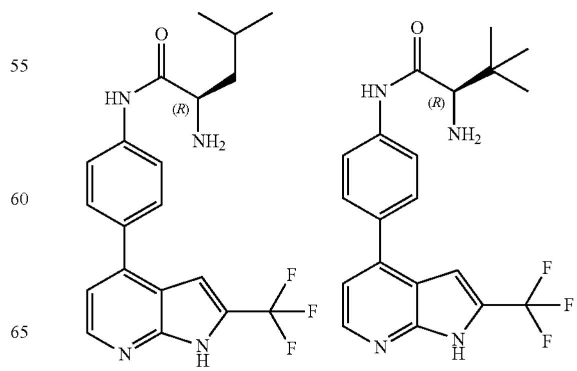

-continued
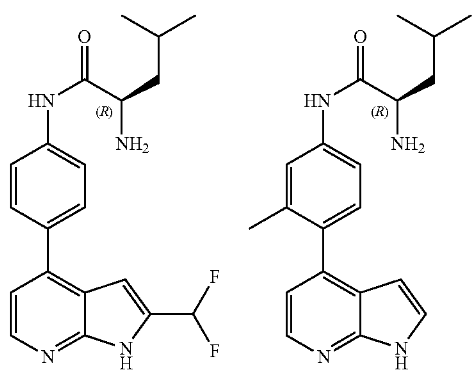
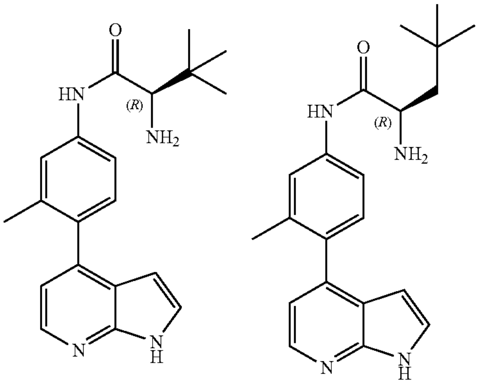
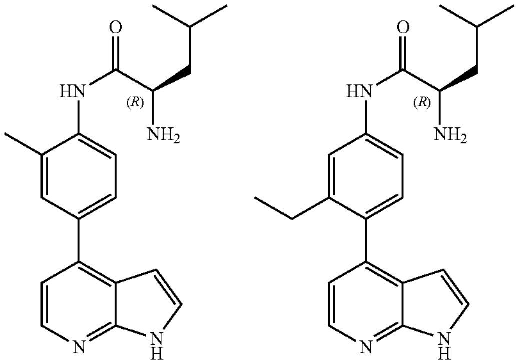
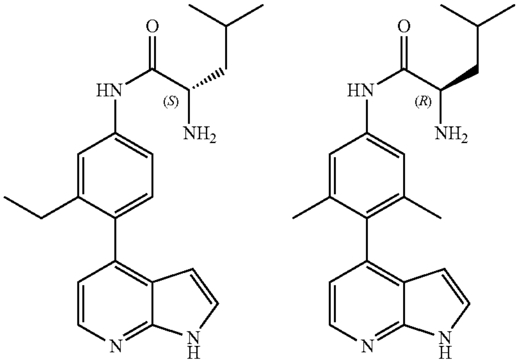
-continued
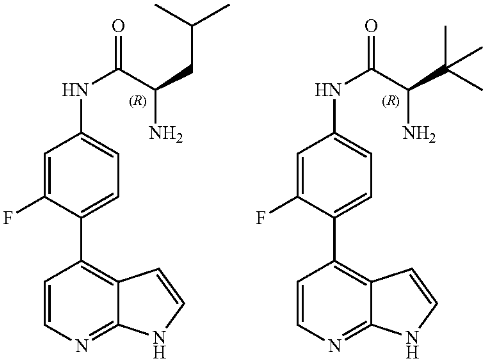
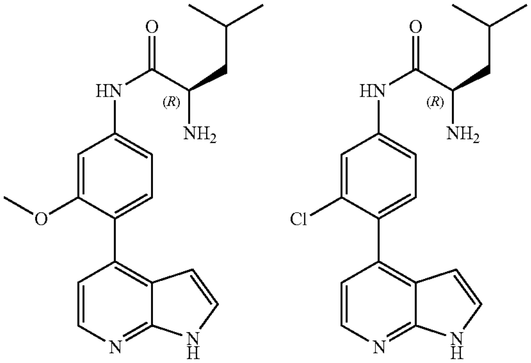
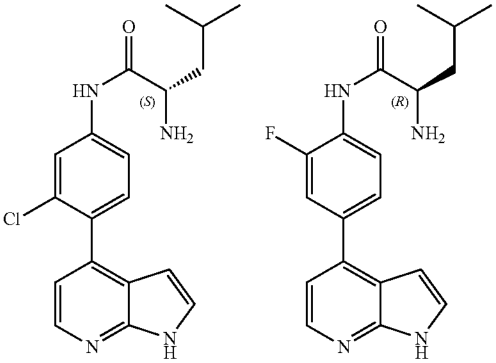
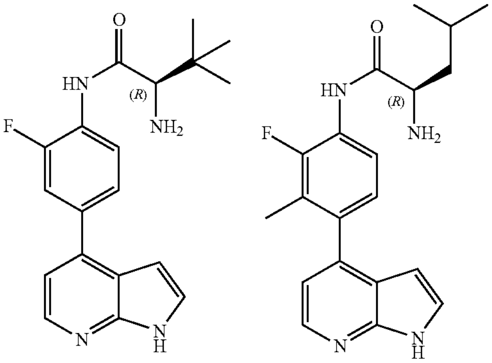

-continued
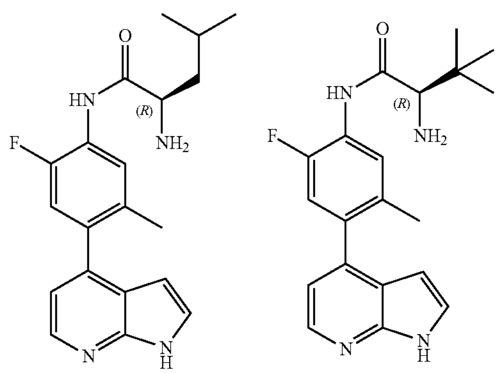
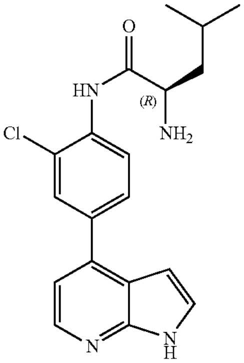
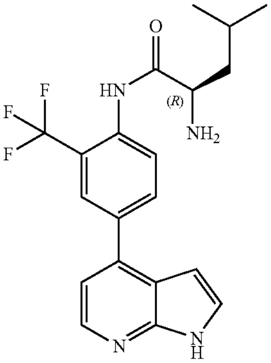
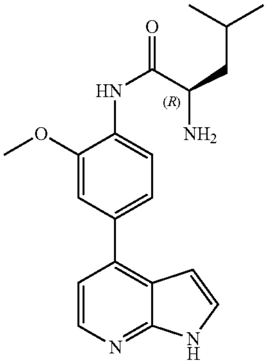
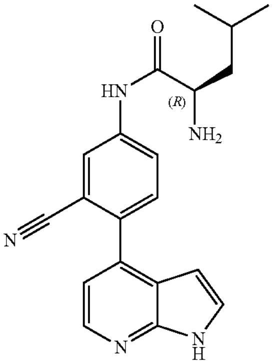
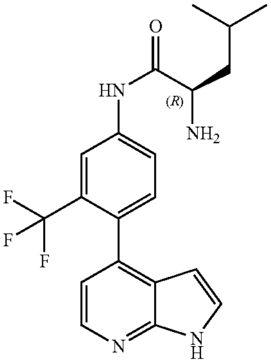
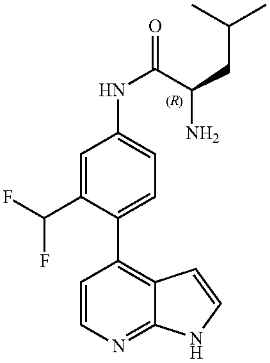
-continued
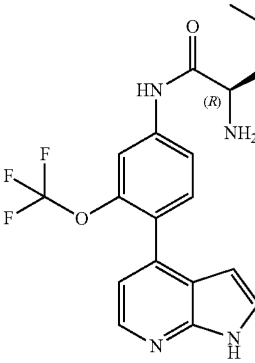
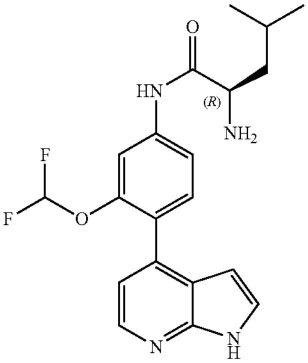
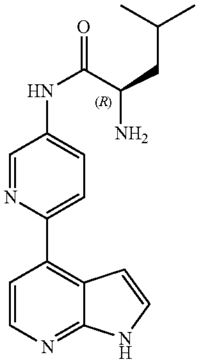
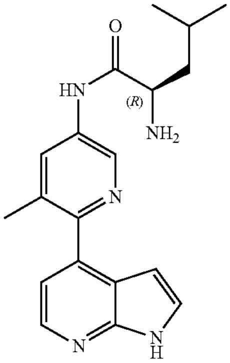
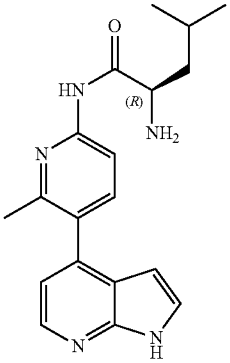
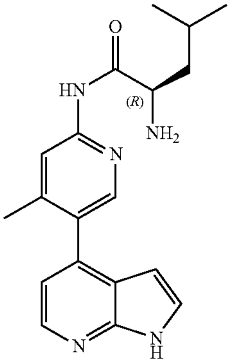
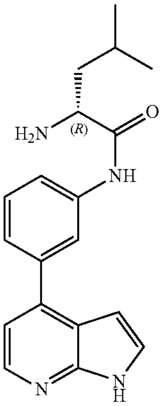

-continued
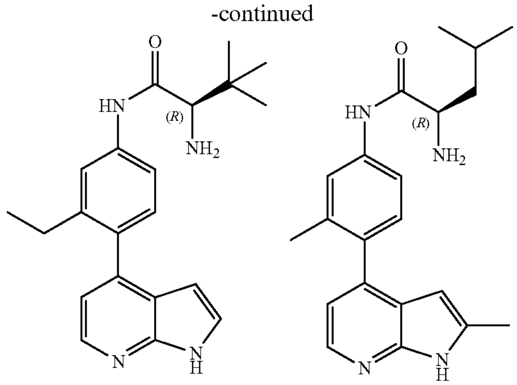
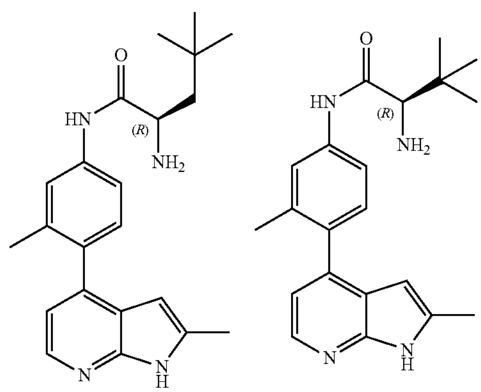
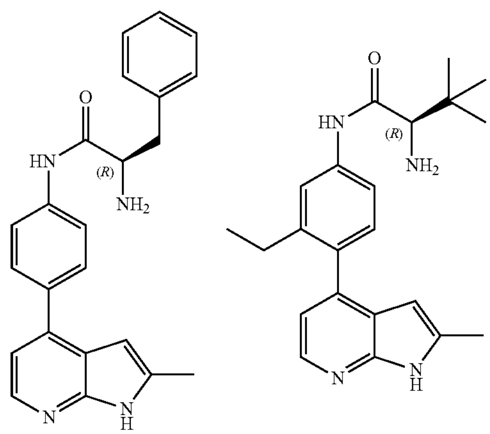
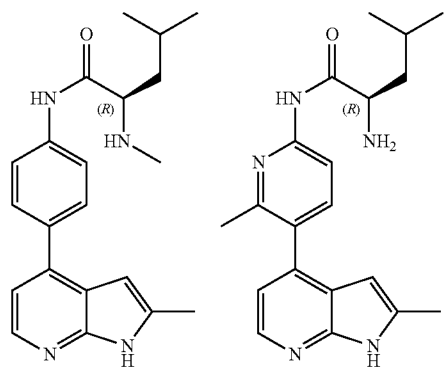
-continued
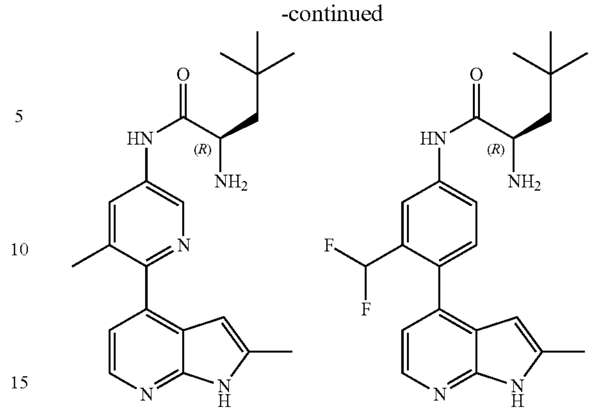
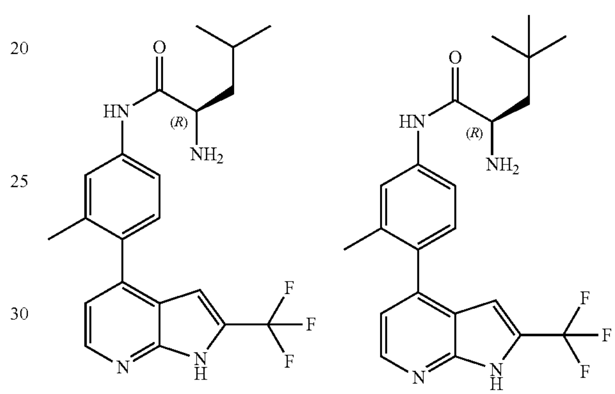
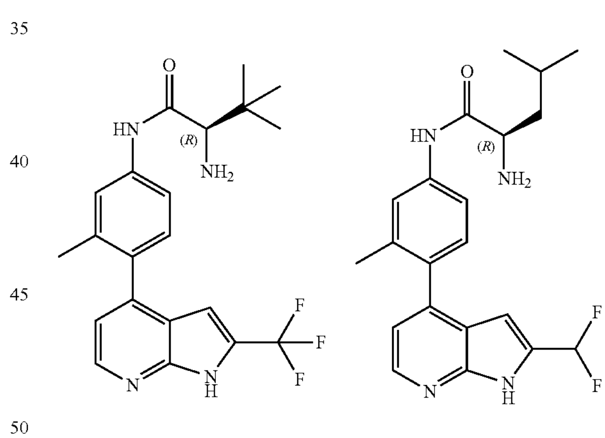
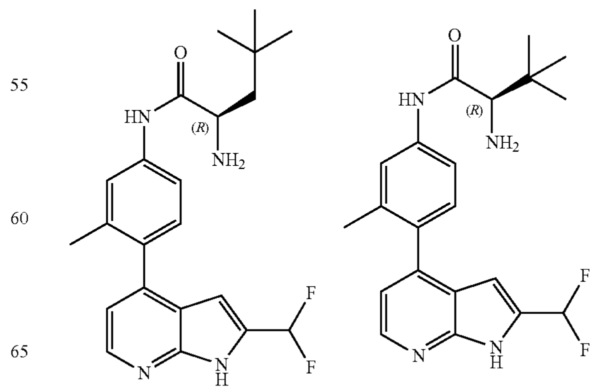

-continued
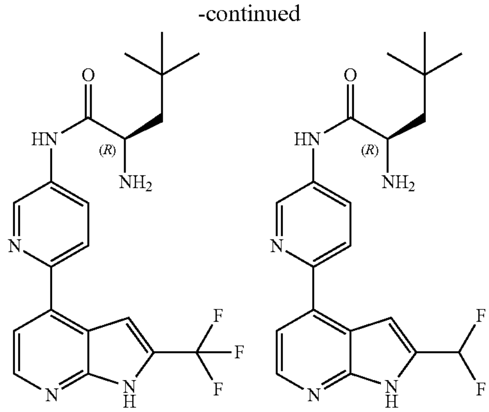
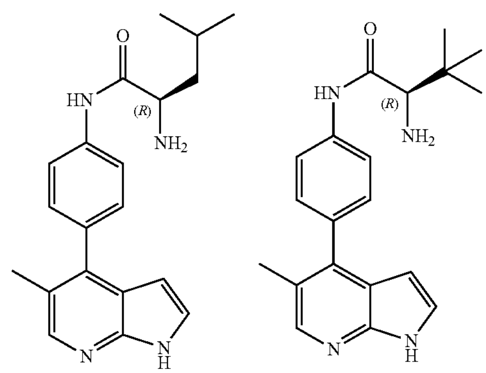
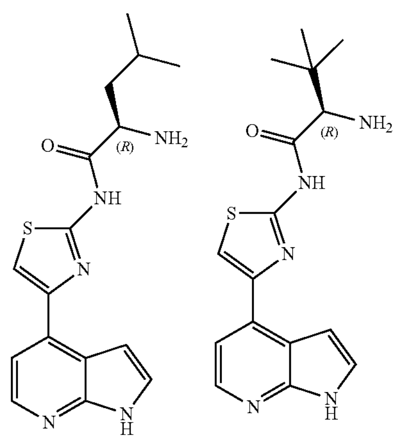
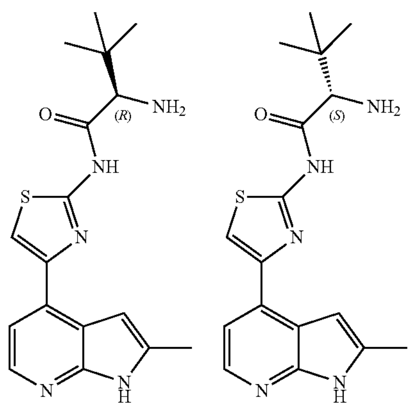
-continued
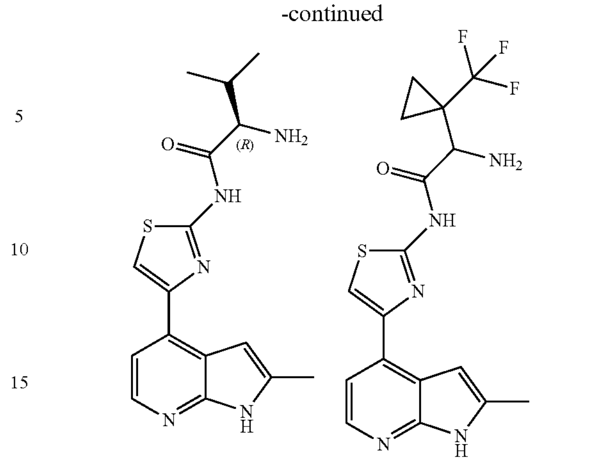
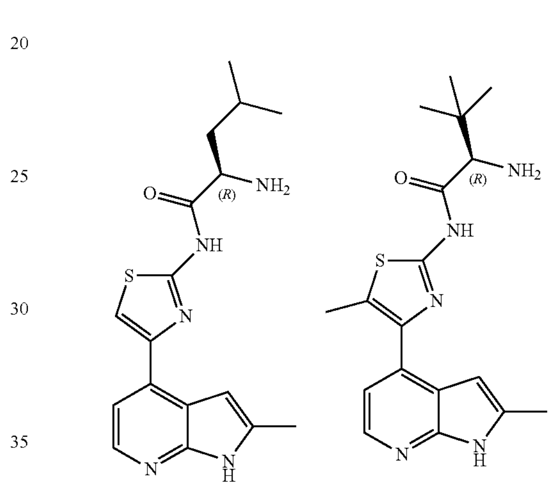
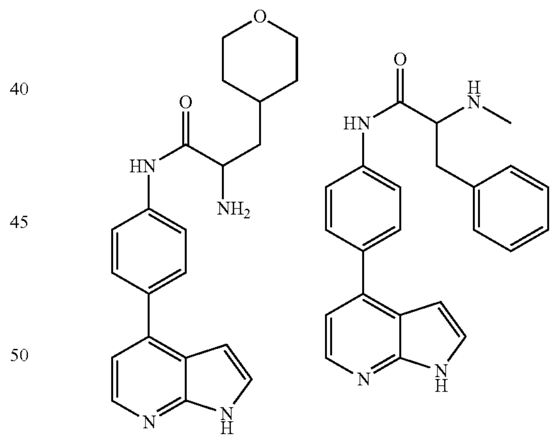
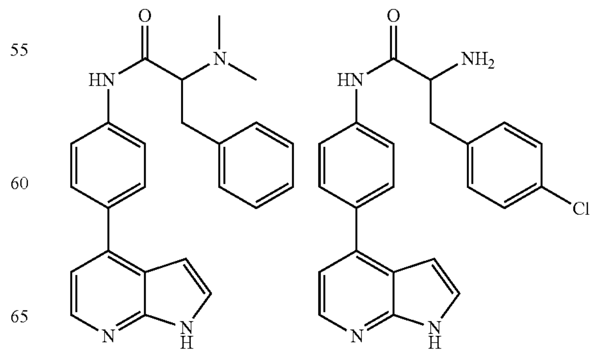

-continued
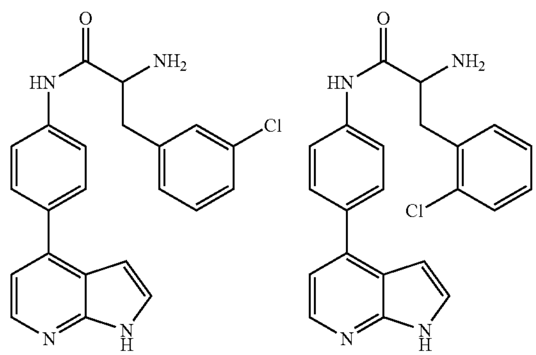
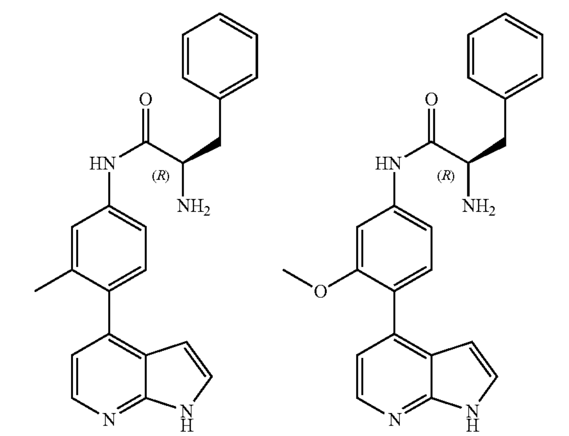
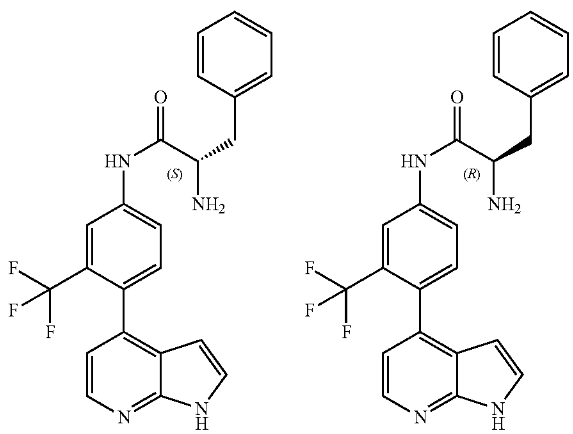
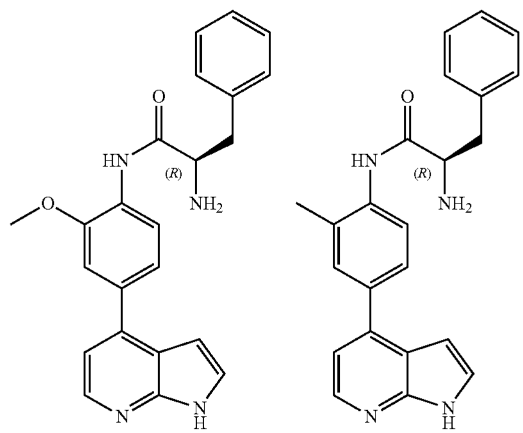
-continued
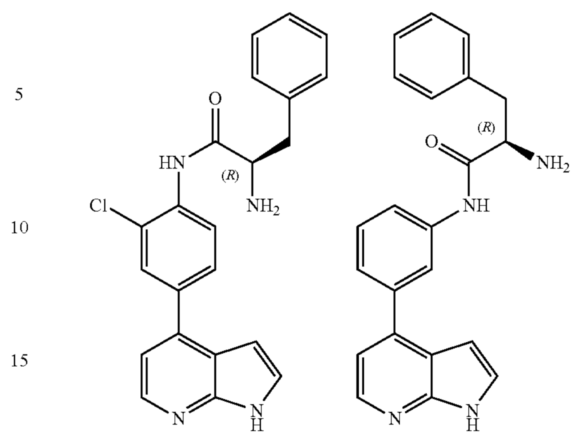
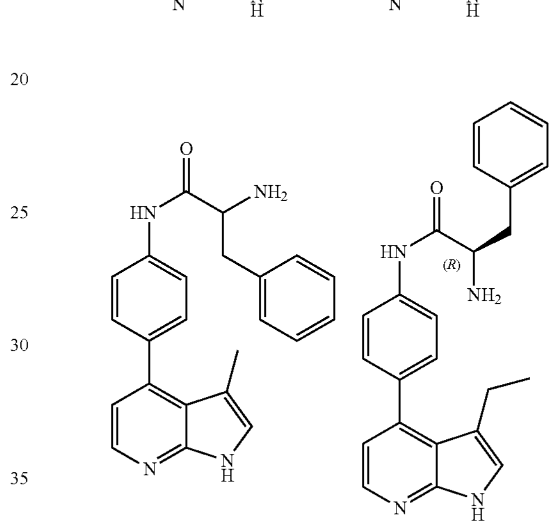
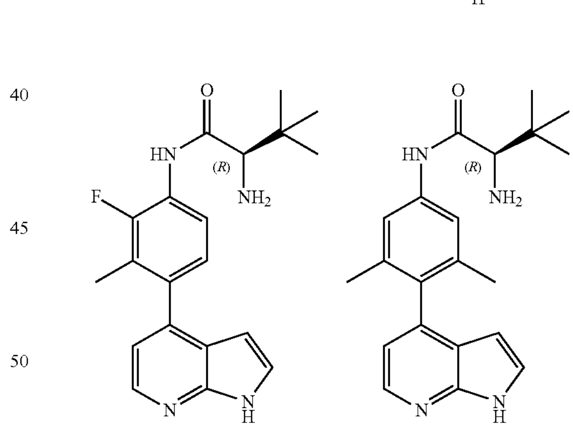
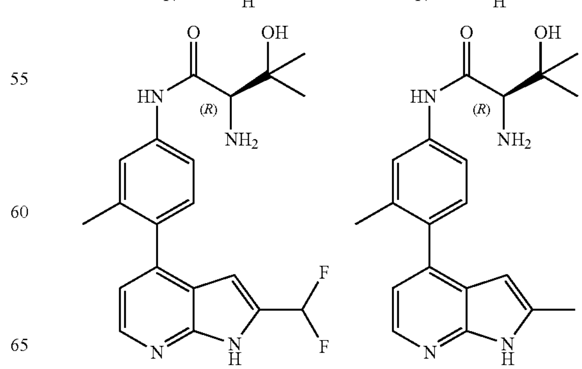

-continued
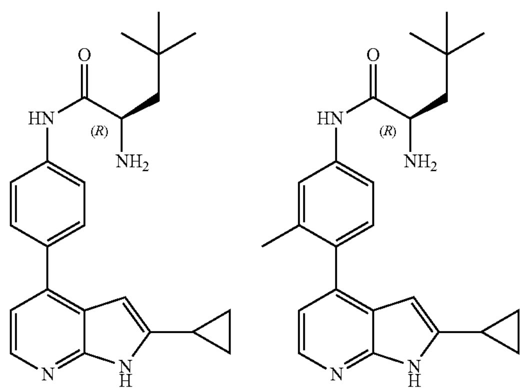
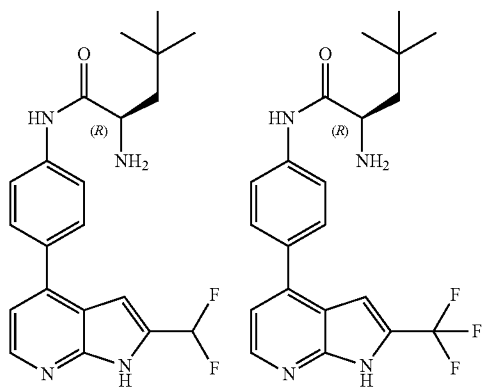
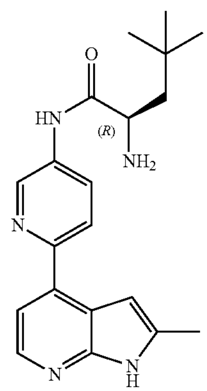
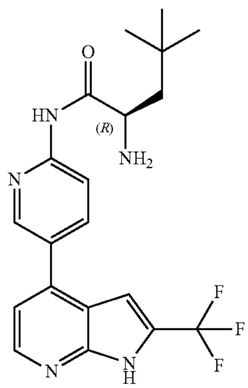
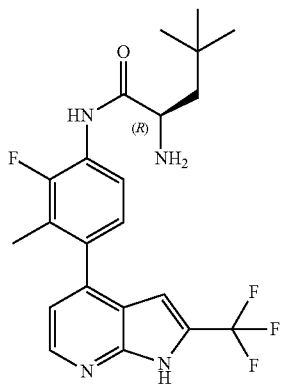
-continued
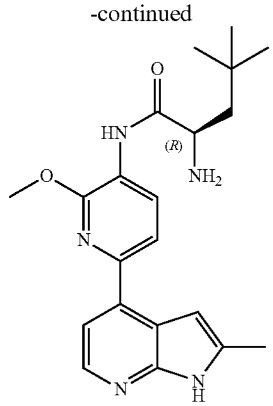
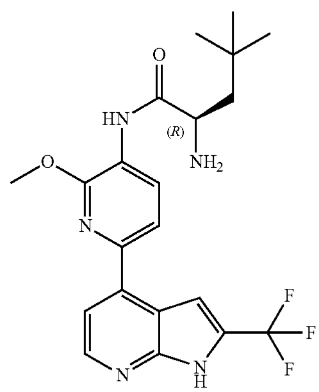
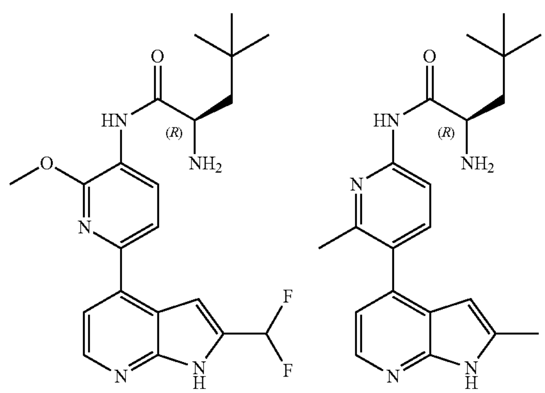
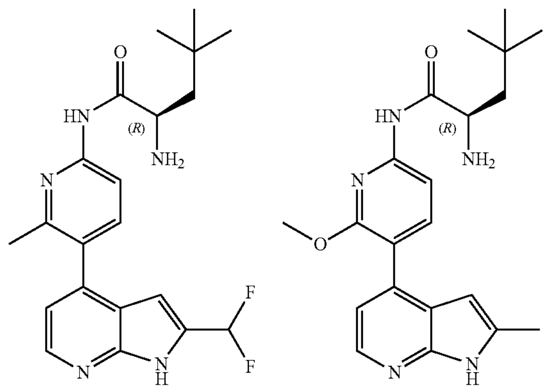

-continued
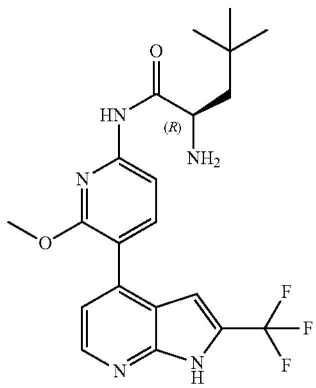
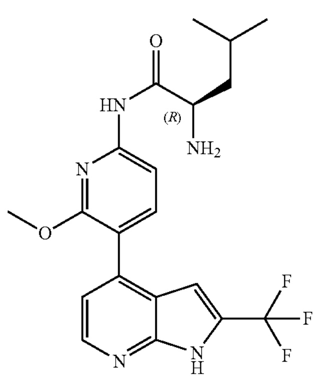
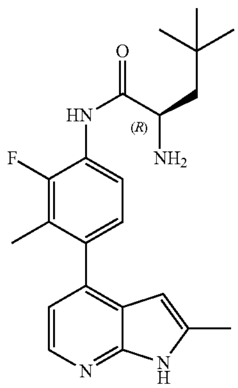
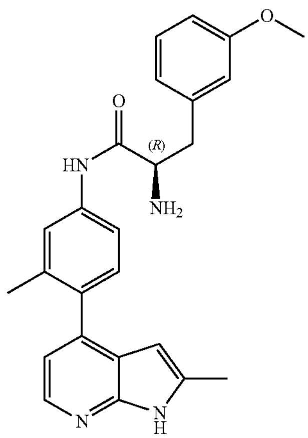
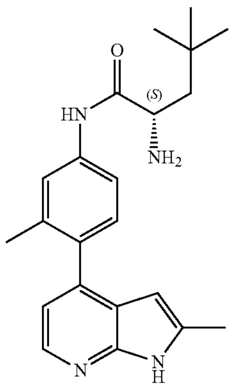
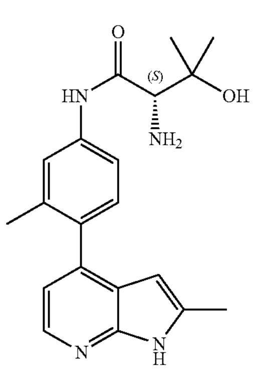
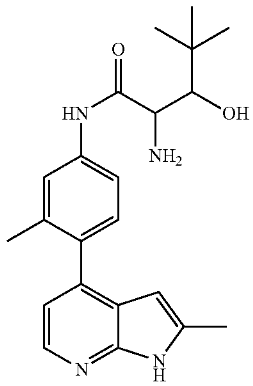
-continued
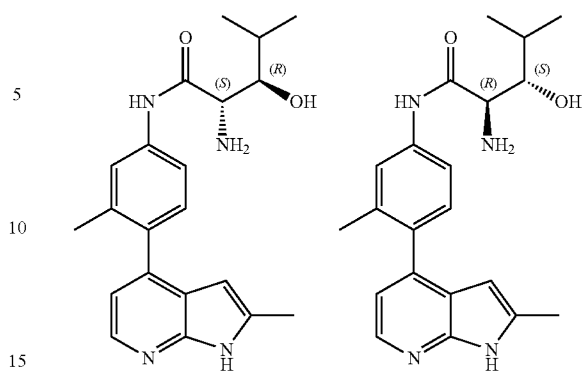
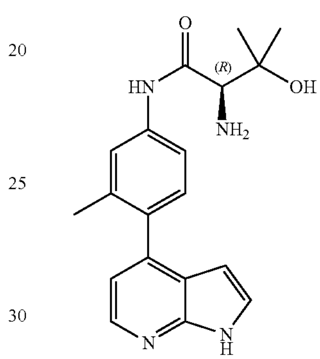
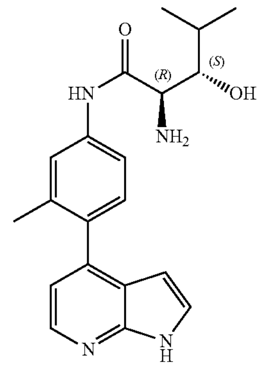
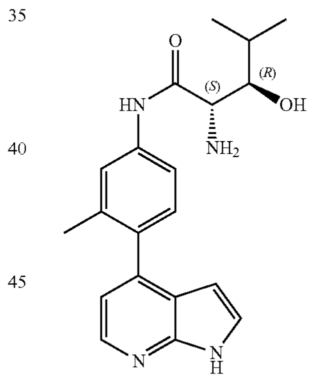
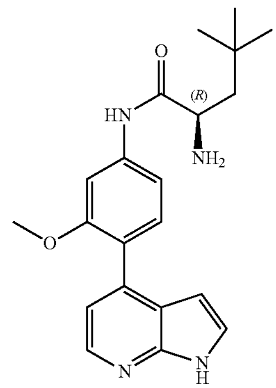
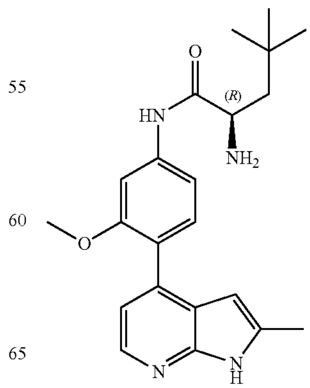
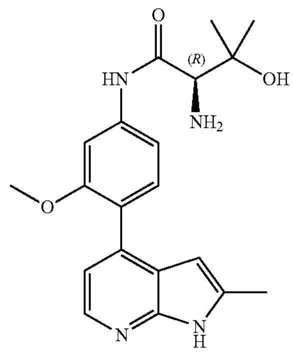

-continued
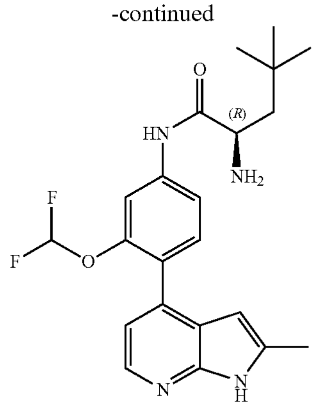
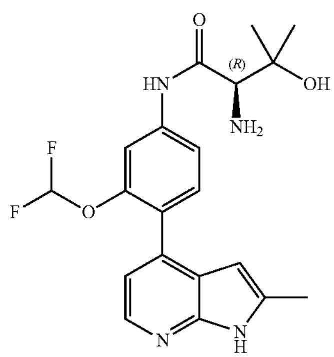
-continued
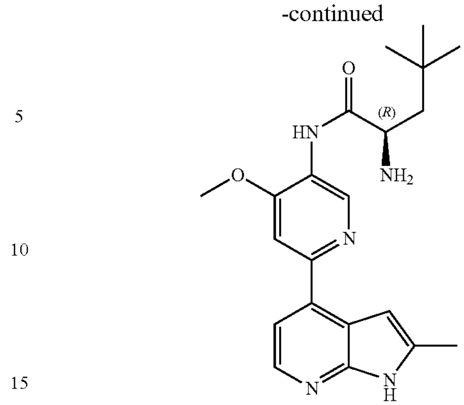
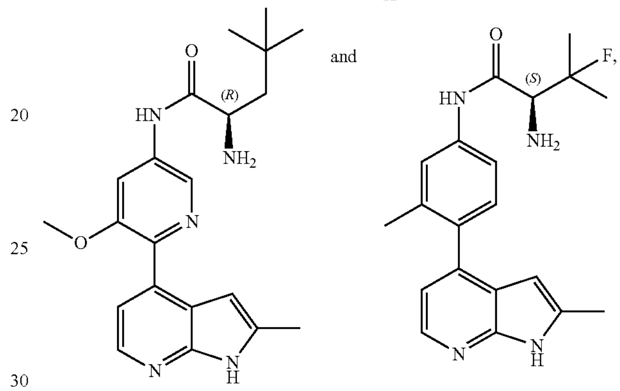
and
and pharmaceutically acceptable salts thereof.
20. A pharmaceutical composition comprising a compound of claim 1, or a pharmaceutically acceptable salt thereof, and a pharmaceutically acceptable carrier.
* * * * *